United States Patent
Pei et al.

(10) Patent No.: US 11,603,373 B2
(45) Date of Patent: Mar. 14, 2023

(54) TDO2 AND IDO1 INHIBITORS

(71) Applicant: Genentech, Inc., South San Francisco, CA (US)

(72) Inventors: Zhonghua Pei, South San Francisco, CA (US); Richard Pastor, South San Francisco, CA (US); Lewis Gazzard, South San Francisco, CA (US); Brendan Parr, South San Francisco, CA (US); Wendy Liu, South San Francisco, CA (US); Rohan Mendonca, South San Francisco, CA (US); Guosheng Wu, Beijing (CN); Po-wai Yuen, Beijing (CN)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 16/626,219

(22) PCT Filed: Jun. 20, 2018

(86) PCT No.: PCT/US2018/038508
§ 371 (c)(1),
(2) Date: Dec. 23, 2019

(87) PCT Pub. No.: WO2019/005559
PCT Pub. Date: Jan. 3, 2019

(65) Prior Publication Data
US 2020/0123163 A1    Apr. 23, 2020

(30) Foreign Application Priority Data
Jun. 28, 2017 (WO) ............... PCT/CN2017/090525

(51) Int. Cl.
| | |
|---|---|
| *C07D 221/00* | (2006.01) |
| *C07D 335/00* | (2006.01) |
| *C07D 487/04* | (2006.01) |
| *C07D 471/08* | (2006.01) |
| *A61P 31/00* | (2006.01) |
| *A61P 35/00* | (2006.01) |
| *A61P 37/00* | (2006.01) |

(52) U.S. Cl.
CPC ......... *C07D 487/04* (2013.01); *C07D 221/00* (2013.01); *C07D 335/00* (2013.01)

(58) Field of Classification Search
CPC .......... A61P 37/00; A61P 35/00; A61P 31/00; C07D 471/08; C07D 221/00; C07D 335/00; C07D 487/04
See application file for complete search history.

(56) References Cited

U.S. PATENT DOCUMENTS 10,800,780 B2 * 10/2020 Lin .................... C07D 519/00
2017/0118750 A1    4/2017 Kikuma

FOREIGN PATENT DOCUMENTS

| EP | 3 287 461 | | 2/2018 |
|---|---|---|---|
| WO | 2021214237 | A1 | 10/2012 |
| WO | WO 2016/037026 | | 3/2016 |
| WO | 2016059412 | A1 | 4/2016 |
| WO | WO2016/165613 | | 10/2016 |
| WO | WO2016/169421 | | 10/2016 |
| WO | WO2017/107979 | | 6/2017 |

OTHER PUBLICATIONS

International Search Report for International Application PCT/US2018/038508 dated Aug. 27, 2018, 3 pages.

* cited by examiner

*Primary Examiner* — Sun Jae Yoo
(74) *Attorney, Agent, or Firm* — McDonnell Boehnen Hulbert & Berghoff LLP

(57) ABSTRACT

Presently provided are inhibitors of cellularly expressed TD02 and IDO1, and pharmaceutical compositions thereof, useful for modulating an activity of tryptophan 2,3 dioxygenase and indoleamine 2,3-dioxygenase 1; treating immunosuppression; treating a medical conditions that benefit from the inhibition of tryptophan degradation; enhancing the effectiveness of an anti-cancer treatment comprising administering an anti-cancer agent; and treating tumor-specific immunosuppression associated with cancer.

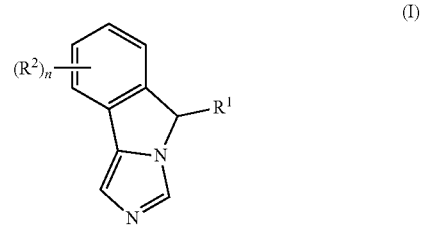

(I)

17 Claims, No Drawings

TDO2 AND IDO1 INHIBITORS

CROSS-REFERENCES TO RELATED APPLICATIONS

This application is a U.S. national phase application of International Patent Application no. PCT/US2018/038508, filed Jun. 20, 2018, which claims the benefit of priority of International Patent Application no. PCT/CN2017/090525, filed Jun. 28, 2017, the disclosure of each of which is hereby incorporated herein by reference in its entirety.

BACKGROUND OF THE INVENTION

Field of the Invention

The present disclosure relates to compounds and methods for inhibition of tryptophan 2,3-dioxygenase (TDO2) and indoleamine 2,3-dioxygenase 1 (IDO1); further the disclosure relates to method of treatment of diseases and disorders mediated by tryptophan deficiency.

Summary of the Related Art

Tryptophan (Trp) is an essential amino acid required for the biosynthesis of proteins, niacin and the neurotransmitter 5-hydroxytryptamine (serotonin). The enzymes indoleamine 2,3-dioxygenase 1 (also known as INDO1 or IDO1), indoleamine-2,3-dioxygenase 2 (INDOL1 or IDO2) and tryptophan-2,3-dioxygenase (TDO2) catalyze the first and rate limiting step in the degradation of L-tryptophan to N-formyl-kynurenine. Although these enzymes catalyze the same reaction, differential expression and compartmentalization of IDO1 and TDO2 in different tissues is thought to mediate their different biological roles. IDO1 is normally expressed in cells of the gastrointestinal and pulmonary epithelia, epididymus, placenta, pDCs in draining lymph nodes and tumor cells. IDO2 is expressed mainly in brain and placenta, but certain splice variants are also detected in liver, small intestine, spleen, placenta, thymus lung, brain, kidney and colon. TDO2 is expressed mainly in liver, and controls the flux of dietary Trp to the serotonin and kynurenine pathways, and is also expressed in tumors and tumor cell lines.

Several lines of evidence suggest that IDO1 and TDO2 are involved in induction of immune tolerance. Studies of mammalian pregnancy, tumor resistance, chronic infections and autoimmune diseases have shown that cells expressing IDO1 can suppress T-cell responses and promote tolerance. Accelerated Trp catabolism has been observed in diseases and disorders associated with cellular immune activation, such as infection, malignancy, autoimmune diseases and AIDS, as well as during pregnancy. It was proposed that IDO1 is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, Adv. Exp. Med. Biol., 294: 425-35). To this end, it has recently been shown that IDO1 inhibition can enhance the levels of virus-specific T cells and, concomitantly, reduce the number of virally infected macrophages in a mouse model of HIV (Portula et al., 2005, Blood, 106:2382-90).

IDO1 is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, Symp. Soc. Exp. Biol. 7: 320-38). Anatomic separation of mother and fetus and antigenic immaturity of the fetus cannot fully explain fetal allograft survival. Recent attention has focused on immunologic tolerance of the mother. Because IDO1 is expressed by human syncytiotrophoblast cells and systemic tryptophan concentration falls during normal pregnancy, it was hypothesized that IDO1 expression at the maternal-fetal interface is necessary to prevent immunologic rejection of the fetal allografts. To test this hypothesis, pregnant mice (carrying syngeneic or allogeneic fetuses) were exposed to 1MT, and a rapid, T cell-induced rejection of all allogeneic concepti was observed. Thus, by catabolizing tryptophan, the mammalian conceptus appears to suppress T-cell activity and defends itself against rejection, and blocking tryptophan catabolism during murine pregnancy allows maternal T cells to provoke fetal allograft rejection (Munn, et al., 1998, Science 281: 1191-3).

Further evidence for a tumoral immune resistance mechanism based on tryptophan degradation by IDO1 comes from the observation that most human tumors constitutively express IDO1, and that expression of IDO1 by immunogenic mouse tumor cells prevents their rejection by preimmunized mice. This effect is accompanied by a lack of accumulation of specific T cells at the tumor site and can be partly reverted by systemic treatment of mice with an inhibitor of IDO1, in the absence of noticeable toxicity. Thus, it was suggested that the efficacy of therapeutic vaccination of cancer patients might be improved by concomitant administration of an IDO1 inhibitor (Uyttenhove et al., 2003, Nature Med., 9: 1269-74). It has also been shown that the IDO1 inhibitor, 1-MT, can synergize with chemotherapeutic agents to reduce tumor growth in mice, suggesting that IDO1 inhibition may also enhance the anti-tumor activity of conventional cytotoxic therapies (Muller et al., 2005, Nature Med., 11:312-9).

A similar situation has been observed with TDO2. It has been shown that a significant proportion of primary human tumors express elevated levels of TDO2 or TDO2 plus IDO1 (Pilotte et al. 2012, P.N.A.S). Moreover, pharmacological inhibition of TDO2 activity with TDO2 inhibitors, leads to immune-mediated rejection of tumors overexpressing TDO2, which means that TDO2, just as seen in IDO1, can mediate tumor-promoting immunosuppressive effects.

Small molecule inhibitors of IDO1 are being developed to treat or prevent IDO1-related diseases such as those described above. For example, PCT Publication WO 99/29310 reports methods for altering T cell-mediated immunity comprising altering local extracellular concentrations of tryptophan and tryptophan metabolites, using an inhibitor of IDO1 such as 1-methyl-DL-tryptophan, p-(3-benzofuranyl)-DL-alanine, p-[3-benzo(b)thienyl]-DL-alanine, and 6-nitro-L-tryptophan) (Munn, 1999). Reported in WO 03/087347, also published as European Patent 1501918, are methods of making antigen-presenting cells for enhancing or reducing T cell tolerance (Munn, 2003). Compounds having indoleamine-2,3-dioxygenase (IDO) inhibitory activity are further reported in WO 2004/094409; WO 2009/073620; WO 2009/132238; WO 2011/056652 and WO 2012/142237. In particular, the compounds of WO 2012/142237 encompass a series of tricyclic imidazoisoindoles with potent IDO1 inhibitory activity.

SUMMARY OF THE INVENTION

We recognized that in light of the experimental data indicating a role for IDO1 and/or TDO2 in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO1 and/or TDO2 activity are desirable. Specific or dual inhibitors of IDO1 and TDO2 can be used to activate T cells and therefore enhance T cell activation when the T cells are suppressed by pregnancy, malignancy or a virus such as HIV. Inhibition of IDO1 and/or TDO2 may also be an important treatment strategy for patients with neurological or neuropsychiatric diseases or disorders such as depression. The compounds, compositions and methods herein help meet the current need for IDO1 and TDO2 modulators.

In this disclosure, we describe novel structures related to imidazoisoindoles that can exert combined inhibition of tryptophan degradation mediated by both IDO1 and TDO2 enzymes.

In one aspect, the invention comprises compounds according to the formula (I),

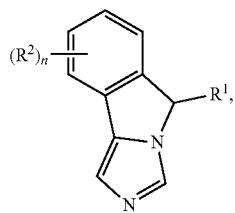

(I)

or a stereoisomer thereof, or a pharmaceutically acceptable salt thereof, wherein
$R^1$ is a spirocyclic ring system,

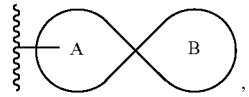

wherein
ring A is $C_{3-8}$cycloalkyl;
ring B is 3-8 membered heterocyclyl or $C_{3-8}$cycloalkyl; and
$R^1$ is substituted by one, two, three, or four $R^a$ groups, wherein each $R^a$ is independently oxo, halogen, cyano, nitro, $C_{1-6}$alkyl, —$C_{1-6}$haloalkyl, $C_{1-6}$alkyl-cyano, —OR, —$NR_2$, —SR, —C(O)OR, —C(O)N(R)$_2$, —C(O)R, —N(R) C(O)R, —S(O)R, —S(O)OR, —S(O)N(R)$_2$, —S(O)$_2$R, —S(O)$_2$OR, —S(O)$_2$N(R)$_2$, —P(O)R$_2$, —OC(O)R, —OC(O)OR, —OC(O)N(R)$_2$, —N(R)C(O)R, —N(R)C(O)OR or —N(R)C(O)N(R)$_2$;
n is 0, 1, 2, 3 or 4;
each $R^2$ is independently halogen, cyano, $C_{1-6}$alkyl, $C_3$cycloalkyl, —$C_{1-6}$haloalkyl, —OR, —$NR_2$ or —SR; and
each R is independently hydrogen, $C_{1-6}$alkyl, $C_{1-6}$haloalkyl, $C_{1-6}$alkyl-O—$C_{1-6}$alkyl, —$C_{1-6}$alkyl-NHC(O)H, optionally substituted $C_{3-6}$cycloalkyl, optionally substituted 4-10 membered heterocycloalkyl, optionally substituted —$C_{1-6}$alkyl-(4-10 membered heterocycloalkyl), optionally substituted heteroaryl, optionally substituted —$C_{1-6}$alkyl-heteroaryl;

provided that ring A is substituted with —$NR_2$ or —OH on a carbon atom adjacent to the carbon atom bonded to the 5H-imidazo[5,1-a]isoindolyl.

In an embodiment, the invention provides compounds of formula (I), wherein ring A is substituted with —OH on a carbon atom adjacent to the carbon atom bonded to the 5H-imidazo[5,1-a]isoindolyl.

In another embodiment, the invention provides compounds of formula (I), wherein ring A is substituted with —OH on a carbon atom adjacent to the carbon atom bonded to the 5H-imidazo[5,1-a]isoindolyl and n is 0. In other embodiments, the invention provides compounds of formula (I), wherein ring A is substituted with —OH on a carbon atom adjacent to the carbon atom bonded to the 5H-imidazo[5,1-a]isoindolyl and n is 1.

In another aspect, pharmaceutical compositions are provided comprising a pharmaceutically acceptable excipient, diluent, or carrier, and a compound according to formula (I).

In another aspect, pharmaceutical compositions are provided comprising a pharmaceutically acceptable excipient, diluent, or carrier, a compound according to formula (I) and a second therapeutic agent.

In another aspect, a kit is provided comprising a pharmaceutically acceptable excipient, diluent, or carrier, a compound according to formula (I) and a second therapeutic agent.

In another aspect methods are provided for
a) modulating an activity of IDO1 and/or TDO2 in a cell-free system or in a cell (ex vivo or in vivo) comprising contacting an IDO1 and/or TDO2 with a modulation effective amount of a compound according to formula (I), or a pharmaceutical composition comprising a compound according to formula (I);
b) treating IDO1 and/or TDO2 mediated immunosuppression in a subject in need thereof, comprising administering an effective inhibiting amount of a compound according to formula (I), or a pharmaceutical composition comprising a compound according to formula (I);
c) treating a medical condition that benefits from the inhibition of tryptophan degradation mediated by IDO1 and/or TDO2 comprising administering an effective amount of a compound of formula (I), or a pharmaceutical composition comprising a compound according to formula (I);
d) enhancing the effectiveness of an anti-cancer treatment comprising administering an anti-cancer agent and a compound according to formula (I), or a pharmaceutical composition comprising a compound according to formula (I); and
e) treating immunosuppression associated with cancer comprising administering an effective amount of a compound according to formula (I), or a pharmaceutical composition comprising a compound according to formula (I).

In another aspect, the invention comprises use of any genus of compounds or species defined herein for the manufacture of a medicament for the treatment of medical conditions that benefit from the inhibition of enzymatic activity of IDO1 and/or TDO2.

In another aspect, the invention comprises any genus of compounds or species defined herein for use in the inhibition of enzymatic activity of IDO1 and/or TDO2 and the treatment of medical conditions that benefit from the inhibition of enzymatic activity of IDO1 and/or TDO2.

In another aspect, the invention comprises use of any genus of compounds or species defined herein for the treatment of immunosuppression associated with cancer, infectious diseases, or viral infections.

DETAILED DESCRIPTION OF THE INVENTION

The present invention is directed to small molecules that inhibit the enzymatic activity of IDO1 and TDO2. Alignment between IDO1 and IDO2 amino acid sequences reveals highly conserved features that mediate heme and substrate binding. Even though the amino acid sequence identity between IDO1 and IDO2 or IDO1 and TDO2 are not particularly high, significant residues determined to be important for catalytic activity by IDO1 and TDO2 mutagenesis and by crystallographic analysis are highly conserved between IDO1, IDO2 and TDO2, suggesting a structural and functional analogy in the mechanism of tryophan dioxygenation. Despite these structural similarities at the active site, IDO1 and TDO2 have different substrate specificity with TDO2 being almost exclusively specific for L-Trp and L-Trp derivatives substituted at the 5- and 6-positions of the indole group, while IDO1 can accept and oxygenate a wider variety of substrates such as D-Trp, tryptamine, serotonin and 1-methyl-L-Trp. These minor structural differences in the active site of IDO1 and TDO2 determine that these two proteins show differential response to the same enzymatic inhibitor molecules, with some inhibitors showing TDO2-specific response, others showing IDO1-specific response and some showing dual IDO1 and TDO2 inhibition. Moreover, the specificity of IDO1 and TDO2 inhibition by a particular class of small molecule inhibitors depends on whether IDO1 and TDO2 activity is measured using bioassays that employ recombinant purified IDO1 and/or TDO2 protein, or IDO1 and/or TDO2 protein expressed within a cell. For example, compounds described in patent applications WO2012142237 and WO2014159248 show potent IDO1 inhibition when tested against the purified recombinant protein and against cellularly expressed IDO1, or against recombinant purified TDO2 protein. However, compounds of that class show a remarkable 10-100 fold decreased potency when tested against TDO2 expressed within a cell. Therefore, those compounds are not likely to contribute to significant inhibition of TDO2 in vivo. For this reason, the present invention describes a novel class of molecules that show potent IDO1 and TDO2 inhibition in cellular bioassays and in vivo.

In one aspect, the invention provides compounds of formula (I),

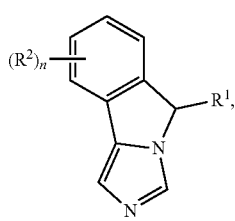

(I)

or a stereoisomer thereof, or a pharmaceutically acceptable salt thereof, wherein $R^1$ is a spirocyclic ring system,

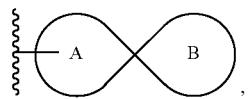

wherein
ring A is $C_{3-8}$cycloalkyl;
ring B is 3-8 membered heterocyclyl or $C_{3-8}$cycloalkyl; and
$R^1$ is substituted by one, two, three, or four $R^a$ groups, wherein each $R^a$ is independently oxo, halogen, cyano, nitro, $C_{1-6}$alkyl, —$C_{1-6}$haloalkyl, $C_{1-6}$alkyl-cyano, —OR, —$NR_2$, —SR, —C(O)OR, —C(O)N(R)$_2$, —C(O)R, —N(R)C(O)R, —S(O)R, —S(O)OR, —S(O)N(R)$_2$, —S(O)$_2$R, —S(O)$_2$OR, —S(O)$_2$N(R)$_2$, —P(O)R$_2$, —OC(O)R, —OC(O)OR, —OC(O)N(R)$_2$, —N(R)C(O)R, —N(R)C(O)OR or —N(R)C(O)N(R)$_2$;
n is 0, 1, 2, 3 or 4;
each $R^2$ is independently halogen, cyano, $C_{1-6}$alkyl, $C_3$cycloalkyl, —$C_{1-6}$haloalkyl, —OR, —$NR_2$ or —SR; and
each R is independently hydrogen, $C_{1-6}$alkyl, $C_{1-6}$haloalkyl, $C_{1-6}$alkyl-O—$C_{1-6}$alkyl, —$C_{1-6}$alkyl-NHC(O)H, optionally substituted $C_{3-6}$cycloalkyl, optionally substituted 4-10 membered heterocycloalkyl, optionally substituted —$C_{1-6}$alkyl-(4-10 membered heterocycloalkyl), optionally substituted heteroaryl, optionally substituted —$C_{1-6}$alkyl-heteroaryl;
provided that ring A is substituted with —$NR_2$ or —OH on a carbon atom adjacent to the carbon atom bonded to the 5H-imidazo[5,1-a]isoindolyl.

In an embodiment, the invention provides compounds of formula (I), wherein ring A is substituted with —OH on a carbon atom adjacent to the carbon atom bonded to the 5H-imidazo[5,1-a]isoindolyl.

In another embodiment, the invention provides compounds of formula (I), wherein ring A is substituted with —OH on a carbon atom adjacent to the carbon atom bonded to the 5H-imidazo[5,1-a]isoindolyl and n is 0. In other embodiments, the invention provides compounds of formula (I), wherein ring A is substituted with —OH on a carbon atom adjacent to the carbon atom bonded to the 5H-imidazo[5,1-a]isoindolyl and n is 1.

The invention further comprises subgenera and species of formula (I) that are any combination of species and genera of structural formula (I), n, $R^1$, and $R^2$, as defined herein below. So, for example, the invention also comprises the subgenus of compounds of structural formula (I) where n is defined as in (1c) below, $R^1$ is defined in (2h) below, and $R^2$ is defined in (3k) below.

n is Selected from One of the Following Groups (1a)-(1k):
(1a) n is 1, 2, 3, or 4.
(1b) n is 0, 1, 2, or 3.
(1c) n is 0, 1, or 2.
(1d) n is 0 or 1.
(1e) n is 1 or 2.
(1f) n is 2 or 3.
(1g) n is 1.
(1h) n is 2.
(1i) n is 3.
(1j) n is 4.
(1k) n is 0.

$R^2$ is Selected from One of the Following Groups (2a)-(2t):

(2a) $R^2$ is independently halogen, cyano, $C_{1-6}$alkyl, $C_3$cycloalkyl, —$C_{1-6}$haloalkyl, —OR, —$NR_2$ or —SR.
(2b) $R^2$ is independently halogen, cyano, $C_{1-6}$alkyl, $C_3$cycloalkyl, —OR, —SR or —$NR_2$.
(2c) $R^2$ is independently halogen, cyano, $C_{1-6}$alkyl, $C_3$cycloalkyl, —SR or —OR.
(2d) $R^2$ is independently halogen, $C_{1-6}$alkyl, $C_3$cycloalkyl, or —OR.
(2e) $R^2$ is independently halogen, cyano, $C_{1-6}$alkyl, —SR or —OR.
(2f) $R^2$ is independently halogen, $C_{1-6}$alkyl or —OR.
(2g) $R^2$ is independently halogen or —OR.
(2h) $R^2$ is independently $C_{1-6}$alkyl or —OR.
(2i) $R^2$ is independently —OR.
(2j) $R^2$ is independently halogen, methyl or —OR.
(2k) $R^2$ is independently halogen, methyl, —OH or —OMe.
(2l) $R^2$ is independently chloro, fluoro, methyl or —OR.
(2m) $R^2$ is independently chloro, fluoro, methyl, —OH or —OMe.
(2n) $R^2$ is independently chloro, fluoro, methyl or —OH.
(2o) $R^2$ is independently fluoro, methyl or —OH.
(2p) $R^2$ is independently fluoro or —OH.
(2q) $R^2$ is independently fluoro or methyl.
(2r) $R^2$ is fluoro.
(2s) $R^2$ is methyl.
(2t) $R^2$ is —OH.

$R^1$ is Selected from One of the Following Groups (3a)-(3 mm):

(3a) $R^1$ is a spirocyclic ring system

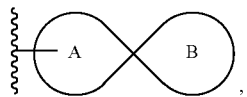

wherein
ring A is $C_{3-8}$cycloalkyl;
ring B is 3-8 membered heterocyclyl or $C_{4-6}$cycloalkyl.

(3b) $R^1$ is a spirocyclic ring system,

wherein
ring A is $C_{4-6}$cycloalkyl;
ring B is 4-8 membered heterocyclyl or $C_{3-8}$cycloalkyl.

(3c) $R^1$ is a spirocyclic ring system,

wherein
ring A is $C_{5-8}$cycloalkyl;
ring B is 5-8 membered heterocyclyl.

(3d) $R^1$ is a spirocyclic ring system

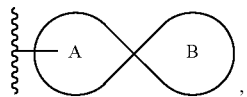

wherein
ring A is $C_{4-7}$cycloalkyl;
ring B is 4-7 membered heterocyclyl.

(3e) $R^1$ is a spirocyclic ring system,

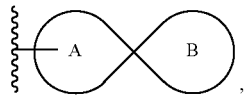

wherein
ring A is $C_{4-6}$cycloalkyl;
ring B is 4-6 membered heterocyclyl or $C_{4-6}$cycloalkyl.

(3f) $R^1$ is a spirocyclic ring system,

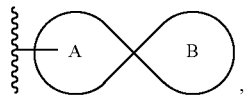

wherein
ring A is $C_{5-6}$cycloalkyl;
ring B is 5-6 membered heterocyclyl.

(3g) $R^1$ is a spirocyclic ring system,

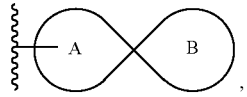

wherein
ring A is $C_{3-8}$cycloalkyl;
ring B is piperidinyl, pyrrolidinyl, azetidinyl, 8-azabicyclo[3.2.1]octane or cyclohexyl.

(3h) $R^1$ is a spirocyclic ring system,

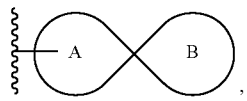

wherein
ring A is $C_{4-7}$cycloalkyl;
ring B is piperidinyl.

(3i) $R^1$ is a spirocyclic ring system,

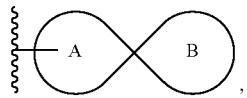

wherein
ring A is $C_{4-6}$cycloalkyl;
ring B is piperidinyl.

(3j) $R^1$ is a spirocyclic ring system

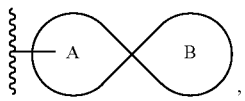

wherein
  ring A is $C_{3-8}$cycloalkyl;
  ring B is pyrrolidinyl.
(3k) $R^1$ is a spirocyclic ring system,

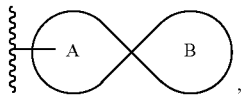

wherein
  ring A is $C_{4-7}$cycloalkyl;
  ring B is pyrrolidinyl.
(3l) $R^1$ is a spirocyclic ring system,

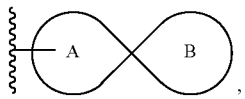

wherein
  ring A is $C_{4-6}$cycloalkyl;
  ring B is pyrrolidinyl.
(3m) $R^1$ is a spirocyclic ring system,

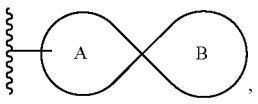

wherein
  ring A is cyclobutyl or cyclopentyl;
  ring B is azetidinyl, piperidinyl, 8-azabicyclo[3.2.1]octanyl, cyclohexyl or tetrahydro-2H-thiopyran 1,1-dioxidyl.
(3n) $R^1$ is a spirocyclic ring system,

wherein
  ring A is cyclobutyl;
  ring B is 4-8 membered heterocyclyl.
(3o) $R^1$ is a spirocyclic ring system,

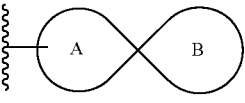

wherein
  ring A is cyclobutyl;
  ring B is piperidinyl, azetidinyl, 8-azabicyclo[3.2.1]octane or cyclohexyl.
(3p) $R^1$ is a spirocyclic ring system,

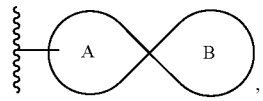

wherein
  ring A is cyclobutyl;
  ring B is 6-8 membered heterocyclyl.
(3q) $R^1$ is a spirocyclic ring system,

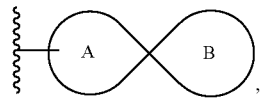

wherein
  ring A is cyclopentyl;
  ring B is 3-8 membered heterocyclyl.
(3r) $R^1$ is a spirocyclic ring system,

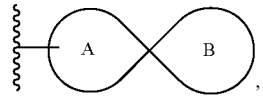

wherein
  ring A is cyclopentyl;
  ring B is 4-8 membered heterocyclyl.
(3s) $R^1$ is a spirocyclic ring system,

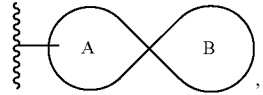

wherein
  ring A is cyclopentyl;
  ring B is piperidinyl, azetidinyl, 8-azabicyclo[3.2.1]octane or cyclohexyl.
(3t) $R^1$ is a spirocyclic ring system,

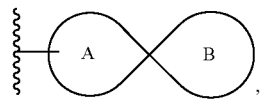

wherein
  ring A is cyclopentyl;
  ring B is 6-8 membered heterocyclyl.
(3u) Any of groups (3a)-(3t), wherein $R^1$ is substituted by one, two, three, or four $R^1$ groups, wherein each $R^a$ is independently oxo, halogen, cyano, nitro, $C_{1-6}$alkyl, $C_{1-6}$haloalkyl, $C_{1-6}$alkyl-cyano, —OR, —$NR_2$, —SR, —C(O)OR, —C(O)N(R)$_2$, —C(O)R, —N(R)C(O)R, —S(O)R, —S(O)OR, —S(O)N(R)$_2$, —S(O)$_2$R, —S(O)$_2$OR, —S(O)$_2$N(R)$_2$, —P(O)R$_2$, —OC(O)R, —OC(O)OR, —OC(O)N(R)₂, —N(R)C(O)R, —N(R)C(O)OR or —N(R)C(O)N(R)₂.

(3v) Any of groups (3a)-(3t), wherein R¹ is substituted by one, two or three R¹ groups, wherein each R¹ is independently oxo, halogen, cyano, nitro, C₁₋₆alkyl, —C₁₋₆haloalkyl, C₁₋₆alkyl-cyano, —OR, —NR₂, —SR, —C(O)OR, —C(O)N(R)₂, —C(O)R, —N(R)C(O)R, —S(O)R, —S(O)OR, —S(O)N(R)₂, —S(O)₂R, —S(O)₂OR, —S(O)₂N(R)₂, —P(O)R₂, —OC(O)R, —OC(O)OR, —OC(O)N(R)₂, —N(R)C(O)R, —N(R)C(O)OR or —N(R)C(O)N(R)₂.

(3w) Any of groups (3a)-(3t), wherein R¹ is substituted by one or two Rᵃ groups, wherein each R¹ is independently oxo, halogen, cyano, nitro, C₁₋₆alkyl, —C₁₋₆haloalkyl, C₁₋₆alkyl-cyano, —OR, —NR₂, —SR, —C(O)OR, —C(O)N(R)₂, —C(O)R, —N(R)C(O)R, —S(O)R, —S(O)OR, —S(O)N(R)₂, —S(O)₂R, —S(O)₂OR, —S(O)₂N(R)₂, —P(O)R₂, —OC(O)R, —OC(O)OR, —OC(O)N(R)₂, —N(R)C(O)R, —N(R)C(O)OR or —N(R)C(O)N(R)₂.

(3x) Any of groups (3a)-(3t), wherein R¹ is substituted by one R¹ groups, wherein each R¹ is independently oxo, halogen, cyano, nitro, C₁₋₆alkyl, —C₁₋₆haloalkyl, C₁₋₆alkyl-cyano, —OR, —NR₂, —SR, —C(O)OR, —C(O)N(R)₂, —C(O)R, —N(R)C(O)R, —S(O)R, —S(O)OR, —S(O)N(R)₂, —S(O)₂R, —S(O)₂OR, —S(O)₂N(R)₂, —P(O)R₂, —OC(O)R, —OC(O)OR, —OC(O)N(R), —N(R)C(O)R, —N(R)C(O)OR or —N(R)C(O)N(R)₂.

(3y) R¹ is

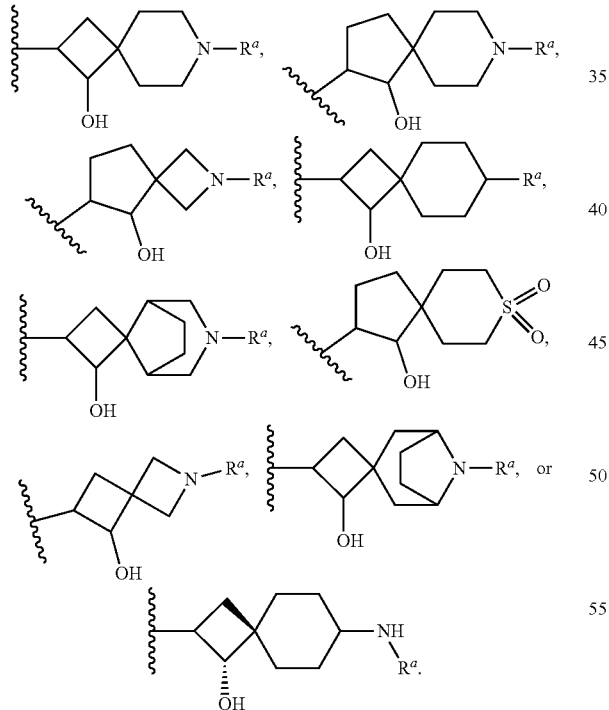

(3z) Group (3y), wherein R¹ is oxo, halogen, cyano, nitro, C₁₋₆alkyl, —C₁₋₆haloalkyl, C₁₋₆ alkyl-cyano, —OR, —NR₂, —SR, —C(O)OR, —C(O)N(R)₂, —C(O)R, —S(O)R, —S(O)OR, —S(O)N(R)₂, —S(O)₂R, —S(O)₂OR, —S(O)₂N(R)₂, —P(O)R₂, —OC(O)R, —OC(O)OR, —OC(O)N(R)₂, —N(R)C(O)R, —N(R)C(O)OR or —N(R)C(O)N(R)₂.

(3aa) Group (3y), wherein R¹ is C₁₋₆alkyl, —C(O)OR, —C(O)N(R)₂, —C(O)R, —S(O)N(R)₂, —S(O)₂R, —P(O)R₂, —OC(O)R, —OC(O)OR or —OC(O)N(R)₂.

(3bb) Group (3y), wherein R¹ is —C(O)OR, —C(O)R, —S(O)N(R)₂, —S(O)₂R or —P(O)R₂.

(3cc) R¹ is

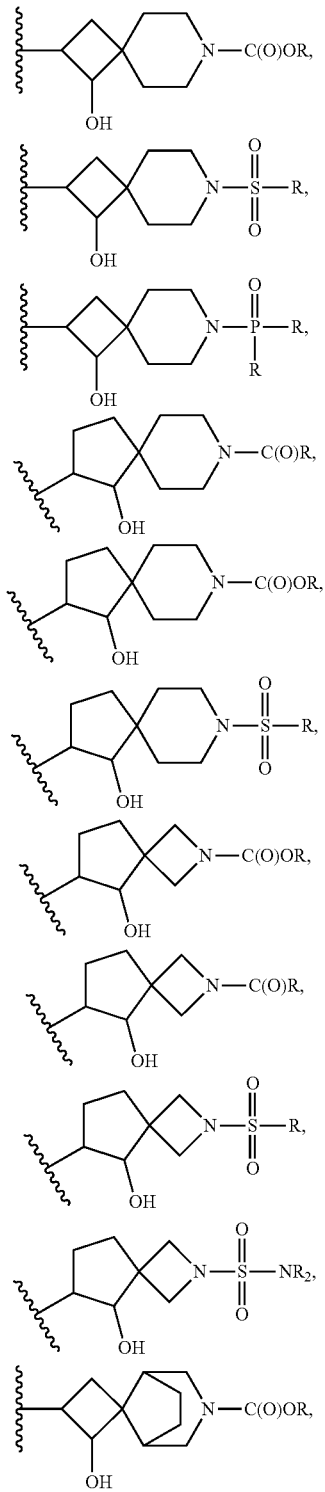

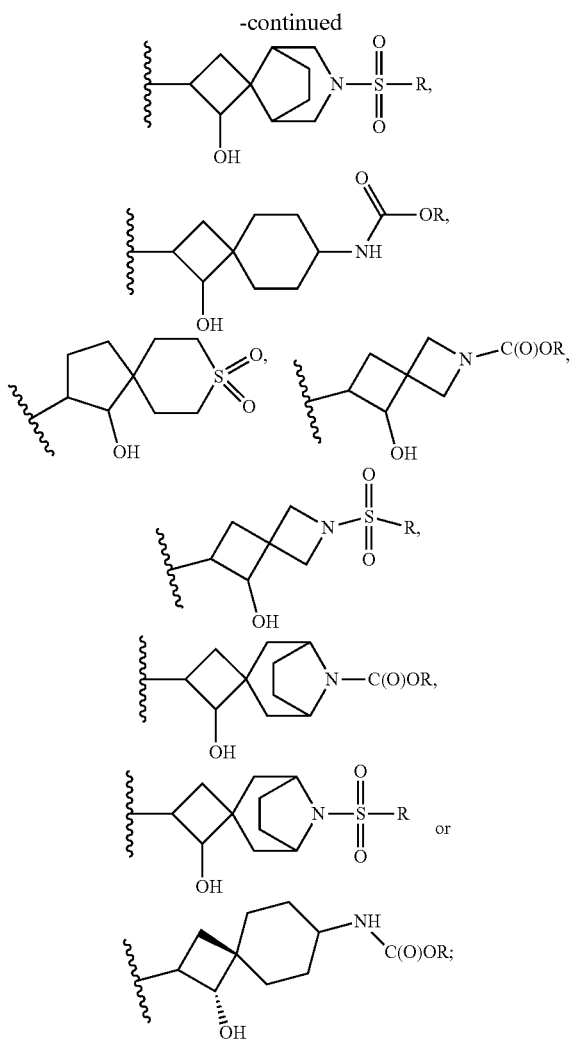

where each R is independently hydrogen, C$_{1-6}$alkyl, C$_{1-6}$haloalkyl, C$_{1-6}$alkyl-O—C$_{1-6}$alkyl, —C$_{1-6}$alkyl-NHC(O)H, —C$_{1-6}$alkyl-CN, —C$_{1-6}$alkyl-C(O)NMe$_2$, optionally substituted C$_{3-6}$cycloalkyl, optionally substituted 4-10 membered heterocycloalkyl, optionally substituted —C$_{1-6}$alkyl-(4-10 membered heterocycloalkyl) or optionally substituted heteroaryl or optionally substituted —C$_{1-6}$alkyl-heteroaryl.

(3dd) Any of groups (3a)-(3cc), where each R is independently C$_{1-6}$alkyl, C$_{1-6}$haloalkyl, C$_{1-6}$alkyl-O—C$_{1-6}$alkyl, —C$_{1-6}$alkyl-CN, optionally substituted C$_{3-6}$cycloalkyl, optionally substituted 4-10 membered heterocycloalkyl, optionally substituted —C$_{1-6}$alkyl-(4-10 membered heterocycloalkyl), optionally substituted heteroaryl or optionally substituted —C$_{1-6}$alkyl-heteroaryl.

(3ee) Any of groups (3a)-(3cc), where each R is independently hydrogen, C$_{1-6}$alkyl, C$_{1-6}$haloalkyl, C$_{1-6}$alkyl-O—C$_{1-6}$alkyl, C$_{1-6}$alkyl-NHC(O)H, —C$_{1-6}$alkyl-C(O)NMe$_2$, —C$_{1-6}$alkyl-CN, C$_{3-6}$cycloalkyl, 4-10 membered heterocycloalkyl, —C$_{1-6}$alkyl-(4-10 membered heterocycloalkyl), heteroaryl or —C$_{1-6}$alkyl-heteroaryl.

(3ff) Any of groups (3a)-(3cc), where each R is independently hydrogen, C$_{1-6}$alkyl, C$_{1-6}$haloalkyl optionally substituted C$_{1-6}$cycloalkyl, optionally substituted 4-10 membered heterocycloalkyl, optionally substituted —C$_{1-6}$alkyl-(4-10 membered heterocycloalkyl), optionally substituted heteroaryl or optionally substituted —C$_{1-6}$alkyl-heteroaryl.

(3gg) Any of groups (3a)-(3cc), where each R is independently hydrogen, C$_{1-6}$alkyl, C$_{1-6}$haloalkyl, C$_{1-6}$alkyl-O—C$_{1-6}$alkyl, optionally substituted C$_{3-6}$cycloalkyl, optionally substituted 4-10 membered heterocycloalkyl or optionally substituted —C$_{1-6}$alkyl-(4-10 membered heterocycloalkyl.

(3hh) Any of groups (3a)-(3cc), where each R is independently hydrogen, C$_{1-6}$alkyl, C$_{1-6}$haloalkyl, C$_{1-6}$alkyl-O—C$_{1-6}$alkyl, —C$_{1-6}$alkyl-NHC(O)H, —C$_{1-6}$alkyl-C(O)NMe$_2$, —C$_{1-6}$alkyl-CN, optionally substituted C$_{3-6}$cycloalkyl, optionally substituted heteroaryl or optionally substituted —C$_{1-6}$alkyl-heteroaryl.

(3ii) Any of groups (3a)-(3cc), where each R is independently hydrogen, C$_{1-6}$alkyl, C$_{1-6}$haloalkyl, optionally substituted C$_{3-6}$cycloalkyl, optionally substituted 4-10 membered heterocycloalkyl, optionally substituted —C$_{1-6}$alkyl-(4-10 membered heterocycloalkyl), optionally substituted heteroaryl or optionally substituted —C$_{1-6}$alkyl-heteroaryl.

(3jj) Any of groups (3a)-(3cc), where each R is independently hydrogen, methyl, ethyl, isopropyl, tert-butyl, fluoromethyl, difluoromethyl, —CH$_2$CHF$_2$, —(CH$_2$)$_2$—O—CH$_3$, —CH(CH$_3$)NHC(O)H, —(CH$_2$)$_2$—C(O)NMe$_2$, —CH$_2$CN, cyclopropyl, difluorocyclopropyl, cyclopropane-1-carbonitrile, cyclobutyl, pyrazolyl, imidazolyl, isoxazolyl, pyridinyl, phenyl, piperidinyl, indolin-2-one, 6,7-dihydro-5H-pyrazolo[5,1-b][1,3]oxazinyl, —CH$_2$-piperidin-2-one, piperidin-2-one, 1-methylpiperidin-2-one, triazolyl, —CH(CH$_3$)-triazolyl, pyrazolyl, tetrahydro-2H-pyranyl, tetrahydrofuranyl, tetrahydro-2H-pyranyl, —CH$_2$-tetrahydro-2H-pyranyl, pyrrolidinone, —CH$_2$-pyrrolidinone, -1-methylpyrrolidinone, —CH$_2$-1-methylpyrrolidinone, -methylisoxazolyl, —CH$_2$-methylisoxazolyl, 1-methyl-1H-pyrazolyl, —(CH$_2$)$_2$-(1-methyl-1H-pyrazolyl), 1H-imidazolyl, 1H-tetrazolyl, —CH$_2$-1H-tetrazolyl, methylisoxazolyl, —CH$_2$-3-methylisoxazolyl, piperidine-1-carboxamide, 1,1-dioxidotetrahydrothiophenyl or 5,6,7,8-tetrahydro-[1,2,4]triazolo[4,3-a]pyridinyl.

(3kk) Any of groups (3a)-(3cc), where each R is independently hydrogen, methyl, ethyl, isopropyl, tert-butyl, fluoromethyl, difluoromethyl, —CH$_2$CHF$_2$, —(CH$_2$)$_2$—O—CH$_3$, —CH(CH$_3$)NHC(O)H, —(CH$_2$)$_2$—C(O)NMe$_2$, —CH$_2$CN, cyclopropyl, difluorocyclopropyl, cyclopropane-1-carbonitrile, cyclobutyl, 1-methylpyrazol-4-yl, 1-methyl-1H-pyrazol-3-yl, 1,3,5-trimethylpyrazol-4-yl, 1,3,5-trimethyl-1H-pyrazol-4-yl, 1,2-dimethyl-1H-imidazol-4-yl, 3,5-dimethylisoxazol-4-yl, 4-methylpyridin-3-yl, —(CH$_2$)$_2$-pyridin-3-yl, phenyl-N-methylacetamide, —CH$_2$-piperidin-1-yl, 1-methylindolin-2-one, 6,7-dihydro-5H-pyrazolo[5,1-b][1,3]oxazinyl, —CH$_2$-piperidin-2-one, 1-methylpiperidin-2-one, —CH(CH$_3$)—(1H-1,2,4-triazol-1-yl), 1-methyl-1H-pyrazol-3-yl, tetrahydro-2H-pyran-4-yl, tetrahydrofuran-3-yl, —CH$_2$-(tetrahydro-2H-pyran-4-yl), —CH$_2$-(pyrrolidin-2-one), —CH$_2$-(1-methylpyrrolidin-2-one), —CH$_2$-(5-methylisoxazol-3-yl), —(CH$_2$)$_2$-(1-methyl-1H-pyrazol-4-yl), 1H-imidazolyl-4-yl, —CH$_2$-(1H-tetrazol-5-yl), —CH$_2$-(3-methylisoxazol-5-yl), piperidine-1-carboxamide, 1,1-dioxidotetrahydrothiophen-3-yl or 5,6,7,8-tetrahydro-triazolo[4,3-a]pyridin-6-yl.

(3ll) Any of groups (3a)-(3cc), where each R is independently hydrogen, methyl, ethyl, isopropyl, tert-butyl, fluoromethyl, difluoromethyl, —CH$_2$CHF$_2$, —(CH$_2$)$_2$—O—CH$_3$, —CH(CH$_3$)NHC(O)H, —(CH$_2$)$_2$—C(O)NMe$_2$ or —CH$_2$CN.

(3 mm) Any of groups (3a)-(3cc), where each R is independently hydrogen, methyl, cyclopropyl, difluorocyclopropyl, cyclopropane-1-carbonitrile, cyclobutyl, I-methylpyrazol-4-yl, 1-methyl-1H-pyrazol-3-yl, 1,3,5-trimethylpyrazol-4-yl, 1,3,5-trimethyl-1H-pyrazol-4-yl, 1,2-dimethyl-1H-imidazol-4-yl, 3,5-dimethylisoxazol-4-yl, 4-methylpyridin-3-yl, —(CH$_2$)$_2$-pyridin-3-yl, phenyl-N-methylacetamide, —CH$_2$-piperidin-1-yl, 1-methylindolin-2-one, 6,7-dihydro-5H-pyrazolo[5,1-b][1,3]oxazinyl, —CH$_2$-piperidin-2-one, 1-methylpiperidin-2-one, —CH(CH$_3$)—(1H-1,2,4-triazol-1-yl), 1-methyl-1H-pyrazol-3-yl, tetrahydro-2H-pyran-4-yl, tetrahydrofuran-3-yl, —CH$_2$-(tetrahydro-2H-pyran-4-yl), —CH$_2$-(pyrrolidin-2-one), —CH$_2$-(1-methylpyrrolidin-2-one), —CH$_2$-(5-methylisoxazol-3-yl), —(CH$_2$)$_2$-(1-methyl-1H-pyrazol-4-yl), 1H-imidazol-4-yl, —CH$_2$-(1H-tetrazol-5-yl), —CH$_2$-(3-methylisoxazol-5-yl), piperidine-1-carboxamide, 1,1-dioxidotetrahydrothiophen-3-yl or 5,6,7,8-tetrahydro-[1,2,4]triazolo[4,3-a]pyridin-6-yl.

(3nn) R$^1$ is

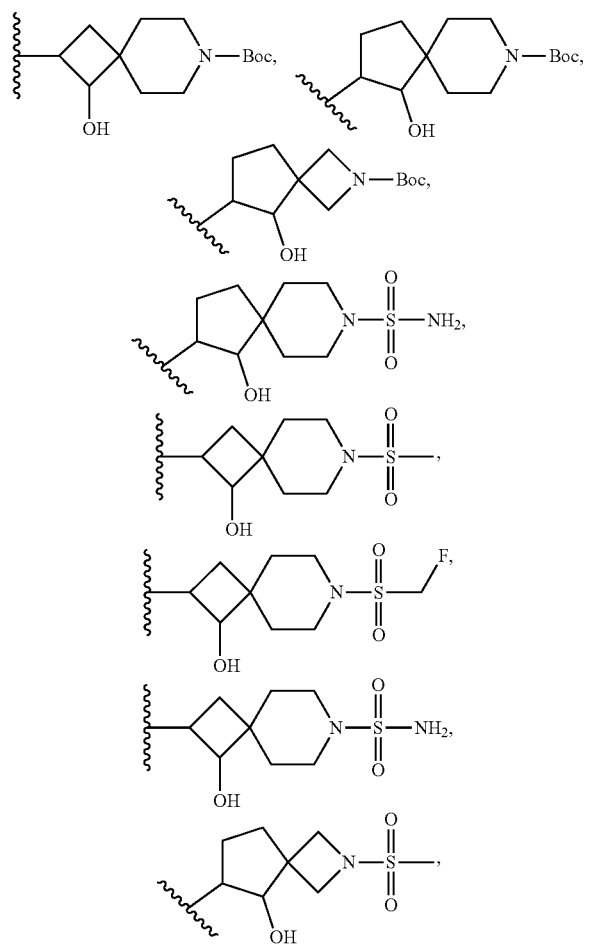

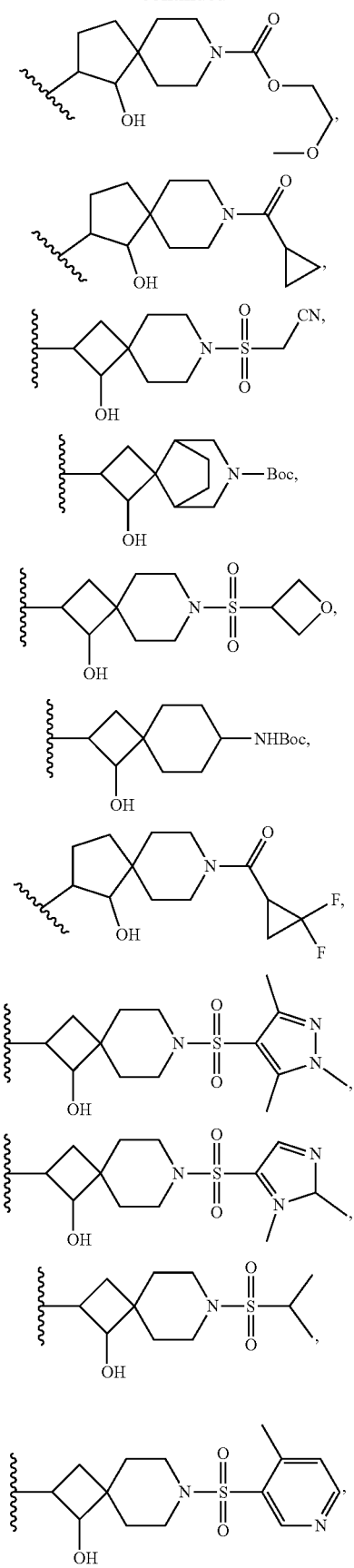

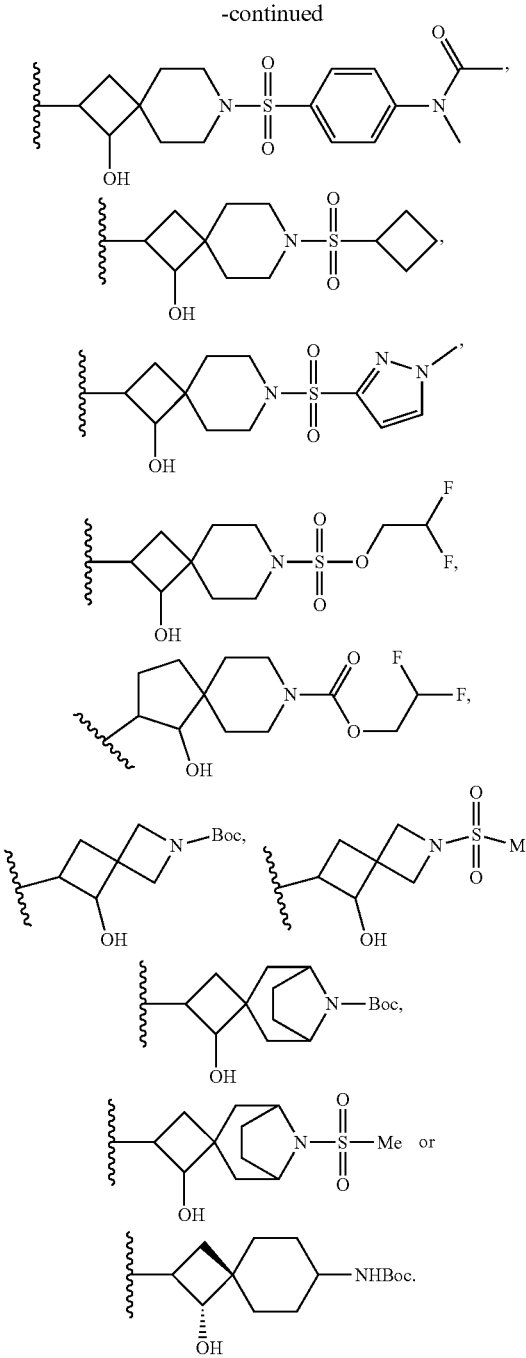

(3oo) R¹ is

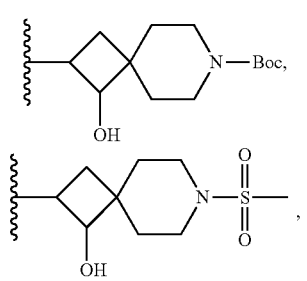

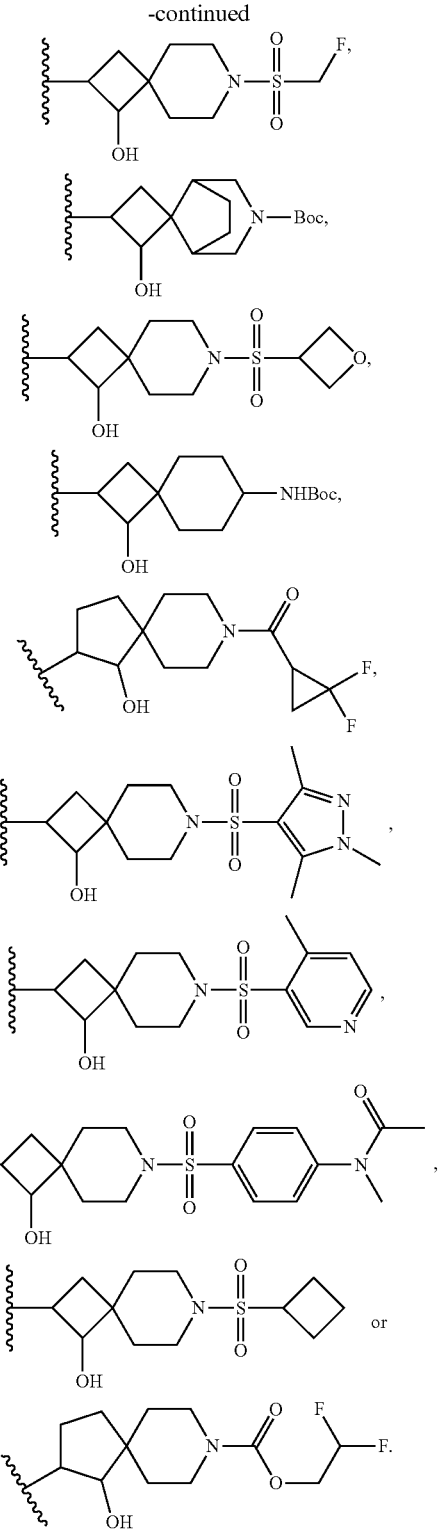

The invention further comprises subgenera and species of formula (I) that are any combination of species and genera of structural formula (I) can be any of formula (Ia)-(Ii) wherein n, R² and R¹ are defined above. So, for example, the invention also comprises the subgenus of compounds of structural formula (Ie) where n is defined as in (1g) above, and R² is defined in (2r) above.

Structural Formula I is One of Formulae (Ia)-(Ii):

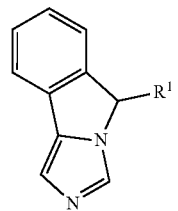
(Ia)

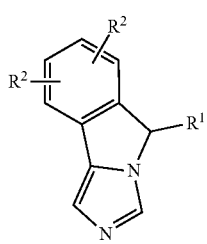
(Ib)

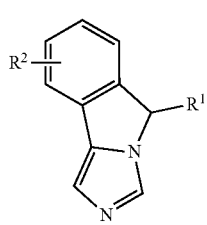
(Ic)

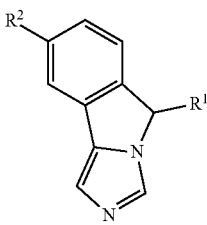
(Id)

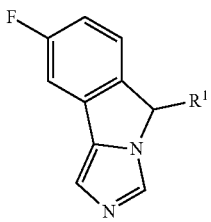
(Ie)

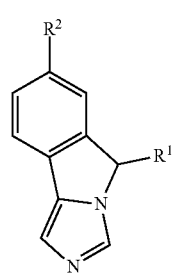
(If)

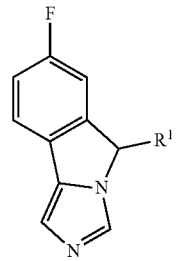
(Ig)

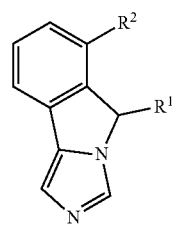
(Ih)

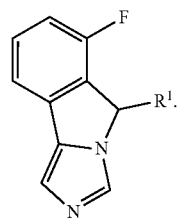
(Ii)

Particular embodiments of this aspect of the invention include compounds of any one of the formulae (I) and (Ia)-(Ii), each as defined in each of the following rows, wherein each entry is a group number as defined above (e.g., (2r) refers to $R^2$ is fluoro), an "X" indicates that the variable is defined by another group in the embodiment (e.g., in embodiment (1)-X below, $R^1$ is defined in Formula (X)) and a dash "-" indicates that the variable is as defined for Formula (I) or (Ia)-(Ii) or defined according to any one of the applicable variable definitions (1a)-(3 mm) [e.g., when the entry for $R^2$ is a dash, it can be either as defined for Formula (I) or (Ia)-(Ii), or any one of definitions (2a)-(2t)]:

|  | (I) | n | $R^2$ | $R^1$ |
|---|---|---|---|---|
| (1)-1 | (I) | (1a) | (2a) | (3e) |
| (1)-2 | (I) | (1a) | (2b) | (3f) |
| (1)-3 | (I) | (1a) | (2f) | (3k) |
| (1)-4 | (I) | (1a) | (2h) | (3u) |
| (1)-5 | (I) | (1a) | (2k) | (3v) |
| (1)-6 | (I) | (1a) | (2n) | (3e) |
| (1)-7 | (I) | (1b) | (2a) | (3ee) |
| (1)-8 | (I) | (1b) | (2b) | (3ii) |
| (1)-9 | (I) | (1b) | (2f) | (3jj) |
| (1)-10 | (I) | (1b) | (2h) | (3kk) |
| (1)-11 | (I) | (1b) | (2k) | (3ll) |
| (1)-12 | (I) | (1b) | (2n) | (3mm) |
| (1)-13 | (I) | (1c) | — | (3nn) |
| (1)-14 | (I) | (1c) | (2b) | (3oo) |
| (1)-15 | (I) | — | (2f) | (3e) |
| (1)-16 | (I) | (1c) | (2h) | (3f) |
| (1)-17 | (I) | (1c) | (2k) | (3k) |
| (1)-18 | (I) | (1c) | (2n) | (3ll) |
| (1)-19 | (I) | (1e) | (2a) | (3mm) |
| (1)-20 | (I) | (1e) | — | (3nn) |
| (1)-21 | (I) | (1e) | (2f) | (3oo) |
| (1)-22 | (I) | (1e) | (2h) | (3kk) |
| (1)-23 | (I) | (1e) | (2k) | (3e) |
| (1)-24 | (I) | (1e) | (2n) | (3f) |

-continued

| (1) | n | R² | R¹ |
|---|---|---|---|
| (1)-25 | (I) | (1f) | (2a) | (3k) |
| (1)-26 | (I) | (1f) | (2b) | (3u) |
| (1)-27 | (I) | (1f) | (2f) | (3nn) |
| (1)-28 | (I) | — | (2h) | (3oo) |
| (1)-29 | (I) | (1f) | (2k) | (3v) |
| (1)-30 | (I) | (1f) | — | (3e) |
| (1)-31 | (Ia) | X | X | (3ee) |
| (1)-32 | (Ia) | X | X | (3ii) |
| (1)-33 | (Ia) | X | X | (3jj) |
| (1)-34 | (Ia) | X | X | (3kk) |
| (1)-35 | (Ia) | X | X | (3mm) |
| (1)-36 | (Ia) | X | X | (3nn) |
| (1)-37 | (Ia) | X | X | (3f) |
| (1)-38 | (Ia) | X | X | (3k) |
| (1)-39 | (Ia) | X | X | (3u) |
| (1)-40 | (Ia) | X | X | (3k) |
| (1)-11 | (Ia) | X | X | (3u) |
| (1)-42 | (Ia) | X | X | (3v) |
| (1)-43 | (Ia) | X | X | (3e) |
| (1)-44 | (Ia) | X | X | (3ee) |
| (1)-45 | (Ia) | X | X | (3e) |
| (1)-46 | (Ia) | X | X | (3f) |
| (1)-47 | (Ia) | X | X | — |
| (1)-48 | (Ia) | X | X | (3u) |
| (1)-49 | (Ia) | X | X | (3mm) |
| (1)-50 | (Ia) | X | X | (3nn) |
| (1)-51 | (Ia) | X | X | (3oo) |
| (1)-52 | (Ia) | X | X | (3mm) |
| (1)-53 | (Ia) | X | X | (3nn) |
| (1)-54 | (Ia) | X | X | (3u) |
| (1)-55 | (Ia) | X | X | (3v) |
| (1)-56 | (Ia) | X | X | (3e) |
| (1)-57 | (Ia) | X | X | (3ee) |
| (1)-58 | (Ia) | X | X | — |
| (1)-59 | (Ia) | X | X | (3f) |
| (1)-60 | (Ib) | X | (2a) | (3k) |
| (1)-61 | (Ib) | X | (2b) | (3u) |
| (1)-62 | (Ib) | X | (2f) | (3kk) |
| (1)-63 | (Ib) | X | (2h) | (3mm) |
| (1)-64 | (Ib) | X | (2k) | (3nn) |
| (1)-65 | (Ib) | X | (2n) | (3u) |
| (1)-66 | (Ib) | X | (2a) | (3v) |
| (1)-67 | (Ib) | X | (2b) | (3e) |
| (1)-68 | (Ib) | X | — | (3ee) |
| (1)-69 | (Ib) | X | (2h) | (3mm) |
| (1)-70 | (Ib) | X | (2k) | (3nn) |
| (1)-71 | (Ib) | X | (2n) | (3f) |
| (1)-72 | (Ib) | X | (2b) | — |
| (1)-73 | (Ib) | X | (2f) | (3u) |
| (1)-74 | (Ib) | X | (2h) | (3jj) |
| (1)-75 | (Ib) | X | (2b) | (3kk) |
| (1)-76 | (Ib) | X | (2f) | (3u) |
| (1)-77 | (Ib) | X | (2h) | — |
| (1)-78 | (Ib) | X | (2b) | (3e) |
| (1)-79 | (Ib) | X | (2f) | (3ee) |
| (1)-80 | (Ib) | X | (2h) | (3e) |
| (1)-81 | (Ib) | X | (2a) | (3f) |
| (1)-82 | (Ib) | X | (2b) | (3k) |
| (1)-83 | (Ib) | X | (2f) | (3u) |
| (1)-84 | (Ib) | X | (2h) | (3ll) |
| (1)-85 | (Ib) | X | (2k) | (3mm) |
| (1)-86 | (Ib) | X | — | (3nn) |
| (1)-87 | (Ib) | X | (2b) | (3oo) |
| (1)-88 | (Ib) | X | (2f) | (3u) |
| (1)-89 | (Ib) | X | (2h) | (3v) |
| (1)-90 | (Ib) | X | (2b) | (3e) |
| (1)-91 | (Ic) | X | (2c) | (3ee) |
| (1)-92 | (Ic) | X | (2h) | — |
| (1)-93 | (Ic) | X | (2k) | (3nn) |
| (1)-94 | (Ic) | X | (2n) | (3kk) |
| (1)-95 | (Ic) | X | (2b) | (3u) |
| (1)-96 | (Ic) | X | (2f) | (3mm) |
| (1)-97 | (Ic) | X | (2h) | (3nn) |
| (1)-98 | (Ic) | X | (2b) | (3oo) |
| (1)-99 | (Ic) | X | — | (3kk) |
| (1)-100 | (Ic) | X | (2j) | (3mm) |
| (1)-100 | (Ic) | X | (2h) | (3nn) |
| (1)-102 | (Ic) | X | (2a) | (3f) |
| (1)-103 | (Ic) | X | (2b) | (3k) |
| (1)-104 | (Ic) | X | (2f) | — |
| (1)-105 | (Ic) | X | (2h) | (3k) |
| (1)-106 | (Ic) | X | (2k) | (3ll) |
| (1)-107 | (Ic) | X | (2n) | (3v) |
| (1)-108 | (Ic) | X | (2b) | (3e) |
| (1)-109 | (Ic) | X | (2f) | (3ee) |
| (1)-110 | (Ic) | X | (2h) | (3mm) |
| (1)-111 | (Ic) | X | (2b) | (3nn) |
| (1)-112 | (Ic) | X | (2c) | (3ll) |
| (1)-113 | (Ic) | X | (2h) | (3mm) |
| (1)-114 | (Ic) | X | (2k) | (3nn) |
| (1)-115 | (Ic) | X | (2n) | (3oo) |
| (1)-116 | (Ic) | X | (2a) | (3ii) |
| (1)-117 | (Ic) | X | (2b) | (3jj) |
| (1)-118 | (Ic) | X | (2f) | (3kk) |
| (1)-119 | (Ic) | X | (2h) | (3e) |
| (1)-120 | (Ic) | X | — | (3f) |
| (1)-121 | (Id) | X | (2n) | (3k) |
| (1)-122 | (Id) | X | (2c) | (3u) |
| (1)-123 | (Id) | X | (2h) | (3k) |
| (1)-124 | (Id) | X | (2k) | (3u) |
| (1)-125 | (Id) | X | (2n) | (3v) |
| (1)-126 | (Id) | X | (2k) | (3e) |
| (1)-127 | (Id) | X | (2n) | — |
| (1)-128 | (Id) | X | (2f) | (3e) |
| (1)-129 | (Id) | X | (2h) | (3f) |
| (1)-130 | (Id) | X | — | (3k) |
| (1)-131 | (Id) | X | (2n) | (3u) |
| (1)-132 | (Id) | X | (2a) | (3jj) |
| (1)-133 | (Id) | X | — | (3kk) |
| (1)-134 | (Id) | X | (2f) | — |
| (1)-135 | (Id) | X | (2h) | (3nn) |
| (1)-136 | (Id) | X | (2k) | (3jj) |
| (1)-137 | (Id) | X | (2n) | (3kk) |
| (1)-138 | (Id) | X | (2a) | (3k) |
| (1)-139 | (Id) | X | (2b) | (3u) |
| (1)-140 | (Id) | X | (2f) | (3v) |
| (1)-141 | (Id) | X | — | (3e) |
| (1)-142 | (Id) | X | (2k) | (3ee) |
| (1)-143 | (Id) | X | (2f) | (3mm) |
| (1)-144 | (Id) | X | (2a) | (3nn) |
| (1)-145 | (Id) | X | (2b) | (3c) |
| (1)-146 | (Id) | X | — | (3kk) |
| (1)-147 | (Id) | X | (2h) | (3ll) |
| (1)-148 | (Id) | X | (2k) | (3mm) |
| (1)-149 | (Id) | X | (2n) | (3nn) |
| (1)-150 | (Id) | X | (2n) | — |
| (1)-151 | (Ie) | X | X | (3v) |
| (1)-152 | (Ie) | X | X | (3e) |
| (1)-153 | (Ie) | X | X | (3ee) |
| (1)-154 | (Ie) | X | X | (3e) |
| (1)-155 | (Ie) | X | X | (3f) |
| (1)-156 | (Ie) | X | X | (3k) |
| (1)-157 | (Ie) | X | X | (3u) |
| (1)-158 | (Ie) | X | X | (3kk) |
| (1)-159 | (Ie) | X | X | (3ll) |
| (1)-160 | (Ie) | X | X | (3mm) |
| (1)-161 | (Ie) | X | X | (3nn) |
| (1)-162 | (Ie) | X | X | — |
| (1)-163 | (Ie) | X | X | (3ii) |
| (1)-164 | (Ie) | X | X | (3jj) |
| (1)-165 | (Ie) | X | X | (3kk) |
| (1)-166 | (Ie) | X | X | (3mm) |
| (1)-167 | (Ie) | X | X | (3nn) |
| (1)-168 | (Ie) | X | X | (3ii) |
| (1)-169 | (Ie) | X | X | (3jj) |
| (1)-170 | (Ie) | X | X | (3kk) |
| (1)-171 | (Ie) | X | X | (3mm) |
| (1)-172 | (Ie) | X | X | (3nn) |
| (1)-173 | (Ie) | X | X | (3ll) |
| (1)-174 | (Ie) | X | X | — |
| (1)-175 | (Ie) | X | X | (3nn) |
| (1)-176 | (Ie) | X | X | (3oo) |
| (1)-177 | (Ie) | X | X | (3e) |
| (1)-178 | (Ie) | X | X | (3ee) |

-continued

|         | (I)  | n | R² | R¹     |
|---------|------|---|-----|--------|
| (1)-179 | (Ie) | X | X   | (3mm)  |
| (1)-180 | (Ie) | X | X   | —      |
| (1)-181 | (If) | X | (2a)| (3f)   |
| (1)-182 | (If) | X | (2b)| (3k)   |
| (1)-183 | (If) | X | —   | (3u)   |
| (1)-184 | (If) | X | (2h)| (3ll)  |
| (1)-185 | (If) | X | (2k)| (3mm)  |
| (1)-186 | (If) | X | (2n)| —      |
| (1)-187 | (If) | X | (2f)| (3oo)  |
| (1)-188 | (If) | X | —   | (3kk)  |
| (1)-189 | (If) | X | (2k)| (3e)   |
| (1)-190 | (If) | X | (2n)| (3ee)  |
| (1)-191 | (If) | X | (2a)| (3f)   |
| (1)-192 | (If) | X | (2b)| (3k)   |
| (1)-193 | (If) | X | (2f)| (3u)   |
| (1)-194 | (If) | X | (2h)| (3v)   |
| (1)-195 | (If) | X | (2k)| (3c)   |
| (1)-196 | (If) | X | (2n)| (3ee)  |
| (1)-197 | (If) | X | (2f)| (3kk)  |
| (1)-198 | (If) | X | (2h)| (3ll)  |
| (1)-199 | (If) | X | (2k)| (3mm)  |
| (1)-200 | (If) | X | (2n)| (3nn)  |
| (1)-201 | (If) | X | (2f)| (3oo)  |
| (1)-202 | (If) | X | (2h)| (3mm)  |
| (1)-203 | (If) | X | (2k)| (3nn)  |
| (1)-204 | (If) | X | (2n)| (3ii)  |
| (1)-205 | (If) | X | (2a)| (3jj)  |
| (1)-206 | (If) | X | (2b)| (3kk)  |
| (1)-207 | (If) | X | (2f)| —      |
| (1)-208 | (If) | X | (2h)| (3nn)  |
| (1)-209 | (If) | X | (2k)| (3e)   |
| (1)-210 | (If) | X | —   | (3kk)  |
| (1)-211 | (Ig) | X | X   | (3ll)  |
| (1)-212 | (Ig) | X | X   | (3mm)  |
| (1)-213 | (Ig) | X | X   | (3nn)  |
| (1)-214 | (Ig) | X | X   | (3oo)  |
| (1)-215 | (Ig) | X | X   | (3mm)  |
| (1)-216 | (Ig) | X | X   | (3nn)  |
| (1)-217 | (Ig) | X | X   | (3k)   |
| (1)-218 | (Ig) | X | X   | —      |
| (1)-219 | (Ig) | X | X   | (3v)   |
| (1)-220 | (Ig) | X | X   | (3e)   |
| (1)-221 | (Ig) | X | X   | (3ee)  |
| (1)-222 | (Ig) | X | X   | (3kk)  |
| (1)-223 | (Ig) | X | X   | (3ll)  |
| (1)-224 | (Ig) | X | X   | (3mm)  |
| (1)-225 | (Ig) | X | X   | (3nn)  |
| (1)-226 | (Ig) | X | X   | (3oo)  |
| (1)-227 | (Ig) | X | X   | (3jj)  |
| (1)-228 | (Ig) | X | X   | —      |
| (1)-229 | (Ig) | X | X   | (3e)   |
| (1)-230 | (Ig) | X | X   | (3e)   |
| (1)-231 | (Ig) | X | X   | (3kk)  |
| (1)-232 | (Ig) | X | X   | (3ll)  |
| (1)-233 | (Ig) | X | X   | (3mm)  |
| (1)-234 | (Ig) | X | X   | (3nn)  |
| (1)-235 | (Ig) | X | X   | (3oo)  |
| (1)-236 | (Ig) | X | X   | (3kk)  |
| (1)-237 | (Ig) | X | X   | (3e)   |
| (1)-238 | (Ig) | X | X   | (3f)   |
| (1)-239 | (Ig) | X | X   | (3k)   |
| (1)-240 | (Ig) | X | X   | (3u)   |
| (1)-241 | (Ih) | X | (2b)| (3u)   |
| (1)-242 | (Ih) | X | —   | (3v)   |
| (1)-243 | (Ih) | X | (2h)| —      |
| (1)-244 | (Ih) | X | (2k)| (3ee)  |
| (1)-243 | (Ih) | X | (2n)| (3ii)  |
| (1)-246 | (Ih) | X | (2f)| (3jj)  |
| (1)-247 | (Ih) | X | (2h)| (3kk)  |
| (1)-248 | (Ih) | X | (2k)| (3e)   |
| (1)-249 | (Ih) | X | —   | (3f)   |
| (1)-250 | (Ih) | X | (2a)| (3k)   |
| (1)-251 | (Ih) | X | (2b)| (3mm)  |
| (1)-252 | (Ih) | X | (2f)| (3nn)  |
| (1)-253 | (Ih) | X | (2h)| (3oo)  |
| (1)-254 | (Ih) | X | (2k)| (3e)   |
| (1)-255 | (Ih) | X | (2n)| (3k)   |
| (1)-256 | (Ih) | X | (2f)| (3u)   |
| (1)-257 | (Ih) | X | (2h)| (3v)   |
| (1)-258 | (Ih) | X | (2k)| (3e)   |
| (1)-259 | (Ih) | X | (2n)| (3ee)  |
| (1)-260 | (Ih) | X | (2f)| (3ii)  |
| (1)-261 | (Ih) | X | (2h)| —      |
| (1)-262 | (Ih) | X | (2k)| (3kk)  |
| (1)-263 | (Ih) | X | (2n)| (3e)   |
| (1)-264 | (Ih) | X | —   | (3f)   |
| (1)-265 | (Ih) | X | (2b)| (3k)   |
| (1)-266 | (Ih) | X | (2f)| (3kk)  |
| (1)-267 | (Ih) | X | (2h)| (3e)   |
| (1)-268 | (Ih) | X | (2k)| (3f)   |
| (1)-269 | (Ih) | X | (2n)| (3k)   |
| (1)-270 | (Ih) | X | —   | (3u)   |
| (1)-271 | (Ii) | X | X   | (3ll)  |
| (1)-272 | (Ii) | X | X   | (3mm)  |
| (1)-273 | (Ii) | X | X   | (3nn)  |
| (1)-274 | (Ii) | X | X   | (3oo)  |
| (1)-275 | (Ii) | X | X   | (3v)   |
| (1)-276 | (Ii) | X | X   | (3e)   |
| (1)-277 | (Ii) | X | X   | (3ee)  |
| (1)-278 | (Ii) | X | X   | (3e)   |
| (1)-279 | (Ii) | X | X   | (3f)   |
| (1)-280 | (Ii) | X | X   | (3k)   |
| (1)-281 | (Ii) | X | X   | (3u)   |
| (1)-282 | (Ii) | X | X   | (3mm)  |
| (1)-283 | (Ii) | X | X   | (3nn)  |
| (1)-284 | (Ii) | X | X   | (3k)   |
| (1)-285 | (Ii) | X | X   | (3u)   |
| (1)-286 | (Ii) | X | X   | (3v)   |
| (1)-287 | (Ii) | X | X   | (3e)   |
| (1)-288 | (Ii) | X | X   | (3ee)  |
| (1)-289 | (Ii) | X | X   | (3ii)  |
| (1)-290 | (Ii) | X | X   | (3jj)  |
| (1)-291 | (Ii) | X | X   | (3kk)  |
| (1)-292 | (Ii) | X | X   | (3e)   |
| (1)-293 | (Ii) | X | X   | —      |
| (1)-294 | (Ii) | X | X   | (3k)   |
| (1)-295 | (Ii) | X | X   | (3ll)  |
| (1)-296 | (Ii) | X | X   | (3mm)  |
| (1)-297 | (Ii) | X | X   | (3nn)  |
| (1)-298 | (Ii) | X | X   | (3oo)  |
| (1)-299 | (Ii) | X | X   | (3mm)  |
| (1)-300 | (Ii) | X | X   | (3nn)  |
| (1)-301 | (Ia) | X | X   | (3nnn) |
| (1)-302 | (Ia) | X | X   | (3ooo) |
| (1)-303 | (Ia) | X | X   | (3ppp) |
| (1)-304 | (Ia) | X | X   | (3qqq) |
| (1)-305 | (Ia) | X | X   | (3rrr) |
| (1)-306 | (Ia) | X | X   | (3sss) |
| (1)-307 | (Ia) | X | X   | (3ttt) |
| (1)-308 | (Ia) | X | X   | (3uuu) |
| (1)-309 | (Ia) | X | X   | (3vvv) |
| (1)-310 | (Ia) | X | X   | (3www) |
| (1)-311 | (Ia) | X | X   | (3xxx) |
| (1)-312 | (Ia) | X | X   | (3yyy) |
| (1)-313 | (Ia) | X | X   | (3zzz) |
| (1)-314 | (Ia) | X | X   | (3aaaa)|
| (1)-315 | (Ia) | X | X   | (3bbbb)|
| (1)-316 | (Ia) | X | X   | (3cccc)|

In an embodiment, the invention comprises compounds of Formula (II),

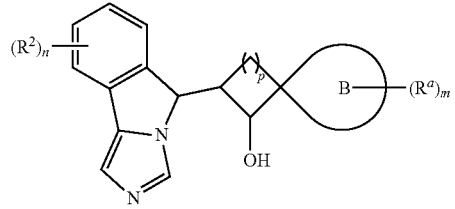
(II)

which is a compound of Formula (I) wherein
ring B is as defined above for formula (I);
m is 0, 1, 2, 3 or 4;
each $R^a$ is independently oxo, halogen, cyano, nitro, $C_{1-6}$alkyl, —$C_{1-6}$haloalkyl, $C_{1-6}$alkyl-cyano, —OR, —NR$_2$, —SR, —C(O)OR, —C(O)N(R)$_2$, —C(O)R, —N(R)C(O)R, —S(O)R, —S(O)OR, —S(O)N(R)$_2$, —S(O)$_2$R, —S(O)$_2$OR, —S(O)$_2$N(R)$_2$, —P(O)R$_2$, —OC(O)R, —OC(O)OR, —OC(O)N(R)$_2$, —N(R)C(O)R, —N(R)C(O)OR or —N(R)C(O)N(R)$_2$;
p is 1, 2 or 3;
n is 0, 1, 2, 3 or 4;
each $R^2$ is independently halogen, cyano, $C_{1-6}$alkyl, $C_3$cycloalkyl, —$C_{1-6}$haloalkyl, —OR, —NR$_2$ or —SR; and
each R is independently hydrogen, $C_{1-6}$alkyl, $C_{1-6}$haloalkyl, $C_{1-6}$alkyl-O—$C_{1-6}$alkyl, $C_{1-6}$alkyl-NHC(O)H, optionally substituted $C_{3-6}$cycloalkyl, optionally substituted 4-10 membered heterocycloalkyl, optionally substituted $C_{1-6}$alkyl-(4-10 membered heterocycloalkyl), optionally substituted heteroaryl, optionally substituted —$C_{1-6}$alkyl-heteroaryl.

In one embodiment, the invention comprises compounds of Formula (II) wherein p is 1. In other embodiments, p is 2 and n is 0. In other embodiments, m is 1 and n is 0.

The invention further comprises subgenera of formula (II) in which the substituents are selected as any and all combinations of one or more of structural formula (II), $R^2$, $R^a$, m, n, p, R and ring B, as defined herein, including without limitation, the following:

Structural Formula I s One of Formulae (IIa)-(IIp):

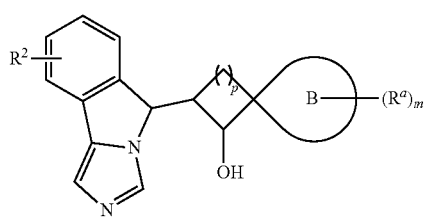
(IIa)

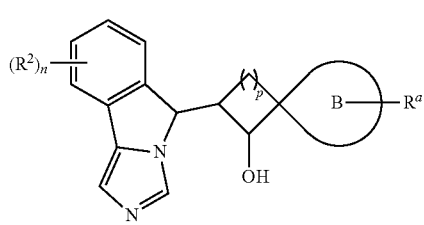
(IIb)

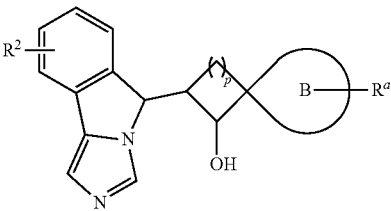
(IIc)

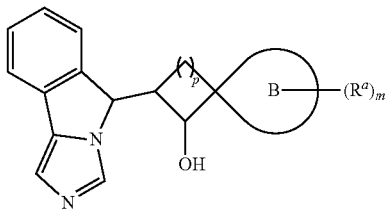
(IId)

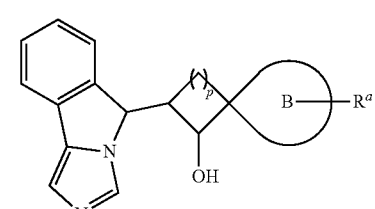
(IIe)

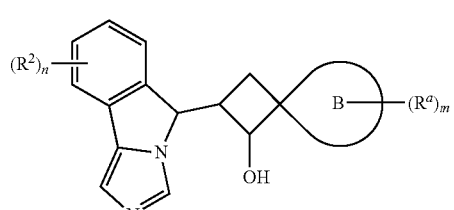
(IIf)

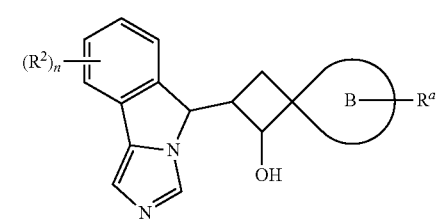
(IIg)

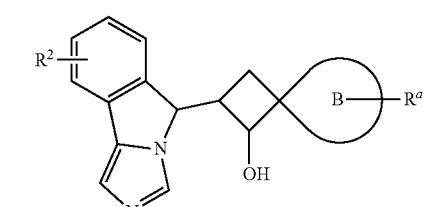
(IIh)

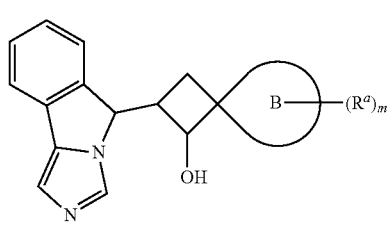
(IIi)

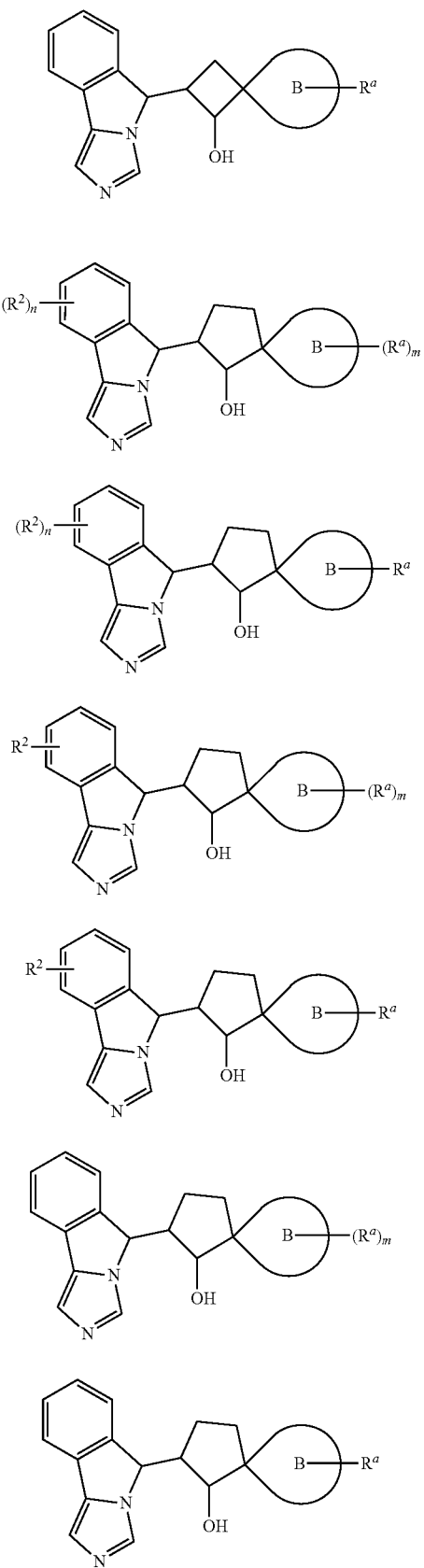

Ring B is Selected from One of the Following Groups (4a)-(4ss):

(4a) Ring B is 3-8 membered heterocyclyl.
(4b) Ring B is 4 8 membered heterocyclyl or $C_{4-6}$cycloalkyl.
(4c) Ring B is 5-8 membered heterocyclyl.
(4d) Ring B is 6-8 membered heterocyclyl or $C_{4-6}$cycloalkyl.
(4e) Ring B is 4-7 membered heterocyclyl.
(4f) Ring B is 4-6 membered heterocyclyl or $C_{4-6}$cycloalkyl.
(4g) Ring B is 5-8 membered heterocyclyl.
(4h) Ring B is 5-6 membered heterocyclyl.
(4i) Ring B is piperidinyl, pyrrolidinyl, 8-azabicyclo[3.2.1]octane, cyclopentyl or tetrahydro-2H-thiopyran 1,1-dioxide.
(4j) Ring B is piperidinyl, pyrrolidinyl or 8-azabicyclo[3.2.1]octane.
(4k) Ring B is pyrrolidinyl or 8-azabicyclo[3.2.1]octane.
(4l) Ring B is piperidinyl, cyclopentyl or 8-azabicyclo[3.2.1]octane.
(4m) Ring B is piperidinyl or pyrrolidinyl.
(4n) Ring B is piperidinyl, pyrrolidinyl or tetrahydro-2H-thiopyran 1,1-dioxide.
(4o) Ring B is pyrrolidinyl, 8-azabicyclo[3.2.1]octane or tetrahydro-2H-thiopyran 1,1-dioxide.
(4p) Ring B is piperidinyl, cyclopentyl, 8-azabicyclo[3.2.1]octane or tetrahydro-2H-thiopyran 1,1-dioxide.
(4q) Ring B is piperidinyl.
(4r) Ring B is pyrrolidinyl.
(4s) Ring B is 8-azabicyclo[3.2.1]octane.
(4t) Ring B is cyclopentyl.
(4u) Any of groups (4a)-(4t), wherein Ring B is substituted by one, two, three, or four $R^a$ groups, wherein each $R^a$ is independently oxo, halogen, cyano, nitro, $C_{1-6}$alkyl, —$C_{1-6}$haloalkyl, $C_{1-6}$alkyl-cyano, —OR, —NR$_2$, —SR, —C(O)OR, —C(O)N(R)$_2$, —C(O)R, —N(R)C(O)R, —S(O)R, —S(O)OR, —S(O)N(R)$_2$, —S(O)$_2$R, —S(O)$_2$OR, —S(O)$_2$N(R)$_2$, —P(O)R$_2$, —OC(O)R, —OC(O)OR, —OC(O)N(R)$_2$, —N(R)C(O)R, —N(R)C(O)OR or —N(R)C(O)N(R)$_2$.
(4v) Any of groups (4a)-(4t), wherein Ring B is substituted by one, two or three $R^1$ groups, wherein each $R^1$ is independently oxo, halogen, cyano, nitro, $C_{1-6}$alkyl, —$C_{1-6}$haloalkyl, $C_{1-6}$ alkyl-cyano, —OR, —NR$_2$, —SR, —C(O)OR, —C(O)N(R)$_2$, —C(O)R, —N(R)C(O)R, —S(O)R, —S(O)OR, —S(O)N(R)$_2$, —S(O)$_2$R, —S(O)$_2$OR, —S(O)$_2$N(R)$_2$, —P(O)R$_2$, —OC(O)R, —OC(O)OR, —OC(O)N(R)$_2$, —N(R)C(O)R, —N(R)C(O)OR or —N(R)C(O)N(R)$_2$.
(4w) Any of groups (4a)-(4t), wherein Ring B is substituted by one or two $R^a$ groups, wherein each $R^a$ is independently oxo, halogen, cyano, nitro, $C_{1-6}$alkyl, —$C_{1-6}$haloalkyl, $C_{1-6}$alkyl-cyano, —OR, —NR$_2$, —SR, —C(O)OR, —C(O)N(R)$_2$, —C(O)R, —N(R)C(O)R, —S(O)R, —S(O)OR, —S(O)N(R)$_2$, —S(O)$_2$R, —S(O)$_2$OR, —S(O)$_2$N(R)$_2$, —P(O)R$_2$, —OC(O)R, —OC(O)OR, —OC(O)N(R), —N(R)C(O)R, —N(R)C(O)OR or —N(R)C(O)N(R)$_2$.
(4x) Any of groups (4a)-(4t), wherein Ring B is substituted by one $R^a$ groups, wherein each $R^a$ is independently oxo, halogen, cyano, nitro, $C_{1-6}$alkyl, —$C_{1-6}$haloalkyl, $C_{1-6}$alkyl-cyano, —OR, —NR$_2$, —SR, —C(O)OR, —C(O)N(R)$_2$, —C(O)R, —N(R)C(O)R, —S(O)R, —S(O)OR, —S(O)N(R)$_2$, —S(O)$_2$R, —S(O)$_2$OR, —S(O)$_2$N(R), —P(O)R$_2$, —OC(O)R, —OC(O)OR, —OC(O)N(R)$_2$, —N(R)C(O)R, —N(R)C(O)OR or —N(R)C(O)N(R)$_2$.

(4y) Ring B is

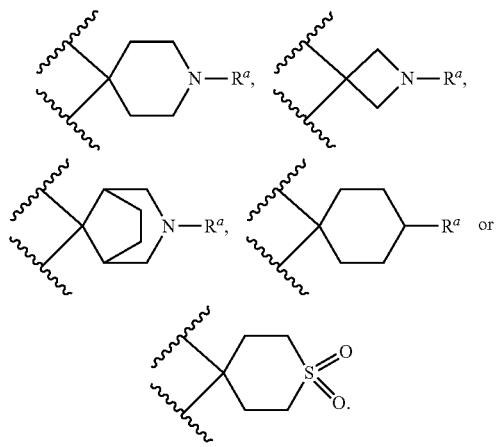

(4 mm) Ring B is

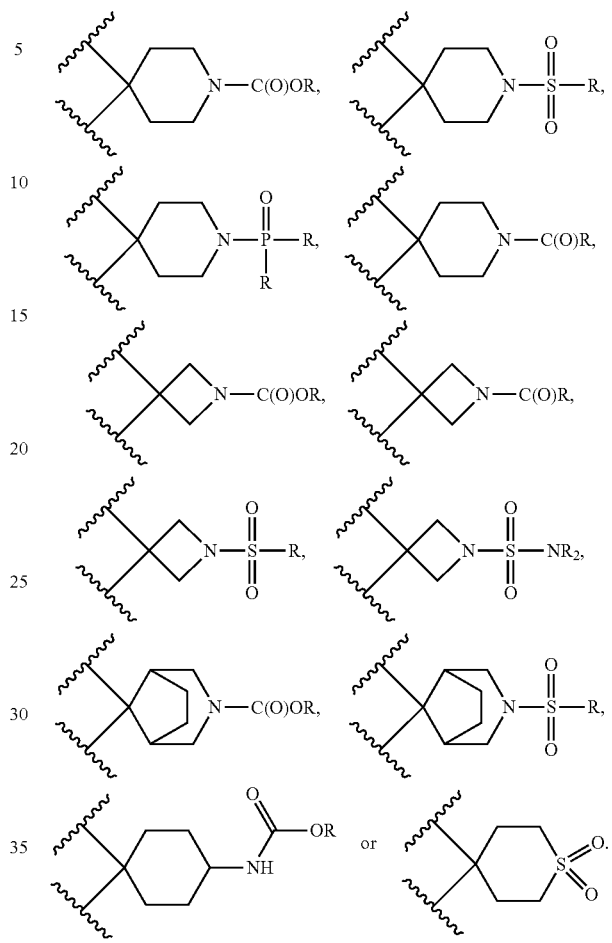

(4z) Group (4y), wherein $R^a$ is $C_{1-6}$alkyl, —$C_{1-6}$haloalkyl, $C_{1-6}$alkyl-cyano, —C(O)OR, —C(O)N(R)$_2$, —C(O)R, —N(R)C(O)R, —S(O)R, —S(O)OR, —S(O)N(R)$_2$, —S(O)$_2$R, —S(O)$_2$OR, —S(O)$_2$N(R)$_2$ or —P(O)R$_2$.

(4aa) Group (4y), wherein $R^a$ is $C_{1-6}$alkyl, —C(O)OR, —C(O)N(R)$_2$, —C(O)R, —N(R)C(O)R, —S(O)R, —S(O)OR, —S(O)N(R)$_2$, —S(O)$_2$R, —S(O)$_2$OR, —S(O)$_2$N(R)$_2$ or —P(O)R$_2$.

(4bb) Group (4y), wherein $R^a$ is —$C_{1-6}$haloalkyl, $C_{1-6}$alkyl-cyano, —C(O)OR, —C(O)N(R)$_2$, —C(O)R, —N(R)C(O)R, —S(O)R, —S(O)OR, —S(O)N(R)$_2$, —S(O)$_2$R, —S(O)$_2$OR, —S(O)$_2$N(R)$_2$ or —P(O)R$_2$.

(4cc) Group (4y), wherein $R^a$ is —C(O)OR, —C(O)N(R)$_2$, —C(O)R, —N(R)C(O)R, —S(O)R, —S(O)OR, —S(O)N(R)$_2$, —S(O)$_2$R, —S(O)$_2$OR, —S(O)$_2$N(R)$_2$ or —P(O)R$_2$.

(4dd) Group (4y), wherein $R^a$ is $C_{1-6}$alkyl, —C(O)OR, —C(O)R, —N(R)C(O)R, —S(O)R, —S(O)OR, —S(O)N(R)$_2$, —S(O)$_2$R, —S(O)$_2$OR, —S(O)$_2$N(R)$_2$ or —P(O)R$_2$.

(4ee) Group (4y), wherein $R^a$ is $C_{1-6}$alkyl, —$C_{1-6}$haloalkyl, $C_{1-6}$alkyl-cyano, —C(O)OR, —C(O)N(R)$_2$, —C(O)R, —N(R)C(O)R, or —P(O)R$_2$.

(4ff) Group (4y), wherein $R^a$ is $C_{1-6}$alkyl, —C(O)OR, —C(O)R, —N(R)C(O)R, —S(O)R, —S(O)OR, —S(O)N(R)$_2$, —S(O)$_2$R, —S(O)$_2$OR, or —S(O)$_2$N(R)$_2$.

(4gg) Group (4y), wherein $R^a$ is —C(O)OR, —C(O)R, —N(R)C(O)R, —S(O)R, —S(O)OR, —S(O)N(R)$_2$, —S(O)$_2$R, —S(O)$_2$OR, or —S(O)$_2$N(R)$_2$.

(4hh) Group (4y), wherein $R^a$ is —C(O)OR, —C(O)R, —N(R)C(O)R, —S(O)$_2$R, —S(O)$_2$N(R)$_2$ or —P(O)R$_2$.

(4ii) Group (4y), wherein R is —C(O)OR, —C(O)R—N(R)C(O)R, or —P(O)R$_2$.

(4jj) Group (4y), wherein $R^a$ is —S(O)$_2$R, —S(O)$_2$N(R)$_2$ or —P(O)R$_2$.

(4kk) Group (4y), wherein $R^1$ is —C(O)OR—N(R)C(O)R, or —C(O)R.

(4ll) Group (4y), wherein $R^a$ is —S(O)$_2$R or —S(O)$_2$N(R)$_2$.

where each R is independently hydrogen, $C_{1-6}$alkyl, $C_{1-6}$haloalkyl, $C_{1-6}$alkyl-O—$C_{1-6}$alkyl or $C_{1-6}$cycloalkyl.

(4nn) Any of groups (4u)-(4 mm), where each R is independently hydrogen, $C_{1-6}$alkyl, $C_{1-6}$haloalkyl, $C_{1-6}$alkyl-O—$C_{1-6}$alkyl, optionally substituted $C_{3-6}$cycloalkyl, optionally substituted 4-10 membered heterocycloalkyl or optionally substituted —$C_{1-6}$alkyl-(4-10 membered heterocycloalkyl.

(4oo) Any of groups (4u)-(4 mm), where each R is independently hydrogen, $C_{1-6}$alkyl, $C_{1-6}$haloalkyl, $C_{1-6}$alkyl-O—$C_{1-6}$alkyl, —$C_{1-6}$alkyl-NHC(O)H, —$C_{1-6}$ alkyl-C(O)NMe$_2$, —$C_{1-6}$alkyl-CN, optionally substituted $C_{3-6}$cycloalkyl, optionally substituted heteroaryl or optionally substituted —$C_{1-6}$alkyl-heteroaryl.

(4pp) Any of groups (4u)-(4 mm), where each R is independently hydrogen, $C_{1-6}$alkyl, $C_{1-6}$haloalkyl, optionally substituted $C_{3-6}$cycloalkyl, optionally substituted 4-10 membered heterocycloalkyl, optionally substituted —$C_{1-6}$alkyl-(4-10 membered heterocycloalkyl), optionally substituted heteroaryl or optionally substituted —$C_{1-6}$alkyl-heteroaryl.

(4qq) Any of groups (4u)-(4 mm), where each R is independently hydrogen, methyl, ethyl, isopropyl, tert-butyl, fluoromethyl, difluoromethyl, —CH$_2$CHF$_2$, —(CH$_2$)$_2$—O—CH$_3$, —CH(CH$_3$)NHC(O)H, —(CH$_2$)$_2$—C(O)NMe$_2$, —CH$_2$CN, cyclopropyl, difluorocyclopropyl, cyclopropane-1-carbonitrile, cyclobutyl, pyrazolyl, imidazolyl, isoxazolyl, pyridinyl, phenyl, piperidinyl, indolin-2-one, 6,7-dihydro-5H-pyrazolo[5,1-b][1,3]oxazinyl, —CH$_2$-piperidin-2-one, piperidin-2-one, 1-methylpiperidin-2-one, triazolyl, —CH(CH$_3$)-triazolyl, pyrazolyl, tetrahydro-2H-pyranyl, tetrahydrofuranyl, tetrahydro-2H-pyranyl, —CH$_2$-tetrahydro-2H-pyranyl, pyrrolidinone, —CH$_2$-pyrrolidinone, -1-methylpyrrolidinone, —CH$_2$-1-methylpyrolidinone, -methylisoxazolyl, —CH$_2$-methylisoxazolyl, 1-methyl-1H-pyrazolyl, —(CH$_2$)$_2$-(1-methyl-1H-pyrazolyl), 1H-imidazolyl, 1H-tetrazolyl, —CH$_2$-1H-tetrazolyl, methylisoxazolyl, —CH$_2$-3-methylisoxazolyl, piperidin-1-carboxamide, 1,1-dioxidotetrahydrothiophenyl or 5,6,7,8-tetrahydro-[1,2,4]triazolo[4,3-a]pyridinyl.

(4rr) Any of groups (4u)-(4 mm), where each R is independently hydrogen, methyl, cyclopropyl, difluorocyclopropyl, cyclopropane-1-carbonitrile, cyclobutyl, 1-methylpyrazol-4-yl, 1-methyl-1H-pyrazol-3-yl, 1,3,5-trimethylpyrazol-4-yl, 1,3,5-trimethyl-1H-pyrazol-4-yl, 1,2-dimethyl-1H-imidazol-4-yl, 3,5-dimethylisoxazol-4-yl, 4-methylpyridin-3-yl, —(CH$_2$)$_2$-pyridin-3-yl, phenyl-N-methylacetamide, —CH$_2$-piperidin-1-yl, 1-methylindolin-2-one, 6,7-dihydro-5H-pyrazolo[5,1-b][1,3]oxazinyl, —CH$_2$-piperidin-2-one, 1-methylpiperidin-2-one, —CH(CH$_3$)-(1H-1,2,4-triazol-1-yl), 1-methyl-1H-pyrazol-3-yl, tetrahydro-2H-pyran-4-yl, tetrahydrofuran-3-yl, —CH$_2$-(tetrahydro-2H-pyran-4-yl), —CH$_2$-(pyrrolidin-2-one), —CH$_2$-(1-methylpyrrolidin-2-one), —CH$_2$-(5-methylisoxazol-3-yl), —(CH$_2$)$_2$-(1-methyl-1H-pyrazol-4-yl), 1H-imidazol-4-yl, —CH$_2$-(1H-tetrazol-5-yl), —CH$_2$-(3-methylisoxazol-5-yl), piperidine-1-carboxamide, 1,1-dioxidotetrahydrothiophen-3-yl or 5,6,7,8-tetrahydro-[1,2,4]triazolo[4,3-a]pyridin-6-yl.

(4ss) Ring B is

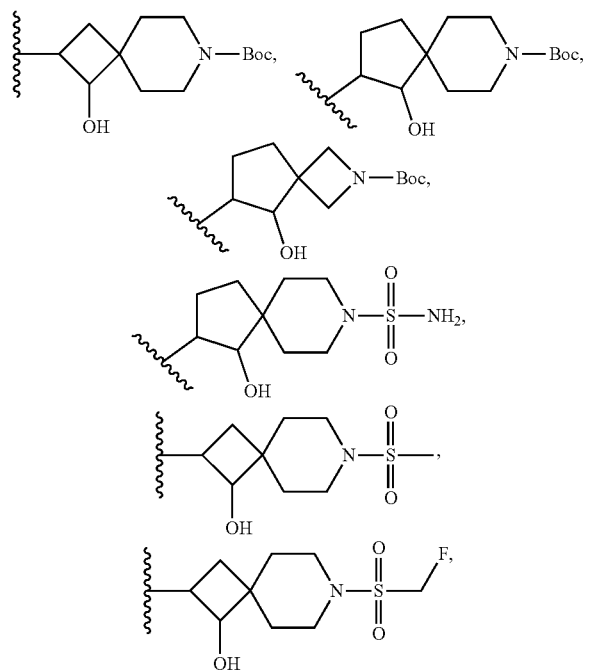

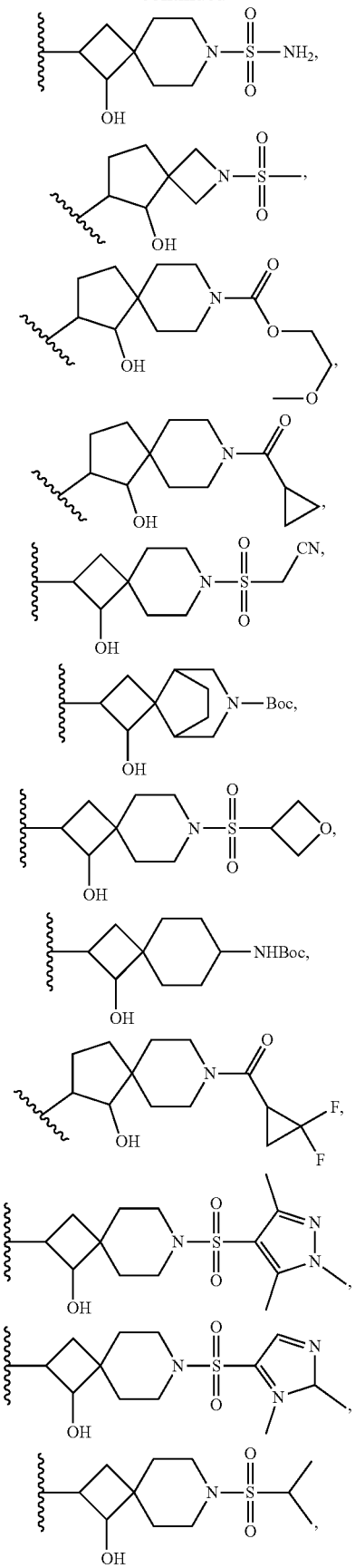

-continued

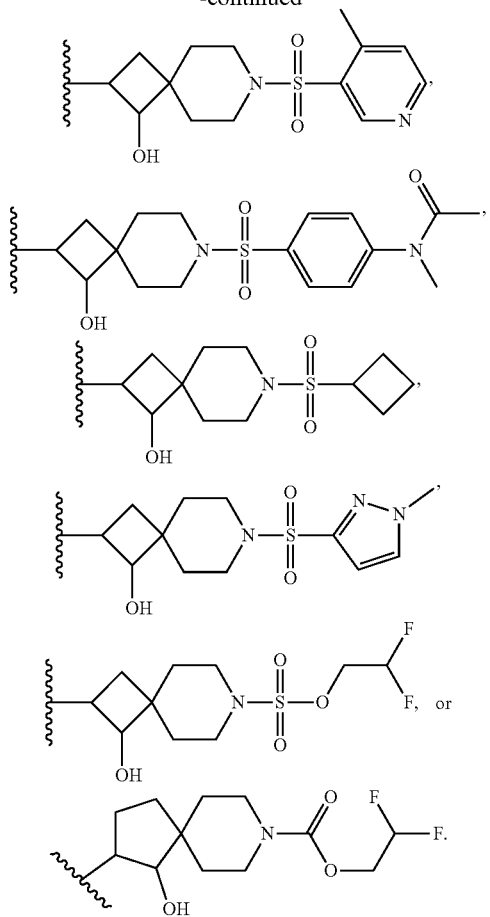

In another embodiment, the invention comprises compounds of Formula (III),

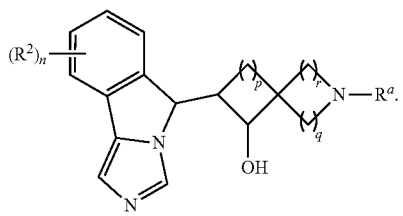
(III)

which is a compound of Formula (I) wherein
  $R^a$ is $C_{1-6}$alkyl, —$C_{1-6}$haloalkyl, $C_{1-6}$alkyl-cyano, —C(O)OR, —C(O)N(R)$_2$, —C(O)R, —N(R)C(O)R, —S(O)R, —S(O)OR, —S(O)N(R)$_2$, —S(O)$_2$R, —S(O)$_2$OR, —S(O)$_2$N(R)$_2$ or —P(O)R$_2$;
  p is 1, 2 or 3;
  q is 1, 2 or 3;
  r is 1, 2 or 3;
  n is 0, 1, 2, 3 or 4;
  each $R^2$ is independently halogen, cyano, $C_{1-6}$alkyl, $C_3$cycloalkyl, —$C_{1-6}$haloalkyl, —OR, —NR$_2$ or —SR; and
  each R is independently hydrogen, $C_{1-6}$alkyl, $C_{1-6}$haloalkyl, $C_{1-6}$alkyl-O—$C_{1-6}$alkyl, —$C_{1-6}$alkyl-NHC(O)H, optionally substituted $C_{3-6}$cycloalkyl, optionally substituted 4-10 membered heterocycloalkyl, optionally substituted —$C_{1-6}$alkyl-(4-10 membered heterocycloalkyl), optionally substituted heteroaryl, optionally substituted —$C_{1-6}$alkyl-heteroaryl.

In one embodiment, the invention comprises compounds of Formula (III) wherein n is 0. In other embodiments, n is 1.

In one embodiment, the invention comprises compounds of Formula (II) wherein p is 1, 2 or 3, q is 1, 2 or 3, and r is 1, 2 or 3; or p is 1 or 2, q is 1, 2 or 3, and r is 1, 2 or 3; or p is 1 or 2, q is 1 or 2, and r is 1 or 2; or p is 1 or 2, q is 1 or 2, and r is 1 or 2; or p is 2, q is 1 or 2, and r is 1 or 2; or p is, q is 2, and r is 2; or p is 2, q is 2, and r is 2; or p is 1, q is 1, and r is 1 or p is 2, q is 1, and r is 1.

The invention further comprises subgenera of formula (III) in which the substituents are selected as any and all combinations of one or more of structural formula (III), $R^2$, $R^a$, n, m, p, q or r, as defined herein, including without limitation, the following:

Structural Formula I is One of Formulae (IIIa)-(IIIp):

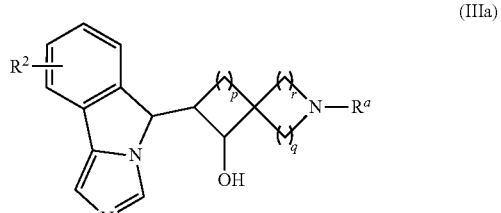
(IIIa)

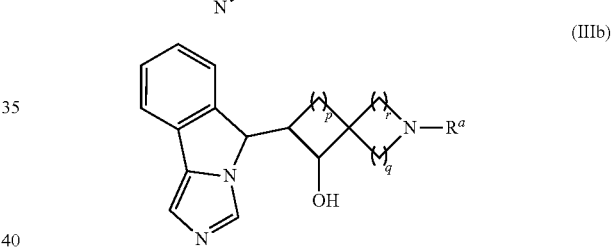
(IIIb)

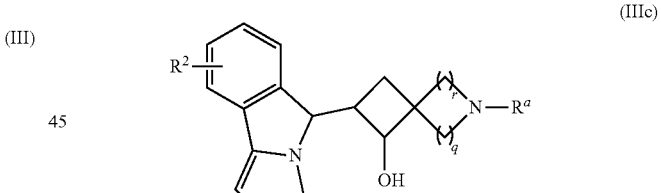
(IIIc)

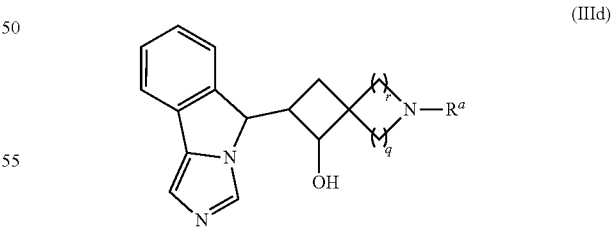
(IIId)

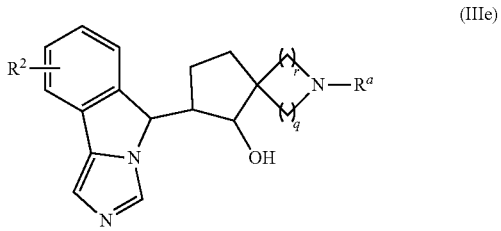
(IIIe)

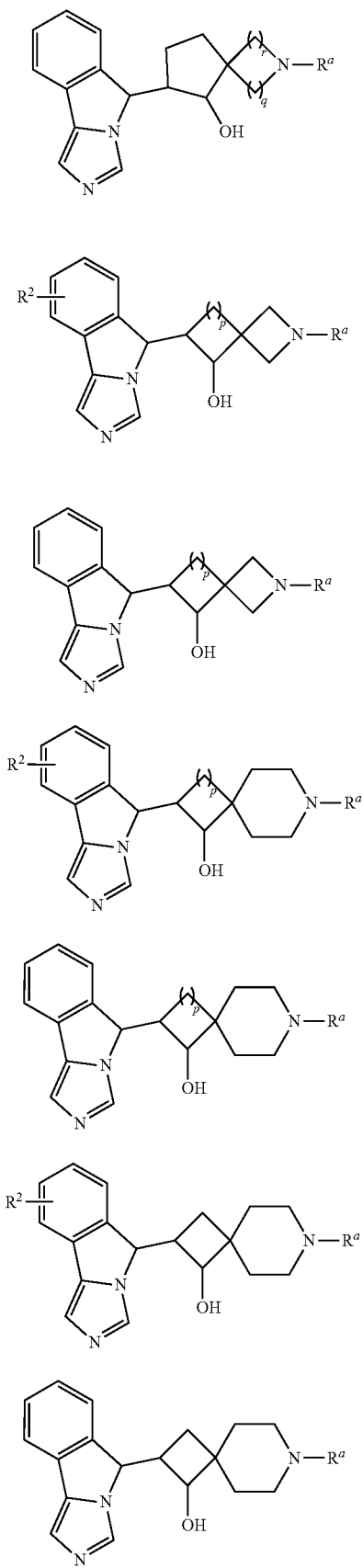
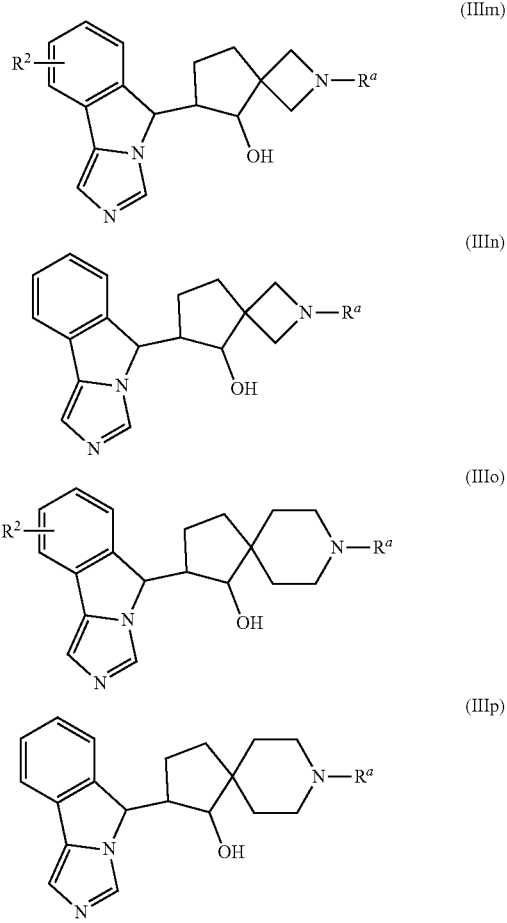

Rᵃ is Selected from One of the Following Groups (6a)-(6r):

(6a) $R^a$ is $C_{1-6}$alkyl, —$C_{1-6}$haloalkyl, $C_{1-6}$alkyl-cyano, —C(O)OR, —C(O)N(R)₂, —C(O)R, —N(R)C(O)R, —S(O)R, —S(O)OR, —S(O)N(R)₂, —S(O)₂R, —S(O)₂OR, —S(O)₂N(R)₂ or —P(O)R₂.

(6b) $R^a$ is $C_{1-6}$alkyl, —C(O)OR, —C(O)N(R)₂, —C(O)R, —N(R)C(O)R, —S(O)R, —S(O)OR, —S(O)N(R)₂, —S(O)₂R, —S(O)₂OR, —S(O)₂N(R)₂ or —P(O)R₂.

(6c) $R^a$ is —$C_{1-6}$haloalkyl, $C_{1-6}$alkyl-cyano, —C(O)OR, —C(O)N(R)₂, —C(O)R, —N(R)C(O)R, —S(O)R, —S(O)OR, —S(O)N(R)₂, —S(O)₂R, —S(O)₂OR, —S(O)₂N(R)₂ or —P(O)R₂.

(6d) $R^a$ is —C(O)OR, —C(O)N(R)₂, —C(O)R, —N(R)C(O)R, —S(O)R, —S(O)OR, —S(O)N(R)₂, —S(O)₂R, —S(O)₂OR, —S(O)₂N(R)₂ or —P(O)R₂.

(6e) $R^a$ is $C_{1-6}$alkyl, —C(O)OR, —C(O)R, —N(R)C(O)R, —S(O)R, —S(O)OR, —S(O)N(R)₂, —S(O)₂R, —S(O)₂OR, —S(O)₂N(R)₂ or —P(O)R₂.

(6f) $R^a$ is $C_{1-6}$alkyl, —$C_{1-6}$haloalkyl, $C_{1-6}$alkyl-cyano, —C(O)OR, —C(O)N(R)₂, —C(O)R, —N(R)C(O)R, or —P(O)R₂.

(6g) $R^a$ is $C_{1-6}$alkyl, —C(O)OR, —C(O)R, —N(R)C(O)R, —S(O)R, —S(O)OR, —S(O)N(R)₂, —S(O)₂R, —S(O)₂OR, or —S(O)₂N(R)₂.

(6h) $R^a$ is —C(O)OR, —C(O)R, —N(R)C(O)R, —S(O)R, —S(O)OR, —S(O)N(R)₂, —S(O)₂R, —S(O)₂OR, or —S(O)₂N(R)₂.

(6i) $R^a$ is —C(O)OR, —C(O)R, —N(R)C(O)R, —S(O)₂R, —S(O)₂N(R)₂ or —P(O)R₂.

(6j) $R^a$ is —C(O)OR, —C(O)R, —N(R)C(O)R or —P(O)R$_2$.
(6k) $R^a$ is —S(O)$_2$R, —S(O)$_2$N(R)$_2$ or —P(O)R$_2$.
(6l) $R^a$ is —C(O)OR, —N(R)C(O)R or —C(O)R.
(6m) $R^a$ is —S(O)$_2$R or —S(O)$_2$N(R)$_2$.
(6n) Any of groups (6a)-(6m), where each R is independently hydrogen, C$_{1-6}$alkyl, C$_{1-6}$haloalkyl, C$_{1-6}$alkyl-O—C$_{1-6}$alkyl, —C$_{1-6}$alkyl-NHC(O)H, —C$_{1-6}$alkyl-CN, —C$_{1-6}$alkyl-C(O)NMe$_2$, optionally substituted C$_{3-4}$cycloalkyl, optionally substituted 4-10 membered heterocycloalkyl, optionally substituted —C$_{1-6}$alkyl-(4-10 membered heterocycloalkyl) or optionally substituted heteroaryl or optionally substituted —C$_{1-6}$alkyl-heteroaryl.
(6o) Any of groups (6a)-(6m), where each R is independently hydrogen, C$_{1-6}$alkyl, C$_{1-6}$haloalkyl, C$_{1-6}$alkyl-O—C$_{1-6}$alkyl, —C$_{1-6}$alkyl-NHC(O)H, —C$_{1-6}$alkyl-C(O)NMe$_2$, —C$_{1-6}$alkyl-CN, C$_{3-6}$cycloalkyl, 4-10 membered heterocycloalkyl, —C$_{1-6}$alkyl-(4-10 membered heterocycloalkyl), heteroaryl or —C$_{1-6}$alkyl-heteroaryl.
(6p) Any of groups (6a)-(6m), where each R is independently hydrogen, methyl, ethyl, isopropyl, tert-butyl, fluoromethyl, difluoromethyl, —CH$_2$CHF$_2$, —(CH$_2$)$_2$—O—CH$_3$, —CH(CH$_3$)NHC(O)H, —(CH$_2$)$_2$—C(O)NMe$_2$, —CH$_2$CN, cyclopropyl, difluorocyclopropyl, cyclopropane-1-carbonitrile, cyclobutyl, pyrazolyl, imidazolyl, isoxazolyl, pyridinyl, phenyl, piperidinyl, indolin-2-one, 6,7-dihydro-5K-pyrazolo[5,1-b][1,3]oxazinyl, —CH$_2$-piperidin-2-one, piperidin-2-one, 1-methylpiperidin-2-one, triazolyl, —CH(CH$_3$)-triazolyl, pyrazolyl, tetrahydro-2H-pyranyl, tetrahydrofuranyl, tetrahydro-2H-pyranyl, —CH$_2$-tetrahydro-2H-pyranyl, pyrrolidinone, —CH$_2$-pyrrolidinone, -1-methylpyrrolidinone, —CH$_2$-1-methylpyrrolidinone, -methylisoxazolyl, —CH$_2$-methylisoxazolyl, 1-methyl-1H-pyrazolyl, —(CH$_2$)$_2$-(1-methyl-1H-pyrazolyl), 1H-imidazolyl, 1H-tetrazolyl, —CH$_2$-1H-tetrazolyl, methylisoxazolyl, —CH$_2$-3-methylisoxazolyl, piperidine-1-carboxamide, 1,1-dioxidotetrahydrothiophenyl or 5,6,7,8-tetrahydro-[1,2,4]triazolo[4,3-a]pyridinyl.
(6q) Any of groups (6a)-(6m), where each R is independently hydrogen, methyl, ethyl, isopropyl, tert-butyl, fluoromethyl, difluoromethyl, —CH$_2$CHF$_2$, —(CH$_2$)$_2$—O—CH$_3$, —CH(CH$_3$)NHC(O)H, —(CH$_2$)$_2$—C(O)NMe$_2$, —CH$_2$CN, cyclopropyl, difluorocyclopropyl, cyclopropane-1-carbonitrile, cyclobutyl, 1-methylpyrazol-4-yl, 1-methyl-1H-pyrazol-3-yl, 1,3,5-trimethylpyrazol-4-yl, 1,3,5-trimethyl-1H pyrazol-4-yl, 1,2-dimethyl-1H-imidazol-4-yl, 3,5-dimethylisoxazol-4-yl, 4-methylpyridin-3-yl, —(CH$_2$)$_2$-pyridin-3-yl, phenyl-N-methylacetamide, —CH$_2$-piperidin-1-yl, 1-methyl-indolin-2-one, 6,7-dihydro-5H-pyrazolo[5,1-b][1,3]oxazinyl, —CH$_2$-piperidin-2-one, 1-methylpiperidin-2-one, —CH(CH$_3$)—(1H-1,2,4-triazol-1-yl), 1-methyl-1H-pyrazol-3-yl, tetrahydro-2H-pyran-4-yl, tetrahydrofuran-3-yl, —CH$_2$-(tetrahydro-2H-pyran-4-yl), —CH$_2$-(pyrrolidin-2-one), —CH$_2$-(1-methylpyrrolidin-2-one), —CH$_2$-(5-methylisoxazol-3-yl), —(CH$_2$)$_2$-(1-methyl-1H-pyrazol-4-yl), 1H-imidazol-4-yl, —CH$_2$-(1H-tetrazol-5-yl), —CH$_2$-(3-methylisoxazol-5-yl), piperidine-1-carboxamide, 1,1-dioxidotetrahydrothiophen-3-yl or 5,6,7,8-tetrahydro-[1,2,4]triazolo[4,3-a]pyridin-6-yl.
(6r) Any of groups (6a)-(6m), where each R is independently hydrogen, methyl, ethyl, isopropyl, tert-butyl, fluoromethyl, difluoromethyl, —CH$_2$CHF$_2$, —(CH$_2$)$_2$—O—CH$_3$, —CH(CH$_3$)NHC(O)H, —(CH$_2$)$_2$—C(O)NMe$_2$, —CH$_2$CN, cyclopropyl, difluorocyclopropyl, cyclopropane-1-carbonitrile, cyclobutyl, 1-methylpyrazol-4-yl, 1-methyl-1H-pyrazol-3-yl, 1,3,5-trimethylpyrazol-4-yl, 1,3,5-trimethyl-1H-pyrazol-4-yl, 1,2-dimethyl-1H-imidazol-4-yl, 3,5-dimethylisoxazol-4-yl, 4-methylpyridin-3-yl, —(CH$_2$)$_2$-pyridin-3-yl, phenyl-N-methylacetamide, —CH$_2$-piperidin-1-yl, 1-methyl-indolin-2-one, 6,7-dihydro-5H-pyrazolo[5,1-b][1,3]oxazinyl, —CH$_2$-piperidin-2-one, 1-methylpiperidin-2-one, —CH(CH$_3$)-(1H-1,2,4-triazol-1-yl), 1-methyl-1H-pyrazol-3-yl, tetrahydro-2H-pyran-4-yl, tetrahydrofuran-3-yl, —CH$_2$-(tetrahydro-2H-pyran-4-yl), —CH$_2$-(pyrrolidin-2-one), —CH$_2$-(1-methylpyrrolidin-2-one), —CH$_2$—(S-methylisoxazol-3-yl), —(CH$_2$)$_2$-(1-methyl-1H-pyrazol-4-yl), 1H-imidazol-4-yl, —CH$_2$-(1H-tetrazol-5-yl), —CH$_2$-(3-methylisoxazol-5-yl), piperidine-1-carboxamide, 1,1-dioxidotetrahydrothiophen-3-yl or 5,6,7,8-tetrahydro-[1,2,4]triazolo[4,3-a]pyridin-6-yl.

Particular embodiments of this aspect of the invention include compounds of any one of the formulae (I), (IIa)-(IIi), (III) and (IIIa)-(IIIp), each as defined in each of the following rows, wherein each entry is a group number as defined above (e.g., (6m) refers to $R^a$ is —S(O)$_2$R or —S(O)$_2$N(R)$_2$), an "X" indicates that the variable is defined by another group in the embodiment (e.g., in embodiment (2)-11 below, $R^a$ is defined in group (4z)) and a dash "-" indicates that the variable is as defined for Formula (II)-(IIIp) or defined according to any one of the applicable variable definitions (5a)-(6r) [e.g., when the entry for $R^a$ is a dash, it can be either as defined for Formula (II)-(IIIp) or any one of definitions (6a)-(6r)]:

|  | (II) or (III) | Ring B | $R^a$ |
| --- | --- | --- | --- |
| (2)-1 | (IIa) | (4b) | — |
| (2)-2 | (IIa) | (4f) | — |
| (2)-3 | (IIa) | (4i) | — |
| (2)-1 | (IIa) | (4j) | — |
| (2)-5 | (IIa) | (4l) | — |
| (2)-6 | (IIa) | (4m) | — |
| (2)-7 | (IIa) | (4q) | — |
| (2)-8 | (IIa) | (4q) | — |
| (2)-9 | (IIa) | (4x) | X |
| (2)-10 | (IIa) | (4y) | — |
| (2)-11 | (IIa) | (4z) | X |
| (2)-12 | (IIa) | (4aa) | X |
| (2)-13 | (IIa) | (4ff) | X |
| (2)-14 | (IIa) | (4hh) | X |
| (2)-15 | (IIa) | (4jj) | X |
| (2)-16 | (IIa) | (4mm) | X |
| (2)-17 | (IIa) | (4nn) | X |
| (2)-18 | (IIa) | (4pp) | X |
| (2)-19 | (IIa) | (4qq) | X |
| (2)-20 | (IIa) | (4ss) | X |
| (2)-21 | (IId) | (4b) | — |
| (2)-22 | (IId) | (4f) | — |
| (2)-23 | (IId) | (4i) | — |
| (2)-24 | (IId) | (4j) | — |
| (2)-25 | (IId) | (4l) | — |
| (2)-26 | (IId) | (4m) | — |
| (2)-27 | (IId) | (4q) | — |
| (2)-28 | (IId) | (4q) | — |
| (2)-29 | (IId) | (4x) | X |
| (2)-30 | (IId) | (4y) | — |
| (2)-31 | (IId) | (4z) | X |
| (2)-32 | (IId) | (4aa) | X. |
| (2)-33 | (IId) | (4ff) | X |
| (2)-34 | (IId) | (4hh) | X |
| (2)-35 | (IId) | (4jj) | X |

| | (II) or (III) | Ring B | R$^a$ |
|---|---|---|---|
| (2)-36 | (IId) | (4mm) | X |
| (2)-37 | (IId) | (4nn) | X |
| (2)-38 | (IId) | (4pp) | X |
| (2)-39 | (IId) | (4qq) | X |
| (2)-10 | (IId) | (4ss) | X |
| (2)-11 | (IIe) | (4b) | — |
| (2)-12 | (IIe) | (4f) | — |
| (2)-13 | (IIe) | (4i) | — |
| (2)-14 | (IIe) | (4j) | — |
| (2)-15 | (IIe) | (4l) | — |
| (2)-16 | (IIe) | (4m) | — |
| (2)-17 | (IIe) | (4q) | — |
| (2)-18 | (IIe) | (4q) | — |
| (2)-19 | (IIe) | (4x) | X |
| (2)-50 | (IIe) | (4y) | — |
| (2)-51 | (IIe) | (4z) | X |
| (2)-52 | (IIe) | (4aa) | X |
| (2)-53 | (IIe) | (4ff) | X |
| (2)-54 | (IIe) | (4hh) | X |
| (2)-55 | (IIe) | (4jj) | X |
| (2)-56 | (IIe) | (4mm) | X |
| (2)-57 | (IIe) | (4nn) | X |
| (2)-58 | (IIe) | (4pp) | X |
| (2)-59 | (IIe) | (4qq) | X |
| (2)-60 | (IIe) | (4ss) | X |
| (2)-61 | (IIh) | (4b) | — |
| (2)-62 | (IIh) | (4f) | — |
| (2)-63 | (IIh) | (4i) | — |
| (2)-64 | (IIh) | (4j) | — |
| (2)-65 | (IIh) | (4l) | — |
| (2)-66 | (IIh) | (4m) | — |
| (2)-67 | (IIh) | (4q) | — |
| (2)-68 | (IIh) | (4q) | — |
| (2)-69 | (IIh) | (4x) | X |
| (2)-70 | (IIh) | (4y) | — |
| (2)-71 | (IIh) | (4z) | X |
| (2)-72 | (IIh) | (4aa) | X |
| (2)-73 | (IIh) | (4ff) | X |
| (2)-74 | (IIh) | (4hh) | X |
| (2)-75 | (IIh) | (4jj) | X |
| (2)-76 | (IIh) | (4mm) | X |
| (2)-77 | (IIh) | (4nn) | X |
| (2)-78 | (IIh) | (4pp) | X |
| (2)-79 | (IIh) | (4qq) | X |
| (2)-80 | (IIh) | (4ss) | X |
| (2)-81 | (IIj) | (4b) | — |
| (2)-82 | (IIj) | (4f) | — |
| (2)-83 | (IIj) | (4i) | — |
| (2)-84 | (IIj) | (4j) | — |
| (2)-85 | (IIj) | (4l) | — |
| (2)-86 | (IIj) | (4m) | — |
| (2)-87 | (IIj) | (4q) | — |
| (2)-88 | (IIj) | (4q) | — |
| (2)-89 | (IIj) | (4x) | X |
| (2)-90 | (IIj) | (4y) | — |
| (2)-91 | (IIj) | (4z) | X |
| (2)-92 | (IIj) | (4aa) | X |
| (2)-93 | (IIj) | (4ff) | X |
| (2)-94 | (IIj) | (4hh) | X |
| (2)-95 | (IIj) | (4jj) | X |
| (2)-96 | (IIj) | (4mm) | X |
| (2)-97 | (IIj) | (4nn) | X |
| (2)-98 | (IIj) | (4pp) | X |
| (2)-99 | (IIj) | (4qq) | X |
| (2)-100 | (IIj) | (4ss) | X |
| (2)-101 | (IIn) | (4b) | — |
| (2)-102 | (IIn) | (4f) | — |
| (2)-103 | (IIn) | (4i) | — |
| (2)-104 | (IIn) | (4j) | — |
| (2)-105 | (IIn) | (4l) | — |
| (2)-106 | (IIn) | (4m) | — |
| (2)-107 | (IIn) | (4q) | — |
| (2)-108 | (IIn) | (4q) | — |
| (2)-109 | (IIn) | (4x) | X |
| (2)-110 | (IIn) | (4y) | — |
| (2)-111 | (IIn) | (4z) | X |
| (2)-112 | (IIn) | (4aa) | X |
| (2)-113 | (IIn) | (4ff) | X |
| (2)-114 | (IIn) | (4hh) | X |
| (2)-115 | (IIn) | (4jj) | X |
| (2)-116 | (IIn) | (4mm) | X |
| (2)-117 | (IIn) | (4nn) | X |
| (2)-118 | (IIn) | (4pp) | X |
| (2)-119 | (IIn) | (4qq) | X |
| (2)-120 | (IIn) | (4ss) | X |
| (2)-121 | (IIp) | (4b) | — |
| (2)-122 | (IIp) | (4f) | — |
| (2)-123 | (IIp) | (4i) | — |
| (2)-124 | (IIp) | (4j) | — |
| (2)-125 | (IIp) | (4l) | — |
| (2)-126 | (IIp) | (4m) | — |
| (2)-127 | (IIp) | (4q) | — |
| (2)-128 | (IIp) | (4q) | — |
| (2)-129 | (IIp) | (4x) | X |
| (2)-130 | (IIp) | (4y) | — |
| (2)-131 | (IIp) | (4z) | X |
| (2)-132 | (IIp) | (4aa) | X |
| (2)-133 | (IIp) | (4ff) | X |
| (2)-134 | (IIp) | (4hh) | X |
| (2)-135 | (IIp) | (4jj) | X |
| (2)-136 | (IIp) | (4mm) | X |
| (2)-137 | (IIp) | (4nn) | X |
| (2)-138 | (IIp) | (4pp) | X |
| (2)-139 | (IIp) | (4qq) | X |
| (2)-140 | (IIp) | (4ss) | X |
| (2)-141 | (IIIa) | X | (6a) |
| (2)-142 | (IIIa) | X | (6b) |
| (2)-143 | (IIIa) | X | (6c) |
| (2)-144 | (IIIa) | X | (6d) |
| (2)-145 | (IIIa) | X | (6e) |
| (2)-146 | (IIIa) | X | (6f) |
| (2)-147 | (IIIa) | X | (6g) |
| (2)-148 | (IIIa) | X | (6h) |
| (2)-149 | (IIIa) | X | (6i) |
| (2)-150 | (IIIa) | X | (6j) |
| (2)-151 | (IIIa) | X | (6k) |
| (2)-152 | (IIIa) | X | (6l) |
| (2)-153 | (IIIa) | X | (6m) |
| (2)-154 | (IIIa) | X | (6n) |
| (2)-155 | (IIIa) | X | (6o) |
| (2)-156 | (IIIa) | X | (6p) |
| (2)-157 | (IIIa) | X | (6q) |
| (2)-158 | (IIIa) | X | (6r) |
| (2)-159 | (IIIb) | X | (6a) |
| (2)-160 | (IIIb) | X | (6b) |
| (2)-161 | (IIIb) | X | (6c) |
| (2)-162 | (IIIb) | X | (6d) |
| (2)-163 | (IIIb) | X | (6e) |
| (2)-164 | (IIIb) | X | (6f) |
| (2)-165 | (IIIb) | X | (6g) |
| (2)-166 | (IIIb) | X | (6h) |
| (2)-167 | (IIIb) | X | (6i) |
| (2)-168 | (IIIb) | X | (6j) |
| (2)-169 | (IIIb) | X | (6k) |
| (2)-170 | (IIIb) | X | (6l) |
| (2)-171 | (IIIb) | X | (6m) |
| (2)-172 | (IIIb) | X | (6n) |
| (2)-173 | (IIIb) | X | (6o) |
| (2)-174 | (IIIb) | X | (6p) |
| (2)-175 | (IIIb) | X | (6q) |
| (2)-176 | (IIIb) | X | (6r) |
| (2)-177 | (IIIc) | X | (6a) |
| (2)-178 | (IIIc) | X | (6b) |
| (2)-179 | (IIIc) | X | (6c) |
| (2)-180 | (IIIc) | X | (6d) |
| (2)-181 | (IIIc) | X | (6e) |
| (2)-182 | (IIIc) | X | (6f) |
| (2)-183 | (IIIc) | X | (6g) |

|  | (II) or (III) | Ring B | $R^a$ |
|---|---|---|---|
| (2)-184 | (IIIc) | X | (6h) |
| (2)-185 | (IIIc) | X | (6i) |
| (2)-186 | (IIIc) | X | (6j) |
| (2)-187 | (IIIc) | X | (6k) |
| (2)-188 | (IIIc) | X | (6l) |
| (2)-189 | (IIIc) | X | (6m) |
| (2)-190 | (IIIc) | X | (6n) |
| (2)-191 | (IIIc) | X | (6o) |
| (2)-192 | (IIIc) | X | (6p) |
| (2)-193 | (IIIc) | X | (6q) |
| (2)-194 | (IIIc) | X | (6r) |
| (2)-195 | (IIIe) | X | (6a) |
| (2)-196 | (IIIe) | X | (6b) |
| (2)-197 | (IIIe) | X | (6c) |
| (2)-198 | (IIIe) | X | (6d) |
| (2)-199 | (IIIe) | X | (6e) |
| (2)-200 | (IIIe) | X | (6f) |
| (2)-201 | (IIIe) | X | (6g) |
| (2)-202 | (IIIe) | X | (6h) |
| (2)-203 | (IIIe) | X | (6i) |
| (2)-204 | (IIIe) | X | (6j) |
| (2)-205 | (IIIe) | X | (6k) |
| (2)-206 | (IIIe) | X | (6l) |
| (2)-207 | (IIIe) | X | (6m) |
| (2)-208 | (IIIe) | X | (6n) |
| (2)-209 | (IIIe) | X | (6o) |
| (2)-210 | (IIIe) | X | (6p) |
| (2)-211 | (IIIe) | X | (6q) |
| (2)-212 | (IIIe) | X | (6r) |
| (2)-213 | (IIIh) | X | (6a) |
| (2)-214 | (IIIh) | X | (6b) |
| (2)-215 | (IIIh) | X | (6c) |
| (2)-216 | (IIIh) | X | (6d) |
| (2)-217 | (IIIh) | X | (6e) |
| (2)-218 | (IIIh) | X | (6f) |
| (2)-219 | (IIIh) | X | (6g) |
| (2)-220 | (IIIh) | X | (6h) |
| (2)-221 | (IIIh) | X | (6i) |
| (2)-222 | (IIIh) | X | (6j) |
| (2)-223 | (IIIh) | X | (6k) |
| (2)-224 | (IIIh) | X | (6l) |
| (2)-225 | (IIIh) | X | (6m) |
| (2)-226 | (IIIh) | X | (6n) |
| (2)-227 | (IIIh) | X | (6o) |
| (2)-228 | (IIIh) | X | (6p) |
| (2)-229 | (IIIh) | X | (6q) |
| (2)-230 | (IIIh) | X | (6r) |
| (2)-231 | (IIIk) | X | (6a) |
| (2)-232 | (IIIk) | X | (6b) |
| (2)-233 | (IIIk) | X | (6c) |
| (2)-234 | (IIIk) | X | (6d) |
| (2)-235 | (IIIk) | X | (6e) |
| (2)-236 | (IIIk) | X | (6f) |
| (2)-237 | (IIIk) | X | (6g) |
| (2)-238 | (IIIk) | X | (6h) |
| (2)-239 | (IIIk) | X | (6i) |
| (2)-240 | (IIIk) | X | (6j) |
| (2)-241 | (IIIk) | X | (6k) |
| (2)-242 | (IIIk) | X | (6l) |
| (2)-243 | (IIIk) | X | (6m) |
| (2)-244 | (IIIk) | X | (6n) |
| (2)-245 | (IIIk) | X | (6o) |
| (2)-246 | (IIIk) | X | (6p) |
| (2)-247 | (IIIk) | X | (6q) |
| (2)-248 | (IIIk) | X | (6r) |
| (2)-249 | (IIIl) | X | (6a) |
| (2)-250 | (IIIl) | X | (6b) |
| (2)-251 | (IIIl) | X | (6c) |
| (2)-252 | (IIIl) | X | (6d) |
| (2)-253 | (IIIl) | X | (6e) |
| (2)-254 | (IIIl) | X | (6f) |
| (2)-255 | (IIIl) | X | (6g) |
| (2)-256 | (IIIl) | X | (6h) |
| (2)-257 | (IIIl) | X | (6i) |
| (2)-258 | (IIIl) | X | (6j) |
| (2)-259 | (IIIl) | X | (6k) |
| (2)-260 | (IIIl) | X | (6l) |
| (2)-261 | (IIIl) | X | (6m) |
| (2)-262 | (IIIl) | X | (6n) |
| (2)-263 | (IIIl) | X | (6o) |
| (2)-264 | (IIIl) | X | (6p) |
| (2)-265 | (IIIl) | X | (6q) |
| (2)-266 | (IIIl) | X | (6r) |
| (2)-267 | (IIIm) | X | (6a) |
| (2)-268 | (IIIm) | X | (6b) |
| (2)-269 | (IIIm) | X | (6c) |
| (2)-270 | (IIIm) | X | (6d) |
| (2)-271 | (IIIm) | X | (6e) |
| (2)-272 | (IIIm) | X | (6f) |
| (2)-273 | (IIIm) | X | (6g) |
| (2)-274 | (IIIm) | X | (6h) |
| (2)-275 | (IIIm) | X | (6i) |
| (2)-276 | (IIIm) | X | (6j) |
| (2)-277 | (IIIm) | X | (6k) |
| (2)-278 | (IIIm) | X | (6l) |
| (2)-279 | (IIIm) | X | (6m) |
| (2)-280 | (IIIm) | X | (6n) |
| (2)-281 | (IIIm) | X | (6o) |
| (2)-282 | (IIIm) | X | (6p) |
| (2)-283 | (IIIm) | X | (6q) |
| (2)-284 | (IIIm) | X | (6r) |
| (2)-285 | (IIIo) | X | (6a) |
| (2)-286 | (IIIo) | X | (6b) |
| (2)-287 | (IIIo) | X | (6c) |
| (2)-288 | (IIIo) | X | (6d) |
| (2)-289 | (IIIo) | X | (6e) |
| (2)-290 | (IIIo) | X | (6f) |
| (2)-291 | (IIIo) | X | (6g) |
| (2)-292 | (IIIo) | X | (6h) |
| (2)-293 | (IIIo) | X | (6i) |
| (2)-294 | (IIIo) | X | (6j) |
| (2)-295 | (IIIo) | X | (6k) |
| (2)-296 | (IIIo) | X | (6l) |
| (2)-297 | (IIIo) | X | (6m) |
| (2)-298 | (IIIo) | X | (6n) |
| (2)-299 | (IIIo) | X | (6o) |
| (2)-300 | (IIIo) | X | (6p) |
| (2)-301 | (IIIo) | X | (6q) |
| (2)-302 | (IIIo) | X | (6r) |

In another aspect, the present disclosure provides compounds that are:

| Ex# | Chemical Structure | Chemical Name |
|---|---|---|
| 1 | 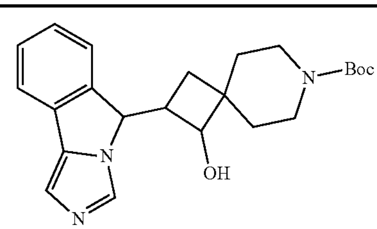 | tert-butyl 1-hydroxy-2-(5H-imidazo[5,1-a]isoindol-5-yl)-7-azaspiro[3.5]nonane-7-carboxylate |

-continued

| Ex# | Chemical Structure | Chemical Name |
|---|---|---|
| 2 | 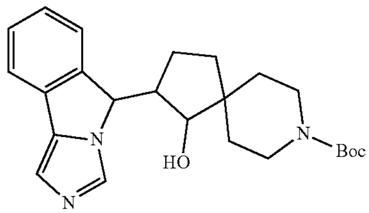 [SMILES: CC(C)(C)OC(=O)N1CCC2(CCC(C3c4ccccc4-c4cncn43)C2O)CC1] | tert-butyl 1-hydroxy-2-(5H-imidazo[5,1-a]isoindol-5-yl)-8-azaspiro[4.5]decane-8-carboxylate |
| 3 | 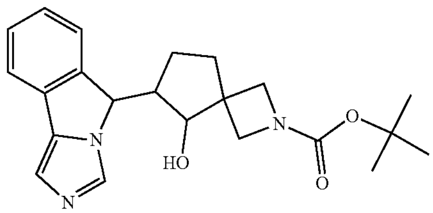 [SMILES: CC(C)(C)OC(=O)N1CC2(CCC(C3c4ccccc4-c4cncn43)C2O)C1] | tert-butyl 5-hydroxy-6-(5H-imidazo[4,3-a]isoindol-5-yl)-2-azaspiro[3.4]octane-2-carboxylate |
| 4 | 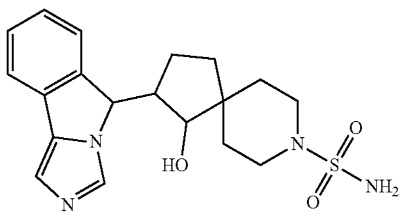 [SMILES: NS(=O)(=O)N1CCC2(CCC(C3c4ccccc4-c4cncn43)C2O)CC1] | 1-hydroxy-2-(5H-imidazo[4,3-a]isoindol-5-yl)-8-azaspiro[4.5]decane-8-sulfonamide |
| 5 | 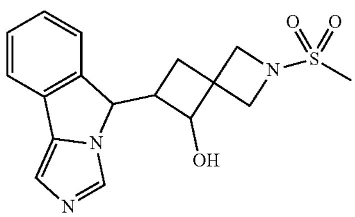 [SMILES: CS(=O)(=O)N1CC2(CC(C3c4ccccc4-c4cncn43)C2O)C1] | 6-(5H-imidazo[1,5-b]isoindol-5-yl)-2-methylsulfonyl-2-azaspiro[3.3]heptan-7-ol |
| 6 | 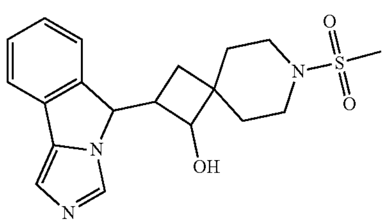 [SMILES: CS(=O)(=O)N1CCC2(CC1)CC(C1c3ccccc3-c3cncn31)C2O] | 2-(5H-imidazo[4,3-a]isoindol-5-yl)-7-methanesulfonyl-7-azaspiro[3.5]nonan-1-ol |
| 7 | 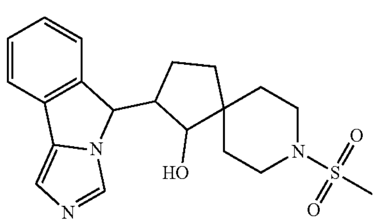 [SMILES: CS(=O)(=O)N1CCC2(CCC(C3c4ccccc4-c4cncn43)C2O)CC1] | 2-(5H-imidazo[5,1-a]isoindol-5-yl)-8-(methylsulfonyl)-8-azaspiro[4.5]decan-1-ol |
| 8 | 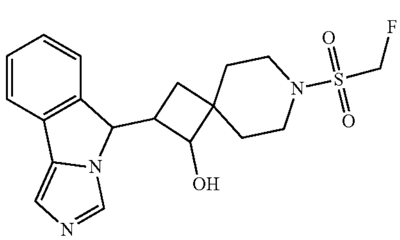 [SMILES: O=S(=O)(CF)N1CCC2(CC1)CC(C1c3ccccc3-c3cncn31)C2O] | 7-fluoromethanesulfonyl-2-(5H-imidazo[4,3-a]isoindol-5-yl)-7-azaspiro[3.5]nonan-1-ol |

| Ex# | Chemical Structure | Chemical Name |
|---|---|---|
| 9 | 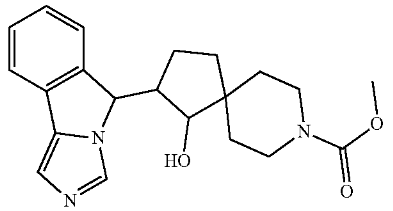 [SMILES: COC(=O)N1CCC2(CCC(C3c4ccccc4-c4cncn43)C2O)CC1] | methyl 1-hydroxy-2-(5H-imidazo[4,3-a]isoindol-5-yl)-8-azaspiro[4.5]decane-8-carboxylate |
| 10 | 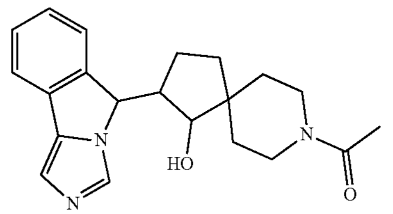 [SMILES: CC(=O)N1CCC2(CCC(C3c4ccccc4-c4cncn43)C2O)CC1] | 1-(1-hydroxy-2-(5H-imidazo[4,3-a]isoindol-5-yl)-8-azaspiro[4.5]decan-8-yl)ethan-1-one |
| 11 | 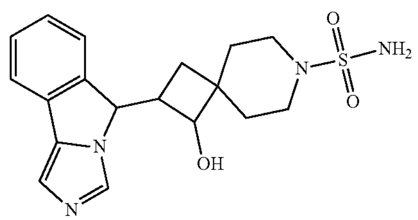 [SMILES: NS(=O)(=O)N1CCC2(CC1)CC(C1c3ccccc3-c3cncn31)C2O] | 1-hydroxy-2-(5H-imidazo[4,3-a]isoindol-5-yl)-7-azaspiro[3.5]nonane-7-sulfonamide |
| 12 | 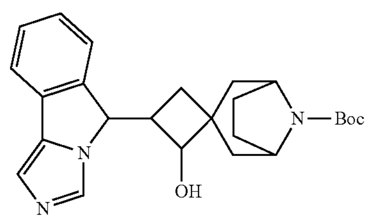 [SMILES: CC(C)(C)OC(=O)N1C2CCC1CC1(CC(C3c4ccccc4-c4cncn43)C1O)C2] | tert-butyl 2'-hydroxy-3'-(5H-imidazo[5,1-a]isoindol-5-yl)-8-azaspiro[bicyclo[3.2.1]octane-3,1'-cyclobutane]-8-carboxylate |
| 13 | 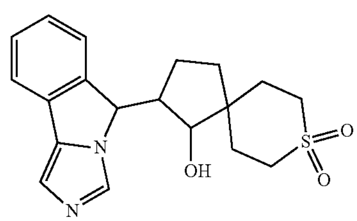 [SMILES: O=S1(=O)CCC2(CCC(C3c4ccccc4-c4cncn43)C2O)CC1] | 1-hydroxy-2-(5H-imidazo[5,1-a]isoindol-5-yl)-8-thiaspiro[4.5]decane 8,8-dioxide |
| 14 | 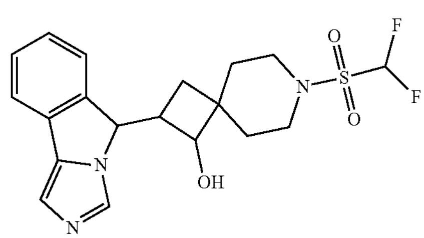 [SMILES: O=S(=O)(C(F)F)N1CCC2(CC1)CC(C1c3ccccc3-c3cncn31)C2O] | 7-((difluoromethyl)sulfonyl)-2-(5H-imidazo[5,1-a]isoindol-5-yl)-7-azaspiro[3.5]nonan-1-ol |
| 15 | 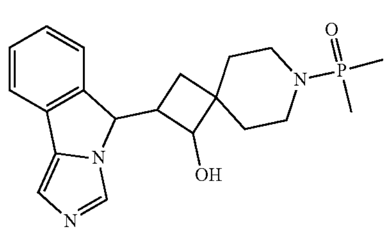 [SMILES: CP(C)(=O)N1CCC2(CC1)CC(C1c3ccccc3-c3cncn31)C2O] | (1-hydroxy-2-(5H-imidazo[5,1-a]isoindol-5-yl)-7-azaspiro[3.5]nonan-7-yl)dimethylphosphine oxide |

| Ex# | Chemical Structure | Chemical Name |
|---|---|---|
| 16 | 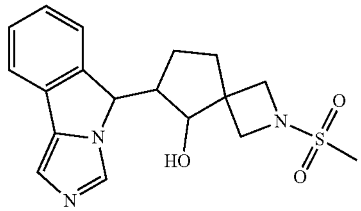 [SMILES: CS(=O)(=O)N1CC2(CCC(C3c4ccccc4-c4cncn43)C2O)C1] | 6-(5H-imidazo[5,1-a]isoindol-5-yl)-2-(methylsulfonyl)-2-azaspiro[3.4]octan-5-ol |
| 17 | 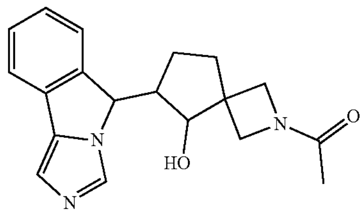 [SMILES: CC(=O)N1CC2(CCC(C3c4ccccc4-c4cncn43)C2O)C1] | 1-(5-hydroxy-6-(5H-imidazo[5,1-a]isoindol-5-yl)-2-azaspiro[3.4]octan-2-yl)ethan-1-one |
| 18 | 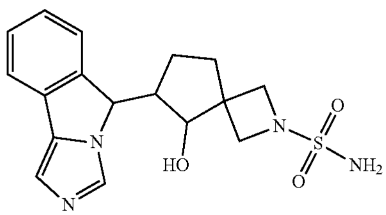 [SMILES: NS(=O)(=O)N1CC2(CCC(C3c4ccccc4-c4cncn43)C2O)C1] | 5-hydroxy-6-(5H-imidazo[5,1-a]isoindol-5-yl)-2-azaspiro[3.4]octane-2-sulfonamide |
| 19 | 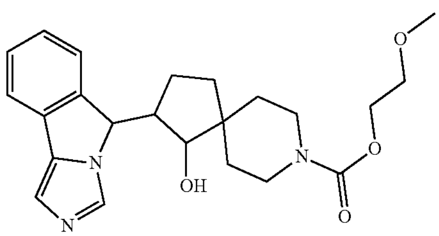 [SMILES: COCCOC(=O)N1CCC2(CCC(C3c4ccccc4-c4cncn43)C2O)CC1] | 2-methoxyethyl 1-hydroxy-2-(5H-imidazo[5,1-a]isoindol-5-yl)-8-azaspiro[4.5]decane-8-carboxylate |
| 20 | 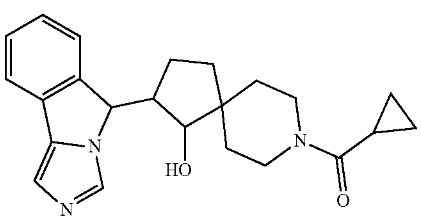 [SMILES: O=C(C1CC1)N1CCC2(CCC(C3c4ccccc4-c4cncn43)C2O)CC1] | cyclopropyl(1-hydroxy-2-(5H-imidazo[5,1-a]isoindol-5-yl)-8-azaspiro[4.5]decan-8-yl)methanone |
| 21 | 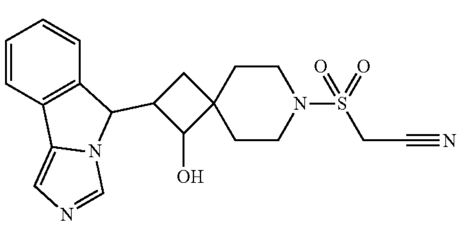 [SMILES: N#CCS(=O)(=O)N1CCC2(CC1)CC(C1c3ccccc3-c3cncn31)C2O] | 2-[[3-hydroxy-2-(5H-imidazo[1,5-b]isoindol-5-yl)-7-azaspiro[3.5]nonan-7-yl]sulfonyl]acetonitrile |
| 22 | 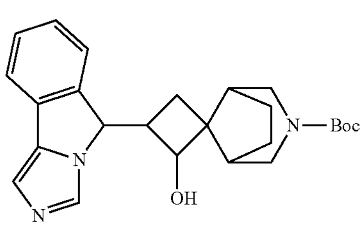 [SMILES: CC(C)(C)OC(=O)N1CC2CCC(C1)C21CC(C2c3ccccc3-c3cncn32)C1O] | tert-butyl 2'-hydroxy-3'-(5H-imidazo[5,1-a]isoindol-5-yl)-3-azaspiro[bicyclo[3.2.1]octane-8,1'-cyclobutane]-3-carboxylate |

| Ex# | Chemical Structure | Chemical Name |
| --- | --- | --- |
| 23 | 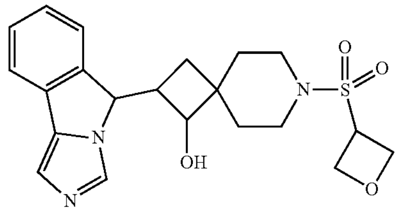 [SMILES: O=S(=O)(C1COC1)N1CCC2(CC1)CC(C1c3ccccc3-c3cncn31)C2O] | 2-(5H-imidazo[1,5-b]isoindol-5-yl)-7-(oxetan-3-ylsulfonyl)-7-azaspiro[3.5]nonan-3-ol |
| 24 | 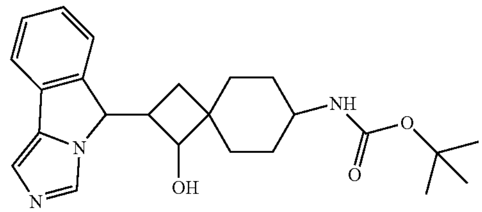 [SMILES: CC(C)(C)OC(=O)NC1CCC2(CC1)CC(C1c3ccccc3-c3cncn31)C2O] | tert-butyl (1-hydroxy-2-(5H-imidazo[5,1-a]isoindol-5-yl)spiro[3.5]nonan-7-yl)carbamate |
| 25 | 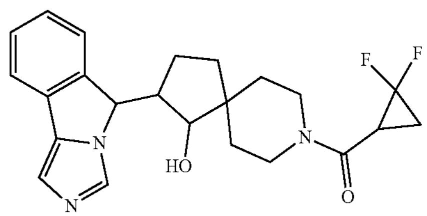 [SMILES: O=C(C1CC1(F)F)N1CCC2(CCC(C3c4ccccc4-c4cncn43)C2O)CC1] | (2,2-difluorocyclopropyl)(1-hydroxy-2-(5H-imidazo[5,1-a]isoindol-5-yl)-8-azaspiro[4.5]decan-8-yl)methanone |
| 26 | 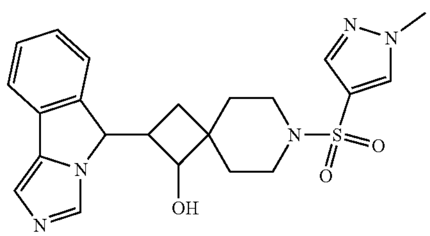 [SMILES: Cn1cc(S(=O)(=O)N2CCC3(CC2)CC(C2c4ccccc4-c4cncn42)C3O)cn1] | 2-(5H-imidazo[1,5-b]isoindol-5-yl)-7-(1-methylpyrazol-4-yl)sulfonyl-7-azaspiro[3.5]nonan-3-ol |
| 27 | 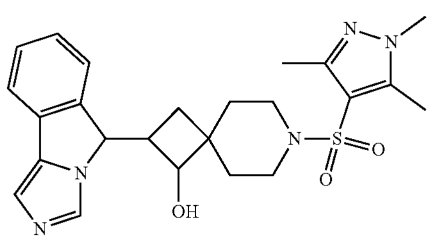 [SMILES: Cc1nn(C)c(C)c1S(=O)(=O)N1CCC2(CC1)CC(C1c3ccccc3-c3cncn31)C2O] | 2-(5H-imidazo[1,5-b]isoindol-5-yl)-7-(1,3,5-trimethylpyrazol-4-yl)sulfonyl-7-azaspiro[3.5]nonan-3-ol |
| 28 | 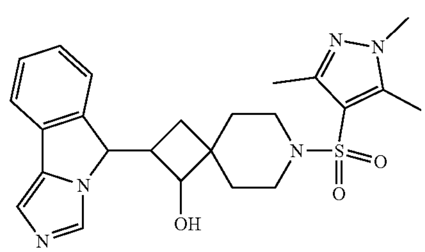 [SMILES: Cc1nn(C)c(C)c1S(=O)(=O)N1CCC2(CC1)CC(C1c3ccccc3-c3cncn31)C2O] | 7-(2,3-dimethylimidazol-4-yl)sulfonyl-2-(5H-imidazo[1,5-b]isoindol-5-yl)-7-azaspiro[3.5]nonan-3-ol |
| 29 | 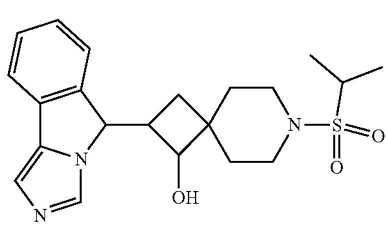 [SMILES: CC(C)S(=O)(=O)N1CCC2(CC1)CC(C1c3ccccc3-c3cncn31)C2O] | 2-(5H-imidazo[1,5-b]isoindol-5-yl)-7-isopropylsulfonyl-7-azaspiro[3.5]nonan-3-ol |

| Ex# | Chemical Structure | Chemical Name |
|---|---|---|
| 30 | 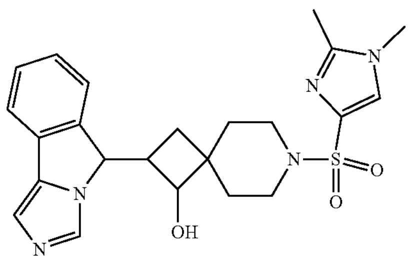 [SMILES: Cc1nc(S(=O)(=O)N2CCC3(CC2)CC(C2c4ccccc4-c4cncn42)C3O)cn1C] | 7-(3,5-dimethylisoxazol-4-yl)sulfonyl-2-(5H-imidazo[1,5-b]isoindol-5-yl)-7-azaspiro[3.5]nonan-3-ol |
| 31 | 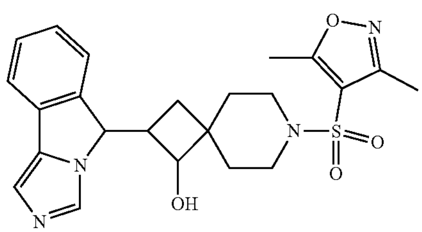 [SMILES: Cc1noc(C)c1S(=O)(=O)N1CCC2(CC1)CC(C1c3ccccc3-c3cncn31)C2O] | 7-(1,2-dimethylimidazol-4-yl)sulfonyl-2-(5H-imidazo[1,5-b]isoindol-5-yl)-7-azaspiro[3.5]nonan-3-ol |
| 32 | 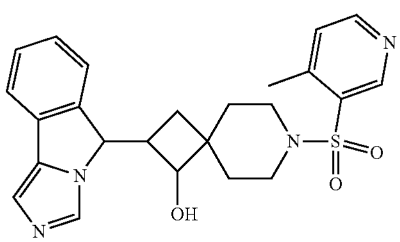 [SMILES: Cc1ccncc1S(=O)(=O)N1CCC2(CC1)CC(C1c3ccccc3-c3cncn31)C2O] | 2-(5H-imidazo[1,5-b]isoindol-5-yl)-7-[(4-methyl-3-pyridyl)sulfonyl]-7-azaspiro[3.5]nonan-3-ol |
| 33 | 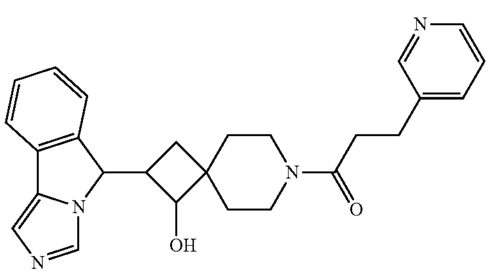 | 1-[3-hydroxy-2-(5H-imidazo[1,5-b]isoindol-5-yl)-7-azaspiro[3.5]nonan-7-yl]-3-(3-pyridyl)propan-1-one |
| 34 | 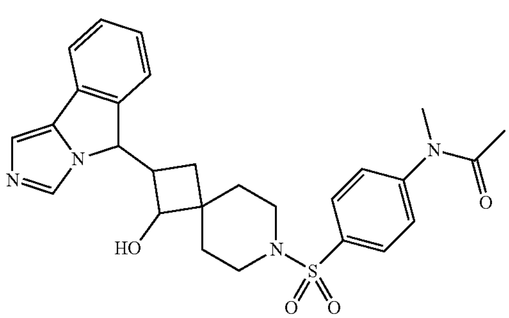 [SMILES: CC(=O)N(C)c1ccc(S(=O)(=O)N2CCC3(CC2)CC(C2c4ccccc4-c4cncn42)C3O)cc1] | N-[4-[[3-hydroxy-2-(5H-imidazo[1,5-b]isoindol-5-yl)-7-azaspiro[3.5]nonan-7-yl]sulfonyl]phenyl]-N-methyl-acetamide |

-continued

| Ex# | Chemical Structure | Chemical Name |
|---|---|---|
| 35 | 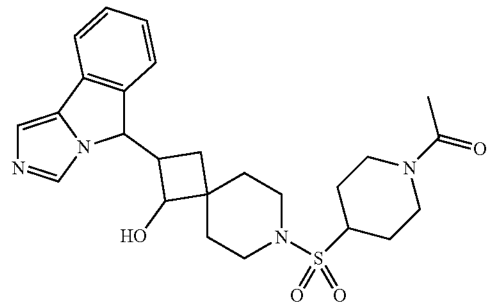 [SMILES: CC(=O)N1CCC(S(=O)(=O)N2CCC3(CC2)CC(C2c4ccccc4-c4cncn42)C3O)CC1] | 1-[4-[[3-hydroxy-2-(5H-imidazo[1,5-b]isoindol-5-yl)-7-azaspiro[3.5]nonan-7-yl]sulfonyl]-1-piperidyl]ethanone |
| 36 | 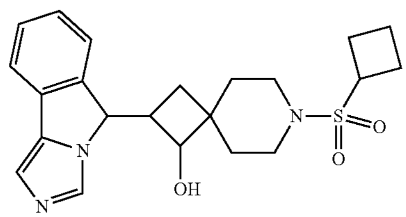 [SMILES: O=S(=O)(C1CCC1)N1CCC2(CC1)CC(C1c3ccccc3-c3cncn31)C2O] | 7-cyclobutylsulfonyl-2-(5H-imidazo[1,5-b]isoindol-5-yl)-7-azaspiro[3.5]nonan-3-ol |
| 37 | 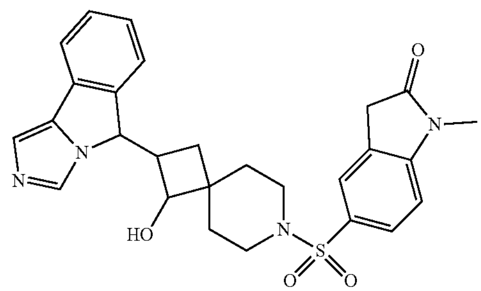 [SMILES: CN1C(=O)Cc2cc(S(=O)(=O)N3CCC4(CC3)CC(C3c5ccccc5-c5cncn53)C4O)ccc21] | 5-[[3-hydroxy-2-(5H-imidazo[1,5-b]isoindol-5-yl)-7-azaspiro[3.5]nonan-7-yl]sulfonyl]-1-methyl-indolin-2-one |
| 38 | 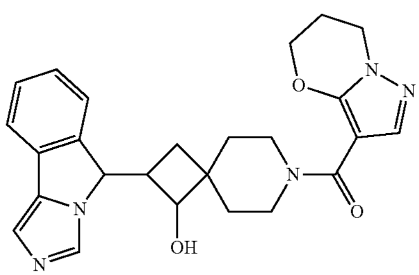 [SMILES: O=C(c1cnn2c1OCCC2)N1CCC2(CC1)CC(C1c3ccccc3-c3cncn31)C2O] | 6,7-dihydro-5H-pyrazolo[5,1-b][1,3]oxazin-3-yl-[3-hydroxy-2-(5H-imidazo[1,5-b]isoindol-5-yl)-7-azaspiro[3.5]nonan-7-yl]methanone |
| 39 | 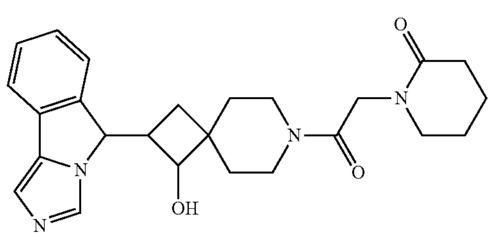 | 1-[2-[3-hydroxy-2-(5H-imidazo[1,5-b]isoindol-5-yl)-7-azaspiro[3.5]nonan-7-yl]-2-oxo-ethyl]piperidin-2-one |
| 40 | 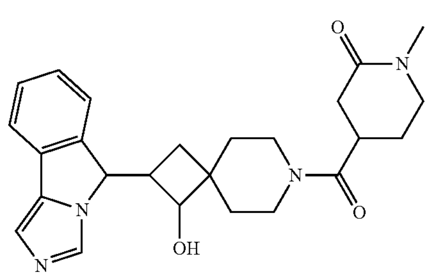 | 4-[3-hydroxy-2-(5H-imidazo[1,5-b]isoindol-5-yl)-7-azaspiro[3.5]nonane-7-carbonyl]-1-methyl-piperidin-2-one |

| Ex# | Chemical Structure | Chemical Name |
|---|---|---|
| 41 | 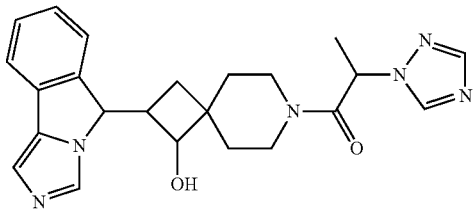 | 1-[3-hydroxy-2-(5H-imidazo[1,5-b]isoindol-5-yl)-7-azaspiro[3.5]nonan-7-yl]-2-(1,2,4-triazol-1-yl)propan-1-one |
| 42 | 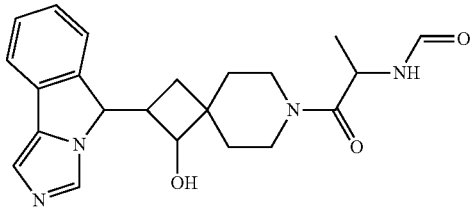 | N-[2-[3-hydroxy-2-(5H-imidazo[1,5-b]isoindol-5-yl)-7-azaspiro[3.5]nonan-7-yl]-1-methyl-2-oxo-ethyl]formamide |
| 43 | 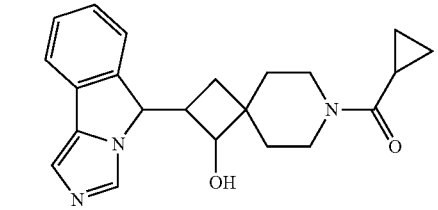 | cyclopropyl-[3-hydroxy-2-(5H-imidazo[1,5-b]isoindol-5-yl)-7-azaspiro[3.5]nonan-7-yl]methanone |
| 44 | 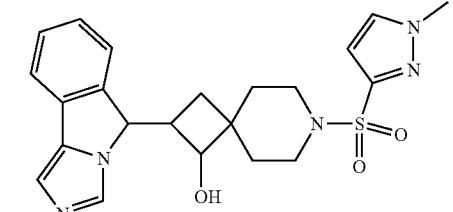 | 2-(5H-imidazo[1,5-b]isoindol-5-yl)-7-(1-methylpyrazol-3-yl)sulfonyl-7-azaspiro[3.5]nonan-3-ol |
| 45 | 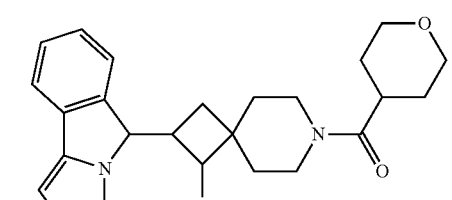 | [3-hydroxy-2-(5H-imidazo[1,5-b]isoindol-5-yl)-7-azaspiro[3.5]nonan-7-yl]-tetrahydropyran-4-yl-methanone |
| 46 | 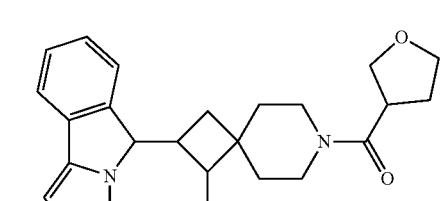 | [3-hydroxy-2-(5H-imidazo[1,5-b]isoindol-5-yl)-7-azaspiro[3.5]nonan-7-yl]-tetrahydrofuran-3-yl-methanone |
| 47 | 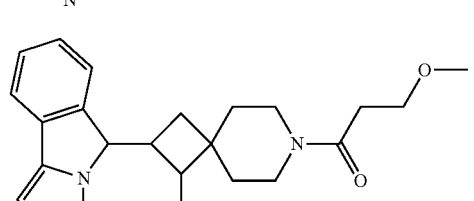 | 1-[3-hydroxy-2-(5H-imidazo[1,5-b]isoindol-5-yl)-7-azaspiro[3.5]nonan-7-yl]-3-methoxy-propan-1-one |

-continued

| Ex# | Chemical Structure | Chemical Name |
|---|---|---|
| 48 | 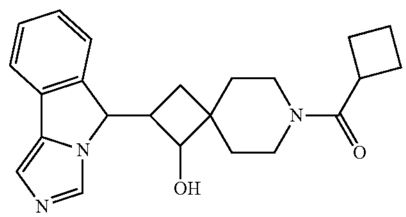 [SMILES: O=C(C1CCC1)N1CCC2(CC1)CC(C1c3ccccc3-c3cncn31)C2O] | cyclobutyl-[3-hydroxy-2-(5H-imidazo[1,5-b]isoindol-5-yl)-7-azaspiro[3.5]nonan-7-yl]methanone |
| 49 | 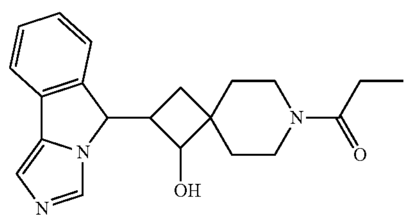 [SMILES: CCC(=O)N1CCC2(CC1)CC(C1c3ccccc3-c3cncn31)C2O] | 1-[3-hydroxy-2-(5H-imidazo[1,5-b]isoindol-5-yl)-7-azaspiro[3.5]nonan-7-yl]propan-1-one |
| 50 | 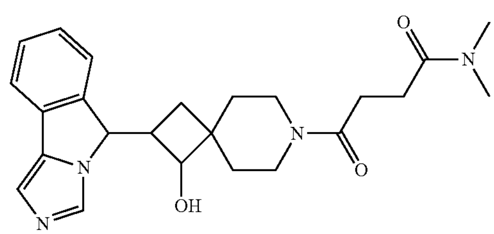 [SMILES: CN(C)C(=O)CCC(=O)N1CCC2(CC1)CC(C1c3ccccc3-c3cncn31)C2O] | 4-[3-hydroxy-2-(5H-imidazo[1,5-b]isoindol-5-yl)-7-azaspiro[3.5]nonan-7-yl]-N,N-dimethyl-4-oxo-butanamide |
| 51 | 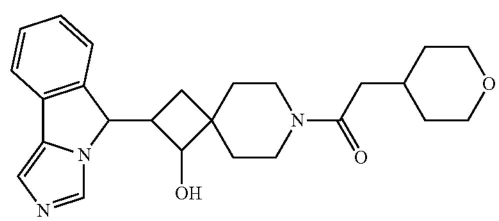 [SMILES: O=C(CC1CCOCC1)N1CCC2(CC1)CC(C1c3ccccc3-c3cncn31)C2O] | 1-[3-hydroxy-2-(5H-imidazo[1,5-b]isoindol-5-yl)-7-azaspiro[3.5]nonan-7-yl]-2-tetrahydropyran-4-yl-ethanone |
| 52 | 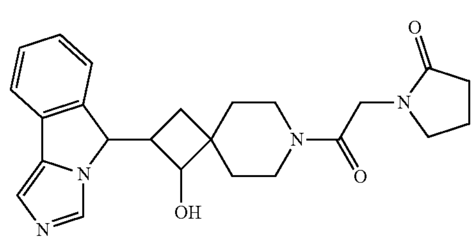 [SMILES: O=C(CN1CCCC1=O)N1CCC2(CC1)CC(C1c3ccccc3-c3cncn31)C2O] | 1-[2-[3-hydroxy-2-(5H-imidazo[1,5-b]isoindol-5-yl)-7-azaspiro[3.5]nonan-7-yl]-2-oxo-ethyl]pyrrolidin-2-one |
| 53 | 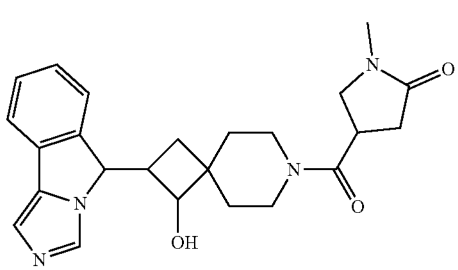 [SMILES: CN1CC(C(=O)N2CCC3(CC2)CC(C2c4ccccc4-c4cncn42)C3O)CC1=O] | 4-[3-hydroxy-2-(5H-imidazo[1,5-b]isoindol-5-yl)-7-azaspiro[3.5]nonane-7-carbonyl]-1-methyl-pyrrolidin-2-one |

| Ex# | Chemical Structure | Chemical Name |
|---|---|---|
| 54 | 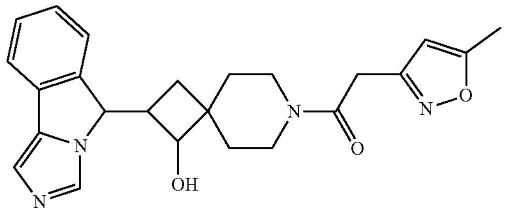 [SMILES: Cc1cc(CC(=O)N2CCC3(CC2)CC(C2c4ccccc4-c4cncn42)C3O)no1] | 1-[3-hydroxy-2-(5H-imidazo[1,5-b]isoindol-5-yl)-7-azaspiro[3.5]nonan-7-yl]-2-(5-methylisoxazol-3-yl)ethanone |
| 55 | 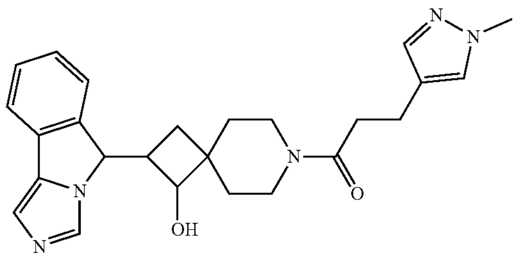 [SMILES: Cn1cc(CCC(=O)N2CCC3(CC2)CC(C2c4ccccc4-c4cncn42)C3O)cn1] | 1-[3-hydroxy-2-(5H-imidazo[1,5-b]isoindol-5-yl)-7-azaspiro[3.5]nonan-7-yl]-3-(1-methylpyrazol-4-yl)propan-1-one |
| 56 | 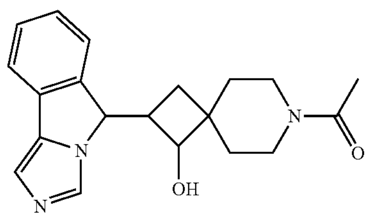 [SMILES: CC(=O)N1CCC2(CC1)CC(C1c3ccccc3-c3cncn31)C2O] | 1-[3-hydroxy-2-(5H-imidazo[1,5-b]isoindol-5-yl)-7-azaspiro[3.5]nonan-7-yl]ethanone |
| 57 | 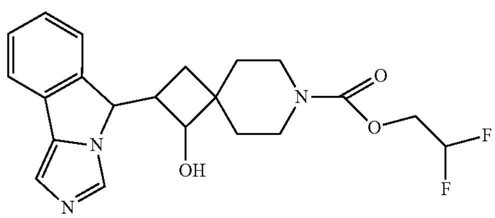 [SMILES: O=C(OCC(F)F)N1CCC2(CC1)CC(C1c3ccccc3-c3cncn31)C2O] | 2,2-difluoroethyl (2S,3R)-3-hydroxy-2-[(5S)-5H-imidazo[1,5-b]isoindol-5-yl]-7-azaspiro[3.5]nonane-7-carboxylate |
| 58 | 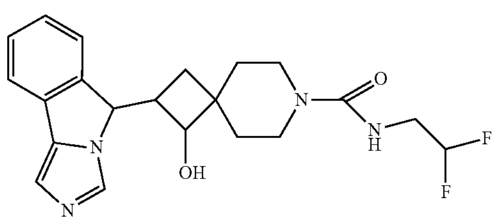 | N-(2,2-difluoroethyl)-3-hydroxy-2-(5H-imidazo[1,5-b]isoindol-5-yl)-7-azaspiro[3.5]nonane-7-carboxamide |
| 59 | 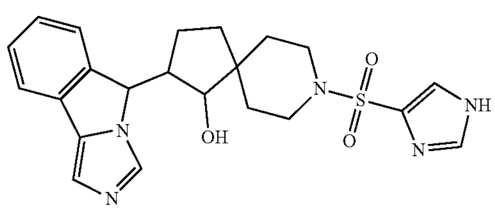 [SMILES: O=S(=O)(c1c[nH]cn1)N1CCC2(CCC(C3c4ccccc4-c4cncn43)C2O)CC1] | 8-((1H-imidazol-4-yl)sulfonyl)-2-(5H-imidazo[5,1-a]isoindol-5-yl)-8-azaspiro[4.5]decan-1-ol |
| 60 | 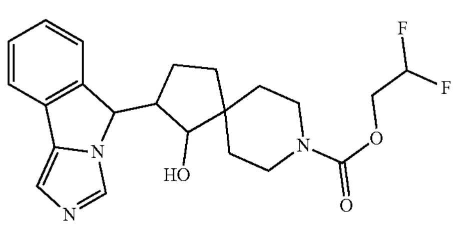 [SMILES: O=C(OCC(F)F)N1CCC2(CCC(C3c4ccccc4-c4cncn43)C2O)CC1] | 2,2-difluoroethyl 1-hydroxy-2-(5H-imidazo[5,1-a]isoindol-5-yl)-8-azaspiro[4.5]decane-8-carboxylate |

-continued

| Ex# | Chemical Structure | Chemical Name |
|---|---|---|
| 61 | 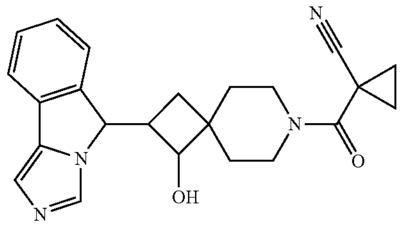 [SMILES: N#CC1(C(=O)N2CCC3(CC2)CC(C2c4ccccc4-c4cncn42)C3O)CC1] | 1-[3-hydroxy-2-(5H-imidazo[1,5-b]isoindol-5-yl)-7-azaspiro[3.5]nonane-7-carbonyl]cyclopropanecarbonitrile |
| 62 | 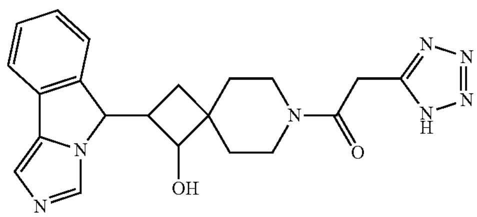 [SMILES: O=C(Cc1nnn[nH]1)N1CCC2(CC1)CC(C1c3ccccc3-c3cncn31)C2O] | 1-[3-hydroxy-2-(5H-imidazo[1,5-b]isoindol-5-yl)-7-azaspiro[3.5]nonan-7-yl]-2-(1H-tetrazol-5-yl)ethanone |
| 63 | 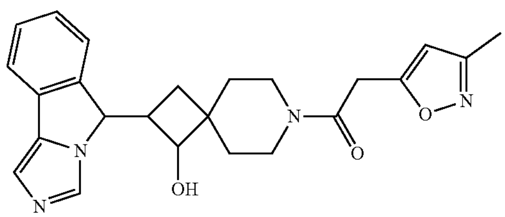 [SMILES: Cc1cc(CC(=O)N2CCC3(CC2)CC(C2c4ccccc4-c4cncn42)C3O)on1] | 1-[3-hydroxy-2-(5H-imidazo[1,5-b]isoindol-5-yl)-7-azaspiro[3.5]nonan-7-yl]-2-(3-methylisoxazol-5-yl)ethanone |
| 64 | 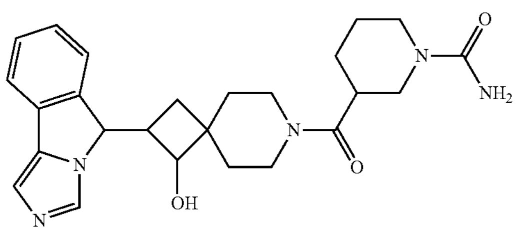 [SMILES: NC(=O)N1CCCC(C(=O)N2CCC3(CC2)CC(C2c4ccccc4-c4cncn42)C3O)C1] | 3-[3-hydroxy-2-(5H-imidazo[1,5-b]isoindol-5-yl)-7-azaspiro[3.5]nonane-7-carbonyl]piperidine-1-carboxamide |
| 65 | 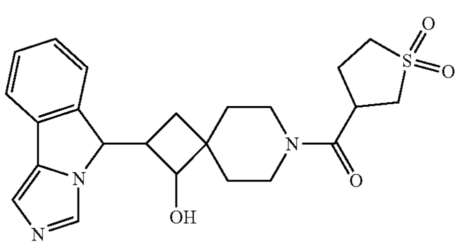 [SMILES: O=C(C1CCS(=O)(=O)C1)N1CCC2(CC1)CC(C1c3ccccc3-c3cncn31)C2O] | (1,1-dioxothiolan-3-yl)-[3-hydroxy-2-(5H-imidazo[1,5-b]isoindol-5-yl)-7-azaspiro[3.5]nonan-7-yl]methanone |
| 66 | 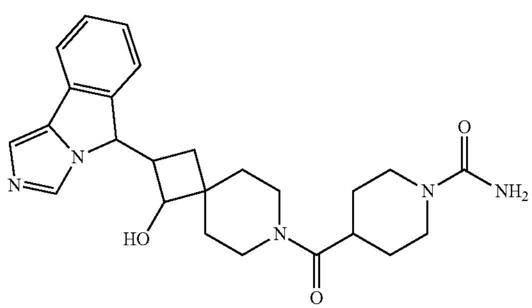 [SMILES: NC(=O)N1CCC(C(=O)N2CCC3(CC2)CC(C2c4ccccc4-c4cncn42)C3O)CC1] | 4-[3-hydroxy-2-(5H-imidazo[1,5-b]isoindol-5-yl)-7-azaspiro[3.5]nonane-7-carbonyl]piperidine-1-carboxamide |

-continued

| Ex# | Chemical Structure | Chemical Name |
|---|---|---|
| 67 | 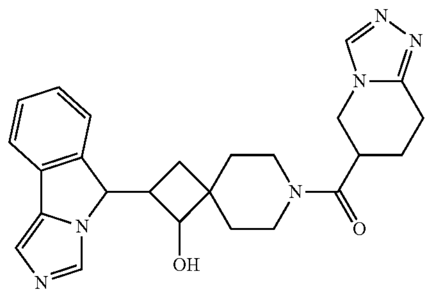 | [3-hydroxy-2-(5H-imidazo[1,5-b]isoindol-5-yl)-7-azaspiro[3.5]nonan-7-yl]-(5,6,7,8-tetrahydro-[1,2,4]triazolo[4,3-a]pyridin-6-yl)methanone |
| 68 | 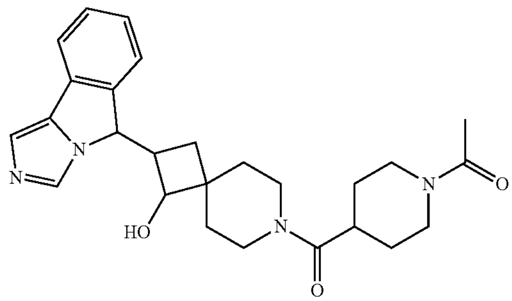 [SMILES: CC(=O)N1CCC(C(=O)N2CCC3(CC2)CC(C2c4ccccc4-c4cncn42)C3O)CC1] | 1-[4-[3-hydroxy-2-(5H-imidazo[1,5-b]isoindol-5-yl)-7-azaspiro[3.5]nonane-7-carbonyl]-1-piperidyl]ethanone |
| 69 | 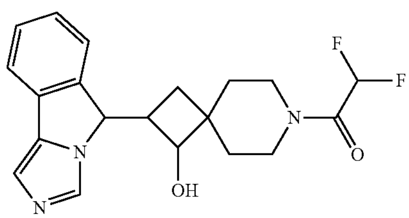 [SMILES: O=C(C(F)F)N1CCC2(CC1)CC(C1c3ccccc3-c3cncn31)C2O] | 2,2-difluoro-1-[3-hydroxy-2-(5H-imidazo[1,5-b]isoindol-5-yl)-7-azaspiro[3.5]nonan-7-yl]ethanone |
| 70 | | 3'-(5H-imidazo[5,1-a]isoindol-5-yl)-3-(methylsulfonyl)-3-azaspiro[bicyclo[3.2.1]octane-8,1'-cyclobutan]-2'-ol | or a pharmaceutically acceptable salt thereof, or an enantiomer or diastereoisomer thereof, or a racemic mixture thereof.

In one embodiment, the compounds of the invention are

| Ex# | Chemical Structure | Chemical Name |
|---|---|---|
| 1a | 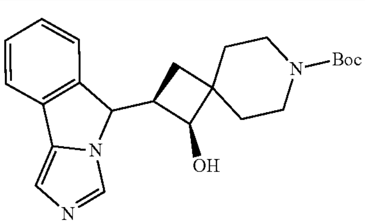 [SMILES: CC(C)(C)OC(=O)N1CCC2(CC1)C[C@H](C1c3ccccc3-c3cncn31)[C@@H]2O] | tert-butyl (1S,2R)-1-hydroxy-2-((R)-5H-imidazo[5,1-a]isoindol-5-yl)-7-azaspiro[3.5]nonane-7-carboxylate |

-continued

| Ex# | Chemical Structure | Chemical Name |
|---|---|---|
| 1b | 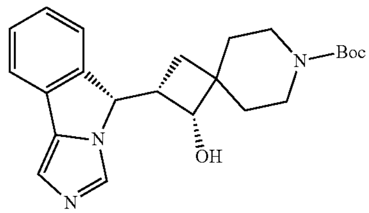 [SMILES: CC(C)(C)OC(=O)N1CCC2(CC1)C[C@@H]([C@H]1c3ccccc3-c3cncn31)[C@H]2O] | tert-butyl (1R,2S)-1-hydroxy-2-((S)-5H-imidazo[5,1-a]isoindol-5-yl)-7-azaspiro[3.5]nonane-7-carboxylate |
| 2a | 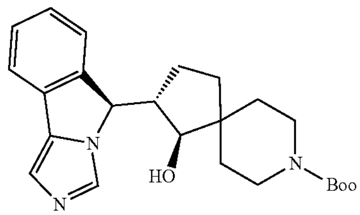 | tert-butyl (1S,2S)-1-hydroxy-2-((R)-5H-imidazo[5,1-a]isoindol-5-yl)-8-azaspiro[4.5]decane-8-carboxylate |
| 2b | 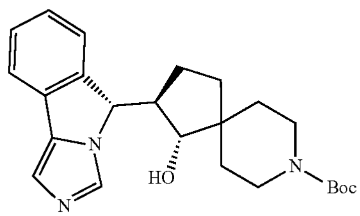 [SMILES: CC(C)(C)OC(=O)N1CCC2(CC[C@H]([C@H]3c4ccccc4-c4cncn43)[C@H]2O)CC1] | tert-butyl (1R,2R)-1-hydroxy-2-((S)-5H-imidazo[5,1-a]isoindol-5-yl)-8-azaspiro[4.5]decane-8-carboxylate |
| 2c | 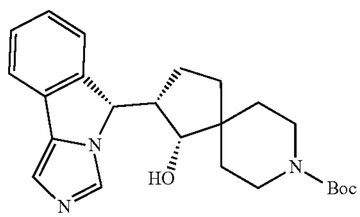 [SMILES: CC(C)(C)OC(=O)N1CCC2(CC[C@@H]([C@H]3c4ccccc4-c4cncn43)[C@H]2O)CC1] | tert-butyl (1R,2S)-1-hydroxy-2-((S)-5H-imidazo[5,1-a]isoindol-5-yl)-8-azaspiro[4.5]decane-8-carboxylate |
| 2d | 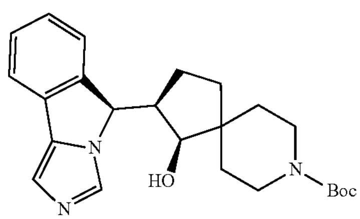 [SMILES: CC(C)(C)OC(=O)N1CCC2(CC[C@H]([C@@H]3c4ccccc4-c4cncn43)[C@@H]2O)CC1] | tert-butyl (1S,2R)-1-hydroxy-2-((R)-5H-imidazo[5,1-a]isoindol-5-yl)-8-azaspiro[4.5]decane-8-carboxylate |
| 3a | 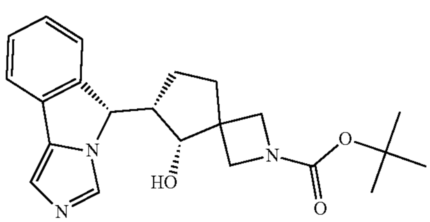 [SMILES: CC(C)(C)OC(=O)N1CC2(CC[C@@H]([C@H]3c4ccccc4-c4cncn43)[C@H]2O)C1] | tert-butyl (5R,6S)-5-hydroxy-6-[(5S)-5H-imidazo[1,5-b]isoindol-5-yl]-2-azaspiro[3.4]octane-2-carboxylate |
| 3b | 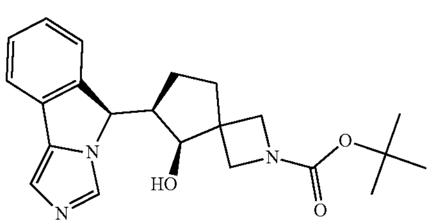 [SMILES: CC(C)(C)OC(=O)N1CC2(CC[C@H]([C@@H]3c4ccccc4-c4cncn43)[C@@H]2O)C1] | tert-butyl (5S,6R)-5-hydroxy-6-[(5R)-5H-imidazo[1,5-b]isoindol-5-yl]-2-azaspiro[3.4]octane-2-carboxylate |

| Ex# | Chemical Structure | Chemical Name |
|---|---|---|
| 3c | 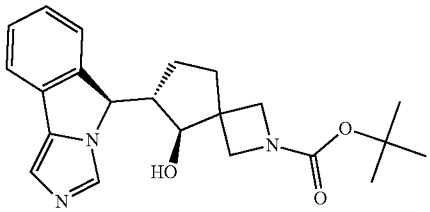 [SMILES: CC(C)(C)OC(=O)N1CC2(CC[C@@H]([C@@H]3c4ccccc4-c4cncn43)[C@@H]2O)C1] | tert-butyl (5S,6S)-5-hydroxy-6-[(5R)-5Himidazo[1,5-b]isoindol-5-yl]-2-azaspiro[3.4]octane-2-carboxylate |
| 3d | 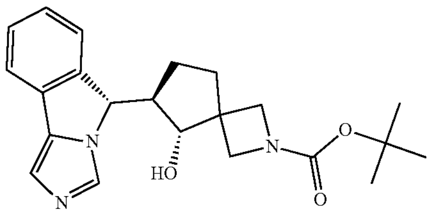 [SMILES: CC(C)(C)OC(=O)N1CC2(CC[C@H]([C@H]3c4ccccc4-c4cncn43)[C@H]2O)C1] | tert-butyl (5R,6R)-5-hydroxy-6-[(5S)-5Himidazo[1,5-b]isoindol-5-yl]-2-azaspiro[3.4]octane-2-carboxylate |
| 3e | 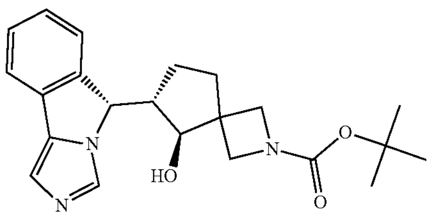 [SMILES: CC(C)(C)OC(=O)N1CC2(CC[C@@H]([C@H]3c4ccccc4-c4cncn43)[C@@H]2O)C1] | tert-butyl (5S,6S)-5-hydroxy-6-[(5S)-5Himidazo[1,5-b]isoindol-5-yl]-2-azaspiro[3.4]octane-2-carboxylate |
| 3f | 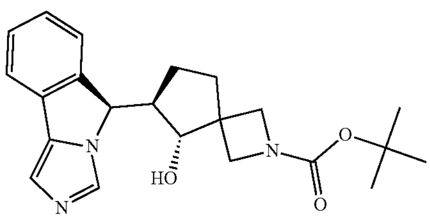 [SMILES: CC(C)(C)OC(=O)N1CC2(CC[C@H]([C@@H]3c4ccccc4-c4cncn43)[C@H]2O)C1] | tert-butyl (5R,6R)-5-hydroxy-6-[(5R)-5Himidazo[1,5-b]isoindol-5-yl]-2-azaspiro[3.4]octane-2-carboxylate |
| 3g | 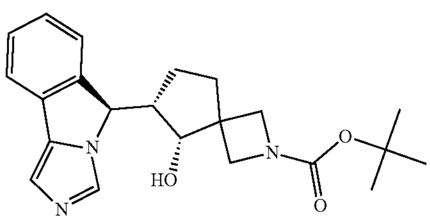 [SMILES: CC(C)(C)OC(=O)N1CC2(CC[C@@H]([C@@H]3c4ccccc4-c4cncn43)[C@H]2O)C1] | tert-butyl (5R,6S)-5-hydroxy-6-[(5R)-5Himidazo[1,5-b]isoindol-5-yl]-2-azaspiro[3.4]octane-2-carboxylate |
| 3h | 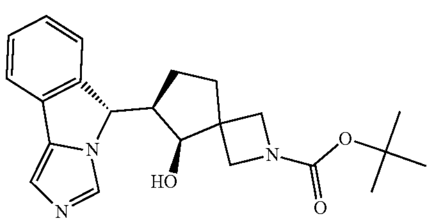 [SMILES: CC(C)(C)OC(=O)N1CC2(CC[C@H]([C@H]3c4ccccc4-c4cncn43)[C@@H]2O)C1] | tert-butyl (5S,6R)-5-hydroxy-6-[(5S)-5Himidazo[1,5-b]isoindol-5-yl]-2-azaspiro[3.4]octane-2-carboxylate |
| 4a | 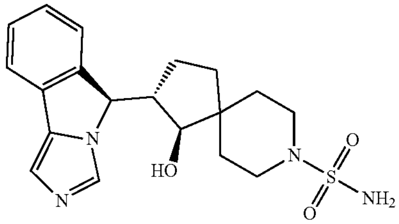 [SMILES: NS(=O)(=O)N1CCC2(CC[C@@H]([C@@H]3c4ccccc4-c4cncn43)[C@@H]2O)CC1] | (1S,2S)-1-hydroxy-2-[(5R)-5H-imidazo[4,3-a]isoindol-5-yl]-8-azaspiro[4.5]decane-8-sulfonamide |

-continued

| Ex# | Chemical Structure | Chemical Name |
|---|---|---|
| 4b | 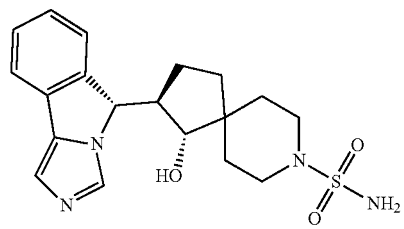 [SMILES: NS(=O)(=O)N1CCC2(CC[C@H]([C@H]3c4ccccc4-c4cncn43)[C@H]2O)CC1] | (1R,2R)-1-hydroxy-2-[(5S)-5H-imidazo[4,3-a]isoindol-5-yl]-8-azaspiro[4.5]decane-8-sulfonamide |
| 4c | 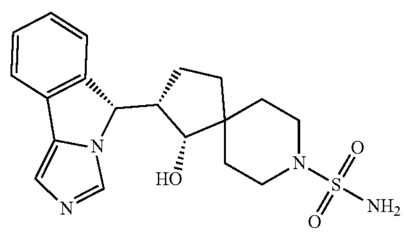 [SMILES: NS(=O)(=O)N1CCC2(CC[C@@H]([C@H]3c4ccccc4-c4cncn43)[C@H]2O)CC1] | (1S,2S)-1-hydroxy-2-[(5R)-5H-imidazo[4,3-a]isoindol-5-yl]-8-azaspiro[4.5]decane-8-sulfonamide |
| 4d | 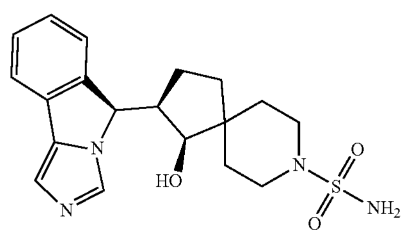 [SMILES: NS(=O)(=O)N1CCC2(CC[C@H]([C@@H]3c4ccccc4-c4cncn43)[C@@H]2O)CC1] | (1R,2R)-1-hydroxy-2-[(5S)-5H-imidazo[4,3-a]isoindol-5-yl]-8-azaspiro[4.5]decane-8-sulfonamide |
| 5 | 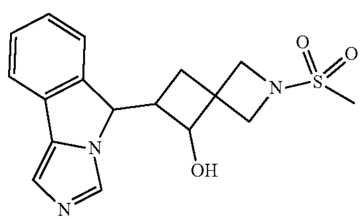 [SMILES: CS(=O)(=O)N1CC2(CC(C3c4ccccc4-c4cncn43)C2O)C1] | 6-(5H-imidazo[1,5-b]isoindol-5-yl)-2-methylsulfonyl-2-azaspiro[3.3]heptan-7-ol |
| 6a | 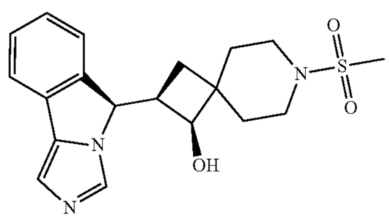 [SMILES: CS(=O)(=O)N1CCC2(CC1)C[C@H]([C@@H]1c3ccccc3-c3cncn31)[C@@H]2O] | (1S,2R)-2-[(5R)-5H-imidazo[4,3-a]isoindol-5-yl]-7-methanesulfonyl-7-azaspiro[3.5]nonan-1-ol |
| 6b | 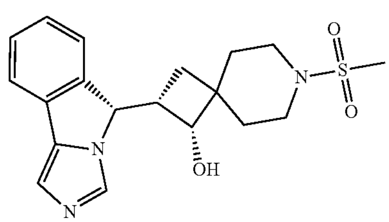 [SMILES: CS(=O)(=O)N1CCC2(CC1)C[C@@H]([C@H]1c3ccccc3-c3cncn31)[C@H]2O] | (1R,2S)-2-[(5S)-5H-imidazo[4,3-a]isoindol-5-yl]-7-methanesulfonyl-7-azaspiro[3.5]nonan-1-ol |
| 6c | 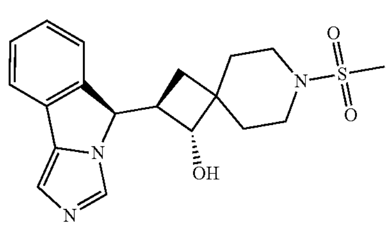 [SMILES: CS(=O)(=O)N1CCC2(CC1)C[C@H]([C@@H]1c3ccccc3-c3cncn31)[C@H]2O] | (1R,2R)-2-[(5R)-5H-imidazo[4,3-a]isoindol-5-yl]-7-methanesulfonyl-7-azaspiro[3.5]nonan-1-ol |

-continued

| Ex# | Chemical Structure | Chemical Name |
|---|---|---|
| 6d | 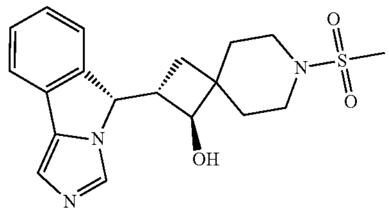 [SMILES: CS(=O)(=O)N1CCC2(CC1)C[C@@H]([C@H]1c3ccccc3-c3cncn31)[C@@H]2O] | (1S,2S)-2-[(5S)-5H-imidazo[4,3-a]isoindol-5-yl]-7-methanesulfonyl-7-azaspiro[3.5]nonan-1-ol |
| 6e | 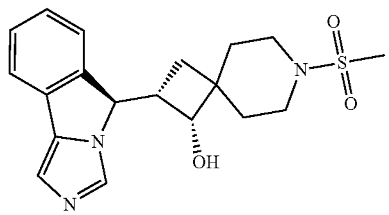 [SMILES: CS(=O)(=O)N1CCC2(CC1)C[C@@H]([C@@H]1c3ccccc3-c3cncn31)[C@H]2O] | (1R,2S)-2-[(5R)-5H-imidazo[4,3-a]isoindol-5-yl]-7-methanesulfonyl-7-azaspiro[3.5]nonan-1-ol |
| 6f | 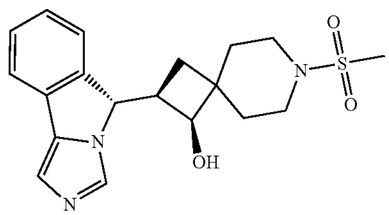 [SMILES: CS(=O)(=O)N1CCC2(CC1)C[C@H]([C@H]1c3ccccc3-c3cncn31)[C@@H]2O] | (1S,2R)-2-[(5S)-5H-imidazo[4,3-a]isoindol-5-yl]-7-methanesulfonyl-7-azaspiro[3.5]nonan-1-ol |
| 6g | 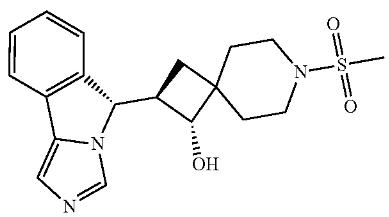 [SMILES: CS(=O)(=O)N1CCC2(CC1)C[C@H]([C@H]1c3ccccc3-c3cncn31)[C@H]2O] | (1R,2S)-2-[(5R)-5H-imidazo[4,3-a]isoindol-5-yl]-7-methanesulfonyl-7-azaspiro[3.5]nonan-1-ol |
| 6h | 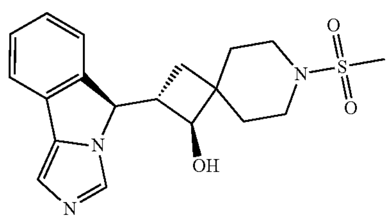 [SMILES: CS(=O)(=O)N1CCC2(CC1)C[C@@H]([C@@H]1c3ccccc3-c3cncn31)[C@@H]2O] | (1S,2R)-2-[(5S)-5H-imidazo[4,3-a]isoindol-5-yl]-7-methanesulfonyl-7-azaspiro[3.5]nonan-1-ol |
| 7a | 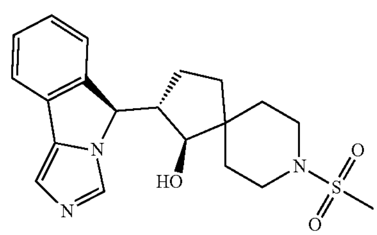 [SMILES: CS(=O)(=O)N1CCC2(CC[C@@H]([C@@H]3c4ccccc4-c4cncn43)[C@@H]2O)CC1] | (1S,2S)-8-(methylsulfonyl)-2-((R)-5H-imidazo[5,1-a]isoindol-5-yl)-8-azaspiro[4.5]decan-1-ol |
| 7b | 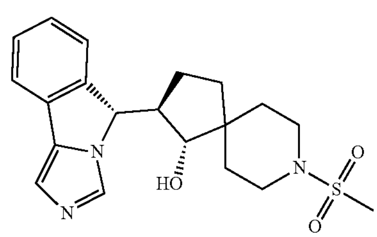 [SMILES: CS(=O)(=O)N1CCC2(CC[C@H]([C@H]3c4ccccc4-c4cncn43)[C@H]2O)CC1] | (1R,2R)-8-(methylsulfonyl)-2-((S)-5H-imidazo[5,1-a]isoindol-5-yl)-8-azaspiro[4.5]decan-1-ol |

| Ex# | Chemical Structure | Chemical Name |
|---|---|---|
| 7c | 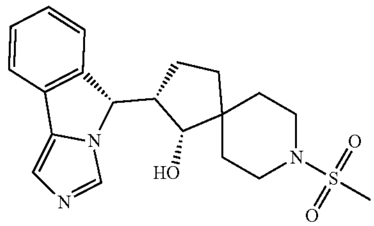 [SMILES: CS(=O)(=O)N1CCC2(CC[C@@H]([C@H]3c4ccccc4-c4cncn43)[C@H]2O)CC1] | (1R,2S)-8-(methylsulfonyl)-2-((S)-5H-imidazo[5,1-a]isoindol-5-yl)-8-azaspiro[4.5]decan-1-ol |
| 7d | 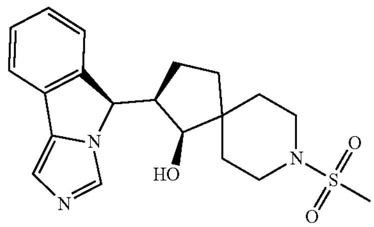 [SMILES: CS(=O)(=O)N1CCC2(CC[C@H]([C@@H]3c4ccccc4-c4cncn43)[C@@H]2O)CC1] | (1S,2R)-8-(methylsulfonyl)-2-((R)-5H-imidazo[5,1-a]isoindol-5-yl)-8-azaspiro[4.5]decan-1-ol |
| 8a | 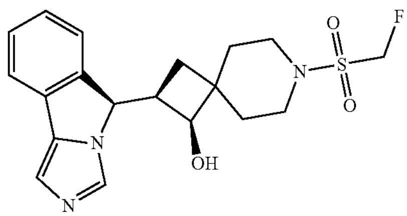 [SMILES: O=S(=O)(CF)N1CCC2(CC1)C[C@H]([C@@H]1c3ccccc3-c3cncn31)[C@@H]2O] | (1S,2R)-7-fluoromethanesulfonyl-2-[(5R)-5H-imidazo[4,3-a]isoindol-5-yl]-7-azaspiro[3.5]nonan-1-ol |
| 8b | 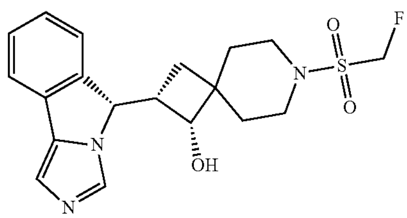 [SMILES: O=S(=O)(CF)N1CCC2(CC1)C[C@@H]([C@H]1c3ccccc3-c3cncn31)[C@H]2O] | (1R,2S)-7-fluoromethanesulfonyl-2-[(5S)-5H-imidazo[4,3-a]isoindol-5-yl]-7-azaspiro[3.5]nonan-1-ol |
| 9a | 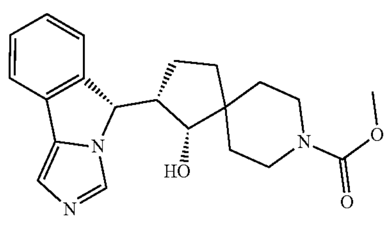 [SMILES: COC(=O)N1CCC2(CC[C@@H]([C@H]3c4ccccc4-c4cncn43)[C@H]2O)CC1] | methyl (1R,2S)-1-hydroxy-2-[(5S)-5H-imidazo[4,3-a]isoindol-5-yl]-8-azaspiro[4.5]decane-8-carboxylate |
| 9b | 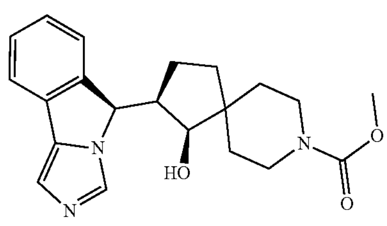 [SMILES: COC(=O)N1CCC2(CC[C@H]([C@@H]3c4ccccc4-c4cncn43)[C@@H]2O)CC1] | methyl (1S,2R)-1-hydroxy-2-[(5R)-5H-imidazo[4,3-a]isoindol-5-yl]-8-azaspiro[4.5]decane-8-carboxylate |
| 10a | 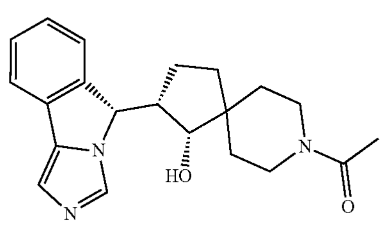 [SMILES: CC(=O)N1CCC2(CC[C@@H]([C@H]3c4ccccc4-c4cncn43)[C@H]2O)CC1] | 1-[(1R,2S)-1-hydroxy-2-[(5S)-5H-imidazo[4,3-a]isoindol-5-yl]-8-azaspiro[4.5]decan-8-yl]ethan-1-one |

| Ex# | Chemical Structure | Chemical Name |
|---|---|---|
| 10b | 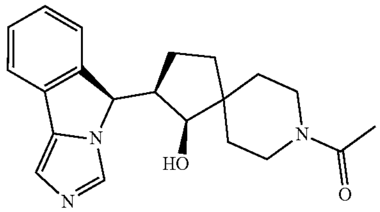 [SMILES: CC(=O)N1CCC2(CC[C@H]([C@@H]3c4ccccc4-c4cncn43)[C@@H]2O)CC1] | 1-[(1S,2R)-1-hydroxy-2-[(5R)-5H-imidazo[4,3-a]isoindol-5-yl]-8-azaspiro[4.5]decan-8-yl]ethan-1-one |
| 11a | 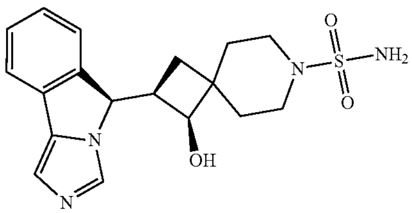 [SMILES: NS(=O)(=O)N1CCC2(CC1)C[C@H]([C@@H]1c3ccccc3-c3cncn31)[C@@H]2O] | (1S,2R)-1-hydroxy-2-[(5R)-5H-imidazo[4,3-a]isoindol-5-yl]-7-azaspiro[3.5]nonane-7-sulfonamide |
| 11b | 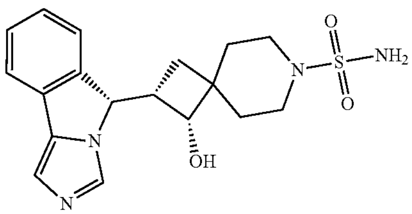 [SMILES: NS(=O)(=O)N1CCC2(CC1)C[C@@H]([C@H]1c3ccccc3-c3cncn31)[C@H]2O] | (1R,2S)-1-hydroxy-2-[(5S)-5H-imidazo[4,3-a]isoindol-5-yl]-7-azaspiro[3.5]nonane-7-sulfonamide |
| 11c | 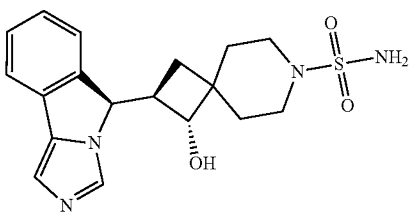 [SMILES: NS(=O)(=O)N1CCC2(CC1)C[C@H]([C@@H]1c3ccccc3-c3cncn31)[C@H]2O] | (1R,2R)-1-hydroxy-2-[(5R)-5H-imidazo[4,3-a]isoindol-5-yl]-7-azaspiro[3.5]nonane-7-sulfonamide |
| 11d | 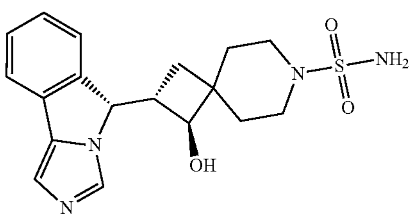 [SMILES: NS(=O)(=O)N1CCC2(CC1)C[C@@H]([C@H]1c3ccccc3-c3cncn31)[C@@H]2O] | (1S,2S)-1-hydroxy-2-[(5S)-5H-imidazo[4,3-a]isoindol-5-yl]-7-azaspiro[3.5]nonane-7-sulfonamide |
| 11e | 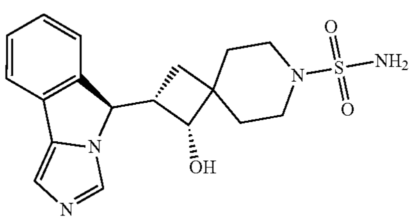 [SMILES: NS(=O)(=O)N1CCC2(CC1)C[C@@H]([C@@H]1c3ccccc3-c3cncn31)[C@H]2O] | (1R,2S)-1-hydroxy-2-[(5R)-5H-imidazo[4,3-a]isoindol-5-yl]-7-azaspiro[3.5]nonane-7-sulfonamide |
| 11f | 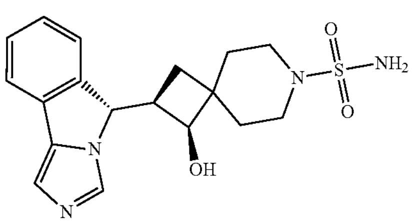 [SMILES: NS(=O)(=O)N1CCC2(CC1)C[C@H]([C@H]1c3ccccc3-c3cncn31)[C@@H]2O] | (1S,2R)-1-hydroxy-2-[(5S)-5H-imidazo[4,3-a]isoindol-5-yl]-7-azaspiro[3.5]nonane-7-sulfonamide |

-continued

| Ex# | Chemical Structure | Chemical Name |
|---|---|---|
| 11g | 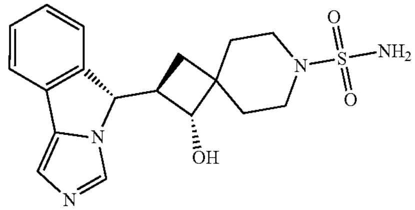 [SMILES: NS(=O)(=O)N1CCC2(CC1)C[C@H]([C@H]1c3ccccc3-c3cncn31)[C@H]2O] | (1R,2R)-1-hydroxy-2-[(5S)-5H-imidazo[4,3-a]isoindol-5-yl]-7-azaspiro[3.5]nonane-7-sulfonamide |
| 11h | 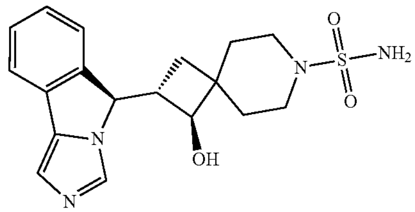 [SMILES: NS(=O)(=O)N1CCC2(CC1)C[C@@H]([C@@H]1c3ccccc3-c3cncn31)[C@@H]2O] | (1S,2S)-1-hydroxy-2-[(5R)-5H-imidazo[4,3-a]isoindol-5-yl]-7-azaspiro[3.5]nonane-7-sulfonamide |
| 12a | 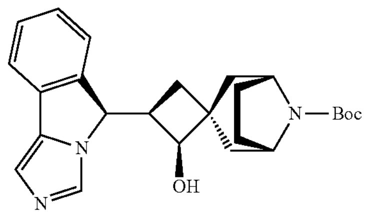 | tert-butyl (1R,2'S,3r,3'R,5S)-2'-hydroxy-3'-((R)-5H-imidazo[5,1-a]isoindol-5-yl)-8-azaspiro[bicyclo[3.2.1]octane-3,1'-cyclobutane]-8-carboxylate |
| 12b | 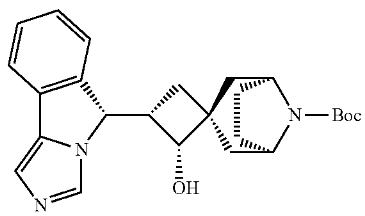 | tert-butyl (1R,2'R,3s,3'S,5S)-2'-hydroxy-3'-((S)-5H-imidazo[5,1-a]isoindol-5-yl)-8-azaspiro[bicyclo[3.2.1]octane-3,1'-cyclobutane]-8-carboxylate |
| 12c | 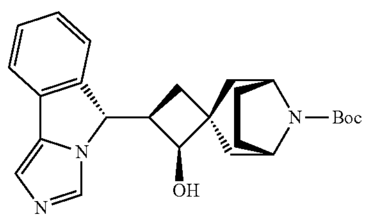 | tert-butyl (1R,2'S,3r,3'R,5S)-2'-hydroxy-3'-((S)-5H-imidazo[5,1-a]isoindol-5-yl)-8-azaspiro[bicyclo[3.2.1]octane-3,1'-cyclobutane]-8-carboxylate |
| 12d | 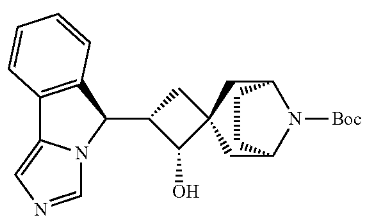 | tert-butyl (1R,2'R,3s,3'S,5S)-2'-hydroxy-3'-((R)-5H-imidazo[5,1-a]isoindol-5-yl)-8-azaspiro[bicyclo[3.2.1]octane-3,1'-cyclobutane]-8-carboxylate |
| 12e | 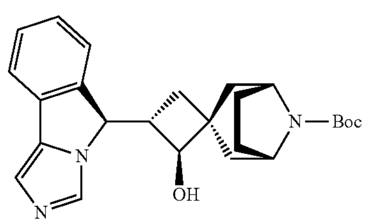 | tert-butyl (1R,2'S,3r,3'S,5S)-2'-hydroxy-3'-((R)-5H-imidazo[5,1-a]isoindol-5-yl)-8-azaspiro[bicyclo[3.2.1]octane-3,1'-cyclobutane]-8-carboxylate |

-continued

| Ex# | Chemical Structure | Chemical Name |
|---|---|---|
| 12f | 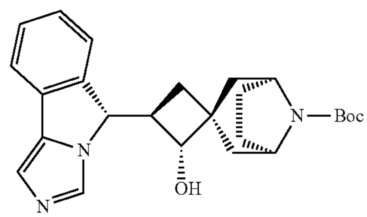 | tert-butyl (1R,2'R,3s,3'R,5S)-2'-hydroxy-3'-((S)-5H-imidazo[5,1-a]isoindol-5-yl)-8-azaspiro[bicyclo[3.2.1]octane-3,1'-cyclobutane]-8-carboxylate |
| 12g | 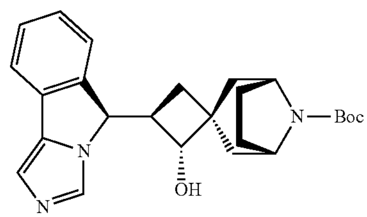 | tert-butyl (1R,2'R,3s,3'R,5S)-2'-hydroxy-3'-((R)-5H-imidazo[5,1-a]isoindol-5-yl)-8-azaspiro[bicyclo[3.2.1]octane-3,1'-cyclobutane]-8-carboxylate |
| 12h | 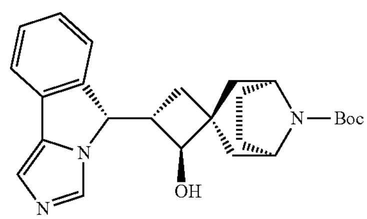 | tert-butyl (1R,2'S,3s,3'S,5S)-2'-hydroxy-3'-((S)-5H-imidazo[5,1-a]isoindol-5-yl)-8-azaspiro[bicyclo[3.2.1]octane-3,1'-cyclobutane]-8-carboxylate |
| 12i | 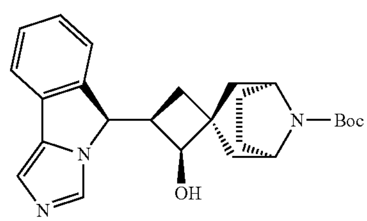 | tert-butyl (1R,2'S,3s,3'R,5S)-2'-hydroxy-3'-((R)-5H-imidazo[5,1-a]isoindol-5-yl)-8-azaspiro[bicyclo[3.2.1]octane-3,1'-cyclobutane]-8-carboxylate |
| 12j | 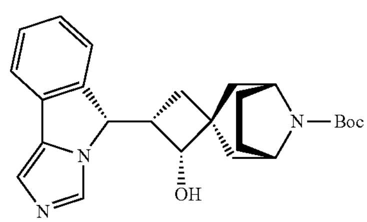 | tert-butyl (1R,2'R,3r,3'S,5S)-2'-hydroxy-3'-((S)-5H-imidazo[5,1-a]isoindol-5-yl)-8-azaspiro[bicyclo[3.2.1]octane-3,1'-cyclobutane]-8-carboxylate |
| 12k | 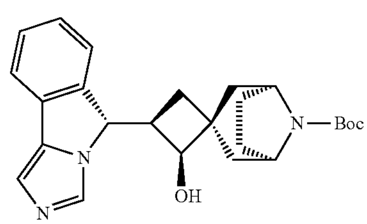 | tert-butyl (1R,2'S,3s,3'R,5S)-2'-hydroxy-3'-((S)-5H-imidazo[5,1-a]isoindol-5-yl)-8-azaspiro[bicyclo[3.2.1]octane-3,1'-cyclobutane]-8-carboxylate |
| 12l | 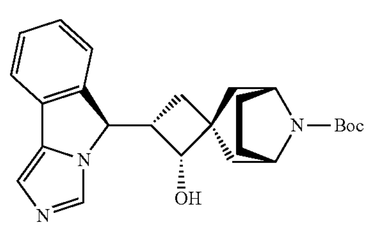 | tert-butyl (1R,2'R,3r,3'S,5S)-2'-hydroxy-3'-((R)-5H-imidazo[5,1-a]isoindol-5-yl)-8-azaspiro[bicyclo[3.2.1]octane-3,1'-cyclobutane]-8-carboxylate |

| Ex# | Chemical Structure | Chemical Name |
|---|---|---|
| 12m | 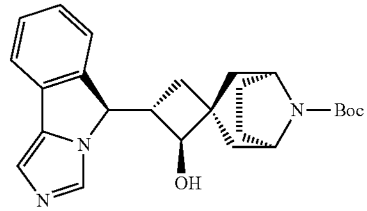 | tert-butyl (1R,2'S,3s,3'S,5S)-2'-hydroxy-3'-((R)-5H-imidazo[5,1-a]isoindol-5-yl)-8-azaspiro[bicyclo[3.2.1]octane-3,1'-cyclobutane]-8-carboxylate |
| 13a | 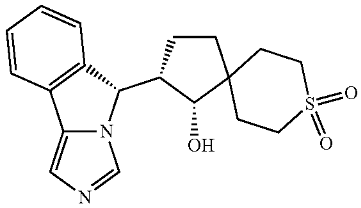 [SMILES: O=S1(=O)CCC2(CC[C@@H]([C@H]3c4ccccc4-c4cncn43)[C@H]2O)CC1] | (1R,2S)-1-hydroxy-2-((S)-5H-imidazo[5,1-a]isoindol-5-yl)-8-thiaspiro[4.5]decane 8,8-dioxide |
| 13b | 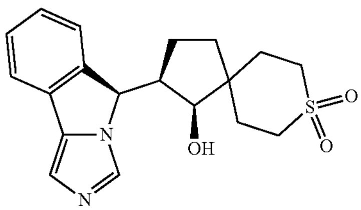 [SMILES: O=S1(=O)CCC2(CC[C@H]([C@@H]3c4ccccc4-c4cncn43)[C@@H]2O)CC1] | (1S,2R)-1-hydroxy-2-((R)-5H-imidazo[5,1-a]isoindol-5-yl)-8-thiaspiro[4.5]decane 8,8-dioxide |
| 14a | 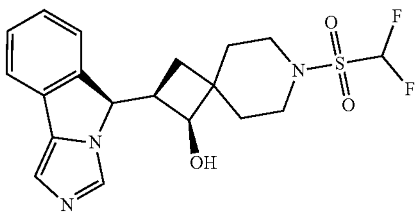 [SMILES: O=S(=O)(C(F)F)N1CCC2(CC1)C[C@H]([C@@H]1c3ccccc3-c3cncn31)[C@@H]2O] | (1S,2R)-7-difluoromethanesulfonyl-2-[(5R)-5H-imidazo(4,3-a]isoindol-5-yl]-7-azaspiro[3.5]nonan-1-ol |
| 14b | 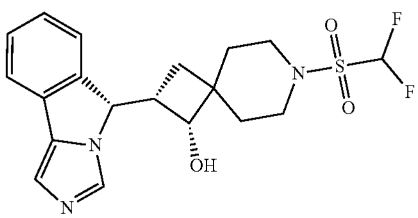 [SMILES: O=S(=O)(C(F)F)N1CCC2(CC1)C[C@@H]([C@H]1c3ccccc3-c3cncn31)[C@H]2O] | (1R,2S)-7-difluoromethanesulfonyl-2-[(5S)-5H-imidazo[4,3-a]isoindol-5-yl]-7-azaspiro[3.5]nonan-1-ol |
| 15a | 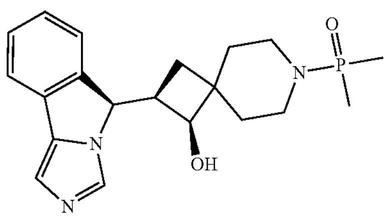 [SMILES: CP(C)(=O)N1CCC2(CC1)C[C@H]([C@@H]1c3ccccc3-c3cncn31)[C@@H]2O] | (2S,3R)-7-dimethylphosphoryl-2-[(5S)-5H-imidazo[1,5-b]isoindol-5-yl]-7-azaspiro[3.5]nonan-3-ol |
| 15b | 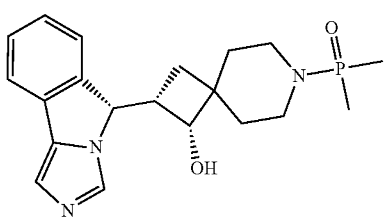 [SMILES: CP(C)(=O)N1CCC2(CC1)C[C@@H]([C@H]1c3ccccc3-c3cncn31)[C@H]2O] | (2R,3S)-7-dimethylphosphoryl-2-[(5R)-5H-imidazo[1,5-b]isoindol-5-yl]-7-azaspiro[3.5]nonan-3-ol |

| Ex# | Chemical Structure | Chemical Name |
|---|---|---|
| 16 | 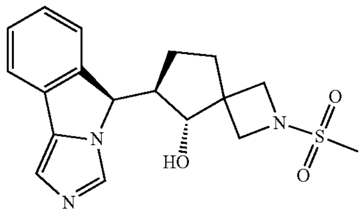 [SMILES: CS(=O)(=O)N1CC2(CC[C@H]([C@@H]3c4ccccc4-c4cncn43)[C@H]2O)C1] | (5R,6R)-6-[(5R)-5H-imidazo[4,3-a]isoindol-5-yl]-2-methanesulfonyl-2-azaspiro[3.4]octan-5-ol |
| 17a | 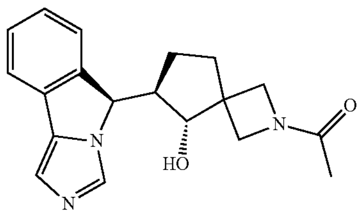 [SMILES: CC(=O)N1CC2(CC[C@H]([C@@H]3c4ccccc4-c4cncn43)[C@H]2O)C1] | 1-((5R,6R)-5-hydroxy-6-((R)-5H-imidazo[5,1-a]isoindol-5-yl)-2-azaspiro[3.4]octan-2-yl)ethan-1-one |
| 18a | 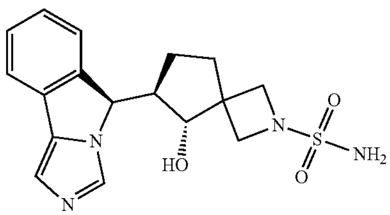 [SMILES: NS(=O)(=O)N1CC2(CC[C@H]([C@@H]3c4ccccc4-c4cncn43)[C@H]2O)C1] | (5R,6R)-5-hydroxy-6-((R)-5H-imidazo[5,1-a]isoindol-5-yl)-2-azaspiro[3.4]octane-2-sulfonamide |
| 19a | 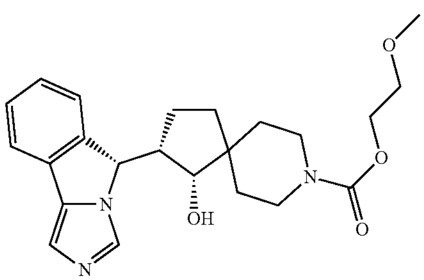 [SMILES: COCCOC(=O)N1CCC2(CC[C@@H]([C@H]3c4ccccc4-c4cncn43)[C@H]2O)CC1] | 2-methoxyethyl (3S,4R)-4-hydroxy-3-[(5S)-5H-imidazo[1,5-b]isoindol-5-yl]-8-azaspiro[4.5]decane-8-carboxylate |
| 20a | 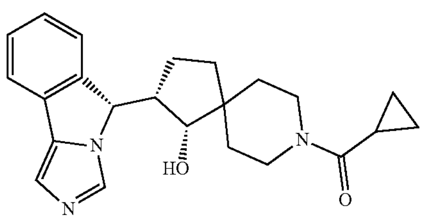 [SMILES: O=C(C1CC1)N1CCC2(CC[C@@H]([C@H]3c4ccccc4-c4cncn43)[C@H]2O)CC1] | cyclopropyl-[(3S,4R)-4-hydroxy-3-[(5S)-5H-imidazo[1,5-b]isoindol-5-yl]-8-azaspiro[4.5]decan-8-yl]ethanone |
| 21a | 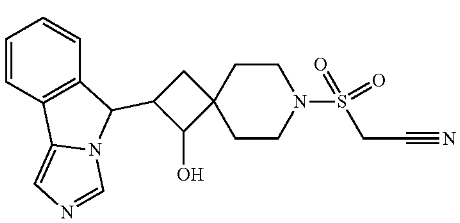 [SMILES: N#CCS(=O)(=O)N1CCC2(CC1)CC(C1c3ccccc3-c3cncn31)C2O] | 2-[[3-hydroxy-2-(5H-imidazo[1,5-b]isoindol-5-yl)-7-azaspiro[3.5]nonan-7-yl]sulfonyl]acetonitrile |
| 21b | 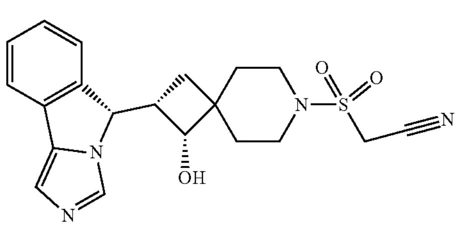 | (2S,3R)-2-[[3-hydroxy-2-((5S)-5H-imidazo[1,5-b]isoindol-5-yl)-7-azaspiro[3.5]nonan-7-yl]sulfonyl]acetonitrile |

| Ex# | Chemical Structure | Chemical Name |
|---|---|---|
| 21c | 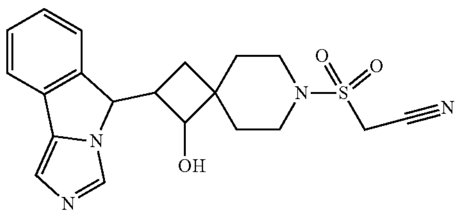 [SMILES: N#CCS(=O)(=O)N1CCC2(CC1)CC(C1c3ccccc3-c3cncn31)C2O] | (2R,3S)-2-[[3-hydroxy-2-((5R)-5H-imidazo[1,5-b]isoindol-5-yl)-7-azaspiro[3.5]nonan-7-yl]sulfonyl]acetonitrile |
| 22a | 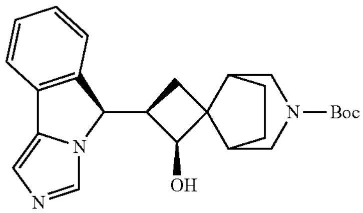 | tert-butyl (2'S,3'R)-2'-hydroxy-3'-((R)-5H-imidazo[5,1a]isoindol-5-yl)-3-azaspiro[bicyclo[3.2.1]octane-8,1'-cyclobutane]-3-carboxylate |
| 22b | 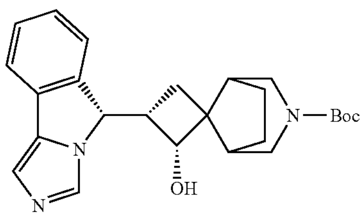 | tert-butyl (2'R,3'S)-2'-hydroxy-3'-((S)-5H-imidazo[5,1-a]isoindol-5-yl)-3-azaspiro[bicyclo[3.2.1]octane-8,1'-cyclobutane]-3-carboxylate |
| 22c | 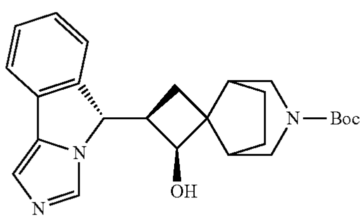 | tert-butyl (2'S,3'R)-2'-hydroxy-3'-((S)-5H-imidazo[5,1-a]isoindol-5-yl)-3-azaspiro[bicyclo[3.2.1]octane-8,1'-cyclobutane]-3-carboxylate |
| 22d | 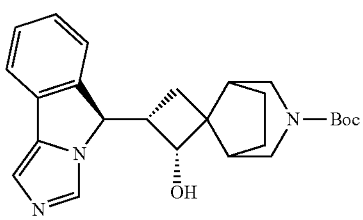 | tert-butyl (2'R,3'S)-2'-hydroxy-3'-((R)-5H-imidazo[5,1-a]isoindol-5-yl)-3-azaspiro[bicyclo[3.2.1]octane-8,1'-cyclobutane]-3-carboxylate |
| 22e | 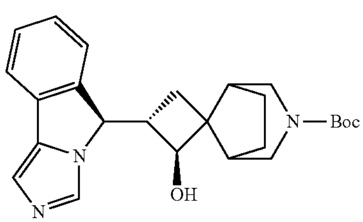 | tert-butyl (2'S,3'S)-2'-hydroxy-3'-((R)-5H-imidazo[5,1-a]isoindol-5-yl)-3-azaspiro[bicyclo[3.2.1]octane-8,1'-cyclobutane]-3-carboxylate |
| 22f | 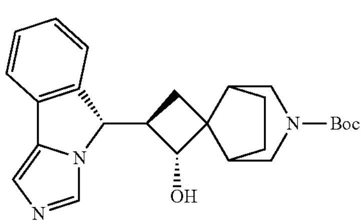 | tert-butyl (2'R,3'R)-2'-hydroxy-3'-((S)-5H-imidazo[5,1-a]isoindol-5-yl)-3-azaspiro[bicyclo[3.2.1]octane-8,1'-cyclobutane]-3-carboxylate |

-continued

| Ex# | Chemical Structure | Chemical Name |
|---|---|---|
| 22g | 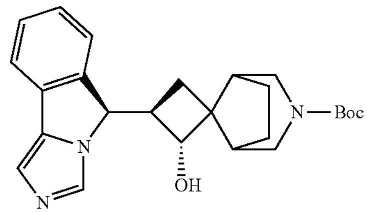 | tert-butyl (2'R,3'R)-2'-hydroxy-3'-((R)-5H-imidazo[5,1-a]isoindol-5-yl)-3-azaspiro[bicyclo[3.2.1]octane-8,1'-cyclobutane]-3-carboxylate |
| 22h | 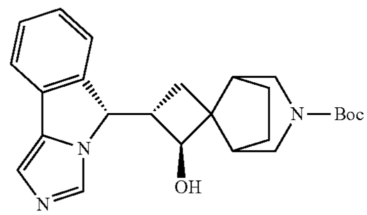 | tert-butyl (2'S,3'S)-2'-hydroxy-3'-((S)-5H-imidazo[5,1-a]isoindol-5 yl) 3 azaspiro[bicyclo[3.2.1]octane-8,1'-cyclobutane]-3-carboxylate |
| 23a | 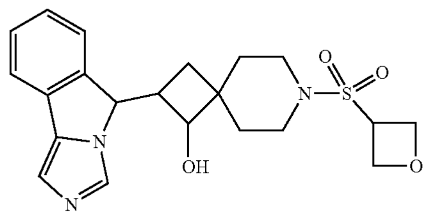 [SMILES: O=S(=O)(C1COC1)N1CCC2(CC1)CC(C1c3ccccc3-c3cncn31)C2O] | 2-(5H-imidazo[1,5-b]isoindol-5-yl)-7-(oxetan-3-ylsulfonyl)-7-azaspiro[3.5]nonan-3-ol |
| 23b | 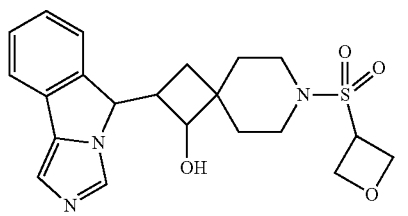 [SMILES: O=S(=O)(C1COC1)N1CCC2(CC1)CC(C1c3ccccc3-c3cncn31)C2O] | (2R,3S)-2-((5S)5H-imidazo[1,5-b]isoindol-5-yl)-7-(oxetan-3-ylsulfonyl)-7-azaspiro[3.5]nonan-3-ol |
| 23c | 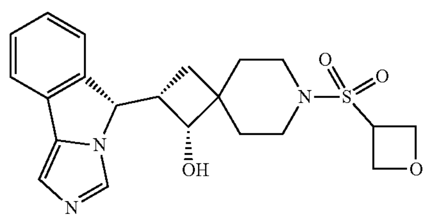 [SMILES: O=S(=O)(C1COC1)N1CCC2(CC1)C[C@@H]([C@H]1c3ccccc3-c3cncn31)[C@H]2O] | (2S,3R)-2-[(5S)-5H-imidazo[1,5-b]isoindol-5-yl]-7-(oxetan-3-ylsulfonyl)-7-azaspiro[3.5]nonan-3-ol |
| 24a | 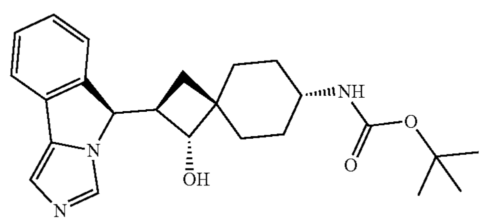 [SMILES: CC(C)(C)OC(=O)N[C@H]1CC[C@@]2(CC1)C[C@H]([C@@H]1c3ccccc3-c3cncn31)[C@H]2O] | tert-butyl ((1R,2R,4s,7S)-1-hydroxy-2-((R)-5H-imidazo[5,1-a]isoindol-5-yl)spiro[3.5]nonan-7-yl)carbamate |
| 24b | 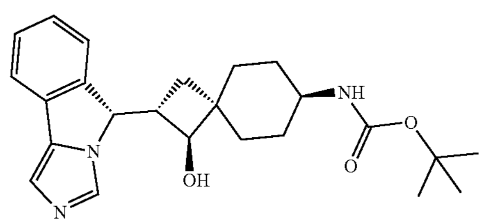 [SMILES: CC(C)(C)OC(=O)N[C@H]1CC[C@@]2(CC1)C[C@@H]([C@H]1c3ccccc3-c3cncn31)[C@@H]2O] | tert-butyl ((1S,2S,4s,7R)-1-hydroxy-2-((S)-5H-imidazo[5,1-a]isoindol-5-yl)spiro[3.5]nonan-7-yl)carbamate |

-continued

| Ex# | Chemical Structure | Chemical Name |
|---|---|---|
| 24c | 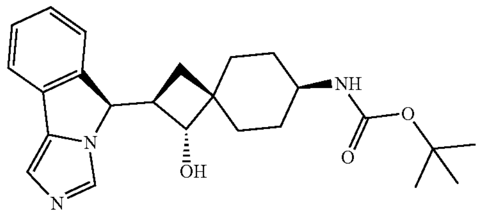 [SMILES: CC(C)(C)OC(=O)N[C@H]1CC[C@]2(CC1)C[C@H]([C@@H]1c3ccccc3-c3cncn31)[C@H]2O] | tert-butyl ((1R,2R,4r,7R)-1-hydroxy-2-((S)-5H-imidazo[5,1-a]isoindol-5-yl)spiro[3.5]nonan-7-yl)carbamate |
| 24d | 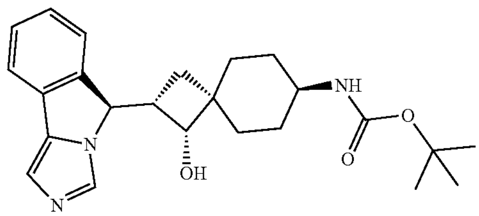 [SMILES: CC(C)(C)OC(=O)N[C@H]1CC[C@@]2(CC1)C[C@@H]([C@@H]1c3ccccc3-c3cncn31)[C@H]2O] | tert-butyl ((1R,2S,4s,7S)-1-hydroxy-2-((R)-5H-imidazo[5,1-a]isoindol-5-yl)spiro[3.5]nonan-7-yl)carbamate |
| 24e | 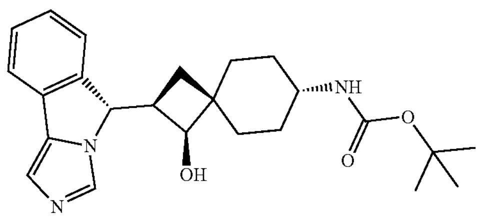 [SMILES: CC(C)(C)OC(=O)N[C@H]1CC[C@@]2(CC1)C[C@H]([C@H]1c3ccccc3-c3cncn31)[C@@H]2O] | tert-butyl ((1S,2R,4s,7R)-1-hydroxy-2-((S)-5H-imidazo[5,1-a]isoindol-5-yl)spiro[3.5]nonan-7-yl)carbamate |
| 24f | 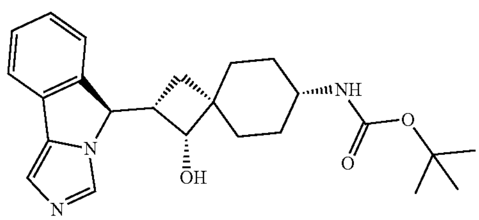 [SMILES: CC(C)(C)OC(=O)N[C@H]1CC[C@]2(CC1)C[C@@H]([C@@H]1c3ccccc3-c3cncn31)[C@H]2O] | tert-butyl ((1R,2S,4r,7R)-1-hydroxy-2-((R)-5H-imidazo[5,1-a]isoindol-5-yl)spiro[3.5]nonan-7-yl)carbamate |
| 24g | 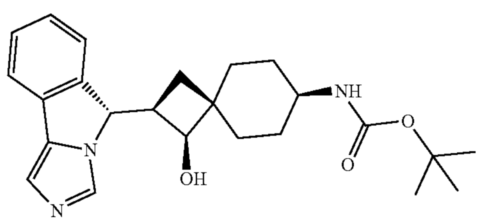 [SMILES: CC(C)(C)OC(=O)N[C@H]1CC[C@]2(CC1)C[C@H]([C@H]1c3ccccc3-c3cncn31)[C@@H]2O] | tert-butyl ((1S,2R,4r,7S)-1-hydroxy-2-((S)-5H-imidazo[5,1-a]isoindol-5-yl)spiro[3.5]nonan-7-yl)carbamate |
| 24h | 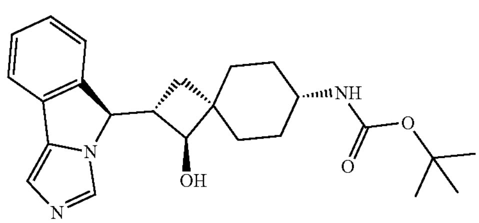 [SMILES: CC(C)(C)OC(=O)N[C@H]1CC[C@]2(CC1)C[C@@H]([C@@H]1c3ccccc3-c3cncn31)[C@@H]2O] | tert-butyl ((1S,2S,4r,7S)-1-hydroxy-2-((R)-5H-imidazo[5,1-a]isoindol-5-yl)spiro[3.5]nonan-7-yl)carbamate |
| 24i | 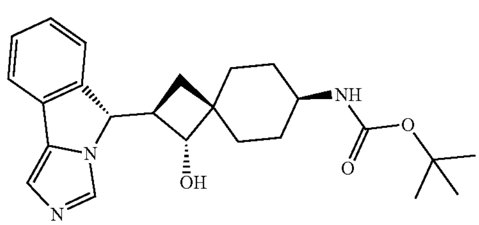 [SMILES: CC(C)(C)OC(=O)N[C@H]1CC[C@]2(CC1)C[C@H]([C@H]1c3ccccc3-c3cncn31)[C@H]2O] | tert-butyl ((1R,2R,4r,7R)-1-hydroxy-2-((S)-5H-imidazo[5,1-a]isoindol-5-yl)spiro[3.5]nonan-7-yl)carbamate |

| Ex# | Chemical Structure | Chemical Name |
|---|---|---|
| 24j | 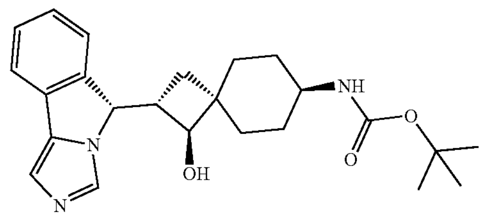 [SMILES: CC(C)(C)OC(=O)N[C@H]1CC[C@@]2(CC1)C[C@@H]([C@H]1c3ccccc3-c3cncn31)[C@@H]2O] | tert-butyl ((1S,2S,4s,7R)-1-hydroxy-2-((S)-5H-imidazo[5,1-a]isoindol-5-yl)spiro[3.5]nonan-7-yl)carbamate |
| 24k | 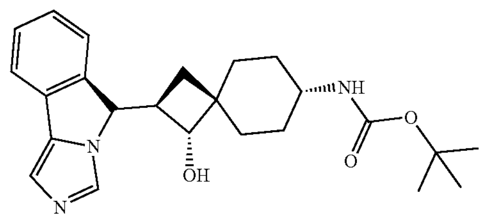 | tert-butyl ((1S,2S,4s,7R)-1-hydroxy-2-((S)-5H-imidazo[5,1-a]isoindol-5-yl)spiro[3.5]nonan-7-yl)carbamate |
| 24l | 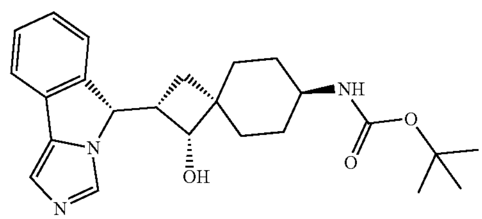 [SMILES: CC(C)(C)OC(=O)N[C@H]1CC[C@@]2(CC1)C[C@@H]([C@H]1c3ccccc3-c3cncn31)[C@H]2O] | tert-butyl ((1R,2S,4s,7S)-1-hydroxy-2-((S)-5H-imidazo[5,1-a]isoindol-5-yl)spiro[3.5]nonan-7-yl)carbamate |
| 24m | 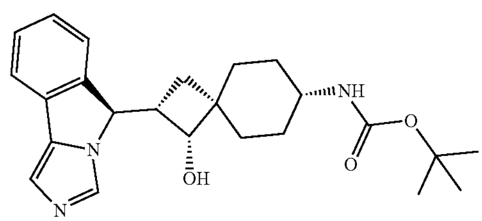 [SMILES: CC(C)(C)OC(=O)N[C@H]1CC[C@]2(CC1)C[C@@H]([C@@H]1c3ccccc3-c3cncn31)[C@H]2O] | tert-butyl ((1R,2S,4r,7R)-1-hydroxy-2-((R)-5H-imidazo[5,1-a]isoindol-5-yl)spiro[3.5]nonan-7-yl)carbamate |
| 24n | 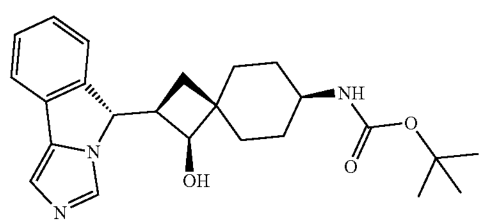 [SMILES: CC(C)(C)OC(=O)N[C@H]1CC[C@]2(CC1)C[C@H]([C@H]1c3ccccc3-c3cncn31)[C@@H]2O] | tert-butyl ((1S,2R,4r,7S)-1-hydroxy-2-((S)-5H-imidazo[5,1-a]isoindol-5-yl)spiro[3.5]nonan-7-yl)carbamate |
| 24o | 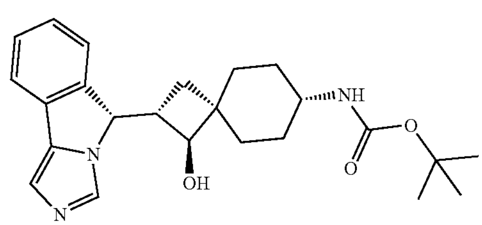 [SMILES: CC(C)(C)OC(=O)N[C@H]1CC[C@]2(CC1)C[C@@H]([C@H]1c3ccccc3-c3cncn31)[C@@H]2O] | tert-butyl ((1S,2S,4r,7S)-1-hydroxy-2-((S)-5H-imidazo[5,1-a]isoindol-5-yl)spiro[3.5]nonan-7-yl)carbamate |
| 24p | 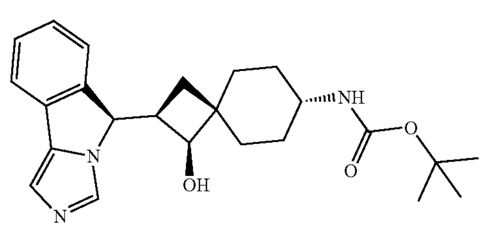 [SMILES: CC(C)(C)OC(=O)N[C@H]1CC[C@@]2(CC1)C[C@H]([C@@H]1c3ccccc3-c3cncn31)[C@@H]2O] | tert-butyl ((1S,2R,4s,7R)-1-hydroxy-2-((R)-5H-imidazo[5,1-a]isoindol-5-yl)spiro[3.5]nonan-7-yl)carbamate |

| Ex# | Chemical Structure | Chemical Name |
|---|---|---|
| 25a | 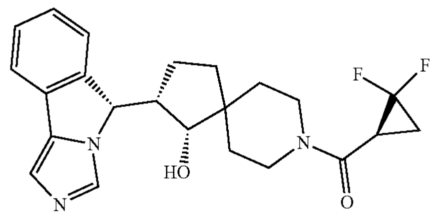 [SMILES: O=C([C@@H]1CC1(F)F)N1CCC2(CC[C@@H]([C@H]3c4ccccc4-c4cncn43)[C@H]2O)CC1] | ((S)-2,2-difluorocyclopropyl)((1R,2S)-1-hydroxy-2-((S)-5H-imidazo[5,1-a]isoindol-5-yl)-8-azaspiro[4.5]decan-8-yl)methanone |
| 25b | 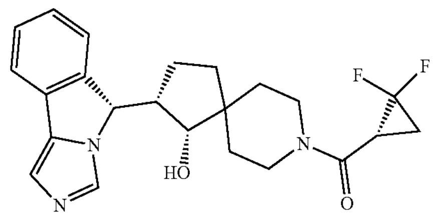 [SMILES: O=C([C@H]1CC1(F)F)N1CCC2(CC[C@@H]([C@H]3c4ccccc4-c4cncn43)[C@H]2O)CC1] | ((R)-2,2-difluorocyclopropyl)((1R,2S)-1-hydroxy-2-((S)-5H-imidazo[5,1-a]isoindol-5-yl)-8-azaspiro[4.5]decan-8-yl)methanone |
| 26 | 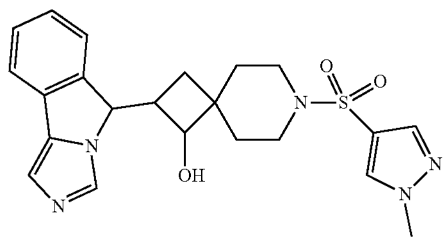 [SMILES: Cn1cc(S(=O)(=O)N2CCC3(CC2)CC(C2c4ccccc4-c4cncn42)C3O)cn1] | 2-(5H-imidazo[1,5-b]isoindol-5-yl)-7-(1-methylpyrazol-4-yl)sulfonyl-7-azaspiro[3.5]nonan-3-ol |
| 27 | 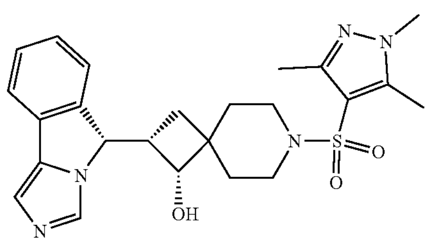 [SMILES: Cc1nn(C)c(C)c1S(=O)(=O)N1CCC2(CC1)C[C@@H]([C@H]1c3ccccc3-c3cncn31)[C@H]2O] | 2-(5H-imidazo[1,5-b]isoindol-5-yl)-7-(1,3,5-trimethylpyrazol-4-yl)sulfonyl-7-azaspiro[3.5]nonan-3-ol |
| 28 | 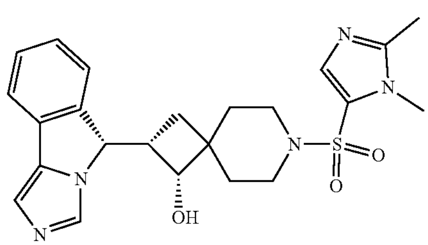 [SMILES: Cc1ncc(S(=O)(=O)N2CCC3(CC2)C[C@@H]([C@H]2c4ccccc4-c4cncn42)[C@H]3O)n1C] | (1R,2S)-2-((S)-5H-imidazo[5,1-a]isoindol-5-yl)-7-((1,3,5-trimethyl-1H-pyrazol-4-yl)sulfonyl)-7-azaspiro[3.5]nonan-1-ol |
| 29 | 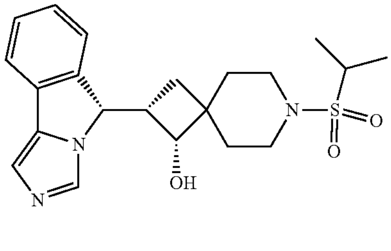 [SMILES: CC(C)S(=O)(=O)N1CCC2(CC1)C[C@@H]([C@H]1c3ccccc3-c3cncn31)[C@H]2O] | (1R,2S)-2-((S)-5H-imidazo[5,1-a]isoindol-5-yl)-7-(isopropylsulfonyl)-7-azaspiro[3.5]nonan-1-ol |

| Ex# | Chemical Structure | Chemical Name |
|---|---|---|
| 30 | 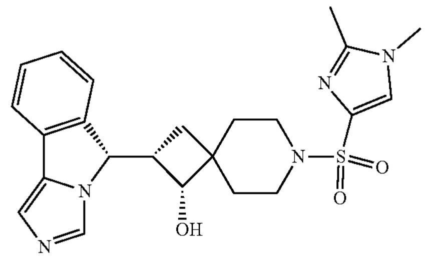 [SMILES: Cc1nc(S(=O)(=O)N2CCC3(CC2)C[C@@H]([C@H]2c4ccccc4-c4cncn42)[C@H]3O)cn1C] | (1R,2S)-7-((1,2-dimethyl-1H-imidazol-4-yl)sulfonyl)-2-((S)-5H-imidazo[5,1-a]isoindol-5-yl)-7-azaspiro[3.5]nonan-1-ol |
| 31 | 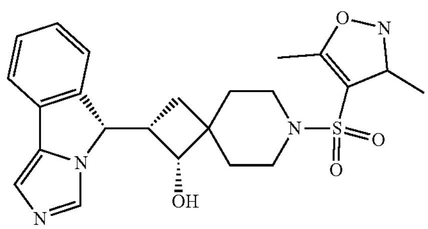 [SMILES: CC1=C(S(=O)(=O)N2CCC3(CC2)C[C@@H]([C@H]2c4ccccc4-c4cncn42)[C@H]3O)C(C)NO1] | (1R,2S)-7-((3,5-dimethylisoxazol-4-yl)sulfonyl)-2-((S)-5H-imidazo[5,1-a]isoindol-5-yl)-7-azaspiro[3.5]nonan-1-ol |
| 32 | 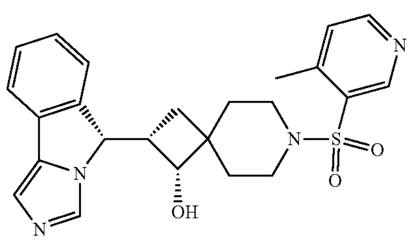 [SMILES: Cc1ccncc1S(=O)(=O)N1CCC2(CC1)C[C@@H]([C@H]1c3ccccc3-c3cncn31)[C@H]2O] | (1R,2S)-2-((S)-5H-imidazo[5,1-a]isoindol-5-yl)-7-((4-methylpyridin-3-yl)sulfonyl)-7-azaspiro[3.5]nonan-1-ol |
| 33 | 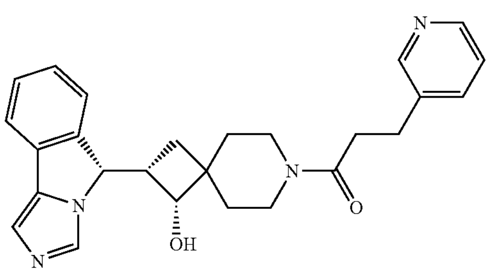 [SMILES: O=C(CCc1cccnc1)N1CCC2(CC1)C[C@@H]([C@H]1c3ccccc3-c3cncn31)[C@H]2O] | 1-((1R,2S)-1-hydroxy-2-((S)-5H-imidazo[5,1-a]isoindol-5-yl)-7-azaspiro[3.5]nonan-7-yl)-3-(pyridin-3-yl)propan-1-one |
| 34 | 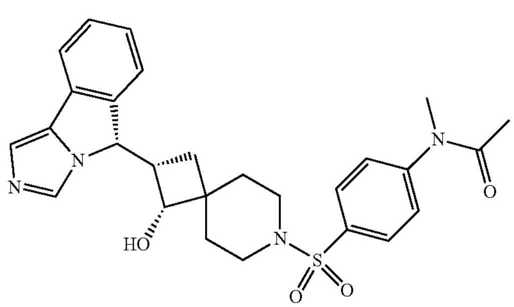 [SMILES: CC(=O)N(C)c1ccc(S(=O)(=O)N2CCC3(CC2)C[C@@H]([C@H]2c4ccccc4-c4cncn42)[C@H]3O)cc1] | N-(4-(((1R,2S)-1-hydroxy-2-((S)-5H-imidazo[5,1-a]isoindol-5-yl)-7-azaspiro[3.5]nonan-7-yl)sulfonyl)phenyl)-N-methylacetamide |
| 35 | 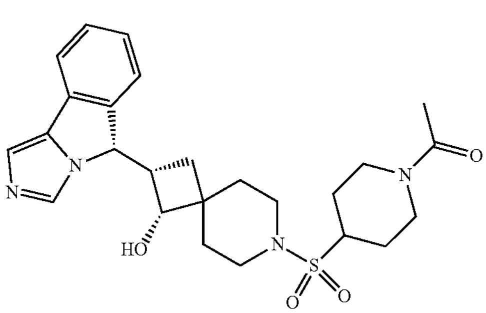 [SMILES: CC(=O)N1CCC(S(=O)(=O)N2CCC3(CC2)C[C@@H]([C@H]2c4ccccc4-c4cncn42)[C@H]3O)CC1] | 1-(4-(((1R,2S)-1-hydroxy-2-((S)-5H-imidazo[5,1-a]isoindol-5-yl)-7-azaspiro[3.5]nonan-7-yl)sulfonyl)piperidin-1-yl)ethan-1-one |

| Ex# | Chemical Structure | Chemical Name |
|---|---|---|
| 36 | 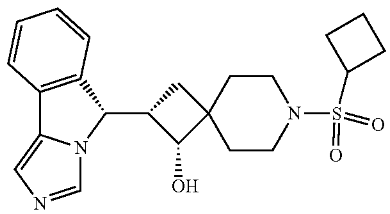 [SMILES: O=S(=O)(C1CCC1)N1CCC2(CC1)C[C@@H]([C@H]1c3ccccc3-c3cncn31)[C@H]2O] | (1R,2S)-7-(cyclobutylsulfonyl)-2-((S)-5H-imidazo[5,1-a]isoindol-5-yl)-7-azaspiro[3.5]nonan-1-ol |
| 37 | 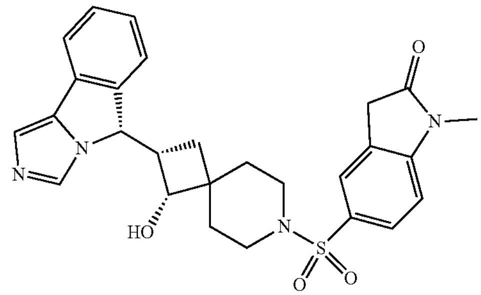 [SMILES: CN1C(=O)Cc2cc(S(=O)(=O)N3CCC4(CC3)C[C@@H]([C@H]3c5ccccc5-c5cncn53)[C@H]4O)ccc21] | 5-(((1R,2S)-1-hydroxy-2-((S)-5H-imidazo[5,1-a]isoindol-5-yl)-7-azaspiro[3.5]nonan-7-yl)sulfonyl)-1-methylindolin-2-one |
| 38 | 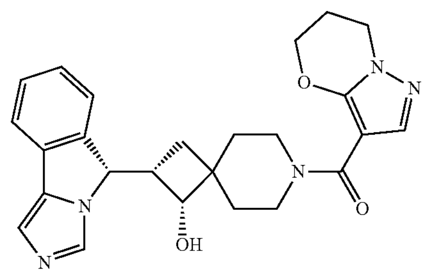 [SMILES: O=C(c1cnn2c1OCCC2)N1CCC2(CC1)C[C@@H]([C@H]1c3ccccc3-c3cncn31)[C@H]2O] | (6,7-dihydro-5H-pyrazolo[5,1-b][1,3]oxazin-3-yl)((1R,2S)-1-hydroxy-2-((S)-5H-imidazo[5,1-a]isoindol-5-yl)-7-azaspiro[3.5]nonan-7-yl)methanone |
| 39 | 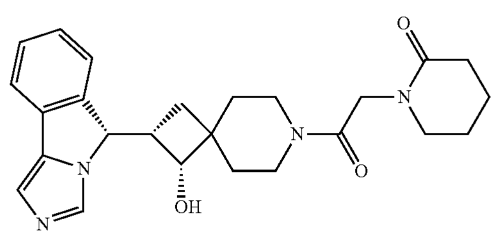 [SMILES: O=C(CN1CCCCC1=O)N1CCC2(CC1)C[C@@H]([C@H]1c3ccccc3-c3cncn31)[C@H]2O] | 1-(2-((1R,2S)-1-hydroxy-2-((S)-5H-imidazo[5,1-a]isoindol-5-yl)-7-azaspiro[3.5]nonan-7-yl)-2-oxoethyl)piperidin-2-one |
| 40 | 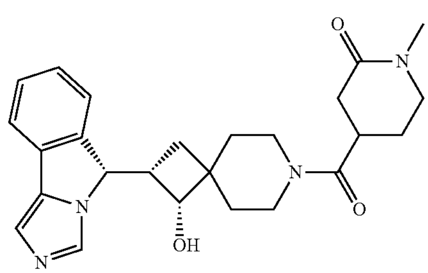 [SMILES: CN1CCC(C(=O)N2CCC3(CC2)C[C@@H]([C@H]2c4ccccc4-c4cncn42)[C@H]3O)CC1=O] | 4-((1R,2S)-1-hydroxy-2-((S)-5H-imidazo[5,1-a]isoindol-5-yl)-7-azaspiro[3.5]nonane-7-carbonyl)-1-methylpiperidin-2-one |
| 41 | 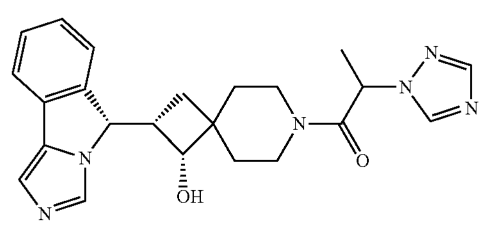 | 1-(((1R,2S)-1-hydroxy-2-((S)-5H-imidazo[5,1-a]isoindol-5-yl)-7-azaspiro[3.5]nonan-7-yl)-2-(1H-1,2,4-triazol-1-yl)propan-1-one |

| Ex# | Chemical Structure | Chemical Name |
|---|---|---|
| 42 | 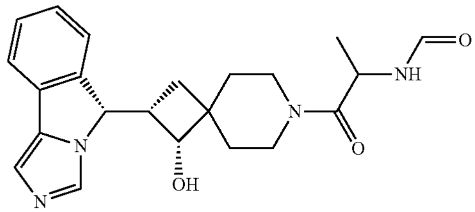 | N-(1-((1R,2S)-1-hydroxy-2-((S)-5H-imidazo[5,1-a]isoindol-5-yl)-7-azaspiro[3.5]nonan-7-yl)-1-oxopropan-2-yl)formamide |
| 43 | 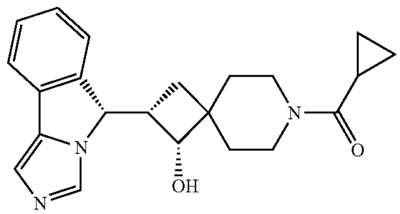 [SMILES: O=C(C1CC1)N1CCC2(CC1)C[C@@H]([C@H]1c3ccccc3-c3cncn31)[C@H]2O] | cyclopropyl((1R,2S)-1-hydroxy-2-((S)-5H-imidazo[5,1-a]isoindol-5-yl)-7-azaspiro[3.5]nonan-7-yl)methanone |
| 44 | 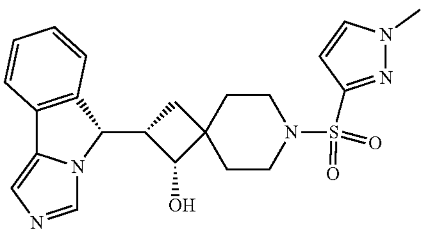 [SMILES: Cn1ccc(S(=O)(=O)N2CCC3(CC2)C[C@@H]([C@H]2c4ccccc4-c4cncn42)[C@H]3O)n1] | (1R,2S)-2-((S)-5H-imidazo[5,1-a]isoindol-5-yl)-7-((1-methyl-1H-pyrazol-3-yl)sulfonyl)-7-azaspiro[3.5]nonan-1-ol |
| 45 | 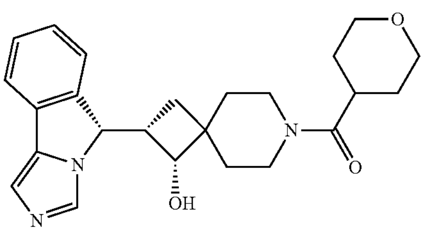 [SMILES: O=C(C1CCOCC1)N1CCC2(CC1)C[C@@H]([C@H]1c3ccccc3-c3cncn31)[C@H]2O] | ((1R,2S)-1-hydroxy-2-((S)-5H-imidazo[5,1-a]isoindol-5-yl)-7-azaspiro[3.5]nonan-7-yl)(tetrahydro-2H-pyran-4-yl)methanone |
| 46 | 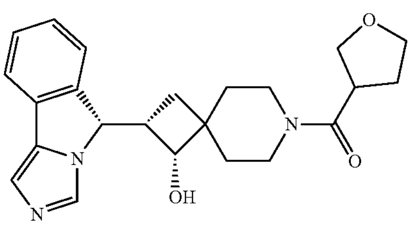 [SMILES: O=C(C1CCOC1)N1CCC2(CC1)C[C@@H]([C@H]1c3ccccc3-c3cncn31)[C@H]2O] | ((1R,2S)-1-hydroxy-2-((S)-5H-imidazo[5,1-a]isoindol-5-yl)-7-azaspiro[3.5]nonan-7-yl)(tetrahydrofuran-3-yl)methanone |
| 47 | 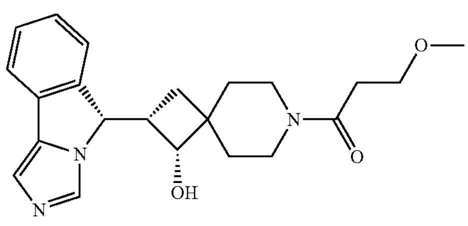 [SMILES: COCCC(=O)N1CCC2(CC1)C[C@@H]([C@H]1c3ccccc3-c3cncn31)[C@H]2O] | 1-((1R,2S)-1-hydroxy-2-((S)-5H-imidazo[5,1-a]isoindol-5-yl)-7-azaspiro[3.5]nonan-7-yl)-3-methoxypropan-1-one |
| 48 | 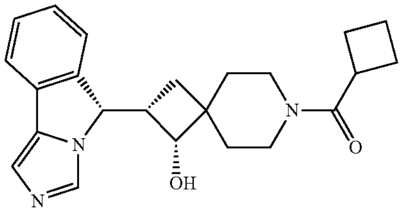 [SMILES: O=C(C1CCC1)N1CCC2(CC1)C[C@@H]([C@H]1c3ccccc3-c3cncn31)[C@H]2O] | cyclobutyl((1R,2S)-1-hydroxy-2-((S)-5H-imidazo[5,1-a]isoindol-5-yl)-7-azaspiro[3.5]nonan-7-yl)methanone |

| Ex# | Chemical Structure | Chemical Name |
|---|---|---|
| 49 | 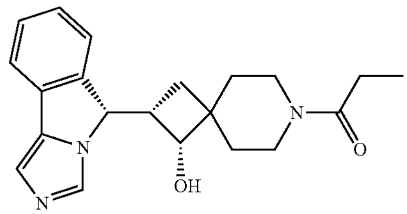 [SMILES: CCC(=O)N1CCC2(CC1)C[C@@H]([C@H]1c3ccccc3-c3cncn31)[C@H]2O] | 1-((1R,2S)-1-hydroxy-2-((S)-5H-imidazo[5,1-a]isoindol-5-yl)-7-azaspiro[3.5]nonan-7-yl])propan-1-one |
| 50 | 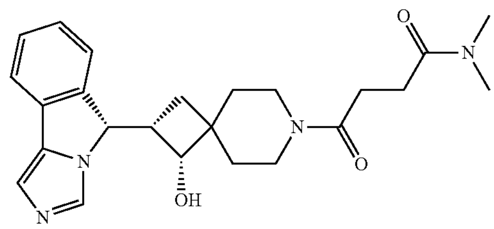 [SMILES: CN(C)C(=O)CCC(=O)N1CCC2(CC1)C[C@@H]([C@H]1c3ccccc3-c3cncn31)[C@H]2O] | 4-((1R,2S)-1-hydroxy-2-((S)-5H-imidazo[5,1-a]isoindol-5-yl)-7-azaspiro[3.5]nonan-7-yl)-N,N-dimethyl-4-oxobutanamide |
| 51 | 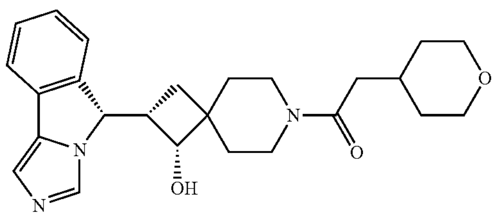 [SMILES: O=C(CC1CCOCC1)N1CCC2(CC1)C[C@@H]([C@H]1c3ccccc3-c3cncn31)[C@H]2O] | 1-((1R,2S)-1-hydroxy-2-((S)-5H-imidazo[5,1-a]isoindol-5-yl)-7-azaspiro[3.5]nonan-7-yl)-2-(tetrahydro-2H-pyran-4-yl)ethan-1-one |
| 52 | 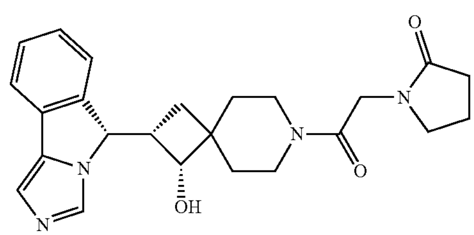 [SMILES: O=C(CN1CCCC1=O)N1CCC2(CC1)C[C@@H]([C@H]1c3ccccc3-c3cncn31)[C@H]2O] | 1-(2-((1R,2S)-1-hydroxy-2-((S)-5H-imidazo[5,1-a]isoindol-5-yl)-7-azaspiro[3.5]nonan-7-yl)-2-oxoethyl)pyrrolidin-2-one |
| 53 | 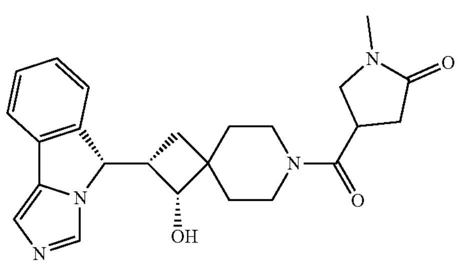 [SMILES: CN1CC(C(=O)N2CCC3(CC2)C[C@@H]([C@H]2c4ccccc4-c4cncn42)[C@H]3O)CC1=O] | 4-((1R,2S)-1-hydroxy-2-((S)-5H-imidazo[5,1-a]isoindol-5-yl)-7-azaspiro[3.5]nonane-7-carbonyl)-1-methylpyrrolidin-2-one |
| 54 | 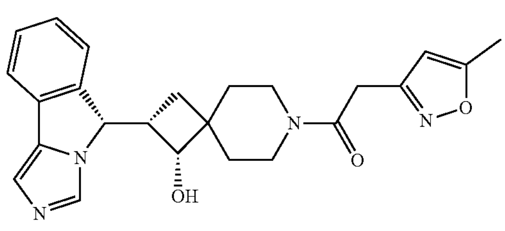 [SMILES: Cc1cc(CC(=O)N2CCC3(CC2)C[C@@H]([C@H]2c4ccccc4-c4cncn42)[C@H]3O)no1] | 1-((1R,2S)-1-hydroxy-2-((S)-5H-imidazo[5,1-a]isoindol-5-yl)-7-azaspiro[3.5]nonan-7-yl)-2-(5-methylisoxazol-3-yl)ethan-1-one |

| Ex# | Chemical Structure | Chemical Name |
|---|---|---|
| 55 | 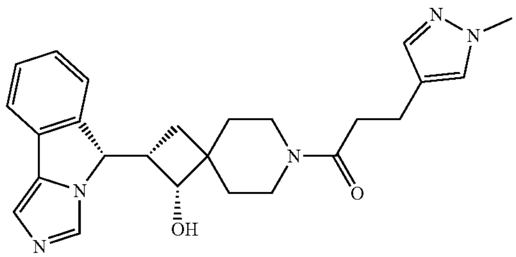 [SMILES: Cn1cc(CCC(=O)N2CCC3(CC2)C[C@@H]([C@H]2c4ccccc4-c4cncn42)[C@H]3O)cn1] | 1-((1R,2S)-1-hydroxy-2-((S)-5H-imidazo[5,1-a]isoindol-5-yl)-7-azaspiro[3.5]nonan-7-yl)-3-(1-methyl-1H-pyrazol-4-yl)propan-1-one |
| 56 | 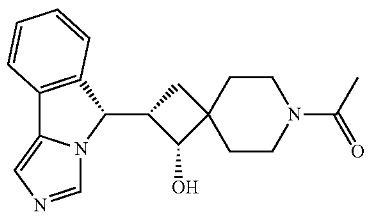 [SMILES: CC(=O)N1CCC2(CC1)C[C@@H]([C@H]1c3ccccc3-c3cncn31)[C@H]2O] | 1-((1R,2S)-1-hydroxy-2-((S)-5H-imidazo[5,1-a]isoindol-5-yl)-7-azaspiro[3.5]nonan-7-yl)ethan-1-one |
| 57 | 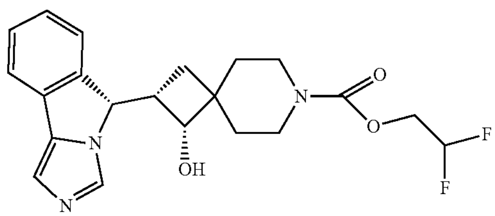 [SMILES: O=C(OCC(F)F)N1CCC2(CC1)C[C@@H]([C@H]1c3ccccc3-c3cncn31)[C@H]2O] | 2,2-difluoroethyl (1R,2S)-1-hydroxy-2-((S)-5H-imidazo[5,1-a]isoindol-5-yl)-7-azaspiro[3.5]nonane-7-carboxylate |
| 58 | 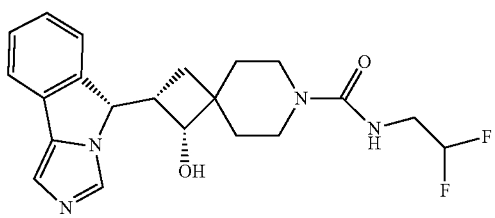 [SMILES: O=C(NCC(F)F)N1CCC2(CC1)C[C@@H]([C@H]1c3ccccc3-c3cncn31)[C@H]2O] | (1R,2S)-N-(2,2-difluoroethyl)-1-hydroxy-2-((S)-5H-imidazo[5,1-a]isoindol-5-yl)-7-azaspiro[3.5]nonane-7-carboxamide |
| 59 | 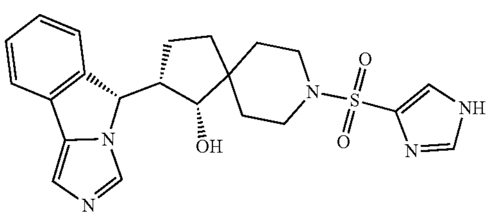 [SMILES: O=S(=O)(c1c[nH]cn1)N1CCC2(CC[C@@H]([C@H]3c4ccccc4-c4cncn43)[C@H]2O)CC1] | (1R,2S)-8-((1H-imidazol-4-yl)sulfonyl)-2-((S)-5H-imidazo[5,1-a]isoindol-5-yl)-8-azaspiro[4.5]decan-1-ol |
| 60 | 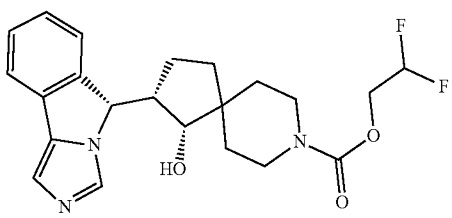 [SMILES: O=C(OCC(F)F)N1CCC2(CC[C@@H]([C@H]3c4ccccc4-c4cncn43)[C@H]2O)CC1] | 2,2-difluoroethyl (3S,4R)-4-hydroxy-3-[(5S)-5H-imidazo[1,5-b]isoindol-5-yl]-8-azaspiro[4.5]decane-8-carboxylate |
| 61 | 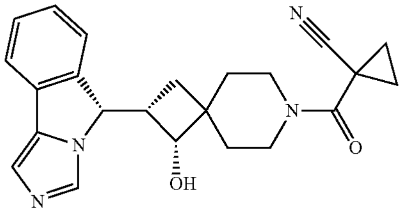 [SMILES: N#CC1(C(=O)N2CCC3(CC2)C[C@@H]([C@H]2c4ccccc4-c4cncn42)[C@H]3O)CC1] | 1-((1R,2S)-1-hydroxy-2-((S)-5H-imidazo[5,1-a]isoindol-5-yl)-7-azaspiro[3.5]nonane-7-carbonyl)cyclopropane-1-carbonitrile |

-continued

| Ex# | Chemical Structure | Chemical Name |
|---|---|---|
| 62 | 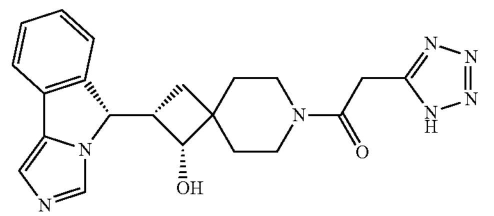 [SMILES: O=C(Cc1nnn[nH]1)N1CCC2(CC1)C[C@@H]([C@H]1c3ccccc3-c3cncn31)[C@H]2O] | 1-((1R,2S)-1-hydroxy-2-((S)-5H-imidazo[5,1-a]isoindol-5-yl)-7-azaspiro[3.5]nonan-7-yl)-2-(1H-tetrazol-5-yl)ethan-1-one |
| 63 | 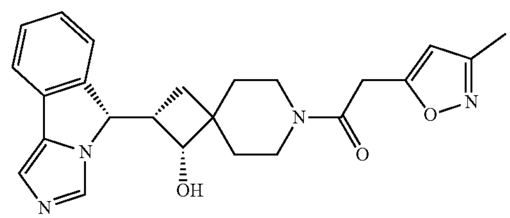 [SMILES: Cc1cc(CC(=O)N2CCC3(CC2)C[C@@H]([C@H]2c4ccccc4-c4cncn42)[C@H]3O)on1] | 1-((1R,2S)-1-hydroxy-2-((S)-5H-imidazo[5,1-a]isoindol-5-yl)-7-azaspiro[3.5]nonan-7-yl)-2-(3-methylisoxazol-5-yl)ethan-1-one |
| 64 | 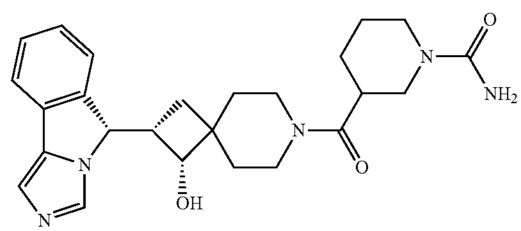 [SMILES: NC(=O)N1CCCC(C(=O)N2CCC3(CC2)C[C@@H]([C@H]2c4ccccc4-c4cncn42)[C@H]3O)C1] | 3-((1R,2S)-1-hydroxy-2-((S)-5H-imidazo[5,1-a]isoindol-5-yl)-7-azaspiro[3.5]nonane-7-carbonyl)piperidine-1-carboxamide |
| 65 | 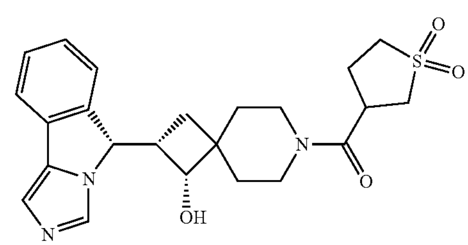 [SMILES: O=C(C1CCS(=O)(=O)C1)N1CCC2(CC1)C[C@@H]([C@H]1c3ccccc3-c3cncn31)[C@H]2O] | (1,1-dioxidotetrahydrothiophen-3-yl)((1R,2S)-1-hydroxy-2-((S)-5H-imidazo[5,1-a]isoindol-5-yl)-7-azaspiro[3.5]nonan-7-yl)methanone |
| 66 | 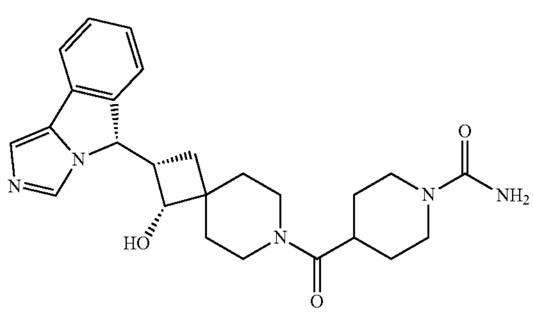 [SMILES: NC(=O)N1CCC(C(=O)N2CCC3(CC2)C[C@@H]([C@H]2c4ccccc4-c4cncn42)[C@H]3O)CC1] | 4-((1R,2S)-1-hydroxy-2-((S)-5H-imidazo[5,1-a]isoindol-5-yl)-7-azaspiro[3.5]nonane-7-carbonyl)piperidine-1-carboxamide |
| 67 | 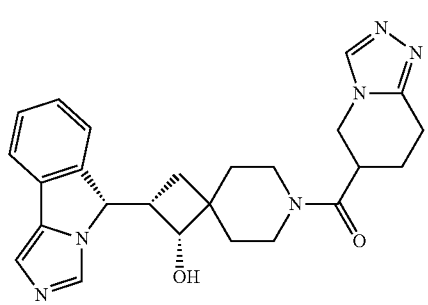 [SMILES: O=C(C1CCc2nncn2C1)N1CCC2(CC1)C[C@@H]([C@H]1c3ccccc3-c3cncn31)[C@H]2O] | ((1R,2S)-1-hydroxy-2-((S)-5H-imidazo[5,1-a]isoindol-5-yl)-7-azaspiro[3.5]nonan-7-yl)(5,6,7,8-tetrahydro-[1,2,4]triazolo[4,3-a]pyridin-6-yl)methanone |

| Ex# | Chemical Structure | Chemical Name |
|---|---|---|
| 68 | 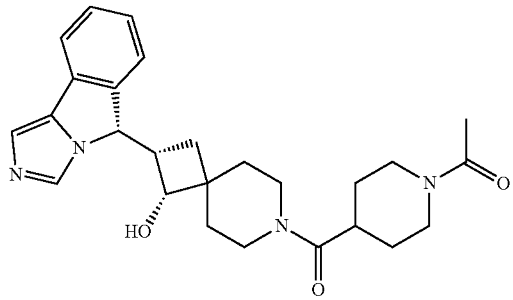 [SMILES: CC(=O)N1CCC(C(=O)N2CCC3(CC2)C[C@@H]([C@H]2c4ccccc4-c4cncn42)[C@H]3O)CC1] | 1-(4-(((1R,2S)-1-hydroxy-2-((S)-5H-imidazo[5,1-a]isoindol-5-yl)-7-azaspiro[3.5]nonane-7-carbonyl)piperidin-1-yl)ethan-1-one |
| 69 | 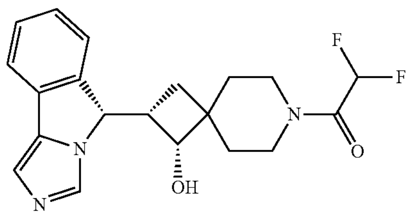 [SMILES: O=C(C(F)F)N1CCC2(CC1)C[C@@H]([C@H]1c3ccccc3-c3cncn31)[C@H]2O] | 2,2-difluoro-1-((1R,2S)-1-hydroxy-2-((S)-5H-imidazo[5,1-a]isoindol-5-yl)-7-azaspiro[3.5]nonan-7-yl)ethan-1-one |
| 70 | | (2'R,3'R)-3'-((R)-5H-imidazo[5,1-a]isoindol-5-yl)-3-(methylsulfonyl)-3-azaspiro[bicyclo[3.2.1]octane-8,1'-cyclobutan]-2'-ol | or a pharmaceutically acceptable salt thereof.

In another embodiment, the compounds of the invention are tert-butyl (1R,2S)-1-hydroxy-2-((S)-5H-imidazo[5,1-a]isoindol-5-yl)-7-azaspiro[3.5]nonane-7-carboxylate tert-butyl (1R,2S)-1-hydroxy-2-((S)-5H-imidazo[5,1-a]isoindol-5-yl)-8-azaspiro[4.5]decane-8-carboxylate tert-butyl (5S,6R)-5-hydroxy-6-[(5R)-5H-imidazo[1,5-b]isoindol-5-yl]-2-azaspiro[3,4]octane-2-carboxylate (1R,2R)-1-hydroxy-2-[(5S)-5H-imidazo[4,3-a]isoindol-5-yl]-8-azaspiro[4.5]decane-8-sulfonamide (1S,2R)-7-[(5S)-5H-imidazo[4,3-a]isoindol-5-yl]-7-methanesulfonyl-7-azaspiro[3.5]nonan-1-ol (1R,2S)-7-fluoromethanesulfonyl-2-[(5S)-5H-imidazo[4,3-a]isoindol-5-yl]-7-azaspiro[3.5]nonan-1-ol (1S,2R)-1-hydroxy-2-[(5S)-5H-imidazo[4,3-a]isoindol-5-yl]-7-azaspiro[3.5]nonane-7-sulfonamide (5R,6R)-6-[(5R)-5H-imidazo[4,3-a]isoindol-5-yl]-2-methanesulfonyl-2-azaspiro[3.4]octan-5-ol 2-methoxyethyl (3S,4R)-4-hydroxy-3-[(5S)-5H-imidazo[1,5-b]isoindol-5-yl]-8-azaspiro[4.5]decane-8-carboxylate cyclopropyl-[(3S,4R)-4-hydroxy-3-[(5S)-5H-imidazo[1,5-b]isoindol-5-yl]-8-azaspiro[4.5]decan-8-yl]methanone (2S,3R)-2-[[3-hydroxy-2-((5 S)-5H-imidazo[1,5-b]isoindol-5-yl)-7-azaspiro[3.5]nonan-7-yl]sulfonyl]acetonitrile tert-butyl (2'R,3'R)-2'-hydroxy-3'-((S)-5H-imidazo[5,1-a]isoindol-5-yl)-3-azaspiro[bicyclo[3.2.1]octane-8,1'-cyclobutane]-3-carboxylate tert-butyl (2'R,3'R)-2'-hydroxy-3'-((R)-5H-imidazo[5,1-a]isoindol-5-yl)-3-azaspiro[bicyclo[3.2.1]octane-8,1'-cyclobutane]-3-carboxylate (2S,3R)-2-[(5S)-5H-imidazo[1,5-b]isoindol-5-yl]-7-(oxetan-3-ylsulfonyl)-7-azaspiro[3.5]nonan-3-ol tert-butyl ((1R,2S,4r,7R)-1-hydroxy-2-((R)-5H-imidazo[5,1-a]isoindol-5-yl)spiro[3.5]nonan-7-yl)carbamate ((S)-2,2-difluorocyclopropyl)((1R,2S)-1-hydroxy-2-((S)-5H-imidazo[5,1-a]isoindol-5-yl)-8-azaspiro[4.5]decan-8-yl)methanone 2-(5H-imidazo[1,5-b]isoindol-5-yl)-7-(1,3,5-trimethylpyrazol-4-yl)sulfonyl-7-azaspiro[3.5]nonan-3-ol (1R,2S)-2-((S)-5H-imidazo[5,1-a]isoindol-5-yl)-7-((1,3,5-trimethyl-1H-pyrazol-4-yl)sulfonyl)-7-azaspiro[3.5]nonan-1-ol (1R,2S)-2-((S)-5H-imidazo[5,1-a]isoindol-5-yl)-7-(isopropylsulfonyl)-7-azaspiro[3.5]nonan-1-ol (1R,2S)-2-((S)-5H-imidazo[5,1-a]isoindol-5-yl)-7-((4-methylpyridin-3-yl)sulfonyl)-7-azaspiro[3.5]nonan-1-ol N-(4-(((1R,2S)-1-hydroxy-2-((S)-5H-imidazo[5,1-a]isoindol-5-yl)-7-azaspiro[3.5]nonan-7-yl)sulfonyl)phenyl)-N-methylacetamide (1R,2S)-7-(cyclobutylsulfonyl)-2-((S)-5H-imidazo[5,1-a]isoindol-5-yl)-7-azaspiro[3.5]nonan-1-ol (1R,2S)-2-((S)-5H-imidazo[5,1-a]isoindol-5-yl)-7-((1-methyl-1H-pyrazol-3-yl)sulfonyl)-7-azaspiro[3.5]nonan-1-ol 2,2-difluoroethyl (1R,2S)-1-hydroxy-2-((S)-5H-imidazo[5,1-a]isoindol-5-yl)-7-azaspiro[3.5]nonane-7-carboxylate 2,2 difluoroethyl (3S,4R)-4-hydroxy-3-[(5S)-5H-imidazo[1,5-b]isoindol-5-yl]-8-azaspiro[4.5]decane-8-carboxylate or a pharmaceutically acceptable salt thereof.

In another embodiment, the compounds of the invention are tert-butyl (1R,2S)-1-hydroxy-2-((S)-5H-imidazo[5,1-a]isoindol-5-yl)-7-azaspiro[3.5]nonane-7-carboxylate
(1S,2R)-2-[(5S)-5H-imidazo[4,3-a]isoindol-5-yl]-7-methanesulfonyl-7-azaspiro[3.5]nonan-1-ol
(1R,2S)-7-flouromethanesulfonyl-2-[(5S)-5H-imidazo[4,3-a]isoindol-5-yl]-7-azaspiro[3.5]nonan-1-ol
tert-butyl (2'R,3'R)-2'-hydroxy-3'-((R)-5H-imidazo[5,1-a]isoindol-5-yl)-3-azaspiro[bicyclo[3.2.1]octane-8,1'-cyclobutane]-3-carboxylate
(2S,3R)-2-[(5S)-5H-imidazo[1,5-b]isoindol-5-yl]-7-(oxetan-3-ylsulfonyl)-7-azaspiro[3.5]nonan-3-ol
tert-butyl ((1R,2S,4r,7R)-1-hydroxy-2-((R)-5H-imidazo[5,1-a]isoindol-5-yl)spiro[3.5]nonan-7-yl)carbamate
((S)-2,2-difluorocyclopropyl)((1R,2S)-1-hydroxy-2-((S)-5H-imidazo[5,1-a]isoindol-5-yl)-8-azaspiro[4.5]decan-8-yl)methanone
2-(5H-imidazo[1,5-b]isoindol-5-yl)-7-(1,3,5-trimethylpyrazol-4-yl)sulfonyl-7-azaspiro[3.5]nonan-3-ol
(1R,2S)-2-((S)-5H-imidazo[5,1-a]isoindol-5-yl)-7-((4-methylpyridin-3-yl)sulfonyl)-7-azaspiro[3.5]nonan-1-ol
N-(4-(((1R,2S)-1-hydroxy-2-((S)-5H-imidazo[5,1-a]isoindol-5-yl)-7-azaspiro[3.5]nonan-7-yl)sulfonyl)phenyl)-N-methylacetamide
(1R,2S)-7-(cyclobutylsulfonyl)-2-((S)-5H-imidazo[5,1-a]isoindol-5-yl)-7-azaspiro[3.5]nonan-1-ol
2,2-difluoroethyl (3S,4R)-4-hydroxy-3-[(5S)-5H-imidazo[1,5-b]isoindol-5-yl]-8-azaspiro[4.5]decane-8-carboxylate or a pharmaceutically acceptable salt thereof.

In another embodiment, the compounds of the invention are

In another embodiment, the compounds of the invention are

The invention further comprises subgenera of formula (I), in which the structure of any of formulae (I), (Ia)-(Ii), (II), (IIa)-(IIp), (III), (IIIa)-(IIIp) comprising the structural element

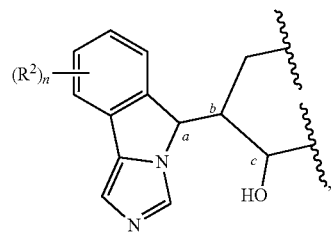

having the stereoisomeric configuration of any of configurations 1-27 below, wherein the stereochemistry of chiral center (labeled "a," "b," and "c" above) is designated as racemic ("-"), "S," or "R":

Structural Formula I is One of Stereoisomeric Configurations (1)-(27):

| Configuration Number | Configuration Structure |
|---|---|
| 1 | 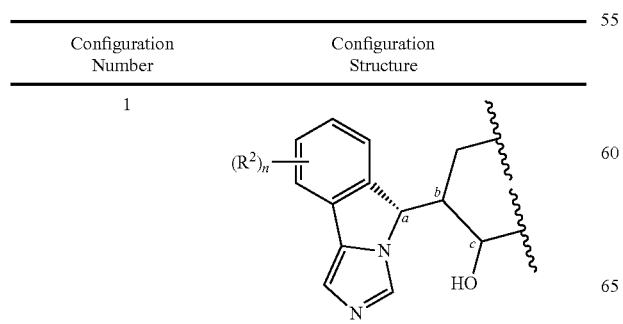 |

-continued

| Configuration Number | Configuration Structure |
|---|---|

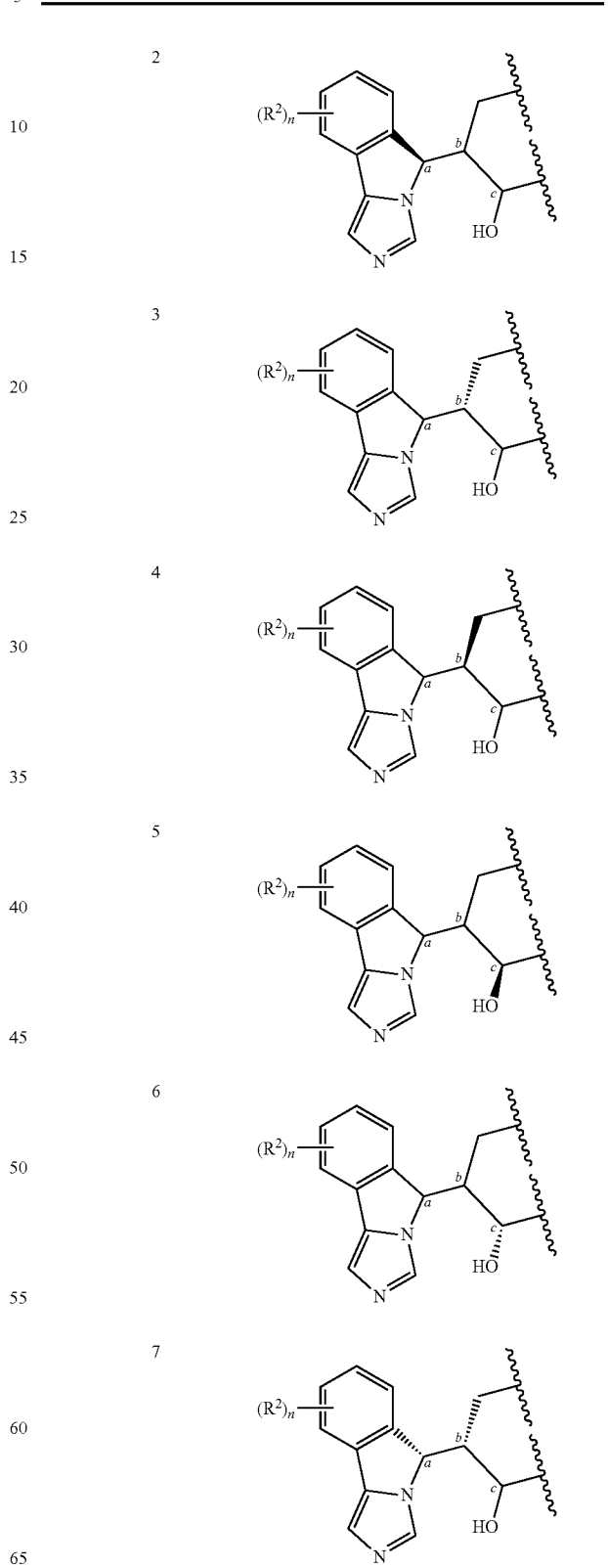

|     | 111 -continued |     | 112 -continued |
| --- | --- | --- | --- |
| Configuration Number | Configuration Structure | Configuration Number | Configuration Structure |
| 8 | | 14 | |
| 9 | | 15 | |
| 10 | | 16 | |
| 11 | | 17 | |
| 12 | | 18 | |
| 13 | | 19 | |

113
-continued

| Configuration Number | Configuration Structure |
|---|---|
| 20 | (structure) |
| 21 | (structure) |
| 22 | (structure) |
| 23 | (structure) |
| 24 | (structure) |
| 25 | (structure) |

114
-continued

| Configuration Number | Configuration Structure |
|---|---|
| 26 | (structure) |
| 27 | (structure) |

In one embodiment, the compounds of the disclosure have a stereoconfiguration of configuration 1, 7, 8, 15, 16 or 19-22.

In another embodiment, the compounds of the disclosure have a stereoconfiguration of configuration 2, 9, 10, 17, 18 or 23-26.

In another embodiment, the compounds of the disclosure are in the stereoconfiguration of configuration 19 or 20.

In one embodiment, the compounds of the disclosure are in the stereoconfiguration of configuration 20.

In another embodiment, the compounds of the disclosure are in the stereoconfiguration of configuration 19.

In another aspect, the present disclosure provides each of compounds 1-70 in each of stereoisomeric configurations 1-27. For example:

| No. | Con. |
|---|---|
| 1 | 1 |
| 1 | 2 |
| 1 | 3 |
| 1 | 4 |
| 1 | 5 |
| 1 | 6 |
| 1 | 7 |
| 1 | 8 |
| 1 | 9 |
| 1 | 10 |
| 1 | 11 |
| 1 | 12 |
| 1 | 13 |
| 1 | 14 |
| 1 | 15 |
| 1 | 16 |
| 1 | 17 |
| 1 | 18 |
| 1 | 19 |
| 1 | 20 |
| 1 | 21 |
| 1 | 22 |
| 1 | 23 |
| 1 | 24 |
| 1 | 25 |
| 1 | 26 |
| 1 | 27 |
| 2 | 1 |
| 2 | 2 |

| No. | Con. |
|---|---|
| 2 | 3 |
| 2 | 4 |
| 2 | 5 |
| 2 | 6 |
| 2 | 7 |
| 2 | 8 |
| 2 | 9 |
| 2 | 10 |
| 2 | 11 |
| 2 | 12 |
| 2 | 13 |
| 2 | 14 |
| 2 | 15 |
| 2 | 16 |
| 2 | 17 |
| 2 | 18 |
| 2 | 19 |
| 2 | 20 |
| 2 | 21 |
| 2 | 22 |
| 2 | 23 |
| 2 | 24 |
| 2 | 25 |
| 2 | 26 |
| 2 | 27 |
| 3 | 1 |
| 3 | 2 |
| 3 | 3 |
| 3 | 4 |
| 3 | 5 |
| 3 | 6 |
| 3 | 7 |
| 3 | 8 |
| 3 | 9 |
| 3 | 10 |
| 3 | 11 |
| 3 | 12 |
| 3 | 13 |
| 3 | 14 |
| 3 | 15 |
| 3 | 16 |
| 3 | 17 |
| 3 | 18 |
| 3 | 19 |
| 3 | 20 |
| 3 | 21 |
| 3 | 22 |
| 3 | 23 |
| 3 | 24 |
| 3 | 25 |
| 3 | 26 |
| 3 | 27 |
| 4 | 1 |
| 4 | 2 |
| 4 | 3 |
| 4 | 4 |
| 4 | 5 |
| 4 | 6 |
| 4 | 7 |
| 4 | 8 |
| 4 | 9 |
| 4 | 10 |
| 4 | 11 |
| 4 | 12 |
| 4 | 13 |
| 4 | 14 |
| 4 | 15 |
| 4 | 16 |
| 4 | 17 |
| 4 | 18 |
| 4 | 19 |
| 4 | 20 |
| 4 | 21 |
| 4 | 22 |
| 4 | 23 |
| 4 | 24 |
| 4 | 25 |

| No. | Con. |
|---|---|
| 4 | 26 |
| 4 | 27 |
| 5 | 1 |
| 5 | 2 |
| 5 | 3 |
| 5 | 4 |
| 5 | 5 |
| 5 | 6 |
| 5 | 7 |
| 5 | 8 |
| 5 | 9 |
| 5 | 10 |
| 5 | 11 |
| 5 | 12 |
| 5 | 13 |
| 5 | 14 |
| 5 | 15 |
| 5 | 16 |
| 5 | 17 |
| 5 | 18 |
| 5 | 19 |
| 5 | 20 |
| 5 | 21 |
| 5 | 22 |
| 5 | 23 |
| 5 | 24 |
| 5 | 25 |
| 5 | 26 |
| 5 | 27 |
| 6 | 1 |
| 6 | 2 |
| 6 | 3 |
| 6 | 4 |
| 6 | 5 |
| 6 | 6 |
| 6 | 7 |
| 6 | 8 |
| 6 | 9 |
| 6 | 10 |
| 6 | 11 |
| 6 | 12 |
| 6 | 13 |
| 6 | 14 |
| 6 | 15 |
| 6 | 16 |
| 6 | 17 |
| 6 | 18 |
| 6 | 19 |
| 6 | 20 |
| 6 | 21 |
| 6 | 22 |
| 6 | 23 |
| 6 | 24 |
| 6 | 25 |
| 6 | 26 |
| 6 | 27 |
| 7 | 1 |
| 7 | 2 |
| 7 | 3 |
| 7 | 4 |
| 7 | 5 |
| 7 | 6 |
| 7 | 7 |
| 7 | 8 |
| 7 | 9 |
| 7 | 10 |
| 7 | 11 |
| 7 | 12 |
| 7 | 13 |
| 7 | 14 |
| 7 | 15 |
| 7 | 16 |
| 7 | 17 |
| 7 | 18 |
| 7 | 19 |
| 7 | 20 |
| 7 | 21 |

117
-continued

| No. | Con. |
|---|---|
| 7 | 22 |
| 7 | 23 |
| 7 | 24 |
| 7 | 25 |
| 7 | 26 |
| 7 | 27 |
| 8 | 1 |
| 8 | 2 |
| 8 | 3 |
| 8 | 4 |
| 8 | 5 |
| 8 | 6 |
| 8 | 7 |
| 8 | 8 |
| 8 | 9 |
| 8 | 10 |
| 8 | 11 |
| 8 | 12 |
| 8 | 13 |
| 8 | 14 |
| 8 | 15 |
| 8 | 16 |
| 8 | 17 |
| 8 | 18 |
| 8 | 19 |
| 8 | 20 |
| 8 | 21 |
| 8 | 22 |
| 8 | 23 |
| 8 | 24 |
| 8 | 25 |
| 8 | 26 |
| 8 | 27 |
| 9 | 1 |
| 9 | 2 |
| 9 | 3 |
| 9 | 4 |
| 9 | 5 |
| 9 | 6 |
| 9 | 7 |
| 9 | 8 |
| 9 | 9 |
| 9 | 10 |
| 9 | 11 |
| 9 | 12 |
| 9 | 13 |
| 9 | 14 |
| 9 | 15 |
| 9 | 16 |
| 9 | 17 |
| 9 | 18 |
| 9 | 19 |
| 9 | 20 |
| 9 | 21 |
| 9 | 22 |
| 9 | 23 |
| 9 | 24 |
| 9 | 25 |
| 9 | 26 |
| 9 | 27 |
| 10 | 1 |
| 10 | 2 |
| 10 | 3 |
| 10 | 4 |
| 10 | 5 |
| 10 | 6 |
| 10 | 7 |
| 10 | 8 |
| 10 | 9 |
| 10 | 10 |
| 10 | 11 |
| 10 | 12 |
| 10 | 13 |
| 10 | 14 |
| 10 | 15 |
| 10 | 16 |
| 10 | 17 |

118
-continued

| No. | Con. |
|---|---|
| 10 | 18 |
| 10 | 19 |
| 10 | 20 |
| 10 | 21 |
| 10 | 22 |
| 10 | 23 |
| 10 | 24 |
| 10 | 25 |
| 10 | 26 |
| 10 | 27 |
| 11 | 1 |
| 11 | 2 |
| 11 | 3 |
| 11 | 4 |
| 11 | 5 |
| 11 | 6 |
| 11 | 7 |
| 11 | 8 |
| 11 | 9 |
| 11 | 10 |
| 11 | 11 |
| 11 | 12 |
| 11 | 13 |
| 11 | 14 |
| 11 | 15 |
| 11 | 16 |
| 11 | 17 |
| 11 | 18 |
| 11 | 19 |
| 11 | 20 |
| 11 | 21 |
| 11 | 22 |
| 11 | 23 |
| 11 | 24 |
| 11 | 25 |
| 11 | 26 |
| 11 | 27 |
| 12 | 1 |
| 12 | 2 |
| 12 | 3 |
| 12 | 4 |
| 12 | 5 |
| 12 | 6 |
| 12 | 7 |
| 12 | 8 |
| 12 | 9 |
| 12 | 10 |
| 12 | 11 |
| 12 | 12 |
| 12 | 13 |
| 12 | 14 |
| 12 | 15 |
| 12 | 16 |
| 12 | 17 |
| 12 | 18 |
| 12 | 19 |
| 12 | 20 |
| 12 | 21 |
| 12 | 22 |
| 12 | 23 |
| 12 | 24 |
| 12 | 25 |
| 12 | 26 |
| 12 | 27 |
| 13 | 1 |
| 13 | 2 |
| 13 | 3 |
| 13 | 4 |
| 13 | 5 |
| 13 | 6 |
| 13 | 7 |
| 13 | 8 |
| 13 | 9 |
| 13 | 10 |
| 13 | 11 |
| 13 | 12 |
| 13 | 13 |

| No. | Con. |
|-----|------|
| 13 | 14 |
| 13 | 15 |
| 13 | 16 |
| 13 | 17 |
| 13 | 18 |
| 13 | 19 |
| 13 | 20 |
| 13 | 21 |
| 13 | 22 |
| 13 | 23 |
| 13 | 24 |
| 13 | 25 |
| 13 | 26 |
| 13 | 27 |
| 14 | 1 |
| 14 | 2 |
| 14 | 3 |
| 14 | 4 |
| 14 | 5 |
| 14 | 6 |
| 14 | 7 |
| 14 | 8 |
| 14 | 9 |
| 14 | 10 |
| 14 | 11 |
| 14 | 12 |
| 14 | 13 |
| 14 | 14 |
| 14 | 15 |
| 14 | 16 |
| 14 | 17 |
| 14 | 18 |
| 14 | 19 |
| 14 | 20 |
| 14 | 21 |
| 14 | 22 |
| 14 | 23 |
| 14 | 24 |
| 14 | 25 |
| 14 | 26 |
| 14 | 27 |
| 15 | 1 |
| 15 | 2 |
| 15 | 3 |
| 15 | 4 |
| 15 | 5 |
| 15 | 6 |
| 15 | 7 |
| 15 | 8 |
| 15 | 9 |
| 15 | 10 |
| 15 | 11 |
| 15 | 12 |
| 15 | 13 |
| 15 | 14 |
| 15 | 15 |
| 15 | 16 |
| 15 | 17 |
| 15 | 18 |
| 15 | 19 |
| 15 | 20 |
| 15 | 21 |
| 15 | 22 |
| 15 | 23 |
| 15 | 24 |
| 15 | 25 |
| 15 | 26 |
| 15 | 27 |
| 16 | 1 |
| 16 | 2 |
| 16 | 3 |
| 16 | 4 |
| 16 | 5 |
| 16 | 6 |
| 16 | 7 |
| 16 | 8 |
| 16 | 9 |
| 16 | 10 |
| 16 | 11 |
| 16 | 12 |
| 16 | 13 |
| 16 | 14 |
| 16 | 15 |
| 16 | 16 |
| 16 | 17 |
| 16 | 18 |
| 16 | 19 |
| 16 | 20 |
| 16 | 21 |
| 16 | 22 |
| 16 | 23 |
| 16 | 24 |
| 16 | 25 |
| 16 | 26 |
| 16 | 27 |
| 17 | 1 |
| 17 | 2 |
| 17 | 3 |
| 17 | 4 |
| 17 | 5 |
| 17 | 6 |
| 17 | 7 |
| 17 | 8 |
| 17 | 9 |
| 17 | 10 |
| 17 | 11 |
| 17 | 12 |
| 17 | 13 |
| 17 | 14 |
| 17 | 15 |
| 17 | 16 |
| 17 | 17 |
| 17 | 18 |
| 17 | 19 |
| 17 | 20 |
| 17 | 21 |
| 17 | 22 |
| 17 | 23 |
| 17 | 24 |
| 17 | 25 |
| 17 | 26 |
| 17 | 27 |
| 18 | 1 |
| 18 | 2 |
| 18 | 3 |
| 18 | 4 |
| 18 | 5 |
| 18 | 6 |
| 18 | 7 |
| 18 | 8 |
| 18 | 9 |
| 18 | 10 |
| 18 | 11 |
| 18 | 12 |
| 18 | 13 |
| 18 | 14 |
| 18 | 15 |
| 18 | 16 |
| 18 | 17 |
| 18 | 18 |
| 18 | 19 |
| 18 | 20 |
| 18 | 21 |
| 18 | 22 |
| 18 | 23 |
| 18 | 24 |
| 18 | 25 |
| 18 | 26 |
| 18 | 27 |
| 19 | 1 |
| 19 | 2 |
| 19 | 3 |
| 19 | 4 |
| 19 | 5 |

| No. | Con. |
|---|---|
| 19 | 6 |
| 19 | 7 |
| 19 | 8 |
| 19 | 9 |
| 19 | 10 |
| 19 | 11 |
| 19 | 12 |
| 19 | 13 |
| 19 | 14 |
| 19 | 15 |
| 19 | 16 |
| 19 | 17 |
| 19 | 18 |
| 19 | 19 |
| 19 | 20 |
| 19 | 21 |
| 19 | 22 |
| 19 | 23 |
| 19 | 24 |
| 19 | 25 |
| 19 | 26 |
| 19 | 27 |
| 20 | 1 |
| 20 | 2 |
| 20 | 3 |
| 20 | 4 |
| 20 | 5 |
| 20 | 6 |
| 20 | 7 |
| 20 | 8 |
| 20 | 9 |
| 20 | 10 |
| 20 | 11 |
| 20 | 12 |
| 20 | 13 |
| 20 | 14 |
| 20 | 15 |
| 20 | 16 |
| 20 | 17 |
| 20 | 18 |
| 20 | 19 |
| 20 | 20 |
| 20 | 21 |
| 20 | 22 |
| 20 | 23 |
| 20 | 24 |
| 20 | 25 |
| 20 | 26 |
| 20 | 27 |
| 21 | 1 |
| 21 | 2 |
| 21 | 3 |
| 21 | 4 |
| 21 | 5 |
| 21 | 6 |
| 21 | 7 |
| 21 | 8 |
| 21 | 9 |
| 21 | 10 |
| 21 | 11 |
| 21 | 12 |
| 21 | 13 |
| 21 | 14 |
| 21 | 15 |
| 21 | 16 |
| 21 | 17 |
| 21 | 18 |
| 21 | 19 |
| 21 | 20 |
| 21 | 21 |
| 21 | 22 |
| 21 | 23 |
| 21 | 24 |
| 21 | 25 |
| 21 | 26 |
| 21 | 27 |
| 22 | 1 |
| 22 | 2 |
| 22 | 3 |
| 22 | 4 |
| 22 | 5 |
| 22 | 6 |
| 22 | 7 |
| 22 | 8 |
| 22 | 9 |
| 22 | 10 |
| 22 | 11 |
| 22 | 12 |
| 22 | 13 |
| 22 | 14 |
| 22 | 15 |
| 22 | 16 |
| 22 | 17 |
| 22 | 18 |
| 22 | 19 |
| 22 | 20 |
| 22 | 21 |
| 22 | 22 |
| 22 | 23 |
| 22 | 24 |
| 22 | 25 |
| 22 | 26 |
| 22 | 27 |
| 23 | 1 |
| 23 | 2 |
| 23 | 3 |
| 23 | 4 |
| 23 | 5 |
| 23 | 6 |
| 23 | 7 |
| 23 | 8 |
| 23 | 9 |
| 23 | 10 |
| 23 | 11 |
| 23 | 12 |
| 23 | 13 |
| 23 | 14 |
| 23 | 15 |
| 23 | 16 |
| 23 | 17 |
| 23 | 18 |
| 23 | 19 |
| 23 | 20 |
| 23 | 21 |
| 23 | 22 |
| 23 | 23 |
| 23 | 24 |
| 23 | 25 |
| 23 | 26 |
| 23 | 27 |
| 24 | 1 |
| 24 | 2 |
| 24 | 3 |
| 24 | 4 |
| 24 | 5 |
| 24 | 6 |
| 24 | 7 |
| 74 | 8 |
| 24 | 9 |
| 24 | 10 |
| 24 | 11 |
| 24 | 12 |
| 24 | 13 |
| 24 | 14 |
| 24 | 15 |
| 24 | 16 |
| 24 | 17 |
| 24 | 18 |
| 24 | 19 |
| 24 | 20 |
| 24 | 21 |
| 24 | 22 |
| 24 | 23 |
| 24 | 24 |

123
-continued

| No. | Con. |
|---|---|
| 24 | 25 |
| 24 | 26 |
| 24 | 27 |
| 25 | 1 |
| 25 | 2 |
| 25 | 3 |
| 25 | 4 |
| 25 | 5 |
| 25 | 6 |
| 25 | 7 |
| 25 | 8 |
| 25 | 9 |
| 25 | 10 |
| 25 | 11 |
| 25 | 12 |
| 25 | 13 |
| 25 | 14 |
| 25 | 15 |
| 25 | 16 |
| 25 | 17 |
| 25 | 18 |
| 25 | 19 |
| 25 | 20 |
| 25 | 21 |
| 25 | 22 |
| 25 | 23 |
| 25 | 24 |
| 25 | 25 |
| 25 | 26 |
| 25 | 27 |
| 26 | 1 |
| 26 | 2 |
| 26 | 3 |
| 26 | 4 |
| 26 | 5 |
| 26 | 6 |
| 26 | 7 |
| 26 | 8 |
| 26 | 9 |
| 26 | 10 |
| 26 | 11 |
| 26 | 12 |
| 26 | 13 |
| 26 | 14 |
| 26 | 15 |
| 26 | 16 |
| 26 | 17 |
| 26 | 18 |
| 26 | 19 |
| 26 | 20 |
| 26 | 21 |
| 26 | 22 |
| 26 | 23 |
| 26 | 24 |
| 26 | 25 |
| 26 | 26 |
| 26 | 27 |
| 27 | 1 |
| 27 | 2 |
| 27 | 3 |
| 27 | 4 |
| 27 | 5 |
| 27 | 6 |
| 27 | 7 |
| 27 | 8 |
| 27 | 9 |
| 27 | 10 |
| 27 | 11 |
| 27 | 12 |
| 27 | 13 |
| 27 | 14 |
| 27 | 15 |
| 27 | 16 |
| 27 | 17 |
| 27 | 18 |
| 27 | 19 |
| 27 | 20 |

124
-continued

| No. | Con. |
|---|---|
| 27 | 21 |
| 27 | 22 |
| 27 | 23 |
| 27 | 24 |
| 27 | 25 |
| 27 | 26 |
| 27 | 27 |
| 28 | 1 |
| 28 | 2 |
| 28 | 3 |
| 28 | 4 |
| 28 | 5 |
| 28 | 6 |
| 28 | 7 |
| 28 | 8 |
| 28 | 9 |
| 28 | 10 |
| 28 | 11 |
| 28 | 12 |
| 28 | 13 |
| 28 | 14 |
| 28 | 15 |
| 28 | 16 |
| 28 | 17 |
| 28 | 18 |
| 28 | 19 |
| 28 | 20 |
| 28 | 21 |
| 28 | 22 |
| 28 | 23 |
| 28 | 24 |
| 28 | 25 |
| 28 | 26 |
| 28 | 27 |
| 29 | 1 |
| 29 | 2 |
| 29 | 3 |
| 29 | 4 |
| 29 | 5 |
| 29 | 6 |
| 29 | 7 |
| 29 | 8 |
| 29 | 9 |
| 29 | 10 |
| 29 | 11 |
| 29 | 12 |
| 29 | 13 |
| 29 | 14 |
| 29 | 15 |
| 29 | 16 |
| 29 | 17 |
| 29 | 18 |
| 29 | 19 |
| 29 | 20 |
| 29 | 21 |
| 29 | 22 |
| 29 | 23 |
| 29 | 24 |
| 29 | 25 |
| 29 | 26 |
| 29 | 27 |
| 30 | 1 |
| 30 | 2 |
| 30 | 3 |
| 30 | 4 |
| 30 | 5 |
| 30 | 6 |
| 30 | 7 |
| 30 | 8 |
| 30 | 9 |
| 30 | 10 |
| 30 | 11 |
| 30 | 12 |
| 30 | 13 |
| 30 | 14 |
| 30 | 15 |
| 30 | 16 |

125
-continued

| No. | Con. |
|---|---|
| 30 | 17 |
| 30 | 18 |
| 30 | 19 |
| 30 | 20 |
| 30 | 21 |
| 30 | 22 |
| 30 | 23 |
| 30 | 24 |
| 30 | 25 |
| 30 | 26 |
| 30 | 27 |
| 31 | 1 |
| 31 | 2 |
| 31 | 3 |
| 31 | 4 |
| 31 | 5 |
| 31 | 6 |
| 31 | 7 |
| 31 | 8 |
| 31 | 9 |
| 31 | 10 |
| 31 | 11 |
| 31 | 12 |
| 31 | 13 |
| 31 | 14 |
| 31 | 15 |
| 31 | 16 |
| 31 | 17 |
| 31 | 18 |
| 31 | 19 |
| 31 | 20 |
| 31 | 21 |
| 31 | 22 |
| 31 | 23 |
| 31 | 24 |
| 31 | 25 |
| 31 | 26 |
| 31 | 27 |
| 32 | 1 |
| 32 | 2 |
| 32 | 3 |
| 32 | 4 |
| 32 | 5 |
| 32 | 6 |
| 32 | 7 |
| 32 | 8 |
| 32 | 9 |
| 32 | 10 |
| 32 | 11 |
| 32 | 12 |
| 32 | 13 |
| 32 | 14 |
| 32 | 15 |
| 32 | 16 |
| 32 | 17 |
| 32 | 18 |
| 32 | 19 |
| 32 | 20 |
| 32 | 21 |
| 32 | 22 |
| 32 | 23 |
| 32 | 24 |
| 32 | 25 |
| 32 | 26 |
| 32 | 27 |
| 33 | 1 |
| 33 | 2 |
| 33 | 3 |
| 33 | 4 |
| 33 | 5 |
| 33 | 6 |
| 33 | 7 |
| 33 | 8 |
| 33 | 9 |
| 33 | 10 |
| 33 | 11 |
| 33 | 12 |

126
-continued

| No. | Con. |
|---|---|
| 33 | 13 |
| 33 | 14 |
| 33 | 15 |
| 33 | 16 |
| 33 | 17 |
| 33 | 18 |
| 33 | 19 |
| 33 | 20 |
| 33 | 21 |
| 33 | 22 |
| 33 | 23 |
| 33 | 24 |
| 33 | 25 |
| 33 | 26 |
| 33 | 27 |
| 34 | 1 |
| 34 | 2 |
| 34 | 3 |
| 34 | 4 |
| 34 | 5 |
| 34 | 6 |
| 34 | 7 |
| 34 | 8 |
| 34 | 9 |
| 34 | 10 |
| 34 | 11 |
| 34 | 12 |
| 34 | 13 |
| 34 | 14 |
| 34 | 15 |
| 34 | 16 |
| 34 | 17 |
| 34 | 18 |
| 34 | 19 |
| 34 | 20 |
| 34 | 21 |
| 34 | 22 |
| 34 | 23 |
| 34 | 24 |
| 34 | 25 |
| 34 | 26 |
| 34 | 27 |
| 35 | 1 |
| 35 | 2 |
| 35 | 3 |
| 35 | 4 |
| 35 | 5 |
| 35 | 6 |
| 35 | 7 |
| 35 | 8 |
| 35 | 9 |
| 35 | 10 |
| 35 | 11 |
| 35 | 12 |
| 35 | 13 |
| 35 | 14 |
| 35 | 15 |
| 35 | 16 |
| 35 | 17 |
| 35 | 18 |
| 35 | 19 |
| 35 | 20 |
| 35 | 21 |
| 35 | 22 |
| 35 | 23 |
| 35 | 24 |
| 35 | 25 |
| 35 | 26 |
| 35 | 27 |
| 36 | 1 |
| 36 | 2 |
| 36 | 3 |
| 36 | 4 |
| 36 | 5 |
| 36 | 6 |
| 36 | 7 |
| 36 | 8 |

127
-continued

| No. | Con. |
|---|---|
| 36 | 9 |
| 36 | 10 |
| 36 | 11 |
| 36 | 12 |
| 36 | 13 |
| 36 | 14 |
| 36 | 15 |
| 36 | 16 |
| 36 | 17 |
| 36 | 18 |
| 36 | 19 |
| 36 | 20 |
| 36 | 21 |
| 36 | 22 |
| 36 | 23 |
| 36 | 24 |
| 36 | 25 |
| 36 | 26 |
| 36 | 27 |
| 37 | 1 |
| 37 | 2 |
| 37 | 3 |
| 37 | 4 |
| 37 | 5 |
| 37 | 6 |
| 37 | 7 |
| 37 | 8 |
| 37 | 9 |
| 37 | 10 |
| 37 | 11 |
| 37 | 12 |
| 37 | 13 |
| 37 | 14 |
| 37 | 15 |
| 37 | 16 |
| 37 | 17 |
| 37 | 18 |
| 37 | 19 |
| 37 | 20 |
| 37 | 21 |
| 37 | 22 |
| 37 | 23 |
| 37 | 24 |
| 37 | 25 |
| 37 | 26 |
| 37 | 27 |
| 38 | 1 |
| 38 | 2 |
| 38 | 3 |
| 38 | 4 |
| 38 | 5 |
| 38 | 6 |
| 38 | 7 |
| 38 | 8 |
| 38 | 9 |
| 38 | 10 |
| 38 | 11 |
| 38 | 12 |
| 38 | 13 |
| 38 | 14 |
| 38 | 15 |
| 38 | 16 |
| 38 | 17 |
| 38 | 18 |
| 38 | 19 |
| 38 | 20 |
| 38 | 21 |
| 38 | 22 |
| 38 | 23 |
| 38 | 24 |
| 38 | 25 |
| 38 | 26 |
| 38 | 27 |
| 39 | 1 |
| 39 | 2 |
| 39 | 3 |
| 39 | 4 |

128
-continued

| No. | Con. |
|---|---|
| 39 | 5 |
| 39 | 6 |
| 39 | 7 |
| 39 | 8 |
| 39 | 9 |
| 39 | 10 |
| 39 | 11 |
| 39 | 12 |
| 39 | 13 |
| 39 | 14 |
| 39 | 15 |
| 39 | 16 |
| 39 | 17 |
| 39 | 18 |
| 39 | 19 |
| 39 | 20 |
| 39 | 21 |
| 39 | 22 |
| 39 | 23 |
| 39 | 24 |
| 39 | 25 |
| 39 | 26 |
| 39 | 27 |
| 40 | 1 |
| 40 | 2 |
| 40 | 3 |
| 40 | 4 |
| 40 | 5 |
| 40 | 6 |
| 40 | 7 |
| 40 | 8 |
| 40 | 9 |
| 40 | 10 |
| 40 | 11 |
| 40 | 12 |
| 40 | 13 |
| 40 | 14 |
| 40 | 15 |
| 40 | 16 |
| 40 | 17 |
| 40 | 18 |
| 40 | 19 |
| 40 | 20 |
| 40 | 21 |
| 40 | 22 |
| 40 | 23 |
| 40 | 24 |
| 40 | 25 |
| 40 | 26 |
| 40 | 27 |
| 41 | 1 |
| 41 | 2 |
| 41 | 3 |
| 41 | 4 |
| 41 | 5 |
| 41 | 6 |
| 41 | 7 |
| 41 | 8 |
| 41 | 9 |
| 41 | 10 |
| 41 | 11 |
| 41 | 12 |
| 41 | 13 |
| 41 | 14 |
| 41 | 15 |
| 41 | 16 |
| 41 | 17 |
| 41 | 18 |
| 41 | 19 |
| 41 | 20 |
| 41 | 21 |
| 41 | 22 |
| 41 | 23 |
| 41 | 24 |
| 41 | 25 |
| 41 | 26 |
| 41 | 27 |

| No. | Con. |
|---|---|
| 42 | 1 |
| 42 | 2 |
| 42 | 3 |
| 42 | 4 |
| 42 | 5 |
| 42 | 6 |
| 42 | 7 |
| 42 | 8 |
| 42 | 9 |
| 42 | 10 |
| 42 | 11 |
| 42 | 12 |
| 42 | 13 |
| 42 | 14 |
| 42 | 15 |
| 42 | 16 |
| 42 | 17 |
| 42 | 18 |
| 42 | 19 |
| 42 | 20 |
| 42 | 21 |
| 42 | 22 |
| 42 | 23 |
| 42 | 24 |
| 42 | 25 |
| 42 | 26 |
| 42 | 27 |
| 43 | 1 |
| 43 | 2 |
| 43 | 3 |
| 43 | 4 |
| 43 | 5 |
| 43 | 6 |
| 43 | 7 |
| 43 | 8 |
| 43 | 9 |
| 43 | 10 |
| 43 | 11 |
| 43 | 12 |
| 43 | 13 |
| 43 | 14 |
| 43 | 15 |
| 43 | 16 |
| 43 | 17 |
| 43 | 18 |
| 43 | 19 |
| 43 | 20 |
| 43 | 21 |
| 43 | 22 |
| 43 | 23 |
| 43 | 24 |
| 43 | 25 |
| 43 | 26 |
| 43 | 27 |
| 44 | 1 |
| 44 | 2 |
| 44 | 3 |
| 44 | 4 |
| 44 | 5 |
| 44 | 6 |
| 44 | 7 |
| 44 | 8 |
| 44 | 9 |
| 44 | 10 |
| 44 | 11 |
| 44 | 12 |
| 44 | 13 |
| 44 | 14 |
| 44 | 15 |
| 44 | 16 |
| 44 | 17 |
| 44 | 18 |
| 44 | 19 |
| 44 | 20 |
| 44 | 21 |
| 44 | 22 |
| 44 | 23 |

| No. | Con. |
|---|---|
| 44 | 24 |
| 44 | 25 |
| 44 | 26 |
| 44 | 27 |
| 45 | 1 |
| 45 | 2 |
| 45 | 3 |
| 45 | 4 |
| 45 | 5 |
| 45 | 6 |
| 45 | 7 |
| 45 | 8 |
| 45 | 9 |
| 45 | 10 |
| 45 | 11 |
| 45 | 12 |
| 45 | 13 |
| 45 | 14 |
| 45 | 15 |
| 45 | 16 |
| 45 | 17 |
| 45 | 18 |
| 45 | 19 |
| 45 | 20 |
| 45 | 21 |
| 45 | 22 |
| 45 | 23 |
| 45 | 24 |
| 45 | 25 |
| 45 | 26 |
| 45 | 27 |
| 46 | 1 |
| 46 | 2 |
| 46 | 3 |
| 46 | 4 |
| 46 | 5 |
| 46 | 6 |
| 46 | 7 |
| 46 | 8 |
| 46 | 9 |
| 46 | 10 |
| 46 | 11 |
| 46 | 12 |
| 46 | 13 |
| 46 | 14 |
| 46 | 15 |
| 46 | 16 |
| 46 | 17 |
| 46 | 18 |
| 46 | 19 |
| 46 | 20 |
| 46 | 21 |
| 46 | 22 |
| 46 | 23 |
| 46 | 24 |
| 46 | 25 |
| 46 | 26 |
| 46 | 27 |
| 47 | 1 |
| 47 | 2 |
| 47 | 3 |
| 47 | 4 |
| 47 | 5 |
| 47 | 6 |
| 47 | 7 |
| 47 | 8 |
| 47 | 9 |
| 47 | 10 |
| 47 | 11 |
| 47 | 12 |
| 47 | 13 |
| 47 | 14 |
| 47 | 15 |
| 47 | 16 |
| 47 | 17 |
| 47 | 18 |
| 47 | 19 |

| No. | Con. |
|---|---|
| 47 | 20 |
| 47 | 21 |
| 47 | 22 |
| 47 | 23 |
| 47 | 24 |
| 47 | 25 |
| 47 | 26 |
| 47 | 27 |
| 48 | 1 |
| 48 | 2 |
| 48 | 3 |
| 48 | 4 |
| 48 | 5 |
| 48 | 6 |
| 48 | 7 |
| 48 | 8 |
| 48 | 9 |
| 48 | 10 |
| 48 | 11 |
| 48 | 12 |
| 48 | 13 |
| 48 | 14 |
| 48 | 15 |
| 48 | 16 |
| 48 | 17 |
| 48 | 18 |
| 48 | 19 |
| 48 | 20 |
| 48 | 21 |
| 48 | 22 |
| 48 | 23 |
| 48 | 24 |
| 48 | 25 |
| 48 | 26 |
| 48 | 27 |
| 49 | 1 |
| 49 | 2 |
| 49 | 3 |
| 49 | 4 |
| 49 | 5 |
| 49 | 6 |
| 49 | 7 |
| 49 | 8 |
| 49 | 9 |
| 49 | 10 |
| 49 | 11 |
| 49 | 12 |
| 49 | 13 |
| 49 | 14 |
| 49 | 15 |
| 49 | 16 |
| 49 | 17 |
| 49 | 18 |
| 49 | 19 |
| 49 | 20 |
| 49 | 21 |
| 49 | 22 |
| 49 | 23 |
| 49 | 24 |
| 49 | 25 |
| 49 | 26 |
| 49 | 27 |
| 50 | 1 |
| 50 | 2 |
| 50 | 3 |
| 50 | 4 |
| 50 | 5 |
| 50 | 6 |
| 50 | 7 |
| 50 | 8 |
| 50 | 9 |
| 50 | 10 |
| 50 | 11 |
| 50 | 12 |
| 50 | 13 |
| 50 | 14 |
| 50 | 15 |

| No. | Con. |
|---|---|
| 50 | 16 |
| 50 | 17 |
| 50 | 18 |
| 50 | 19 |
| 50 | 20 |
| 50 | 21 |
| 50 | 22 |
| 50 | 23 |
| 50 | 24 |
| 50 | 25 |
| 50 | 26 |
| 50 | 27 |
| 51 | 1 |
| 51 | 2 |
| 51 | 3 |
| 51 | 4 |
| 51 | 5 |
| 51 | 6 |
| 51 | 7 |
| 51 | 8 |
| 51 | 9 |
| 51 | 10 |
| 51 | 11 |
| 51 | 12 |
| 51 | 13 |
| 51 | 14 |
| 51 | 15 |
| 51 | 16 |
| 51 | 17 |
| 51 | 18 |
| 51 | 19 |
| 51 | 20 |
| 51 | 21 |
| 51 | 22 |
| 51 | 23 |
| 51 | 24 |
| 51 | 25 |
| 51 | 26 |
| 51 | 27 |
| 52 | 1 |
| 52 | 2 |
| 52 | 3 |
| 52 | 4 |
| 52 | 5 |
| 52 | 6 |
| 52 | 7 |
| 52 | 8 |
| 52 | 9 |
| 52 | 10 |
| 52 | 11 |
| 52 | 12 |
| 52 | 13 |
| 52 | 14 |
| 52 | 15 |
| 52 | 16 |
| 52 | 17 |
| 52 | 18 |
| 52 | 19 |
| 52 | 20 |
| 52 | 21 |
| 52 | 22 |
| 52 | 23 |
| 52 | 24 |
| 52 | 25 |
| 52 | 26 |
| 52 | 27 |
| 53 | 1 |
| 53 | 2 |
| 53 | 3 |
| 53 | 4 |
| 53 | 5 |
| 53 | 6 |
| 53 | 7 |
| 53 | 8 |
| 53 | 9 |
| 53 | 10 |
| 53 | 11 |

-continued

| No. | Con. |
|---|---|
| 53 | 12 |
| 53 | 13 |
| 53 | 14 |
| 53 | 15 |
| 53 | 16 |
| 53 | 17 |
| 53 | 18 |
| 53 | 19 |
| 53 | 20 |
| 53 | 21 |
| 53 | 22 |
| 53 | 23 |
| 53 | 24 |
| 53 | 25 |
| 53 | 26 |
| 53 | 27 |
| 54 | 1 |
| 54 | 2 |
| 54 | 3 |
| 54 | 4 |
| 54 | 5 |
| 54 | 6 |
| 54 | 7 |
| 54 | 8 |
| 54 | 9 |
| 54 | 10 |
| 54 | 11 |
| 54 | 12 |
| 54 | 13 |
| 54 | 14 |
| 54 | 15 |
| 54 | 16 |
| 54 | 17 |
| 54 | 18 |
| 54 | 19 |
| 54 | 20 |
| 54 | 21 |
| 54 | 22 |
| 54 | 23 |
| 54 | 24 |
| 54 | 25 |
| 54 | 26 |
| 54 | 27 |
| 55 | 1 |
| 55 | 2 |
| 55 | 3 |
| 55 | 4 |
| 55 | 5 |
| 55 | 6 |
| 55 | 7 |
| 55 | 8 |
| 55 | 9 |
| 55 | 10 |
| 55 | 11 |
| 55 | 12 |
| 55 | 13 |
| 55 | 14 |
| 55 | 15 |
| 55 | 16 |
| 55 | 17 |
| 55 | 18 |
| 55 | 19 |
| 55 | 20 |
| 55 | 21 |
| 55 | 22 |
| 55 | 23 |
| 55 | 24 |
| 55 | 25 |
| 55 | 26 |
| 55 | 27 |
| 56 | 1 |
| 56 | 2 |
| 56 | 3 |
| 56 | 4 |
| 56 | 5 |
| 56 | 6 |
| 56 | 7 |

-continued

| No. | Con. |
|---|---|
| 56 | 8 |
| 56 | 9 |
| 56 | 10 |
| 56 | 11 |
| 56 | 12 |
| 56 | 13 |
| 56 | 14 |
| 56 | 15 |
| 56 | 16 |
| 56 | 17 |
| 56 | 18 |
| 56 | 19 |
| 56 | 20 |
| 56 | 21 |
| 56 | 22 |
| 56 | 23 |
| 56 | 24 |
| 56 | 25 |
| 56 | 26 |
| 56 | 27 |
| 57 | 1 |
| 57 | 2 |
| 57 | 3 |
| 57 | 4 |
| 57 | 5 |
| 57 | 6 |
| 57 | 7 |
| 57 | 8 |
| 57 | 9 |
| 57 | 10 |
| 57 | 11 |
| 57 | 12 |
| 57 | 13 |
| 57 | 14 |
| 57 | 15 |
| 57 | 16 |
| 57 | 17 |
| 57 | 18 |
| 57 | 19 |
| 57 | 20 |
| 57 | 21 |
| 57 | 22 |
| 57 | 23 |
| 57 | 24 |
| 57 | 25 |
| 57 | 26 |
| 57 | 27 |
| 58 | 1 |
| 58 | 2 |
| 58 | 3 |
| 58 | 4 |
| 58 | 5 |
| 58 | 6 |
| 58 | 7 |
| 58 | 8 |
| 58 | 9 |
| 58 | 10 |
| 58 | 11 |
| 58 | 12 |
| 58 | 13 |
| 58 | 14 |
| 58 | 15 |
| 58 | 16 |
| 58 | 17 |
| 58 | 18 |
| 58 | 19 |
| 58 | 20 |
| 58 | 21 |
| 58 | 22 |
| 58 | 23 |
| 58 | 24 |
| 58 | 25 |
| 58 | 26 |
| 58 | 27 |
| 59 | 1 |
| 59 | 2 |
| 59 | 3 |

135
-continued

| No. | Con. |
|---|---|
| 59 | 4 |
| 59 | 5 |
| 59 | 6 |
| 59 | 7 |
| 59 | 8 |
| 59 | 9 |
| 59 | 10 |
| 59 | 11 |
| 59 | 12 |
| 59 | 13 |
| 59 | 14 |
| 59 | 15 |
| 59 | 16 |
| 59 | 17 |
| 59 | 18 |
| 59 | 19 |
| 59 | 20 |
| 59 | 21 |
| 59 | 22 |
| 59 | 23 |
| 59 | 24 |
| 59 | 25 |
| 59 | 26 |
| 59 | 27 |
| 60 | 1 |
| 60 | 2 |
| 60 | 3 |
| 60 | 4 |
| 60 | 5 |
| 60 | 6 |
| 60 | 7 |
| 60 | 8 |
| 60 | 9 |
| 60 | 10 |
| 60 | 11 |
| 60 | 12 |
| 60 | 13 |
| 60 | 14 |
| 60 | 15 |
| 60 | 16 |
| 60 | 17 |
| 60 | 18 |
| 60 | 19 |
| 60 | 20 |
| 60 | 21 |
| 60 | 22 |
| 60 | 23 |
| 60 | 24 |
| 60 | 25 |
| 60 | 26 |
| 60 | 27 |
| 61 | 1 |
| 61 | 2 |
| 61 | 3 |
| 61 | 4 |
| 61 | 5 |
| 61 | 6 |
| 61 | 7 |
| 61 | 8 |
| 61 | 9 |
| 61 | 10 |
| 61 | 11 |
| 61 | 12 |
| 61 | 13 |
| 61 | 14 |
| 61 | 15 |
| 61 | 16 |
| 61 | 17 |
| 61 | 18 |
| 61 | 19 |
| 61 | 20 |
| 61 | 21 |
| 61 | 22 |
| 61 | 23 |
| 61 | 24 |
| 61 | 25 |
| 61 | 26 |

136
-continued

| No. | Con. |
|---|---|
| 61 | 27 |
| 62 | 1 |
| 62 | 2 |
| 62 | 3 |
| 62 | 4 |
| 62 | 5 |
| 62 | 6 |
| 62 | 7 |
| 62 | 8 |
| 62 | 9 |
| 62 | 10 |
| 62 | 11 |
| 62 | 12 |
| 62 | 13 |
| 62 | 14 |
| 62 | 15 |
| 62 | 16 |
| 62 | 17 |
| 62 | 18 |
| 62 | 19 |
| 62 | 20 |
| 62 | 21 |
| 62 | 22 |
| 62 | 23 |
| 62 | 24 |
| 62 | 25 |
| 62 | 26 |
| 62 | 27 |
| 63 | 1 |
| 63 | 2 |
| 63 | 3 |
| 63 | 4 |
| 63 | 5 |
| 63 | 6 |
| 63 | 7 |
| 63 | 8 |
| 63 | 9 |
| 63 | 10 |
| 63 | 11 |
| 63 | 12 |
| 63 | 13 |
| 63 | 14 |
| 63 | 15 |
| 63 | 16 |
| 63 | 17 |
| 63 | 18 |
| 63 | 19 |
| 63 | 20 |
| 63 | 21 |
| 63 | 22 |
| 63 | 23 |
| 63 | 24 |
| 63 | 25 |
| 63 | 26 |
| 63 | 27 |
| 64 | 1 |
| 64 | 2 |
| 64 | 3 |
| 64 | 4 |
| 64 | 5 |
| 64 | 6 |
| 64 | 7 |
| 64 | 8 |
| 64 | 9 |
| 64 | 10 |
| 64 | 11 |
| 64 | 12 |
| 64 | 13 |
| 64 | 14 |
| 64 | 15 |
| 64 | 16 |
| 64 | 17 |
| 64 | 18 |
| 64 | 19 |
| 64 | 20 |
| 64 | 21 |
| 64 | 22 |

-continued

| No. | Con. |
|---|---|
| 64 | 23 |
| 64 | 24 |
| 64 | 25 |
| 64 | 26 |
| 64 | 27 |
| 65 | 1 |
| 65 | 2 |
| 65 | 3 |
| 65 | 4 |
| 65 | 5 |
| 65 | 6 |
| 65 | 7 |
| 65 | 8 |
| 65 | 9 |
| 65 | 10 |
| 65 | 11 |
| 65 | 12 |
| 65 | 13 |
| 65 | 14 |
| 65 | 15 |
| 65 | 16 |
| 65 | 17 |
| 65 | 18 |
| 65 | 19 |
| 65 | 20 |
| 65 | 21 |
| 65 | 22 |
| 65 | 23 |
| 65 | 24 |
| 65 | 25 |
| 65 | 26 |
| 65 | 27 |
| 66 | 1 |
| 66 | 2 |
| 66 | 3 |
| 66 | 4 |
| 66 | 5 |
| 66 | 6 |
| 66 | 7 |
| 66 | 8 |
| 66 | 9 |
| 66 | 10 |
| 66 | 11 |
| 66 | 12 |
| 66 | 13 |
| 66 | 14 |
| 66 | 15 |
| 66 | 16 |
| 66 | 17 |
| 66 | 18 |
| 66 | 19 |
| 66 | 20 |
| 66 | 21 |
| 66 | 22 |
| 66 | 23 |
| 66 | 24 |
| 66 | 25 |
| 66 | 26 |
| 66 | 27 |
| 67 | 1 |
| 67 | 2 |
| 67 | 3 |
| 67 | 4 |
| 67 | 5 |
| 67 | 6 |
| 67 | 7 |
| 67 | 8 |
| 67 | 9 |
| 67 | 10 |
| 67 | 11 |
| 67 | 12 |
| 67 | 13 |
| 67 | 14 |
| 67 | 15 |
| 67 | 16 |
| 67 | 17 |
| 67 | 18 |

-continued

| No. | Con. |
|---|---|
| 67 | 19 |
| 67 | 20 |
| 67 | 21 |
| 67 | 22 |
| 67 | 23 |
| 67 | 24 |
| 67 | 25 |
| 67 | 26 |
| 67 | 27 |
| 68 | 1 |
| 68 | 2 |
| 68 | 3 |
| 68 | 4 |
| 68 | 5 |
| 68 | 6 |
| 68 | 7 |
| 68 | 8 |
| 68 | 9 |
| 68 | 10 |
| 68 | 11 |
| 68 | 12 |
| 68 | 13 |
| 68 | 14 |
| 68 | 15 |
| 68 | 16 |
| 68 | 17 |
| 68 | 18 |
| 68 | 19 |
| 68 | 20 |
| 68 | 21 |
| 68 | 22 |
| 68 | 23 |
| 68 | 24 |
| 68 | 25 |
| 68 | 26 |
| 68 | 27 |
| 69 | 1 |
| 69 | 2 |
| 69 | 3 |
| 69 | 4 |
| 69 | 5 |
| 69 | 6 |
| 69 | 7 |
| 69 | 8 |
| 69 | 9 |
| 69 | 10 |
| 69 | 11 |
| 69 | 12 |
| 69 | 13 |
| 69 | 14 |
| 69 | 15 |
| 69 | 16 |
| 69 | 17 |
| 69 | 18 |
| 69 | 19 |
| 69 | 20 |
| 69 | 21 |
| 69 | 22 |
| 69 | 23 |
| 69 | 24 |
| 69 | 25 |
| 69 | 26 |
| 69 | 27 |
| 70 | 1 |
| 70 | 2 |
| 70 | 3 |
| 70 | 4 |
| 70 | 5 |
| 70 | 6 |
| 70 | 7 |
| 70 | 8 |
| 70 | 9 |
| 70 | 10 |
| 70 | 11 |
| 70 | 12 |
| 70 | 13 |
| 70 | 14 |

| No. | Con. |
| --- | --- |
| 70 | 15 |
| 70 | 16 |
| 70 | 17 |
| 70 | 18 |
| 70 | 19 |
| 70 | 20 |
| 70 | 21 |
| 70 | 22 |
| 70 | 23 |
| 70 | 24 |
| 70 | 25 |
| 70 | 26 |
| 70 | 27 |

In another aspect, the present disclosure provides a compound according to any one of the preceding aspects includes one or more stable isotopes. The stable isotope may replace any atom, for example, hydrogen, and may include any stable isotope, for example, deuterium.

In another aspect, the present disclosure provides compounds and pharmaceutical compositions comprising the compounds according to any one of the preceding aspects of the invention or any embodiment thereof, together with a pharmaceutically acceptable excipient, diluent, or carrier.

In another aspect, the invention provides methods for treating tryptophan 2,3-dioxygenase (TDO2) mediated immunosuppression in a subject in need thereof, comprising administering an effective tryptophan 2,3-dioxygenase inhibiting amount of a compound or a pharmaceutical composition according to any of the preceding aspects of the invention or any embodiment thereof.

In one embodiment, the immunosuppression is associated with cancer.

In an embodiment, the immunosuppression is tumor-specific immunosuppression associated with cancer.

In another embodiment, the immunosuppression is associated with a cancer, wherein the cancer is colon, pancreas, breast, prostate, lung, brain, ovary, cervix, testes, renal, head, or neck cancer, or lymphoma, leukemia, or melanoma.

In another aspect, the invention provides the use of compounds described by any one of the preceding aspects (and any embodiment thereof), as defined above, for the preparation of a medicament for the treatment of medical conditions that benefit from the inhibition of enzymatic activity of IDO1 and/or TDO2. Medical conditions contemplated in this aspect include all the conditions described herein.

In another aspect, the invention provides a use of compounds described by any one of the preceding aspects (and any embodiment thereof), as defined above, for the preparation of a medicament to stimulate T cell proliferation or to reverse an immunologic state of anergy or immunosuppression.

In another aspect, the invention provides the use of compounds described by any one of the preceding aspects (and any embodiment thereof), as defined above, for the preparation of a medicament for the treatment of immunosuppression associated with cancer or viral infections.

In one embodiment, the invention provides the use of compounds described in to any one of the preceding aspects (and any embodiment thereof), as defined above, for the preparation of a medicament for the treatment of tumor-specific immunosuppression associated with cancer. Preferably, the cancer is cancer of the colon, pancreas, breast, prostate, lung, brain, ovary, cervix, testes, renal, or head and neck, lymphoma, leukemia, melanoma, and the like.

Definitions

Terms used herein may be preceded and/or followed by a single dash, "-", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl, arylalkyl-, and -alkylaryl indicate the same functionality.

Further, certain terms herein may be used as both monovalent and divalent linking radicals as would be familiar to those skilled in the art, and by their presentation linking between two other moieties. For example, an alkyl group can be both a monovalent radical or divalent radical; in the latter case, it would be apparent to one skilled in the art that an additional hydrogen atom is removed from a monovalent alkyl radical to provide a suitable divalent moiety.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC(CH_3)$—, —$CH_2CH(CH_2CH_3)CH_2$—. A $C_x$-$C_y$ alkyl or cycloalkyl (as defined below) represents a Markush group of alkyl or cycloalkyl groups, respectively, with a backbone of x, x+1, x+2 . . . y−1, or y carbon atoms. So, for example, a $C_1$-$C_3$alkyl represents a Marksuh group consisting of $C_1$alkyl (i.e., methyl). $C_2$alkyl (i.e., ethyl), and $C_3$alkyl (i.e., n-propyl and i-propyl).

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[b]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The term "arylalkyl," "-alkylaryl," and "arylalkyl-" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 10 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, 3 or 4). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane and adamantane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or this. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

"Cycloalkenyl" as used herein refers to a monocyclic or a bicyclic cycloalkenyl ring system. Monocyclic ring systems are cyclic hydrocarbon groups containing from 3 to 10 carbon atoms, where such groups are unsaturated (i.e., containing at least one annular carbon-carbon double bond), but not aromatic. Examples of monocyclic ring systems include cyclopentenyl and cyclohexenyl. Bicyclic cycloalkenyl rings are bridged monocyclic rings or a fused bicyclic rings. Bridged monocyclic rings contain a monocyclic cycloalkenyl ring where two non-adjacent carbon atoms of the monocyclic ring are linked by an alkylene bridge of between one and three additional carbon atoms (i.e., a bridging group of the form —(CH$_2$)$_w$—, where w is 1, 2, 3 or 4). Representative examples of bicyclic cycloalkenyls include, but are not limited to, norbornenyl and bicyclo[2.2.2]oct-2-enyl. Fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. The bridged or fused bicyclic cycloalkenyl is attached to the parent molecular moiety through any carbon atom contained within the monocyclic cycloalkenyl ring. Cycloalkenyl groups are optionally substituted with one or two groups which are independently oxo or thia.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring or a monocyclic heteroaryl, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The term "heteroarylalkyl" and "-alkylheteroaryl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, pyridin-4-ylmethyl, pyrimidin-5-ylmethyl, 2-(pyrimidin-2-yl)propyl, thien-2-ylmethyl, and thien-3-ylmethyl.

The term "heterocyclyl" as used herein, means a monocyclic heterocycle, a bicyclic heterocycle or a bridged heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. The bridged heterocycle is a 5, 6 or 7 membered monocyclic heterocycle where two non-adjacent atoms of the monocyclic ring are linked by an alkylene bridge between one and four carbon atoms (i.e., a bridging group of the form —(CH$_2$)$_w$—, where w is 1, 2, 3 or 4). The monocyclic heterocycle can one, two or three heteroatoms selected from the group consisting of O, N and S. Representative examples of bridged heterocycles include, but are not limited to, 8-azabicyclo[3.2.1]octanyl.

The term "hydroxy" as used herein, means an —OH group.

The term "nitro" as used herein, means a —NO$_2$ group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and die like.

The term "spiro" as used herein refers to a cyclic moiety formed by the substituted atom and two available substitutable positions on that same atom. For example, moiety such as

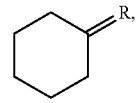

where R is a spiro-cycloalkyl= group includes compounds such as

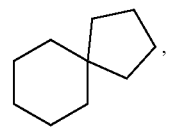

where the spiro-cyclopentyl group is the R group attached to the parent cyclohexyl ring by two single bonds. Similarly, where R is a spiro-heterocyclyl group, such compounds include

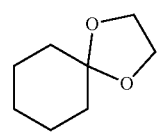

where the spiro-1,3-dioxolanyl ring is the R group attached to the parent cyclohexyl ring by two single bonds.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

As used herein, the term "optionally substituted" means that the referenced chemical structure is unsubstituted or contains at least one substituent selected from the list consisting of halogen, cyano, nitro, $C_{1-6}$alkyl, $C_{1-6}$alkenyl, $C_{1-6}$alkynyl, $C_{1-6}$haloalkyl, —O—$C_{1-6}$alkyl, —O—$C_{1-6}$alkenyl, —O—$C_{1-6}$alkynyl, —O—$C_{1-6}$haloalkyl, $C_{1-6}$alkylcyano, —OH, —OMe, —NH$_2$, —N(H)Me, —NHC(O)Me, —SH and —SMe.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the TDO2 enzyme with a compound includes the administration of a compound described herein to an individual or patient, such as a human, having TDO2, as well as, for example, introducing a compound into a sample containing a cellular or purified preparation containing the TDO2 enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for
  (1) preventing the disease; for example, preventing a disease, condition or disorder in an individual who may be predisposed to the disease, condition or disorder but does not yet experience or display the pathology or symptomotology of the disease;
  (2) inhibiting the disease; for example, inhibiting a disease, condition or disorder in an individual who is experiencing or displaying the pathology or symptomotology of the disease, condition or disorder; or
  (3) ameliorating the disease; for example, ameliorating a disease, condition or disorder in an individual who is experiencing or displaying the pathology or symptomotology of the disease, condition or disorder (i.e., reversing the pathology and/or symptomotology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomotology of the disease, condition or disorder (i.e., reversing or improving the pathology and/or symptomotology) such as decreasing the severity of disease; or (ii) eliciting the referenced biological effect (e.g., TDO2 modulation or tryptophan degradation inhibition).

Manifestation of amelioration of a disease condition with underlying TDO2-mediated immunosuppression may require the concomitant or sequential administration of additional therapeutic agents, such as antineoplastic agents in the case of cancer, or antiretroviral agents in the case of viral diseases. For example, administration of TDO2 inhibitors for the treatment of cancer does not always produce a direct antitumor effect when used as a single agent. However, when combined with chemotherapeutic drugs (antineoplastic) the antitumor effect observed is higher than the sum of effects of each agent alone.

As used herein, the terms "catalytic pocket", "catalytic site", "active site" collectively and indistinctly refer to a region of the enzyme that contains amino acid residues responsible for the substrate binding (charge, hydrophobicity, steric hindrance) and catalytic amino acid residues which act as proton donors or acceptors or are responsible for binding a cofactor and participate in the catalysis of a chemical reaction.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—(CH$_2$)—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

Methods of Use

The compounds and pharmaceutical compositions described herein can modulate activity of the enzyme tryptophan 2,3-dioxygenase (TDO2). The term "modulate" is meant to refer to an ability to decrease activity of an enzyme or receptor. Accordingly, compounds described herein can be used in methods of modulating TDO2 by contacting the enzyme with any one or more of the compounds or compositions described herein. In some embodiments, the compounds described herein can act as inhibitors of TDO2. In further embodiments, the compounds described herein can be used to modulate activity of TDO2 in cell or in an individual in need of modulation of the enzyme by administering a modulating (e.g., inhibiting) amount of a compound described herein.

Further provided are methods of inhibiting the degradation of tryptophan and preventing the production of N-formylkynurenine in a system containing cells expressing TDO2 such as a tissue, living organism, or cell culture. In some embodiments methods of altering (e.g., increasing) extracellular tryptophan levels in a mammal comprise administering an effective amount of a compound or pharmaceutical composition provided herein. Methods of measuring tryptophan levels and tryptophan degradation are routine in the art.

Further provided are methods of inhibiting immunosuppression such as TDO2-mediated immunosuppression in a patient by administering to the patient an effective amount of a compound or composition recited herein. TDO2-mediated immunosuppression has been associated with, for example, cancers, tumor growth, metastasis, infectious diseases (e.g., viral infection), viral replication, etc.

Further provided are methods for treating tumor-specific immunosuppression associated with cancer in a patient by administering to the patient an effective amount of a compound or composition recited herein. Example tumor-specific immunosuppression associated with cancers treatable by the methods herein include immunosuppression associated with cancer of the colon, pancreas, breast, prostate, lung, brain, ovary, cervix, testes, renal, head and neck, lymphoma, leukemia, melanoma, and the like.

For example, a patient undergoing or having completed a course of chemotherapy and/or radiation therapy for the treatment of a disease state, such as a cancer, can benefit from administering to the patient a therapeutically effective amount of a compound or composition recited herein for inhibiting immunosuppression resulting from the disease state and/or treatment thereof.

Further provided are methods of treating diseases associated with activity or expression, including abnormal activity and/or overexpression, of TDO2 in an individual (e.g., patient) by administering to the individual in need of such treatment a therapeutically effective amount or dose of a compound described herein or a pharmaceutical composition thereof. Example diseases can include any disease, disorder or condition that is directly or indirectly linked to expression or activity of the TDO2 enzyme, such as over expression or abnormal activity. An TDO2-associated disease can also include any disease, disorder or condition that can be prevented, ameliorated, or cured by modulating enzyme activity.

Examples of TDO2-associated diseases include cancer, viral infection such as HIV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, inflammatory bowel disease, psoriasis and systemic lupus erythematosusor. Example cancers treatable by the methods herein include cancer of the colon, pancreas, breast, prostate, lung, brain, ovary, cervix, testes, renal, head and neck, lymphoma, leukemia, melanoma, and the like.

Combination Therapy

One or more additional pharmaceutical agents for treatment methods such as, for example, anti-viral agents, chemotherapeutics or other anti-cancer agents, immune enhancers, immunosuppressants, radiation, anti-tumor and antiviral vaccines, cytokine therapy (e.g., IL2, GM-CSF, etc.), and/or indoleamine 2,3-dioxygenase (IDO) inhibitors can be used in combination with the compounds and pharmaceutical compositions described herein for treatment of TDO2-associated diseases, disorders or conditions (as noted above) or for enhancing the effectiveness of the treatment of a disease state or condition, such as cancer. The agents can be combined with the present compounds in a single dosage form, or the agents can be administered simultaneously or sequentially as separate dosage forms.

Therapeutic agents that constitute the standard of care for a particular cancer type or infectious disease are expected to benefit when combined with TDO2 inhibitors of the present invention. For example, for the case of tumors, is it preferable that the tumor is sensitive to the cytotoxic effects of the chemotherapeutic agent in order to stimulate the release of antigens that will eventually mediate an immune response that will be enhanced by addition of TDO2 inhibitors to the combination treatment. A person of skill in the art will know how to select such chemotherapeutic agent based on the clinical characteristics and known sensitivity of each tumor to different antineoplastic agents.

Suitable antiviral agents contemplated for use in combination with the compounds described herein can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2′,3′-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimid-1 nedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol™), docetaxel, mithramycin, deoxyco-formycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4,4-1BB, or antibodies to cytokines (IL-10, TGF-β, etc.).

Other anti-cancer agents also include those that block immune cell migration such as antagonists to chemokine receptors, including CCR2, CCR4 and CCR6.

Other anti-cancer agents also include those that augment the immune system such adoptive T cell transfer.

Anti-cancer vaccines include dendritic cells, synthetic peptides, DNA vaccines and recombinant viruses.

The compounds of the present application can also be used in combination therapy with therapeutic treatments suppressing or inhibiting biologic pathways modulated by PD-1 (programmed cell death protein 1) or its ligand PD-L1. Such therapeutic treatments include those that suppress or inhibit the expression of PD-1 or PD-L1 as well as those that suppress or inhibit the activity of the PD-1 or PD-L1 proteins themselves. Examples of anti-PD-1 compounds include, for example, pembrolizumab, nivolumab, pidilizumab, and BMS 936559. Examples of anti-PD-L1 include, for example, atezolizumab and avelumab.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by a variety of mutes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as anti-viral agents, vaccines, antibodies, immune enhancers, immune suppressants, anti-inflammatory agents and the like.

The following examples are offered for illustrative purposes, and are not intended to limit the disclosure in any manner. Those of skill in the art will readily recognize a variety of noncritical parameters which can be changed or modified to yield essentially the same results. The example compounds below were found to be inhibitors of TDO2 according to one or more of the assays described herein.

Kits.

Also included are pharmaceutical kits useful, for example, in the treatment or prevention of TDO2-associated diseases or disorders, obesity, diabetes and other diseases referred to herein which include one or more containers containing a pharmaceutical composition comprising a therapeutically effective amount of a compound described herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The following examples are offered for illustrative purposes, and are not intended to limit the disclosure in any manner. Those of skill in the art will readily recognize a variety of noncritical parameters which can be changed or modified to yield essentially the same results. The example compounds below were found to be inhibitors of TDO2 according to one or more of the assays described herein.

EXAMPLES

All reagents and solvents were purchased from commercial sources. All commercial reagents and solvents were used as received without further purification. The reactions were monitored using analytical thin layer chromatography (TLC) with 0.25 mm EM Science silica gel plates (60F-254). The developed TLC plates were visualized by short wave UV light (254 nm) or immersion in potassium permanganate solution followed by heating on a hot plate. Flash chromatography was performed with Selecto Scientific silica gel, 32-63 µm particle sizes. All reactions were performed in flame or oven-dried glassware under a nitrogen atmosphere. All reactions were stirred magnetically at ambient temperature unless otherwise indicated. $^1$H NMR spectra were obtained with a Bruker DRX400, Varian VXR400 or VXR300. $^1$H NMR spectra were reported in parts per million (δ) relative to TMS (0.0), DMSO-d6 (2.50) or CD$_3$OD (4.80) as an internal reference. All $^1$H NMR spectra were taken in CDCl3 unless otherwise indicated. The phosphonates were prepared according to the literature procedure: (Patent: U.S. Pat. No. 5,807,892 A1, 1998; Patent: US2012/033245; Patent: US2008/306084 A1, 2008). 1-(azidomethyl)-2,4-dimethoxybenzene was synthesized according to ChemMedChem, 2011, vol. 6, #5, 840-847.

Example 1: tert-butyl 1-hydroxy-2-(5H-imidazo[5,1-a]isoindol-5-yl)-7-azaspiro[3.5]nonane-7-carboxylate

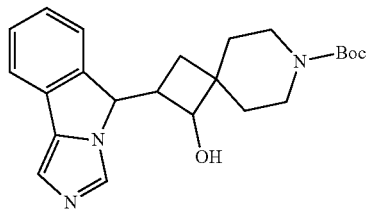 [SMILES: CC(C)(C)OC(=O)N1CCC2(CC1)CC(C1c3ccccc3-c3cncn31)C2O]

tert-butyl (1S,2R)-1-hydroxy-2-((R)-5H-imidazo[5,1-a]isoindol-5-yl)-7-azaspiro[3.5]nonane-7-carboxylate
tert-butyl (1R,2S)-1-hydroxy-2-((S)-5H-imidazo[5,1-a]isoindol-5-yl)-7-azaspiro[3.5]nonane-7-carboxylate Step 1:
tert-butyl(2E)-1-oxo-2-([2-[1-(triphenylmethyl)-1H-imidazol-4-yl]phenyl]methylidene)-7-azaspiro[3.5]nonane-7-carboxylate

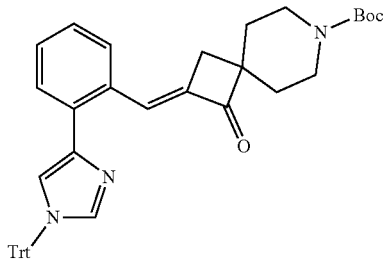

A slurry of tert-butyl1-oxo-7-azaspiro [3.5]nonane-7-carboxylate (2.27 g, 9.49 mmol), 2-[1-(triphenylmethyl)-1H-imidazol-4-yl]benzaldehyde (4.04 g, 9.74 mmol) and $C_a(OH)_2$ (2.10 g, 28.33 mmol) in EtOH (100 mL) were mixed and stirred overnight at 80° C. The solids were filtered out. The resulting mixture was concentrated under vacuum. This resulted in 7.4 g (crude) of tert-butyl(2E)-1-oxo-2-([2-[1-(triphenylmethyl)-1H-imidazol-4-yl]phenyl]methylidene)-7-azaspiro[3.5]nonane-7-carboxylate as a yellow solid. LCMS (ESI) m/z=636.2 [M+H]+

Step 2:
tert-butyl2-[5H-imidazo[4,3-a]isoindol-5-yl]-1-oxo-7-azaspiro[3.5]nonane-7-carboxylate

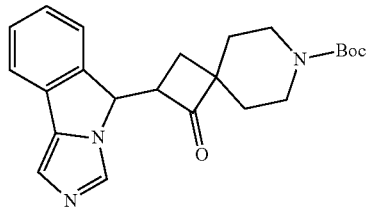 [SMILES: CC(C)(C)OC(=O)N1CCC2(CC1)CC(C1c3ccccc3-c3cncn31)C2=O]

To a solution of tert-butyl(2E)-1-oxo-2-([2-[1-(triphenylmethyl)-1H-imidazol-4-yl]phenyl]methylidene)-7-azaspiro [3.5]nonane-7-carboxylate (7.4 g, 11.64 mmol) in MeOH (150 mL) was added acetic acid (8 mL). The resulting solution was stirred overnight at 70° C. The resulting mixture was concentrated under vacuum. The residue was purified by a silica gel column eluting with DCM/MeOH (97:3) to afford 4 g (87%) of tert-butyl2-[5H-imidazo[4,3-a]isoindol-5-yl]-1-oxo-7-azaspiro[3.5]nonane-7-carboxylate as a yellow solid. LCMS (ESI) m/z=394.2 [M+H]+.

Step 3:
tert-butyl (1S,2R)-1-hydroxy-2-((R)-5H-imidazo[5,1-a]isoindol-5-yl)-7-azaspiro[3.5]nonane-7-carboxylate
tert-butyl (1R,2S)-1-hydroxy-2-((S)-5H-imidazo[5,1-a]isoindol-5-yl)-7-azaspiro[3.5]nonane-7-carboxylate

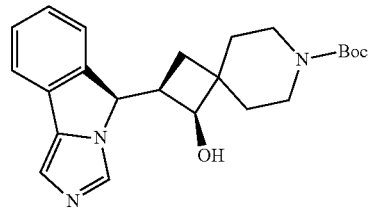

1a

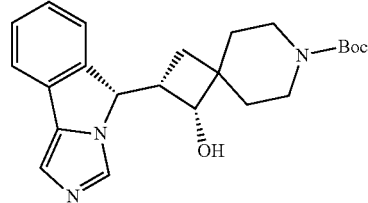

1b

To a solution of tert-butyl2-[5H-imidazo[4,3-a]isoindol-5-yl]-1oxo-7-azaspiro[3.5]nonane-7-carboxylate (8.4 g, 21.35 mmol) in MeOH (150 mL) was added $NaBH_4$ (2.43 g, 64.23 mmol) in portions at 0° C. The resulting solution was stirred for 1 h at room temperature. The reaction was quenched with water (200 mL). The resulting solution was extracted with EtOAc (3×200 mL) and the organic layers combined. The residue was purified by silica gel column eluting with DCM/MeOH (96:4). This resulted in 6.7 g (79%) of tert-butyl1-hydroxy-2-[5H-imidazo[4,3-a]isoindol-5-yl]-7-azaspiro [3.5]nonane-7-carboxylate as a white solid. LCMS (ESI) m/z=396.3 [M+H]+.

The crude product was purified by Combi-Flash and further isolated by chiral separation to afford 2 isomers as white solid.

The absolute configuration of 1a and 1b was assigned arbitrarily.

Example 1a: tert-butyl (1S,2R)-1-hydroxy-2-((R)-5H-imidazo[5,1-a]isoindol-5-yl)-7-azaspiro[3.5]nonane-7-carboxylate. LCMS (ESI) m/z=396.3 [M+H]+. $^1$HNMR (300 MHz, MeOH-d$_4$) δ8.00 (s, 1H), 7.65 (d, J=7.2 Hz, 1H), 7.59 (d, J=7.5 Hz, 1H), 7.41-7.27 (m, 2H), 7.15 (s, 1H), 5.54 (d, J=7.8 Hz, 1H), 4.26-4.23 (m, 1H), 3.60-3.50 (m, 2H), 3.32-3.27 (m, 2H), 2.76-2.71 (m, 1H), 1.88-1.86 (m, 2H), 1.74-1.70 (m, 1H), 1.55-1.50 (m, 3H), 1.47 (s, 9H). tR=2.859 min (CHIRALPAK IA-3, 0.46×5 cm; 3 um, Hex(8 mMNH3):EtOH-90:10, 1.0 mL/min). 1a and 1b are enantiomers.

Example 1b: tert-butyl (1R,2S)-1-hydroxy-2-((S)-5H-imidazo[5,1-a]isoindol-5-yl)-7-azaspiro[3.5]nonane-7-carboxylate. LCMS (ESI) m/z=396.3 [M+H]+. tR=4.930 min (CHIRALPAK IA-3, 0.46×5 cm; 3 um, Hex(8mMNH3):EtOH=90:10, 1.0 mL/min). 1a and 1b are enantiomers.

Example 2: tert-butyl 1-hydroxy-2-(5H-imidazo[5,1-a]isoindol-5-yl)-8-azaspiro[4.5]decane-8-carboxylate

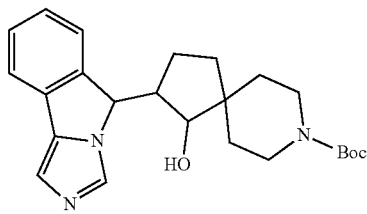 [SMILES: CC(C)(C)OC(=O)N1CCC2(CCC(C3c4ccccc4-c4cncn43)C2O)CC1]

tert-butyl (1S,2S)-1-hydroxy-2-((R)-5H-imidazo[5,1-a]isoindol-5-yl)-8-azaspiro[4.5]decane-8-carboxylate
tert-butyl (1R,2R)-1-hydroxy-2-((S)-5H-imidazo[5,1-a]isoindol-5-yl)-8-azaspiro[4.5]decane-8-carboxylate
tert-butyl (1S,2S)-1-hydroxy-2-((R)-5H-imidazo[5,1-a]isoindol-5-yl)-8-azaspiro[4.5]decane-8 carboxylate
tert-butyl (1R,2R)-1-hydroxy-2-((S)-5H-imidazo[5,1-a]isoindol-5-yl)-8-azaspiro[4.5]decane-8-carboxylate Step 1:
tert-butyl (2E)-1-oxo-2-([2-[1-(triphenylmethyl)-1H-imidazol-4-yl]phenyl]methylidene)-8-azaspiro[4.5]decane-8-carboxylate

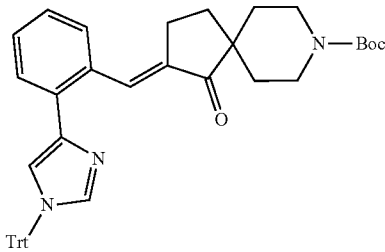

A mixture of tert-butyl 1-oxo-8-azaspiro[4.5]decane-8-carboxylate (3.0 g, 11.84 mmol) and 2-[1-(triphenylmethyl)-1H-imidazol-4-yl]benzaldehyde (5.8 g, 13.99 mmol) in EtOH (100 mL) was added Ca(OH)$_2$ (2.7 g, 36.44 mmol). The resulting solution was stirred for 4 h at 80° C. The resulting mixture was concentrated under vacuum. The resulting solution was diluted with DCM (600 mL). The solid were filtered out. The filtration was concentrated under vacuum. The residue was purified by a silica gel column with EtOAc/PE (30%-80%). This resulted in 7.5 g (97%) of tert-butyl (2E)-1-oxo-2-([2-[1-(triphenylmethyl)-1H-imidazol-4-yl]phenyl]methylidene)-8-azaspiro[4.5]decane-8-carboxylate as a light yellow solid. LCMS (ESI) m/z=650.3 [M+H]$^+$.

Step 2:
tert-butyl 2-[5H-imidazo[4,3-a]isoindol-5-ylidene]-8-azaspiro[4.5]decane-8-carboxylate

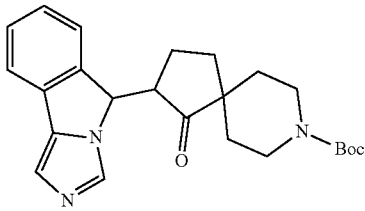 [SMILES: CC(C)(C)OC(=O)N1CCC2(CCC(C3c4ccccc4-c4cncn43)C2=O)CC1]

To a solution of tert-butyl (2E)-1-oxo-2-([2-[1-(triphenylmethyl)-1H-imidazol-4-yl]phenyl]methylidene)-8-azaspiro[4.5]decane-8-carboxylate (7.5 g, 11.54 mmol) in MeOH (120 mL) was added AcOH (24 mL). The resulting solution was stirred for 16 h at 80° C. The resulting mixture was concentrated under vacuum. The resulting residue was diluted with EtOAc (600 mL) and then washed with aq. Na$_2$CO$_3$ (2×100 mL). The organic layers were combined and dried over anhydrous sodium sulfate and concentrated under vacuum. The residue was purified by a silica gel column eluting with DCM/MeOH (0-10%) to give 5.0 g (95%) of tert-butyl 2-[5H-imidazo[4,3-a]isoindol-5-yl]-1-oxo-8-azaspiro[4.5]decane-8-carboxylate as a yellow solid. LCMS (ESI) m/z=408.3 [M+H]$^+$.

Step 3:
tert-butyl (1S,2S)-1-hydroxy-2-((R)-5H-imidazo[5,1-a]isoindol-5-yl)-8-azaspiro[4.5]decane-8-carboxylate
tert-butyl (1R,2R)-1-hydroxy-2-((S)-5H-imidazo[5,1-a]isoindol-5-yl)-8-azaspiro[4.5]decane-8-carboxylate
tert-butyl (1R,2S)-1-hydroxy-2-((S)-5H-imidazo[5,1-a]isoindol-5-yl)-8-azaspiro[4.5]decane-8-carboxylate
tert-butyl (1S,2R)-1-hydroxy-2-((R)-5H-imidazo[5,1-a]isoindol-5-yl)-8-azaspiro[4.5]decane-8-carboxylate 2a
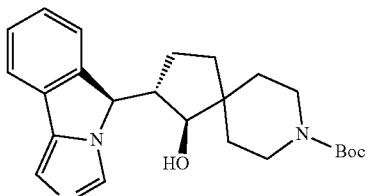

2b
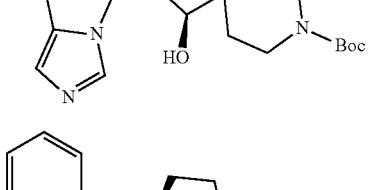

2c
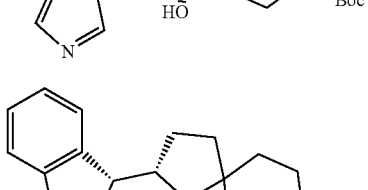

-continued

2d

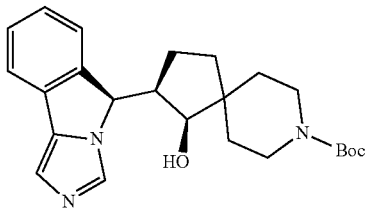

To a solution of tert-butyl 2-[5H-imidazo[4,3-a]isoindol-5-yl]-1-oxo-8-azaspiro[4.5]decane-8-carboxylate (5.0 g, 12.270 mmol) in MeOH (100 mL) was added NaBH$_4$ (2.8 g, 74.01 mmol). The resulting solution was stirred for 20 min at 0° C. The reaction was then quenched by the addition of water (50 mL). The MeOH was removed under vacuum. The resulting solution was extracted with DCM (3×200 mL) and the organic layers combined. The solution was dried over sodium sulfate and concentrated under vacuum. The residue was applied onto a silica gel column with DCM/MeOH (0-10%). This resulted in 4.0 g (80%) of tert-butyl 1-hydroxy-2-[5H-imidazo[4,3-a]isoindol-5-yl]-8-azaspiro[4.5]decane-8-carboxylate as an off-white solid. LCMS (ESI) m/z=410.1 [M+H]$^+$.

The crude product was purified by Prep-HPLC and further isolated by chiral separation to afford 4 isomers as white solids.

1. Column: XBridge Prep C18 OBD Column 19×150 mm 5 um; Mobile Phase A: Water (10 MMOL/L NH4HCO3), Mobile Phase B: ACN; Flow rate: 20 mL/min; Gradient: 20% B to 40% B in 10 min; 254220 nm; Rt: 8.9, 9.65 min
2. Column: Phenomenex Lux 5u Cellulose-4, AX1A Packed, 2.12×25 cm, 5 um; Mobile Phase A: Mobile Phase B: MeOH—HPLC; Flow rate: 20 mL/min; Gradient: 100 B to 100 B in 20 min; 254/220 nm; RT1:7.201; RT2: 15.478
3. Column: CHIRALPAK IA, 2.12×15 cm, 5 um; Mobile Phase A: Hex-HPLC, Mobile Phase B: EtOH—HPLC; Flow rate: 20 mL/min; Gradient: 30 B to 30 B in 30 min; 254/220 nm; RT1: 4.917; RT2: 16.96

The absolute configuration of 2a-2d was assigned arbitrarily.

Example 2a: tert-butyl (1S,2S)-1-hydroxy-2-((R)-5H-imidazo[5,1-a]isoindol-5-yl)-8-azaspiro[4.5]decane-8-carboxylate as a white solid. LCMS (ESI) m/z=410.2 [M+H]; $^1$HNMR (400 MHz, DMSO-d$_6$) δ 8.02 (s, 1H), 7.61 (d, J=7.6 Hz, 1H), 7.53 (d, J=7.6 Hz, 1H), 7.41-7.37 (m, 1H), 7.29-7.25 (m, 1H), 7.15 (s, 1H), 5.47 (d, J=4.0 Hz, 1H), 5.00 (d, J=5.6 Hz, 1H), 3.83-3.63 (m, 2H), 3.56-3.52 (m, 1H), 2.90-2.51 (m, 3H), 1.63-1.49 (m, 3H), 1.39 (s, 9H), 1.35-1.03 (m, 4H), 0.87-0.86 (m, 1H). tR=1.054 min (CHIRALPAK IA-3, 0.46×5 cm; 3 um, Hex(8 mMNH3):EtOH=50:50, 1.0 mL/min). 2a and 2b are enantiomers.

Example 2b: tert-butyl (R,2R)-1-hydroxy-2-((S)-5H-imidazo[5,1-a]isoindol-5-yl)-8-azaspiro[4.5]decane-8-carboxylate. LCMS (ESI) m/z=410.2 [M+H]$^+$. tR=1.572 min (CHIRALPAK IA-3, 0.46×5 cm; 3 um, Hex(8 mMNH3):EtOH-50:50, 1.0 mL/min). 2a and 2b are enantiomers.

Example 2c: tert-butyl (1R,2S)-1-hydroxy-2-((S)-5H-imidazo[5,1-a]isoindol-5-yl)-8-azaspiro[4.5]decane-8-carboxylate as a white solid. LCMS (ESI) m/z=410.2 [M+H]$^+$; $^1$HNMR (400 MHz, DMSO-d6) δ 7.94 (s, 1H), 7.67 (d, J=7.6 Hz, 1H), 7.59 (d, J=7.6 Hz, 1H), 7.40-7.36 (m, 1H), 7.29-7.25 (m, 1H), 7.14 (s, 1H), 5.41 (d, J=4.0 Hz, 1H), 5.33 (d, J=5.6 Hz, 1H), 3.91-3.88 (m, 1H), 3.62-3.58 (m, 1H), 3.47-3.43 (m, 1H), 3.04-2.93 (m, 2H), 2.33-2.28 (m, 1H), 1.73-1.43 (m, 6H), 1.39 (s, 9H), 1.24-1.18 (m, 2H). tR=1.534 min (CHIRALPAK IA-3, 0.46×5 cm; 3 um, Hex(8 mMNH3):EtOH=80:20, 1.0 mL/min). 2c and 2d are enantiomers.

Example 2d: tert-butyl (1S,2R)-1-hydroxy-2-((R)-5H-imidazo[5,1-a]isoindol-5-yl)-8-azaspiro[4.5]decane-8-carboxylate. LCMS (ESI) m/z=410.2 [M+H]$^+$. tR=1.921 min (CHIRALPAK IA-3, 0.46×5 cm; 3 um, Hex(8 mMNH3):EtOH-80:20, 1.0 mL/min). 2c and 2d are enantiomers.

Example 3: tert-butyl 5-hydroxy-6-(5H-imidazo[4,3-a]isoindol-5-yl)-2-azaspiro[3.4]octane-2-carboxylate

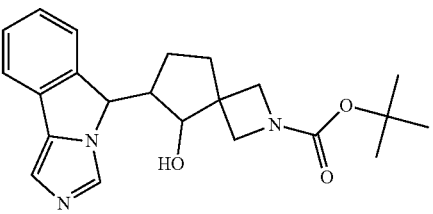 [SMILES: CC(C)(C)OC(=O)N1CC2(CCC(C3c4ccccc4-c4cncn43)C2O)C1]

tert-butyl (5R,6S)-5-hydroxy-6-[(5S)-5H-imidazo[1,5-b]isoindol-5-yl]-2-azaspiro[3.4]octane-2-carboxylate
tert-butyl (5S,6R)-5-hydroxy-6-[(5R)-5H-imidazo[1,5-b]isoindol-5-yl]-2-azaspiro[3.4]octane-2-carboxylate
tert-butyl (5S,6S)-5-hydroxy-6-[(5R)-5H-imidazo[1,5-b]isoindol-5-yl]-2-azaspiro[3.4]octane-2-carboxylate
tert-butyl (5R,6R)-5-hydroxy-6-[(5S)-5H-imidazo[1,5-b]isoindol-5-yl]-2-azaspiro[3.4]octane-2-carboxylate
tert-butyl (5S,6S)-5-hydroxy-6-[(5S)-5H-imidazo[1,5-b]isoindol-5-yl]-2-azaspiro[3.4]octane-2-carboxylate
tert-butyl (5R,6R)-5-hydroxy-6-[(5R)-5H-imidazo[1,5-b]isoindol-5-yl]-2-azaspiro[3.4]octane-2-carboxylate
tert-butyl (5R,6S)-5-hydroxy-6-[(5R)-5H-imidazo[1,5-b]isoindol-5-yl]-2-azaspiro[3.4]octane-2-carboxylate
tert-butyl (5S,6R)-5-hydroxy-6-[(5S)-5H-imidazo[1,5-b]isoindol-5-yl]-2-azaspiro[3.4]octane-2-carboxylate Step 1:
tert-butyl (6E)-5-oxo-6-([2-[1-(triphenylmethyl)-1H-imidazol-4-yl]phenyl]methylidene)-2-azaspiro[3.4]octane-2-carboxylate

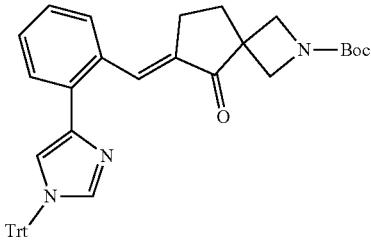

To a solution of tert-butyl 5-oxo-2-azaspiro[3.4]octane-2-carboxylate (2 g, 8.89 mmol), 2-[1-(triphenylmethyl)-1H-imidazol-4-yl]benzadehyde (5.53 g, 13.34 mmol) and Ca(OH)$_2$ (1.64 g, 22.13 mmol) in EtOH (250 mL) was stirred for 6 h at 80° C. The solids were filtered out. The solids were filtered out. The solvent was concentrated under vacuum. The residue was purified by silica gel column eluting with EtOAc/PE (1:2). This resulted in 5.24 g (95%) of tert-butyl (6E)-5-oxo-6-([2-[1-(triphenylmethyl)-1H-imidazol-4-yl]phenyl]methylidene)-2-azaspiro[3.4]octane-2-carboxylate as a light yellow solid. LCMS (ESI) m/z=622.8 [M+H]⁺.

Step 2:
tert-butyl 6-[5H-imidazo[4,3-a]isoindol-5-yl]-5-oxo-2-azaspiro[3.4]octane-2-carboxylate

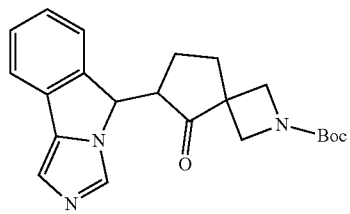 [SMILES: CC(C)(C)OC(=O)N1CC2(CCC(C3c4ccccc4-c4cncn43)C2=O)C1]

A solution of tert-butyl(2E)-1-oxo-2-([2-[1-(triphenylmethyl)-1H-imidazol-4-yl]phenyl]methylidene)-7-azaspiro[3.5]nonane-7-carboxylate (7.4 g, 11.64 mmol) in MeOH (150 mL) was added AcOH (8 mL). The resulting solution was stirred for 1 overnight at 70° C. The resulting mixture was concentrated under vacuum. The residue was purified by a silica gel column eluting with DCM/MeOH (97:3). This resulted in 4 g (87%) of tert-butyl 6-[5H-imidazo[4,3-a]isoindol-5-yl]5-oxo-2-azaspiro[3.4]octane-2-carboxylate as a yellow solid. LCMS (ESI) m/z 380.2 [M+H]⁺.

Step 3:
tert-butyl (5R,6S)-5-hydroxy-6-[(5S)-55H-imidazo[1,5-b]isoindol-5-yl]-2-azaspiro[3.4]octane-2-carboxylate
tert-butyl (5S,6R)-5-hydroxy-6-[(5R)-5H-imidazo[1,5-b]isoindol-5-yl]-2-azaspiro[3.4]octane-2-carboxylate
tert-butyl (5S,6S)-5-hydroxy-6-[(5R)-5H-imidazo[1,5-b]isoindol-5-yl]-2-azaspiro[3.4]octane-2-carboxylate
tert-butyl (5R,6R)-5-hydroxy-6-[(5S)-5H-imidazo[1,5-b]isoindol-5-yl]-2-azaspiro[3.4]octane-2-carboxylate
tert-butyl (5S,6S)-5-hydroxy-6-[(5S)-5H-imidazo[1,5-b]isoindol-5-yl]-2-azaspiro[3.4]octane-2-carboxylate
tert-butyl (5R,6R)-5-hydroxy-6-[(5R)-5Himidazo[1,5-b]isoindol-5-yl]-2-azaspiro[3.4]octane-2-carboxylate
tert-butyl (5R,6S)-5-hydroxy-6-[(R)-5Himidazo[1,5-b]isoindol-5-yl]-2-azaspiro[3.4]octane-2-carboxylate
tert-butyl (5S,6R)-5-hydroxy-6-[(S)-5Himidazo[1,5-b]isoindol-5-yl]-2-azaspiro[3.4]octane-2-carboxylate 3a
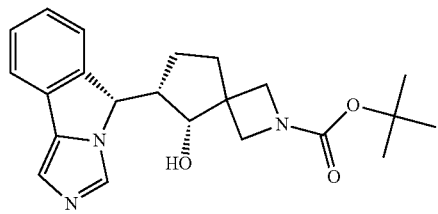

3b
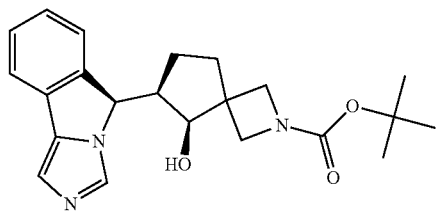

3c
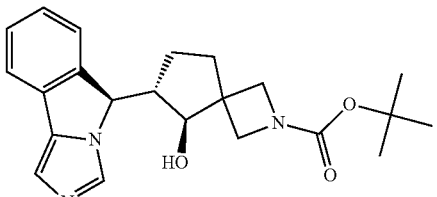

3d
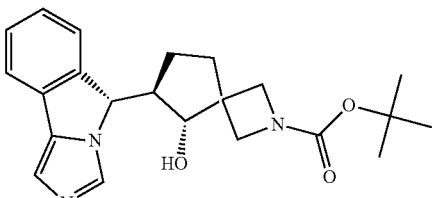

3e
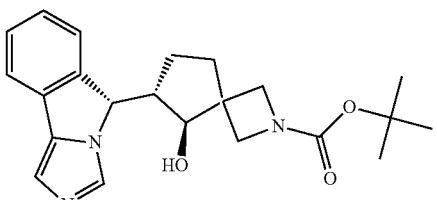

3f
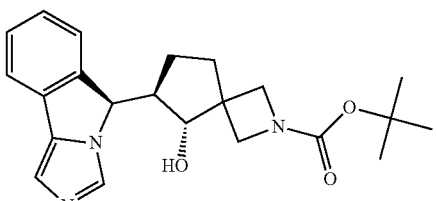

3g
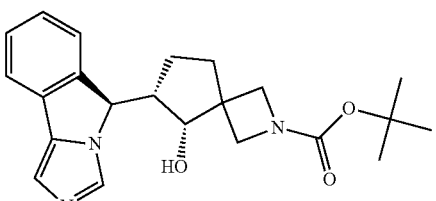

3h
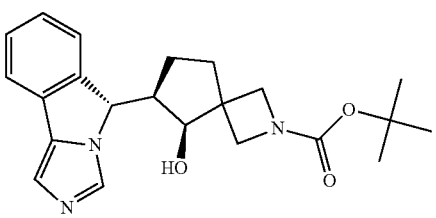

To a solution of tert-butyl 6-[5H-imidazo[4,3-a]isoindol-5-yl]-5-oxo-2-azaspiro[3.4]octane-2-carboxylate (2.7 g, 7.12 mmol) in MeOH (100 mL) was added NaBH₄ (2.16 g, 57.10 mmol) at 0° C. The resulting solution was stirred for 30 in at rt. The reaction was then quenched by the addition of water (50 mL). The resulting solution was extracted with EtOAc (3×100 mL) and the organic layers combined. The resulting mixture was washed with brine (1×50 mL). The mixture was dried over anhydrous sodium sulfate and concentrated under vacuum. The residue was further isolated by Prep-HPLC and chiral separation with the following conditions:

1. Column: XBridge Prep C18 OBD Column 19×150 mm 5 um; Mobile Phase A: Water (10 MMOL/L NH4HCO3), Mobile Phase B: ACN; Flow rate: 20 mL/min; Gradient: 20% B to 65% B in 40 min; 254/220 nm; Rt: 25, 27, 29, 31 min.

2. Column: Chiralpak IC, 2×25 cm, 5um; Mobile Phase A: Hex-HPLC, Mobile Phase B: EtOH—HPLC; Flow rate: 16 mL/min; Gradient: 50 B to 50 B in 14.5 min; 220/254 nm; RT1: 7.71; RT2: 11.843.

3. Column: Phenomenex Lux 5u Cellulose-4, AXIA Packed, 2.12×25 cm, 5 um; Mobile Phase A: Hex(0.1% DEA)-HPLC, Mobile Phase B: EtOH—HPLC; Flow rate: 20 mL/min; Gradient: 30 B to 30 B in 14.5 min; 220/254 nm; RT1: 9.38; RT2: 12.11.

4. Column: CHIRALPAK IC, 2×25 cm, 5um; Mobile Phase A: Hex(0.1% DEA)-HPLC, Mobile Phase B: IPA-HPLC; Flow rate: 16 mL/min; Gradient: 50 B to 50 B in 16 min; 220/254 nm; RT1: 8.588; RT2: 11.281.

5. Column: CHIRALPAK IC, 2×25 cm, 5 um; Mobile Phase A: Hex-HPLC, Mobile Phase B: EtOH—HPLC; Flow rate: 20 mL/min; Gradient: 40 B to 40 B in 16 min; 254/220 nm; RT1: 7.772; RT2: 12.877.

The absolute configuration of 3a-3b was assigned arbitrarily.

Example 3a: tert-butyl (5R,6S)-5-hydroxy-6-[(5S)-5H-imidazo[1,5-b]isoindol-5-yl]-2-azaspiro[3.4]octane-2-carboxylate (18.7 mg, 0.7%) as a light yellow solid. LCMS (ESI) m/z=382.5 [M+H]$^+$. $^1$H NMR (300 MHz, DMSO-d$_6$) δ 7.92 (s, 1H), 7.61 (d, J=7.8 Hz, 1H), 7.53 (d, J=7.8 Hz, 1H), 7.42-7.37 (m, 1H), 7.30-7.24 (m, 1H), 7.13 (s, 1H), 5.44 (d, J=4.2 Hz, 1H), 5.32 (d, J=5.4 Hz, 1H), 4.01-3.99 (m, 1H), 3.66-3.40 (m, 4H), 2.47-2.44 (m, 1H), 1.80-1.73 (m, 1H), 1.60-1.42 (m, 2H), 1.36 (s, 9H), 1.09-0.90 (m, 1H). tR=1.137 min (CHIRALPAK IA-3, 0.46×5 cm; 3 um, Hex (0.1% DEA):EtOH-70:30, 1.0 mL/min). 3a and 3b are enantiomers.

Example 3b: tert-butyl (5S,6R)-5-hydroxy-6-[(5R)-5H-imidazo[1,5-b]isoindol-5-yl]-2-azaspiro[3.4]octane-2-carboxylate (20.7 mg, 0.7%) as a light yellow solid. LCMS (ESI) m/z=382.5 [M+H]$^+$. tR=1.137 min (CHIRALPAK IA-3, 0.46×5 cm; 3 um, Hex(0.1% DEA):EtOH=70:30, 1.0 mL/min). 3a and 3b are enantiomers.

Example 3c: tert-butyl (5R,6S)-5-hydroxy-6-[(5R)-5Himidazo[1,5-b]isoindol-5-yl]-2-azaspiro[3.4]octane-2-carboxylate (4 mg, 0.2%) as a light yellow solid. LCMS (ESI) m/z=382.5 [M+H]$^+$. $^1$H NMR (300 MHz, DMSO-d$_6$) δ 7.95 (s, 1H), 7.59 (d, J=7.2 Hz, 1H), 7.48 (d, J=7.2 Hz, 1H), 7.44-7.22 (m, 2H), 7.18 (s, 1H), 5.65 (d, J=5.5 Hz, 1H), 5.49 (d, J=2.8 Hz, 1H), 4.15-4.05 (m, 1H), 3.94-3.81 (m, 2H), 3.59-3.36 (m, 2H), 2.39-2.28 (m, 1H), 1.75-1.72 (m, 1H), 1.50-1.40 (m, 1H), 2.39 (s, 9H), 1.09-1.00 (m, 1H), 0.61-0.36 (m, 1H). tR=2.411 min (Lux Cellulose-4, 0.46×5 cm; 3 um, Hex(0.1% DEA):EtOH=70:30, 1.0 mL/min). 3c and 3d are enantiomers.

Example 3d: tert-butyl (5R,6R)-5-hydroxy-6-[(5S)-5Himidazo[1,5-b]isoindol-5-yl]-2-azaspiro[3.4]octane-2-carboxylate (2 mg, 0.1%) as a light yellow solid. LCMS (ESI) m/z=382.5 [M+H]$^+$. tR=3.356 min (Lux Cellulose-4, 0.46×5 cm; 3 um, Hex(0.1% DEA):EtOH-70:30, 1.0 mL/min). 3c and 3d are enantiomers.

Example 3e: tert-butyl (5S,6S)-5-hydroxy-6-[(5S)-5Himidazo[1,5-b]isoindol-5-yl]-2-azaspiro[3.4]octane-2-carboxylate (63.6 mg, 2.9%) as a light yellow solid. LCMS (ES) m/z=382.5[M+H]$^+$. $^1$H NMR (300 MHz, DMSO-d$_6$) δ 7.92 (s, 1H), 7.66 (d, J=7.2 Hz, 1H), 7.59 (d, J=7.2 Hz, 1H), 7.41-7.24 (m, 2H), 7.15 (s, 1H), 5.72 (d, J=4.8 Hz, 1-), 5.41 (d, J=7.2 Hz, 1H), 4.19-4.06 (m, 2H), 3.61-3.26 (m, 3H), 2.18-2.14 (m, 1H), 1.94-1.44 (m, 4H), 1.36 (s, 9H). tR=1.784 min (CHIRALPAK IC-3, 0.46×5 cm; 3 um, Hex (0.1% DEA):IPA=50:50, 1.0 mL/min). 3e and 3f are enantiomers.

Example 3f: tert-butyl (5R,6R)-5-hydroxy-6-[(5R)-5Himidazo[1,5-b]isoindol-5-yl]-2-azaspiro[3.4]octane-2-carboxylate (60.7 mg, 2.7%) as a light yellow solid. LCMS (ESI) m/z=382.5 [M+H]$^+$. tR=2.574 min (CHIRALPAK IC-3, 0.46×5 cm; 3 um, Hex(0.1% DEA): IPA=50:50, 1.0 mL/min). 3e and 3f are enantiomers.

Example 3g: tert-butyl (5R,6S)-5-hydroxy-6-[(5R)-5Himidazo[1,5-b]isoindol-5-yl]-2-azaspiro[3.4]octane-2-carboxylate (18 mg, 0.7%) as a light yellow solid. LCMS (ESI) m/z=382.5[M+H]$^+$. $^1$H NMR (300 MHz, DMSO-d$_6$) δ 7.95 (s, 1H), 7.61 (d, J=7.2 Hz, 1H), 7.48 (d, J=7.8 Hz, 1H), 7.41-7.36 (m, 1H), 7.27-7.22 (m, 1H), 7.15 (s, 1H), 5.61 (d, J=5.1 Hz, 1H), 5.28 (d, J=5.1 Hz, 1H), 4.16-4.06 (m, 2H), 3.64-3.62 (m, 1H), 3.50-3.37 (m, 2H), 2.14-1.79 (m, 5H), 1.36 (a, 9H). tR=2.332 min (CHIRALPAK IC-3, 0.46×5 cm; 3 um, Hex(8 mMNH3):EtOH=70:30, 1.0 mL/min). 3g and 3h are enantiomers.

Example 3h: tert-butyl (5S,6R)-5-hydroxy-6-[(5S)-5Himidazo[1,5-b]isoindol-5-yl]-2-azaspiro[3.4]octane-2-carboxylate (20 mg, 0.7%) as a light yellow solid. LCMS (ESI) m/z=382.5 [M+H]$^+$. tR=2.914 mm (CHIRALPAK IC-3, 0.46×5 cm; 3 um, Hex(8 mMNH3):EtOH=70:30, 1.0 mL/min). 3g and 3b are enantiomers.

Example 4: 1-hydroxy-2-(5H-imidazo[4,3-a]isoindol-5-yl)-8-azaspiro[4.5]decane-8-sulfonamide

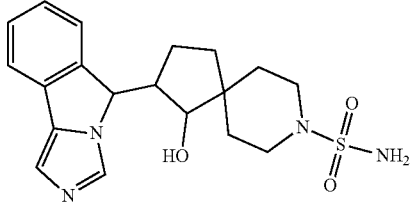 [SMILES: NS(=O)(=O)N1CCC2(CCC(C3c4ccccc4-c4cncn43)C2O)CC1]

(1S,2S)-1-hydroxy-2-[(5R)-5H-imidazo[4,3-a]isoindol-5-yl]-8-azaspiro[4.5]decane-8-sulfonamide
(1R,2R)-1-hydroxy-2-[(5S)-5H-imidazo[4,3-a]isoindol-5-yl]-8-azaspiro[4.5]decane-8-sulfonamide
(1R,2S)-1-hydroxy-2-[(5S)-5H-imidazo[4,3-a]isoindol-5-yl]-8-azaspiro[4.5]decane-8-sulfonamide
(1S,2R)-1-hydroxy-2-[(R)-5H-imidazo[4,3-a]isoindol-5-yl]-8-azaspiro[4.5]decane-8-sulfonamide Step 1:
2-(5H-imidazo[4,3-a]isoindol-5-yl)-8-azaspiro[4.5]decan-1-ol Int-2

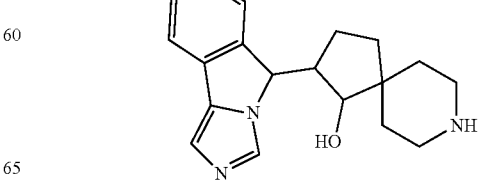

To a solution of tert-butyl 1-hydroxy-2-[5H-imidazo[4,3-a]isoindol-5-yl]-8-azaspiro[4.5]decane-8-carboxylate (200 mg, 0.488 mmol) in DCM (5 mL) was added TFA (2 mL). The solution was stirred for 30 min at room temperature. The resulting mixture was concentrated under vacuum to give 206 mg (crude) of 2-(5H-imidazo[4,3-a]isoindol-5-yl)-8-azaspiro[4.5]decan-1-ol TFA salt as light yellow oil.

Step 2:
(1S,2S)-1-hydroxy-2-[(5R)-5H-imidazo[4,3-a]isoindol-5-yl]-8-azaspiro[4.5]decane-8-sulfonamide
(1R,2R)-1-hydroxy-2-[(5S)-5H-imidazo[4,3-a]isoindol-5-yl]-8-azaspiro[4.5]decane-8-sulfonamide

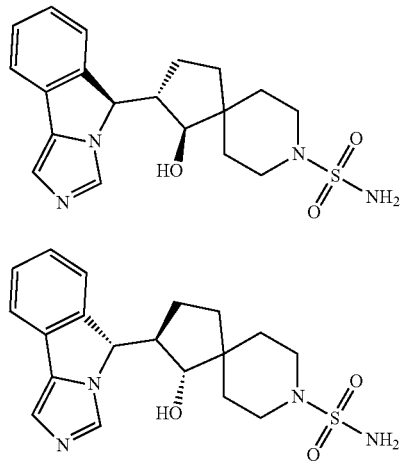

4a

4b

To a solution of [(chlorosulfonyl)imino]methanone (162 mg, 1.15 mmol) in DCM (5 mL) was added tert-butanol (130 mg, 1.75 mmol) at 0° C. The resulting solution was stirred for 30 min at 0° C. The resulting solution was added into a solution of 2-[5H-imidazo[4,3-a]isoindol-5-yl]-8-azaspiro[4.5]decan-1-ol (310 mg, 0.90 mmol) and TEA (0.5 mL, 3.60 mmol) in DCM (10 mL). The resulting solution was stirred for an additional 1 h at it. The reaction was then quenched by the addition of water (50 mL). The reaction mixture was extracted with DCM (3×30 mL) and the organic layers were combined. The organics were dried over anhydrous sodium sulfate and concentrated under vacuum. The residue was purified by a silica gel column eluting with DCM/MeOH (0-7%). This resulted in 350 mg (80%) of tert-butyl N-(1-hydroxy-2-[5H-imidazo[4,3-a]isoindol-5-yl]-8-azaspiro[4.5]decane-8-sulfonyl)carbamate as an off-white solid. LCMS (ESI) m/z=489.3 [M+H]⁺.

A solution of tert-butyl N-(1-hydroxy-2-[5H-imidazo[4,3-a]isoindol-5-yl]-8-azaspiro[4.5]decane-8-sulfonyl)carbamate (350 mg, 0.716 mmol) in DCM (15 mL) was added TFA (5 mL). The resulting solution was stirred for 30 min at room temperature. The resulting mixture was concentrated under vacuum. The crude product was purified by Prep-HPLC and further separated with Chiral-HPLC.

The absolute configuration of 4a-4b was assigned arbitrarily.

Example 4a: (1S,2S)-1-hydroxy-2-[(5R)-5H-imidazo[4,3-a]isoindol-5-yl]-8-azaspiro[4.5]decane-8-sulfonamide (11.3 mg, 14%) as a white solid. LCMS (ESI) m/z=389.3 [M+H]⁺. ¹H NMR (400 MHz, DMSO-d6) δ 8.03 (s, 1H), 7.62 (d, J=7.6 Hz, 1H), 7.54 (d, J=7.6 Hz, 1H), 7.42-7.30 (m, 1H), 7.29-7.25 (m, 1H), 7.16 (s, 1H), 6.63 (s, 2H), 5.47 (d, J=4.0 Hz, 1H), 5.07 (d, J=5.6 Hz, 1H), 3.60-3.55 (m, 1H), 3.28-3.25 (m, 2H), 2.68-2.51 (m, 2H), 2.49-2.45 (m, 1H), 1.74-1.68 (m, 2H), 1.55-1.54 (m, 1H), 1.33-1.01 (m, 4H), 0.86-0.85 (m, 1H). tR=1.342 min (CHIRALPAK IA-3, 0.46×5 cm; 3 um, Hex(8 mMNH3):EtOH=50:50, 1.0 mL/min). 4a and 4b are enantiomers.

Example 4b: (1R,2R)-1-hydroxy-2-[(5S)-5H-imidazo[4,3-a]isoindol-5-yl]-8-azaspiro[4.5]decane-8-sulfonamide (11.0 mg, 14%) as a white solid. LCMS (ESI) m/z=389.3 [M+H]⁺. tR=2.876 min (CHIRALPAK IA-3, 0.46×5 cm; 3 um, Hex(8 mMNH3):EtOH=50:50, 1.0 mL/min). 4a and 4b are enantiomers.

(1R,2S)-1-hydroxy-2-[(5S)-5H-imidazo[4,3-a]isoindol-5-yl]-8-azaspiro[4.5]decane-8-sulfonamide
(1S,2R)-1-hydroxy-2-[(5R)-5H-imidazo[4,3-a]isoindol-5-yl]-8-azaspiro[4.5]decane-8-sulfonamide

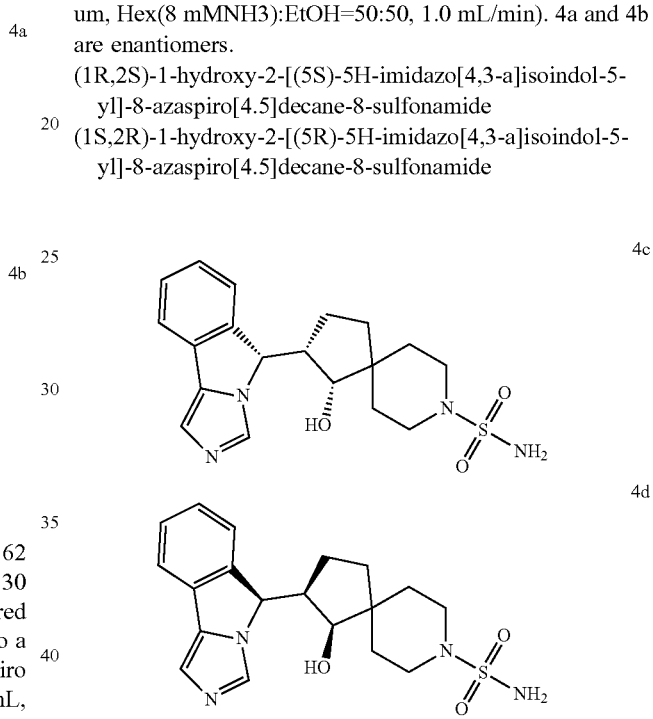

4c

4d

The title compounds were synthesized by the same method of example 4a and 4b.

The absolute configuration of 4c-4d was assigned arbitrarily.

Example 4c: (1S,2S)-1-hydroxy-2-[(5R)-5H-imidazo[4,3-a]isoindol-5-yl]-8-azaspiro[4.5]decane-8-sulfonamide (104.4 mg, 37%) as a white solid. LCMS (ESI) m/z=389.3 [M+H]⁺, ¹HNMR (400 MHz, DMSO-d₆) δ 8.03 (s, 1H), 7.69 (d, J=7.6 Hz, 1H), 7.61 (d, J=7.6 Hz, 1H), 7.42-7.38 (m, 1H), 7.31-7.28 (m, 1H), 7.18 (s, 1H), 6.68 (s, 2H), 5.40 (d, J=4.0 Hz, 1H), 5.38 (d, J=5.6 Hz, 1H), 3.90-3.88 (m, 1H), 3.23-3.20 (m, 1H), 3.08-3.05 (m, 1H), 2.76-2.67 (m, 2H), 2.32-2.29 (m, 1H), 1.78-1.34 (m, 8H). tR=3.132 min (Lux Cellulose-4, 0.46×5 cm; 3 um, Hex(8 mM NH3); EtOH=50:50, 1.0 mL/min). 4c and 4d are enantiomers.

Example 4d: (1R,2R)-1-hydroxy-2-[(5S)-5H-imidazo[4,3-a]isoindol-5-yl]-8-azaspiro[4.5]decane-8-sulfonamide (102.0 mg, 37%) as a white solid. LCMS (ESI) m/z=389.3 [M+H]⁺. tR=2.128 min (Lux Cellulose-4, 0.46×5 cm; 3 um, Hex(8 mM NH3):EtOH=50:50, 1.0 mL/min). 4c and 4 are enantiomers.

Example 5: 6-(5H-imidazo[1,5-b]isoindol-5-yl)-2-methylsulfonyl-2-azaspiro[3.3]heptan-7-ol

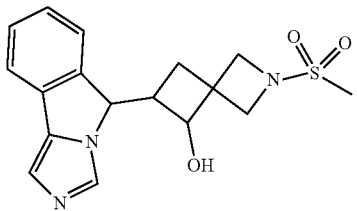 [SMILES: CS(=O)(=O)N1CC2(CC(C3c4ccccc4-c4cncn43)C2O)C1]

Step 1:
tert-butyl (E)-5-oxo-6-(2-(1-trityl-1H-imidazol-4-yl)benzylidene)-2-azaspiro[3.3]heptane-2-carboxylate

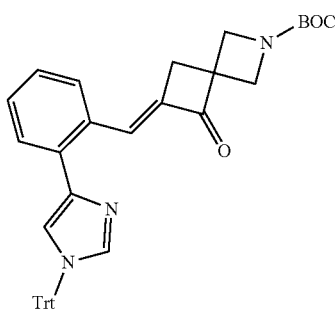

To a mixture of tert-butyl 5-oxo-2-azaspiro[3.3]heptane-2-carboxylate (250 mg, 1.2 mmol) and 2-[1-(triphenylmethyl)-1H-imidazol-4-yl]benzaldehyde (580 mg, 1.4 mmol) in EtOH (10 mL) was added Ca(OH)₂ (270 mg, 3.6 mmol). The resulting solution was stirred for 1 b at room temperature. The resulting mixture was concentrated under vacuum. The resulting solution was diluted with DCM (600 mL). The solid were filtered out. The filtration was concentrated under vacuum. The residue was purified by a silica gel column with EtOAc/PE (30%-80%). This resulted in 700 mg (97%) of the title compound as a light yellow solid. LCMS (ESI) m/z=608.2[M+H]⁺.

Step 2:
tert-butyl-6-(5H-imidazo[5,1-a]isoindol-5-yl)-5-oxo-2-azaspiro[3.3]heptane-2-carboxylate

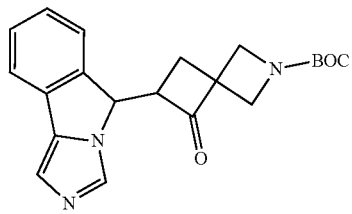 [SMILES: CC(C)(C)OC(=O)N1CC2(CC(C3c4ccccc4-c4cncn43)C2=O)C1]

To a solution of tert-butyl (E)-5-oxo-6-(2-(1-trityl-1H-imidazol-4-yl)benzylidene)-2-azaspiro[3.3]heptane-2-carboxylate (720 mg, 1.15 mmol) in MeOH (12 mL) was added AcOH (2.4 mL). The resulting solution was stirred for 16 h at 80° C. The resulting mixture was concentrated under vacuum. The resulting solution was diluted with EtOAc (60 mL). The resulting mixture was washed with aq. Na₂CO₃ (2×10 mL). The organic layers were combined and dried over anhydrous sodium sulfate and concentrated under vacuum. The residue was purified by a silica gel column eluting with DCM/MeOH (0-10%). This resulted in 480 mg (95%) of tert-butyl 2-[5H-imidazo[4,3-a]isoindol-5-yl]-1-oxo-8-azaspiro[4.5]decane-8-carboxylate as a yellow solid. LCMS (ESI) m/z=366.2 [M+H]⁺.

Step 3:
tert-butyl (5R,6S)-5-hydroxy-6-((S)-5H-imidazo[5,1-a]isoindol-5-yl)-2-azaspiro[3.3]heptane-2-carboxylate

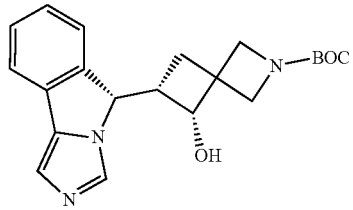 [SMILES: CC(C)(C)OC(=O)N1CC2(C[C@@H]([C@H]3c4ccccc4-c4cncn43)[C@H]2O)C1]

To a solution of tert-butyl-6-(5H-imidazo[5,1-a]isoindol-5-yl)-5-oxo-2-azaspiro[3.3]heptane-2-carboxylate (480 mg, 1.22 mmol) in MeOH (10 mL) was added NaBH₄ (280 mg, 7.4 mmol). The resulting solution was stirred for 20 min at 0° C. The reaction was then quenched by the addition of water (50 mL). The MeOH was removed under vacuum. The resulting solution was extracted with DCM (3×20 mL) and the organic layers combined. The solution was dried over sodium sulfate and concentrated under vacuum. The residue was applied onto a silica gel column with DCM/MeOH (0-10%). This resulted in 400 mg (80%) of tert-butyl-5-hydroxy-6-(5H-imidazo[5,1-a]isoindol-5-yl)-2-azaspiro[3.3]heptane-2-carboxylate as an off-white solid.

The crude product was purified by Prep-HPLC and further isolated by chiral separation to afford the title compound (75 mg) as a white solid.

1. Column: XBridge Prep C18 OBD Column 19×150 mm 5 um; Mobile Phase A: Water (10 MMOL/L NH4HCO3), Mobile Phase B: ACN; Flow rate: 20 mL/min; Gradient: 20% B to 40% B in 10 min; 254220 nm; Rt: 8.9, 9.65 min 2. Column: CHIRALPAK IA, 2.12×15 cm, 5 um; Mobile Phase A: Hex-HPLC, Mobile Phase B: EtOH—HPLC; Flow rate: 20 mL/min; Gradient: 30 B to 30 B in 30 min; 254/220 nm; RT1: 4.917; RT2: 16.96

LCMS (ESI) m/z=368.1 [M+H]⁺; ¹H NMR (400 MHz, DMSO-d6) δ 7.88 (s, 1H), 7.62-7.54 (m, 2H), 7.37 (tt, J=7.3, 0.9 Hz, 1H), 7.26 (td, J=7.6, 1.1 Hz, 1H), 7.14 (s, 1H), 6.25 (d, J=4.8 Hz, 1H), 5.40 (d, J=7.8 Hz, 1H), 4.42 (dd, J=7.0, 4.8 Hz, 1H), 4.15-4.04 (m, 1H), 3.86-3.74 (m, 2H), 3.45-3.26 (m, 2H), 3.17 (d, J=5.2 Hz, 1H), 2.95 (s, 3H), 2.67-2.54 (m, 1H), 1.15 (s, 9H). tR=1.054 min (CHIRALPAK IA-3, 0.46×5 cm; 3 um, Hex(8 mMNH3):EtOH=50:50, 1.0 mL/min).

Step 4:
(5R,6S)-6-((S)-5H-imidazo[5,1-a]isoindol-5-yl)-2-(methylsulfonyl)-2-azaspiro[3.3]heptan-5-ol

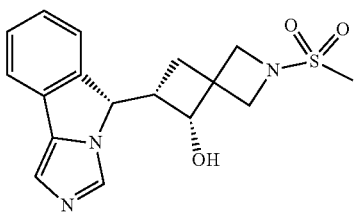 [SMILES: CS(=O)(=O)N1CC2(C[C@@H]([C@H]3c4ccccc4-c4cncn43)[C@H]2O)C1]

A solution of tert-butyl (5R,6S)-5-hydroxy-6-((S)-5H-imidazo[5,1-a]isoindol-5-yl)-2-azaspiro[3.3]heptane-2-carboxylate (50 mg, 0.14 mmol) in 1 mL of DCM was charged with 200 µL of TFA and stirred at room temperature for one hour. The mixture was then concentrated in vacuo and azeotroped twice with MeOH and twice with DCM. The residue was then dissolved in 5 mL of MeOH and charged with 1 g of macroporous polymer supported Ammonium Carbonate resin and sonicated. The resin was then filtered off by vacuum filtration and the solution was concentrated in vacuo. The residue was then dissolved in 1 mL of dimethylacetamide and charged with methane sulfonyl chloride (16 mg, 0.14 mmol) and TEA (42 mg, 0.52 mmol). The crude mixture was then purified by reverse-phase HPLC (0.1% NH₄OH/ACN) to afford the title compound (20 mg, 0.06 mmol, 42% yield) as a white solid.

LCMS (ESI) m/z=346.1 [M+H]⁺; ¹H NMR (400 MHz, DMSO-d6) δ 7.88 (s, 1H), 7.62-7.54 (m, 2H), 7.37 (tt, J=7.3, 0.9 Hz, 1H), 7.26 (td, J=7.6, 1.1 Hz, 1H), 7.14 (s, 1H), 6.25 (d, J=4.8 Hz, 1H), 5.40 (d, J=7.8 Hz, 1H), 4.42 (dd, J=7.0, 4.8 Hz, 1H), 4.15-4.04 (m, 1H), 3.86-3.74 (m, 2H), 3.45-3.26 (m, 2H), 3.17 (d, J=5.2 Hz, 1H), 2.95 (s, 3H), 2.67-2.54 (m, 1H).

Example 6: 2-(5H-imidazo[4,3-a]isoindol-5-yl)-7-methanesulfonyl-7-azaspiro[3.5]nonan-1-ol

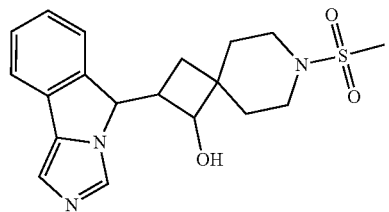 [SMILES: CS(=O)(=O)N1CCC2(CC1)CC(C1c3ccccc3-c3cncn31)C2O]

(1S,2R)-2-[(5R)-5H-imidazo[4,3-a]isoindol-5-yl]-7-methanesulfonyl-7-azaspiro[3.5]nonan-1-ol (1R,2S)-2-[(5S)-5H-imidazo[4,3-a]isoindol-5-yl]-7-methanesulfonyl-7-azaspiro[3.5]nonan-1-ol (1R,2R)-2-[(5R)-5H-imidazo[4,3-a]isoindol-5-yl]-7-methanesulfonyl-7-azaspiro[3.5]nonan-1-ol (1S,2S-2-[(5S)-5H-imidazo[4,3-a]isoindol-5-yl]-7-methanesulfonyl-7-azaspiro[3.5]nonan-1-ol (1R,2S)-2-[(5R)-5H-imidazo[4,3-a]isoindol-5-yl]-7-methanesulfonyl-7-azaspiro[3.5]nonan-1-ol (1S,2R)-2-[(5S)-5H-imidazo[4,3-a]isoindol-5-yl]-7-methanesulfonyl-7-azaspiro[3.5]nonan-1-ol (1R,2R)-2-[(5S)-5H-imidazo[4,3-a]isoindol-5-yl]-7-methanesulfonyl-7-azaspiro[3.5]nonan-1-ol (1S,2S)-2-[(5R)-5H-imidazo[4,3-a]isoindol-5-yl]-7-methanesulfonyl-7-azaspiro[3.5]nonan-1-ol Step 1:
2-(5H-imidazo[4,3-a]isoindol-5-yl)-7-azaspiro[3.5]nonan-1-ol

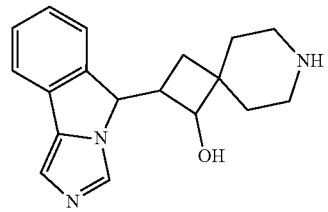

Int-1

To a solution of tert-butyl 1-hydroxy-2-[5H-imidazo[4,3-a]isoindol-5-yl]-8-azaspiro[4.5]decane-8-carboxylate (200 mg, 0.488 mmol) in DCM (5 mL) was added TFA (2 mL). The resulting solution was stirred for 30 min at room temperature. The resulting mixture was concentrated under vacuum. This resulted in 206 mg (crude) of 2-(5H-imidazo[4,3-a]isoindol-5-yl)-7-azaspiro[3.5]nonan-1-ol as light yellow oil.

Step 2:
(1S,2R)-2-[(5R)-5H-imidazo[4,3-a]isoindol-5-yl]-7-methanesulfonyl-7-azaspiro[3.5]nonan-1-ol (1R,2S)-2-[(5S)-5H-imidazo[4,3-a]isoindol-5-yl]-7-methanesulfonyl-7-azaspiro[3.5]nonan-1-ol

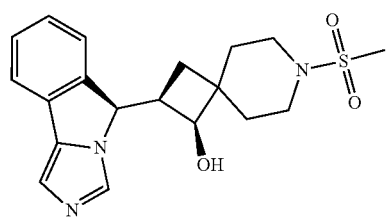

6a

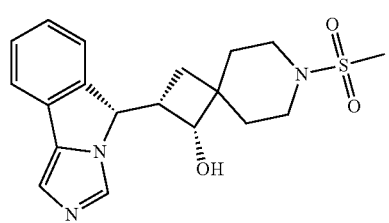

6b

A solution of 2-(5H-imidazo[4,3-a]isoindol-5-yl)-7-azaspiro[3.5]nonan-1-ol (112 mg, 0.38 mmol) in DCM (8 mL) added TEA (0.42 mL, 3.03 mmol). Then MsCl (43 mg, 0.375 mmol) was added at 0° C. The mixture was stirred for 1 h at room temperature. The solution was diluted with DCM (50 mL) and washed with water (50 mL), dried over sodium sulfate and concentrated under vacuum. The residue was applied onto a silica gel column with DCM/MeOH (97:3). The crude product was further isolated by Prep-HPLC and Chiral-HPLC.

The absolute configuration of 6a-6b was assigned arbitrarily.

Example 6a: (1S,2R)-2-[(5R)-5H-imidazo[4,3-a]isoindol-5-yl]-7-methanesulfonyl-7-azaspiro[3.5]nonan-1-ol (21.7 mg, 31%) as a white solid. LCMS (ESI) m/z=374.2 [M+H]⁺. ¹H NMR (400 MHz, DMSO-d₆) δ 7.86 (s, 1H), 7.63-7.57 (m, 2H), 7.40-7.24 (m, 2H), 7.15 (s, 1H), 5.43 (d, J=6.9 Hz, 1H), 5.32 (d, J=6.3 Hz, 1H), 4.08 (dd, J=7.9, 6.2 Hz, 1H), 3.37-3.31 (m, 1H), 3.28-3.24 (m, 1H), 2.95-2.69 (m, 5H), 2.52-2.47 (m, 1H), 1.74-1.54 (m, 4H), 1.45-1.41 (m, 1H), 0.95 (t, J=10.4 Hz, 1H). tR=2.862 min (CHIRALPAK IF-3, 0.46×5 cm; 3 um, Hex(0.1% DEA):EtOH-50:50, 1 mL/min). 6a and 6b are enantiomers.

Example 6b: (1R,2S)-2-[(5S)-5H-imidazo[4,3-a]isoindol-5-yl]-7-methanesulfonyl-7-azaspiro[3.5]nonan-1-ol (24.1 mg, 34%) as a white solid. LCMS (ESI) m/z=374.2 [M+H]⁺. tR=4.22 min (CHIRALPAK IA-3, 0.46×5 cm; 3 um, Hex(8 mMNH3):EtOH=50:50, 1.0 mL/min). 6a and 6b are enantiomers.

(1R,2R)-2-[(5R)-5H-imidazo[4,3-a]isoindol-5-yl]-7-methanesulfonyl-7-azaspiro[3.5]nonan-1-ol (1S,2S)-2-[(5S)-5H-imidazo[4,3-a]isoindol-5-yl]-7-methanesulfonyl-7-azaspiro[3.5]nonan-1-ol

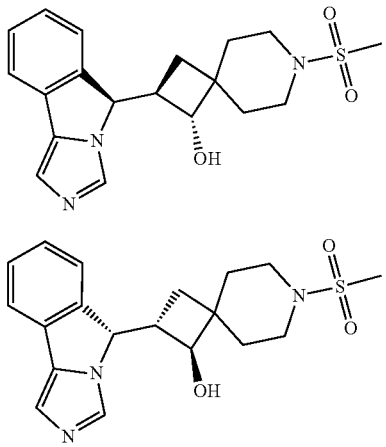

6c

6d

The title compounds were synthesized by the same method of example 6a and 6b The absolute configuration of 6c-6d was assigned arbitrarily.

Example 6c: (1R,2R)-2-[(5R)-5H-imidazo[4,3-a]isoindol-5-yl]-7-methanesulfonyl-7-azaspiro[3.5]nonan-1-ol (43.8 mg, 31%) as a white solid. LCMS (ESI) m/z=374.2 [M+H]⁺. ¹H NMR (400 MHz, DMSO-d₆) δ 7.95 (s, 1H), 7.61 (dd, J=7.2, 1.5 Hz, 1H), 7.39 (t, J=7.5 Hz, 2H), 7.28-7.23 (m, 1H), 7.14 (s, 1H), 5.41 (d, J=8.6 Hz, 1H), 5.26 (d, J=6.7 Hz, 1H), 3.98 (t, J=7.2 Hz, H), 3.37-3.27 (m, 2H), 2.94-2.77 (m, 5H), 2.36-2.30 (m, 1H), 1.86 (dd, J=11.0, 9.5 Hz, 1H), 1.72-1.45 (m, 5H). tR=2.964 min (CHIRALPAK IA-3, 0.46×5 cm; 3 um, (Hex:DCM=5:1):EtOH=50:50, 1.0 mL/min). 6c and 6d are enantiomers.

Example 6d: (1S,2S)-2-[(5S)-5H-imidazo[4,3-a]isoindol-5-yl]-7-methanesulfonyl-7-azaspiro[3.5]nonan-1-ol (49.5 mg, 35%) as a white solid. LCMS (ESI) m/z=374.2 [M+H]⁺. tR=1.119 min (CHIRALPAK IA-3, 0.46×5 cm; 3 um, (Hex:DCM=5:1):EtOH=50:50, 1.0 mL/min). 6c and 6d are enantiomers.

(1R,2S)-2-[(5R)-5H-imidazo[4,3-a]isoindol-5-yl]-7-methanesulfonyl-7-azaspiro[3.5]nonan-1-ol (1S,2R)-2-[(5S)-5H-imidazo[4,3-a]isoindol-5-yl]-7-methanesulfonyl-7-azaspiro[3.5]nonan-1-ol

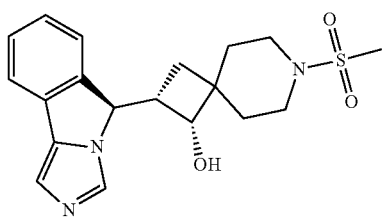

6e

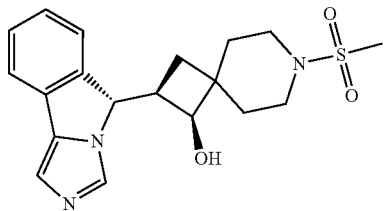

6f

The title compounds were synthesized by the same method of example 6a and 6b. The absolute configuration of 6e-6f was assigned arbitrarily.

Example 6e: (1R,2S)-2-[(5R)-5H-imidazo[4,3-a]isoindol-5-yl]-7-methanesulfonyl-7-azaspiro[3.5]nonan-1-ol (19.1 mg, 6.2%) as a white solid. LCMS (ESI) m/z=374.2 [M+H]⁺. ¹H NMR (400 MHz, DMSO-d₆) δ7.86 (s, 1H), 7.70-7.58 (m, 2H), 7.48-7.24 (m, 2H), 7.14 (d, J=2.9 Hz, 1H), 5.76 (d, J=5.5 Hz, 1H), 5.47 (d, J=8.7 Hz, 1H), 4.12 (dd, J=9.0, 4.8 Hz, 1H), 3.32-2.92 (m, 4H), 2.83 (s, 3H), 2.67-2.52 (m, 1H), 1.94-1.79 (m, 3H), 1.60 (t, J=5.8 Hz, 3H). tR=1.836 min (CHIRALPAK IC-3, 0.46×5 cm; 3 um, Hex(0.1% DEA):IPA=70:30, 1.0 mL/min). 6e and 6f are enantiomers.

Example 6f: (1S,2R)-2-[(5S)-5H-imidazo[4,3-a]isoindol-5-yl]-7-methanesulfonyl-7-azaspiro[3.5]nonan-1-ol (21.3 mg, 7.0%) as a white solid. LCMS (ESI) m/z=374.2 [M+H]⁺. tR=2.94 min (CHIRALPAK IC-3, 0.46×5 cm; 3 um, Hex(0.1% DEA):IPA=70:30, 1.0 mL/min). 6e and 6f are enantiomers.

(1R,2R)-2-[(5S)-5H-imidazo[4,3-a]isoindol-5-yl]-7-methanesulfonyl-7-azaspiro[3.5]nonan-1-ol (1S,2S)-2-[(5R)-5H-imidazo[4,3-a]isoindol-5-yl]-7-methanesulfonyl-7-azaspiro[3.5]nonan-1-ol

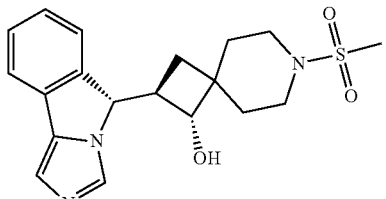

6g

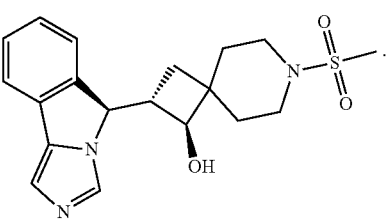

6h

The title compounds were synthesized by the same method of example 6a and 6b. The absolute configuration of 6g-6h was assigned arbitrarily.

Example 6g: (1R,2S)-2-[(5R)-5H-imidazo[4,3-a]isoindol-5-yl]-7-methanesulfonyl-7-azaspiro[3.5]nonan-1-ol (24.2 mg, 52%) as a white solid. LCMS (ESI) m/z=374.2 [M+H]⁺. ¹H NMR (400 MHz, DMSO-d₆) δ7.85 (s, 1H), 7.63-7.60 (m, 1H), 7.41-7.36 (m, 2H), 7.26-7.20 (m, 1H), 7.13 (s, 1H), 5.79 (d, J=6.0 Hz, 1H), 5.42 (d, J=10.6 Hz, 1H), 4.08 (td, J=5.9, 2.9 Hz, 1H), 3.20-2.98 (m, 4H), 2.85 (s, 3H), 2.35-2.19 (m, 2H), 1.95-1.61 (m, 5H). tR=2.279 min (Lux Cellulose-4, 0.46×5 cm; 3 um, Hex(0.1% DEA):EtOH=50:50, 1.0 mL/min). 6g and 6h are enantiomers.

Example 6h: (1S,2R)-2-[(5S)-5H-imidazo[4,3-a]isoindol-5-yl]-7-methanesulfonyl-7-azaspiro[3.5]nonan-1-ol (22.7 mg, 48%) as a white solid. LCMS (ESI) m/z=374.2 [M+H]+. tR=3.761 min (Lux Cellulose-4, 0.46×5 cm; 3 um, Hex (0.1%/DEA):EtOH=50:50, 1.0 mL/min). 6g and 6h are enantiomers.

Example 7: 2-(5H-imidazo[5,1-a]isoindol-5-yl)-8-(methylsulfonyl-8-azaspiro[4.5]decan-1-ol

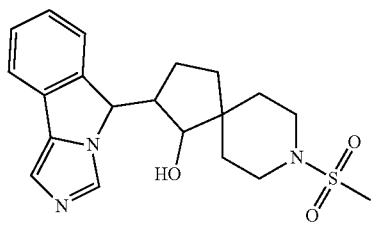 [SMILES: CS(=O)(=O)N1CCC2(CCC(C3c4ccccc4-c4cncn43)C2O)CC1]

(1S,2S)-8-(methylsulfonyl)-2-((R)-5H-imidazo[5,1-a]isoindol-5-yl)-8-azaspiro[4.5]decan-1-ol
(1R,2R)-8-(methylsulfonyl)-2-((S)-5H-imidazo[5,1-a]isoindol-5-yl)-8-azaspiro[4.5]decan-1-ol 7a

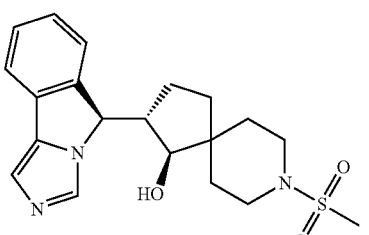

7b

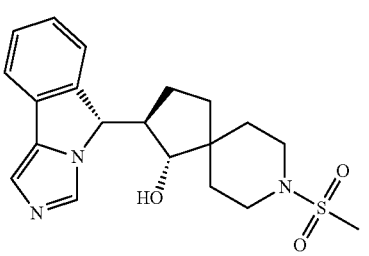

To a solution of 2-(5H-imidazo[4,3-a]isoindol-5-yl)-8-azaspiro[4.5]decan-1-ol (173 mg, 0.056 mmol) in DCM (20 mL) was added TEA (0.4 mL, 2.90 mmol). Then MsCl (62 mg, 0.0.54 mmol) was added at 0° C. The mixture was stirred for 1 h at room temperature. The solution was diluted with DCM (50 mL) then washed with water (50 mL), dried over sodium sulfate and concentrated under vacuum. The residue was purified by silica gel column with DCM/MeOH (0%-10%). The residue was further separated with Chiral-HPLC.

The absolute configuration of 7a-7b was assigned arbitrarily.

Example 7a: (1S,2S)-8-(methylsulfonyl)-2-((R)-5H-imidazo[5,1-a]isoindol-5-yl)-8-azaspiro[4.5]decan-1-ol (4.8 mg, 5%) as a white solid. LCMS (ESI) m/z=388.2 [M+H]+. 1H NMR (400 MHz, DMSO-d6) δ 7.93 (s, 1H), 7.60 (d, J=7.6 Hz, 1H), 7.54 (d, J=7.6 Hz, 1H), 7.41-7.37 (m, 1H), 7.29-7.25 (m, 1H), 7.11 (s, 1H), 5.45 (d, J=4.0 Hz, 1H), 5.08 (d, J=5.6 Hz, 1H), 3.60-3.57 (m, 1H), 3.44-3.35 (m, 2H), 2.82 (s, 3H), 2.81-2.64 (m, 3H), 1.73-1.58 (m, 3H), 1.35-1.04 (m, 4H), 0.88-0.85 (m, 1H). tR=4.843 min (CHIRALPAK IA-3, 0.46×5 cm; 3 um, Hex(0.1% DEA):EtOH=50:50, 1.0 mL/min). 7a and 7b are enantiomers.

Example 7b: (1R,2R)-8-(methylsulfonyl)-2-((S)-5H-imidazo[5,1-a]isoindol-5-yl)-8-azaspiro[4.5]decan-1-ol (8.3 mg, 8%) as a white solid. LCMS (ESI) m/z=388.2 [M+H]+. tR=1.690 min (CHIRALPAK IA-3, 0.46×5 cm; 3 um, Hex (0.1% DEA):EtOH-50:50, 1.0 mL/min). 7a and 7b are enantiomers.

(1R,2S)-8-(methylsulfonyl)-2-((S)-5H-imidazo[5,1-a]isoindol-5-yl)-8-azaspiro[4.5]decan-1-ol (1S,2R)-8-(methylsulfonyl)-2-((R)-5H-imidazo[5,1-a]isoindol-5-yl)-8-azaspiro[4.5]decan-1-ol 7c

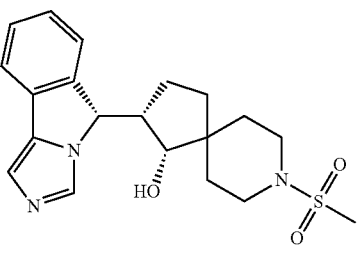

7d

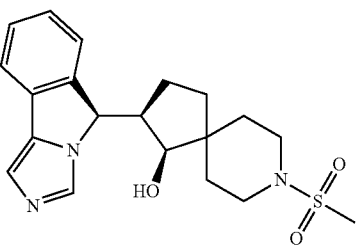

The title compounds were synthesized by the same method of example 7a and 7b.

The absolute configuration of 7c-7d was assigned arbitrarily.

Example 7c: (1R,2S)-8-(methylsulfonyl)-2-((S)-5H-imidazo[5,1-a]isoindol-5-yl)-8-azaspiro[4.5]decan-1-ol (56.1 mg, 24%) as a white solid. LCMS (ESI) m/z=388.2 [M+H]+. 1H NMR (400 MHz, DMSO-d6) δ 7.90 (s, 1H), 7.67 (d, J=7.6 Hz, 1H), 7.59 (d, J=7.6 Hz, 1H), 7.41-7.36 (m, 1H), 7.30-7.25 (m, 1H), 7.13 (s, 1H), 5.40 (d, J=4.0 Hz, 1H), 5.38 (d, J=5.6 Hz, 1H), 3.92-3.89 (m, 1H), 3.39-3.35 (m, 1H), 3.22-3.17 (m, 1H), 2.93-2.86 (m, 1H), 2.84 (s, 3H), 2.83-2.80 (m, 1H), 2.35-2.28 (m, 1H), 1.75-1.52 (m, 6H), 1.35-1.24 (m, 2H). tR=2.258 min (CHIRALPAK IA-3, 0.46×5 cm; 3 um, Hex(8 mMNH3):EtOH=50:50, 1.0 mL/min). 7c and 7d are enantiomers.

Example 7d: (1S,2R)-8-(methylsulfonyl)-2-((R)-5H-imidazo[5,1-a]isoindol-5-yl)-8-azaspiro[4.5]decan-1-ol (8.3 mg, 8%) as a white solid. LCMS (ESI) m/z=388.2 [M+H]+. tR=3.351 min (CHIRALPAK IA-3, 0.46×5 cm; 3 um, Hex(8 mNH3):EtOH=50:50, 1.0 mL/min). 7c and 7d are enantiomers.

Example 8: 7-fluoromethanesulfonyl-2-(5H-imidazo-[4,3-a]isoindol-5-yl)-7-azaspiro[3.5]nonan-1-ol

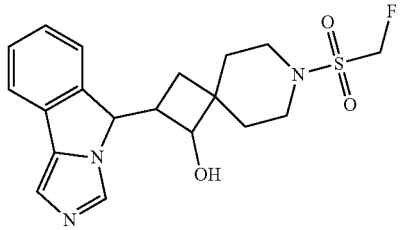 [SMILES: O=S(=O)(CF)N1CCC2(CC1)CC(C1c3ccccc3-c3cncn31)C2O]

(1S,2R)-7-fluoromethanesulfonyl-2-[(5R)-5H-imidazo[4,3-a]isoindol-5-yl]-7-azaspiro[3.5]nonan-1-ol
(1R,2S)-7-fluoromethanesulfonyl-2-[(5S)-5H-imidazo[4,3-a]isoindol-5-yl]-7-azaspiro[3.5]nonan-1-ol 8a

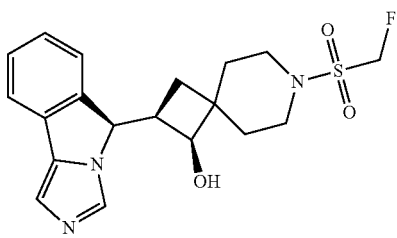

8b

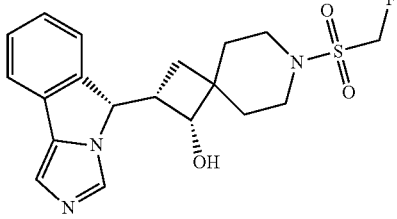

To a mixture of 2-(5H-imidazo[1,5-b]isoindol-5-yl)-7-azaspiro[3.5]nonan-3-ol (200 mg, 0.680 mmol) and TEA (342.58 mg, 3.39 mmol) in DCM (30 mL) was added fluoromethanesulfonyl chloride (358.97 mg, 2.71 mmol). The mixture was stirred at 25° C. for 1 h. The reaction was quenched with water (50 mL). The resulting solution was extracted with EtOAc (3×50 mL) and the organic layers combined. The residue was purified by flash chromatography on silica gel eluting with DCM/MeOH (97:3). The crude product was further isolated by Prep-HPLC and Chiral-HPLC.

The absolute configuration of 8a-8b was assigned arbitrarily.

Example 8a: (1S,2R)-7-fluoromethanesulfonyl-2-[(5R)-5H-imidazo[4,3-a]isoindol-5-yl]-7-azaspiro[3.5]nonan-1-ol (14.1 mg, 5.1%) as a white solid. LCMS (ESI) m/z=392.2 [M+H]$^+$. $^1$H NMR (400 MHz, DMSO-$d_6$) δ 7.86 (s, 1H), 7.65-7.58 (m, 2H), 7.40-7.35 (m, 1H), 7.29-7.24 (m, 1H), 7.14 (s, 1H), 5.80-5.79 (m, 1H), 5.59 (s, 1H), 5.47-5.44 (m, 2H), 4.13 (s, 1H), 3.39-3.36 (m, 1H), 3.29-3.17 (m, 3H), 2.59-2.51 (m, 1H), 1.97-1.93 (m, 1H), 1.90-1.73 (m, 2H), 1.60-1.52 (m, 3H). tR=5.050 min (CHIRALPAK IG-3, 0.46×5 cm; 3 um, Hex(0.1% DBA):EtOH=50:50, 1 mL/min). 8a and 8b are enantiomers.

Example 8b: (1R,2S)-7-fluoromethanesulfonyl-2-[(5S)-5H-imidazo[4,3-a]isoindol-5-yl]-7-azaspiro[3.5]nonan-1-ol (21.5 mg, 7.8%) as a white solid. LCMS (ESI) m/z=392.2 [M+H]$^+$. tR=9.010 min (CHIRALPAK IG-3, 0.46×5 cm; 3 um, Hex(0.1% DEA):EtOH-50:50, 1 mL/min). 8a and 8b are enantiomers.

Example 9: methyl 1-hydroxy-2-(5H-imidazo[4,3-a]isoindol-5-yl)-8-azaspiro[4.5]decane-8-carboxylate

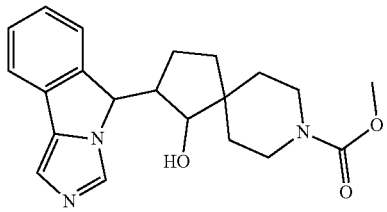 [SMILES: COC(=O)N1CCC2(CCC(C3c4ccccc4-c4cncn43)C2O)CC1]

methyl (1R,2S)-1-hydroxy-2-[(5S)-5H-imidazo[4,3-a]isoindol-5-yl]-8-azaspiro[4.5]decane-8-carboxylate
methyl (1S,2R)-1-hydroxy-2-[(5R)-5H-imidazo[4,3-a]isoindol-5-yl]-8-azaspiro[4.5]decane-8-carboxylate 9a

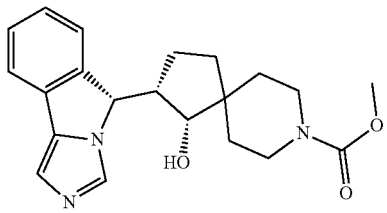

9b

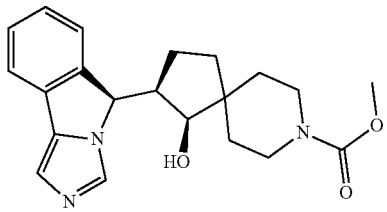

To a solution of 2-(5H-imidazo[4,3-a]isoindol-5-yl)-8-azaspiro[4.5]decan-1-ol (139 mg, 0.450 mmol) in DCM (10 mL) was added TEA (2.0 mL, 14.43 mmol) at it. The mixture was cooled to −65° C. 20 min later, methyl chloroformate (50.49 mg, 0.530 mmol) was added at −65 OC. The mixture was stirred at −65° C. for 1 h. The reaction was quenched with water (20 mL). The mixture was extracted with DCM (3×20 mL). The combined solution was dried over sodium sulfate and concentrated under vacuum. The crude product was purified by Prep-HPLC and further separated with Chiral-HPLC.

The absolute configuration of 9a-9b was assigned arbitrarily.

Example 9a: methyl (1R,2S)-1-hydroxy-2-[(5S)-5H-imidazo[4,3-a]isoindol-5-yl]-8-azaspiro[4.5]decane-8-carboxylate (42.9 mg, 26%) as a white solid. LCMS (ESI) m/z=368.8 [M+H]$^+$. $^1$H NMR (400 MHz, DMSO-$d_6$) δ 8.03 (s, 1H), 7.68 (d, J=7.5 Hz, 1H), 7.61 (d, J=7.5 Hz, 1H), 7.42-7.26 (m, 2H), 7.20 (s, 1H), 5.44 (d, J=4.5 Hz, 1H), 5.38 (d, J=4.5 Hz, 1H), 3.93-3.89 (m, 1H), 3.66-3.60 (m, 1H), 3.57 (s, 3H), 3.51-3.46 (m, 1H), 3.12-3.06 (m, 2H), 2.33-2.32 (m, 1H), 1.79-1.30 (m, 6H), 1.23-1.20 (m, 2H);

tR=1.597 min (CHIRALPAK IF-3, 0.46×5 cm; 3 um, Hex (0.1% DEA):EtOH=50:50, 1.0 mL/min). 9a and 9b are enantiomers.

Example 9b: methyl (1S,2R)-1-hydroxy-2-[(5R)-5H-imidazo[4,3-a]isoindol-5-yl]-8-azaspiro[4.5]decane-8-carboxylate (46.1 mg, 28%) as a white solid. LCMS (ESI) m/z=368.8 [M+H]⁺. tR=2.822 min (CHIRALPAK IF-3, 0.46×5 cm; 3 um, Hex(0.1% DEA):EtOH=50:50, 1.0 mL/min). 9a and 9b are enantiomers.

Example 10: 1-(hydroxy-2-(5H-imidazo[4,3-a]isoindol-5-yl)-8-azaspiro[4.5]decan-8-yl)ethan-1-one

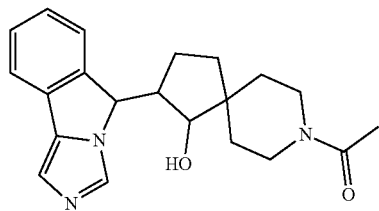 [SMILES: CC(=O)N1CCC2(CCC(C3c4ccccc4-c4cncn43)C2O)CC1]

1-[(1R,2S)-1-hydroxy-2-[(S)-5H-imidazo[4,3-a]isoindol-5-yl]-8-azaspiro[4.5]decan-8-yl]ethan-1-one.
1-[(1S,2R)-1-hydroxy-2-[(5R)-5H-imidazo[4,3-a]isoindol-5-yl]-8-azaspiro[4.5]decan-8-yl]ethan-1-one 10a

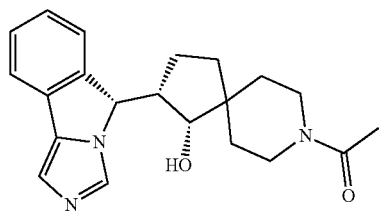

10b

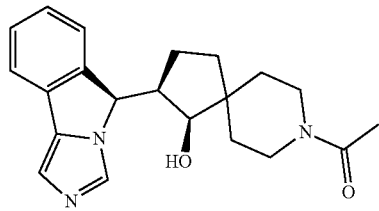

To a solution of 2-(5H-imidazo[4,3-a]isoindol-5-yl)-8-azaspiro[4.5]decan-1-ol (154 mg, 0.50 mmol) in DCM (10 mL) was added TEA (2.0 mL, 14.43 mmol) at rt. Then acetyl chloride (39.58 mg, 0.50 mmol) was added at −60° C. The solution was stirred for 1 h. The reaction was quenched with water (20 mL). Then the mixture was extracted with DCM (3×20 mL). The combined solution was dried over sodium sulfate and concentrated under vacuum. The crude product was purified by Prep-HPLC and further separated with Chiral-HPLC.

The absolute configuration of 10a-10b was assigned arbitrarily.

Example 10a: 1-[(1R,2S)-1-hydroxy-2-[(5S)-5H-imidazo[4,3-a]isoindol-5-yl]-8-azaspiro[4.5]decan-8-yl]ethan-1-one (23.9 mg, 14%) as a white solid. LCMS (ESI) m/z=352.2 [M+H]+; ¹H NMR (300 MHz, DMSO-d₆) δ 7.92 (s, 1H), 7.68 (d, J=7.5 Hz, 1H), 7.59 (d, J=7.5 Hz, 1H), 7.42-7.26 (m, 2H), 7.12 (s, 1H), 5.40 (d, J=4.5 Hz, 1H), 5.37 (d, J=4.5 Hz, 1H), 3.95-3.89 (m, 1H), 3.86-3.37 (m, 2H), 3.21-2.94 (m, 2H), 2.31-2.21 (m, 1H), 1.97 (d, J=8.7 Hz, 3H), 1.75-1.45 (m, 6H), 1.28-1.18 (m, 21H); tR=1.468 min (CHIRALPAK IA-3, 0.46×5 cm; 3 um, Hex(0.1% DEA):EtOH=50:50, 1.0 mL/min). 10a and 10b are enantiomers.

Example 10b: 1-[(1S,2R)-1-hydroxy-2-[(5R)-5H-imidazo[4,3-a]isoindol-5-yl]-8-azaspiro[4.5]decan-8-yl]ethan-1-one (22.1 mg, 12.5%) as a white solid. LCMS (ESI) m/z=368.8 [M+H]⁺. tR=3.037 min (CHIRALPAK IA-3, 0.46×5 cm; 3 um, Hex(0.1% DEA):EtOH=50:50, 1.0 mL/min). 10a and 10b are enantiomers.

Example 11: 1-hydroxy-2-(5H-imidazo[4,3-a]isoindol-5-yl)-7-azaspiro[3.5]nonane-7-sulfonamide

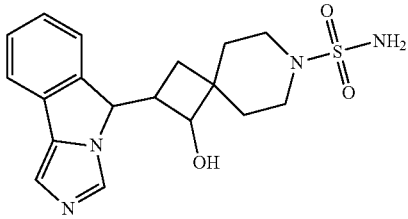 [SMILES: NS(=O)(=O)N1CCC2(CC1)CC(C1c3ccccc3-c3cncn31)C2O]

(1S,2R)-1-hydroxy-2-[(5R)-5H-imidazo[4,3-a]isoindol-5-yl]-7-azaspiro[3.5]nonane-7-sulfonamide
(1R,2S)-1-hydroxy-2-[(5S)-5H-imidazo[4,3-a]isoindol-5-yl]-7-azaspiro[3.5]nonane-7-sulfonamide 11a

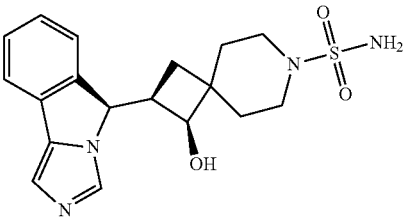

11b

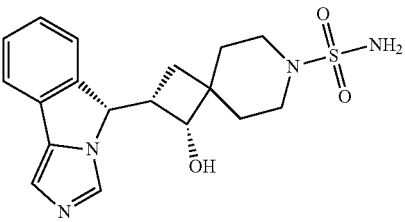

The title compounds were synthesized by the same method of example 4a and 4b.

The absolute configuration of 11a-11b was assigned arbitrarily.

Example 11a: (1S,2R)-1-hydroxy-2-[(5R)-5H-imidazo[4,3-a]isoindol-5-yl]-7-azaspiro[3.5]nonane-7-sulfonamide (38.0 mg, 19%) as a white solid. LCMS (ESI) m/z=375.2 [M+H]⁺. ¹H NMR (400 MHz, DMSO-d₆) δ 7.93 (s, 1H), 7.61-7.58 (m, 2H), 7.41-7.25 (m, 2H), 7.18 (s, 1H), 6.64 (s, 2H), 5.43 (d, J=7.3 Hz, 1H), 5.29 (d, J=6.7 Hz, 1H), 4.06 (t, J=7.2 Hz, 1H), 3.32-3.15 (m, 2H), 2.73-2.51 (m, 2H), 2.50-2.43 (m, 1H), 1.73-1.39 (m, 5H), 1.04 (t, J=10.4 Hz, 1H). tR=8.881 min (CHIRALPAK IG-3, 0.46×5 cm; 3 um, Hex(0.1% DEA): IPA=70:30, 1 mL/min). 11a and 11b are enantiomers.

Example 11b: (1R,2S)-1-hydroxy-2-[(5S)-5H-imidazo[4,3-a]isoindol-5-yl]-7-azaspiro[3.5]nonane-7-sulfonamide (33.8 mg, 17%) as a white solid. LCMS (ESI) m/z=375.2 [M+H]⁺. tR=11.091 min (CHIRALPAK IG-3, 0.46×5 cm; 3 um, Hex(0.1% DEA):IPA=70:30, 1 mL/min). 11a and 11b are enantiomers.

(1R,2R)-1-hydroxy-2-[(5R)-5H-imidazo[4,3-a]isoindol-5-yl]-7-azaspiro[3.5]nonane-7-sulfonamide (1S,2S)-1-hydroxy-2-[(5S)-5H-imidazo[4,3-a]isoindol-5-yl]-7-azaspiro[3.5]nonane-7-sulfonamide

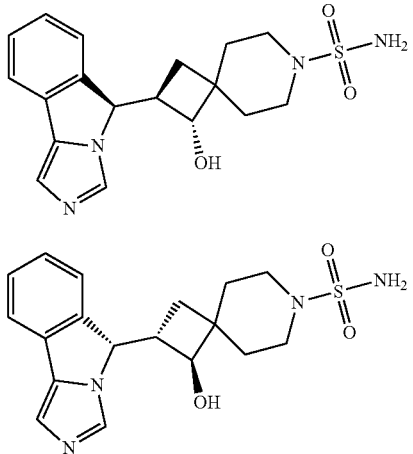

11c

11d

The title compounds were synthesized by the same method of example 4a and 4b.

The absolute configuration of 11c-11d was assigned arbitrarily.

Example 11c: (1R,2R)-1-hydroxy-2-[(5R)-5H-imidazo[4,3-a]isoindol-5-yl]-7-azaspiro[3.5]nonane-7-sulfonamide (74.9 mg, 34%) as a white solid. LCMS (ESI) m/z=375.2 [M+H]⁺. ¹H NMR (400 MHz, DMSO-d₆) δ 8.05 (s, 1H), 7.62 (d, J=7.5 Hz, 1H), 7.43-7.38 (m, 2H), 7.30-7.24 (m, 1H), 7.20 (s, 1H), 6.67 (s, 2H), 5.43 (d, J=8.7 Hz, 1H), 5.24 (d, J=6.9 Hz, 1H), 3.97 (t, J=7.1 Hz, 1H), 3.26-3.18 (m, 2H), 2.75-2.60 (m, 2H), 2.35-2.29 (m, 1H), 1.86-1.64 (m, 3H), 1.58-1.47 (m, 3H). tR=1.297 min (Lux Cellulose-4, 0.46×5 cm; 3 um, Hex(0.1% DEA):EtOH=50:50, 1.0 mL/min). 11c and 11d are enantiomers.

Example 11d: (1S,2S)-1-hydroxy-2-[(5S)-5H-imidazo[4,3-a]isoindol-5-yl]-7-azaspiro[3.5]nonane-7-sulfonamide (66.8 mg, 31%) as a white solid. LCMS (ESI) m/z=375.2 [M+H]⁺. tR=3.276 min (Lux Cellulose-4, 0.46×5 cm; 3 um, Hex(0.1% DEA):EtOH=50:50, 1.0 mL/min). 11c and 11d are enantiomers.

(1R,2S)-1-hydroxy-2-[(5R)-5H-imidazo[4,3-a]isoindol-5-yl]-7-azaspiro[3.5]nonane-7-sulfonamide (1S,2R)-1-hydroxy-2-[(5S)-5H-imidazo[4,3-a]isoindol-5-yl]-7-azaspiro[3.5]nonane-7-sulfonamide

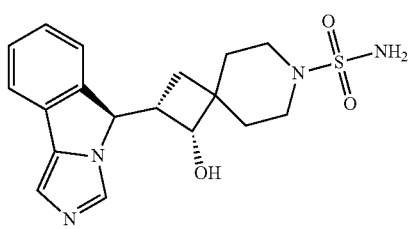

11e

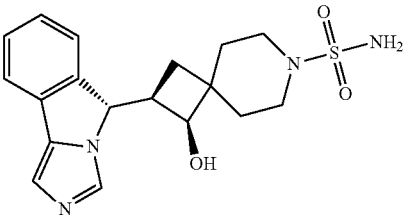

11f

The title compounds were synthesized by the same method of example 4a and 4b.

The absolute configuration of 11e-11f was assigned arbitrarily.

Example 11e: (1R,2S)-1-hydroxy-2-[(5R)-5H-imidazo[4,3-a]isoindol-5-yl]-7-azaspiro[3.5]nonane-7-sulfonamide (76.3 mg, 31%) as a white solid. LCMS (ESI) m/z=375.2 [M+H]⁺. ¹H NMR (400 MHz, DMSO-d₆) δ 7.86 (s, 1H), 7.65-7.58 (m, 2H), 7.40-7.35 (m, 1H), 7.29-7.24 (m, 1H), 7.14 (s, 1H), 6.69 (s, 2H), 5.76 (d, J=5.7 Hz, 1H), 5.46 (d, J=8.9 Hz, 1H), 4.09 (td, J=6.2, 2.9 Hz, 1H), 3.08-2.98 (m, 2H), 2.88-2.76 (m, 2H), 2.63-2.50 (m, 1H), 1.93 (t, J=10.4 Hz, 1H), 1.79-1.73 (m, 2H), 1.60 (t, J=5.5 Hz, 3H). tR=3.997 min (CHIRALPAK IF-3, 0.46×5 cm; 3 um, Hex(8 mMNH3):EtOH=80:20, 1.0 mL/min). 11e and 11f are enantiomers.

Example 11f: (1S,2R)-1-hydroxy-2-[(5S)-5H-imidazo[4,3-a]isoindol-5-yl]-7-azaspiro[3.5]nonane-7-sulfonamide (72.2 mg, 29%) as a white solid. LCMS (ESI) m/z=375.2 [M+H]⁺. tR=5.326 min (CHIRALPAK IF-3, 0.46×5 cm; 3 um, Hex(8 mMNH3):EtOH=80:20, 1.0 mL/min). 11e and 11f are enantiomers.

(1R,2R)-1-hydroxy-2-[(5S)-5H-imidazo[4,3-a]isoindol-5-yl]-7-azaspiro[3.5]nonane-7-sulfonamide (1S,2S)-1-hydroxy-2-[(5R)-5H-imidazo[4,3-a]isoindol-5-yl]-7-azaspiro[3.5]nonane-7-sulfonamide

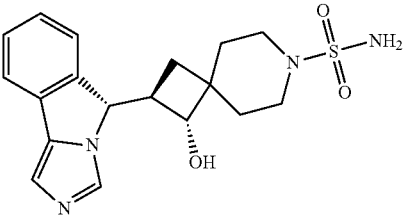

11g

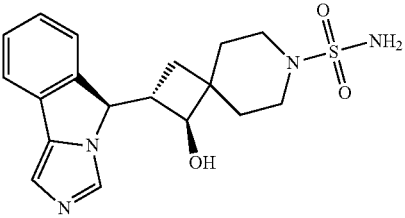

11h

The title compounds were synthesized by the same method of example 4a and 4b.

The absolute configuration of 11g-11h was assigned arbitrarily.

Example 11g: (1R,2R)-1-hydroxy-2-[(5S)-5H-imidazo[4,3-a]isoindol-5-yl]-7-azaspiro[3.5]nonane-7-sulfonamide (17.0 mg, 29%) as a white solid. LCMS (ESI) m/z=375.2 [M+H]+. ¹H NMR (400 MHz, DMSO-d₆) δ 7.89 (s, 1H), 7.62 (d, J=7.6 Hz, 1H), 7.42-7.36 (m, 2H), 7.26-7.21 (m, 1H), 7.15 (s, 1H), 6.71 (s, 2H), 5.79 (d, J=6.1 Hz, 1H), 5.42 (d, J=10.7 Hz, 1H), 4.06 (td, J=6.4, 3.2 Hz, 1H), 3.20-2.98 (m, 2H), 2.89-2.85 (m, 2H), 2.41-2.28 (m, 1H), 2.22 (t, J=10.3 Hz, 1H), 1.92-1.76 (m, 2H), 1.68-1.61 (m, 3H). tR=2.075 min (Lux Cellulose-4, 0.46×5 cm; 3 um, Hex (0.1% DEA):EtOH=50:50, 1.0 mL/min). 11g and 11h are enantiomers.

Example 11h: (1S,2S)-1-hydroxy-2-[(5R)-5H-imidazo[4,3-a]isoindol-5-yl]-7-azaspiro[3.5]nonane-7-sulfonamide (17.4 mg, 29%) as a white solid. LCMS (ESI) m/z=375.2 [M+H]⁺. tR=3.203 min (Lux Cellulose-4, 0.46×5 cm; 3 um, Hex(0.1% DEA):EtOH=50:50, 1.0 mL/min). 11g and 11h are enantiomers.

Example 12: tert-butyl 2'-hydroxy-3'-(5H-imidazo[5,1-a]isoindol-5-yl)-8-azaspiro[bicyclo[3.2.1]octane-3,1'-cyclobutane]-8-carboxylate

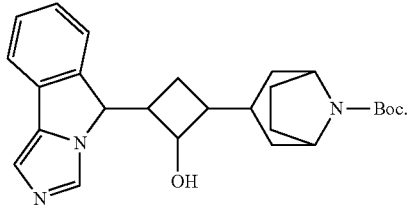 [SMILES: CC(C)(C)OC(=O)N1C2CCC1CC(C1CC(C3c4ccccc4-c4cncn43)C1O)C2]

tert-butyl (1R,2'S,3r,3'R,5S)-2'-hydroxy-3'-((R)-5H-imidazo[5,1-a]isoindol-5-yl)-8-azaspiro[bicyclo[3.2.1]octane-3,1'-cyclobutane]-8-carboxylate
tert-butyl (1R,2'R,3s,3'S,5S)-2'-hydroxy-3'-((S)-5H-imidazo[5,1-a]isoindol-5-yl)-8-azaspiro[bicyclo[3.2.1]octane-3,1'-cyclobutane]-8-carboxylate
tert-butyl (1R,2'S,3r,3'R,5S)-2'-hydroxy-3'-((S)-5H-imidazo[,1-a]isoindol-5-yl)-8-azaspiro[bicyclo[3.2.1]octane-3,1'-cyclobutane]-8-carboxylate
tert-butyl (1R,2'R,3s,3'S,5S)-2'-hydroxy-3'-((R)-5H-imidazo[5,1-a]isoindol-5-yl)-8-azaspiro[bicyclo[3.2.1]octane-3,1'-cyclobutane]-8-carboxylate
tert-butyl (1R,2'S,3r,3'S,5S)-2'-hydroxy-3'-((R)-5H-imidazo[5,1-a]isoindol-5-yl)-8-azaspiro[bicyclo[3.2.1]octane-3,1'-cyclobutane]-8-carboxylate
tert-butyl (1R,2'R,3s,3'R,5S)-2'-hydroxy-3'-((S)-5H-imidazo[5,1-a]isoindol-5-yl)-8-azaspiro[bicyclo[3.2.1]octane-3,1'-cyclobutane]-8-carboxylate
tert-butyl (1R,2'R,3s,3'R,5S)-2'-hydroxy-3'-((R)-5H-imidazo[5,1-a]isoindol-5-yl)-8-azaspiro[bicyclo[3.2.1]octane-3,1'-cyclobutane]-8-carboxylate
tert-butyl (1R,2'S,3s,3'S,5S)-2'-hydroxy-3'-((S)-5H-imidazo[5,1-a]isoindol-5-yl)-8-azaspiro[bicyclo[3.2.1]octane-3,1'-cyclobutane]-8-carboxylate
tert-butyl (1R,2'S,3s,3'R,5S)-2'-hydroxy-3'-((R)-5H-imidazo[5,1-a]isoindol-5-yl)-8-azaspiro[bicyclo[3.2.1]octane-3,1'-cyclobutane]-8-carboxylate
tert-butyl (1R,2'R,3r,3'S,5S)-2'-hydroxy-3'-((S)-5H-imidazo[5,1-a]isoindol-5-yl)-8-azaspiro[bicyclo[3.2.1]octane-3,1'-cyclobutane]-8-carboxylate
tert-butyl (1R,2'S,3s,3'R,5S)-2'-hydroxy-3'-((S)-5H-imidazo[5,1-a]isoindol-5-yl)-8-azaspiro[bicyclo[3.2.1]octane-3,1'-cyclobutane]-8-carboxylate
tort-butyl (1R,2'R,3r,3'S,5S)-2'-hydroxy-3'-((R)-5H-imidazo[5,1-a]isoindol-5-yl)-8-azaspiro[bicyclo[3.2.1]octane-3,1'-cyclobutane]-8-carboxylate
tert-butyl (1R,2'S,3s,3'S,5S)-2'-hydroxy-3'-((R)-5H-imidazo[5,1-a]isoindol-5-yl)-8-azaspiro[bicyclo[3.2.1]octane-3,1'-cyclobutane]-8-carboxylate Step 1:
tert-butyl 2'-oxo-8-azaspiro[bicyclo[3.2.1]octane-3,1'-cyclobutane]-8-carboxylate

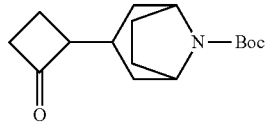 [SMILES: CC(C)(C)OC(=O)N1C2CCC1CC(C1CCC1=O)C2]

Potassium hydroxide (85 mass %, 609 mg, 9.23 mmol) was added to a stirred dimethyl sulfoxide (9.2 mL) solution of tert-butyl 3-oxo-8-azabicyclo[3.2.1]octane-8-carboxylate (1.04 g, 4.62 mmol) and cyclopropyldiphenylsulfonium tetrafluoroborate (1.60 g, 4.85 mmol) at room temperature. After 20 h, the reaction was quenched by dropwise addition of saturated aqueous sodium bicarbonate solution (25 mL). The quenched reaction was extracted with isopropyl acetate (3×25 mL). The organic extracts were combined, washed with brine (25 mL), dried over sodium sulfate, and concentrated. The residue thereby obtained was dissolved in toluene (46 mL). p-Toluenesulfonic acid monohydrate (46 mg, 0.23 mmol) was added to the stirred solution at room temperature. The reaction vessel was fixed with a reflux condenser and warmed to 110° C. After 2 h, the reaction was cooled to room temperature and concentrated. The residue was purified by a silica gel column eluting with heptane/isopropyl acetate (40:60) to afford 483 mg (39%, 79:21 d.r.) tert-butyl 2'-oxospiro[8-azabicyclo[3.2.1]octane-3,1'-cyclobutane]-8-carboxylate as a colorless solid. LCMS (ESI) m/z=266.2 [M+H]⁺.

Step 2:
tert-butyl (E)-2'-oxo-3'-(2-(1-trityl-1H-imidazol-4-yl)benzylidene)-8-azaspiro[bicyclo[3.2.1]octane-3,1'-cyclobutane]-8-carboxylate

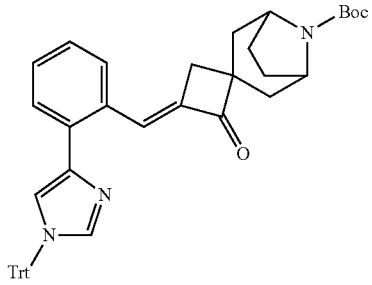

A slurry of tert-butyl 2'-oxospiro[8-azabicyclo[3.2.1]octane-3,1'-cyclobutane]-8-carboxylate (2.65 g, 9.98 mmol), 2-[1-(triphenylmethyl)-1H-imidazol-4-yl]benzaldehyde (4.55 g, 11.0 mmol) and Ca(OH)₂ (1.48 g, 20.0 mmol) in EtOH (33 mL) was stirred for 24 h at 80° C. The reaction was cooled to room temperature and insoluble material was removed by filtration. The filtrate was concentrated. The residue was purified by a silica gel column eluting with DCM/methanol (90:10) to afford 5.60 g (85%) tert-butyl (E)-2'-oxo-3'-(2-(1-trityl-1H-imidazol-4-yl)benzylidene)-8-azaspiro[bicyclo[3.2.1]octane-3,1'-cyclobutane]-8-carboxylate Step 3:
tert-butyl 3'-(5H-imidazo[5,1-a]isoindol-5-yl)-2'-oxo-3-azaspiro[bicyclo[3.2.1]octane-8,1'-cyclobutane]-3-carboxylate

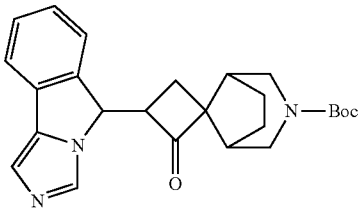 [SMILES: CC(C)(C)OC(=O)N1CC2CCC(C1)C21CC(C2c3ccccc3-c3cncn32)C1=O]

Acetic acid (5.5 mL) was added to a stirred MeOH (55 mL) suspension of tert-butyl (3'E)-2'-oxo-3'-[[2-(1-tritylimidazol-4-yl)phenyl]methylene]spiro[8-azabicyclo[3.2.]octane-3,1'-cyclobutane]-8-carboxylate (5.50 g, 8.31 mmol) at room temperature. The reaction flask was fixed with a reflux condenser and warmed to 70° C. After 6 h, the reaction was cooled to room temperature and concentrated. The residue was suspended in DCM (100 mL) and saturated aqueous sodium bicarbonate solution (100 mL) was added with stirring. The consequent layers were separated. The aqueous layer was extracted with additional DCM (2×50 mL). The organic layers were combined, dried over sodium sulfate, and concentrated. The residue was purified by a silica gel column eluting with DCM/MeOH (95:5) to afford 1.60 g (46%) tert-butyl 3'-(5H-imidazo[1,5-b]isoindol-5-yl)-2'-oxo-spiro[8-azabicyclo[3.2.1]octane-3,1'-cyclobutane]-8-carboxylate as a pale yellow solid. LCMS (ESI) m/z=420.5 [M+H]$^+$.

Step 4:
tert-butyl (1R,2'S,3r,3'R,5S)-2'-hydroxy-3'-((R)-5H-imidazo[5,1-a]isoindol-5-yl)-8-azaspiro[bicyclo[3.2.1]octane-3,1'-cyclobutane]-8-carboxylate
tert-butyl (1R,2'R,3s,3'S,5S)-2'-hydroxy-3'-((S)-5H-imidazo[5,1-a]isoindol-5-yl)-8-azaspiro[bicyclo[3.2.1]octane-3,1'-cyclobutane]-8-carboxylate
tert-butyl (1R,2'S,3r,3'R,5S)-2'-hydroxy-3'-((S)-5H-imidazo[5,1-a]isoindol-5-yl)-8-azaspiro[bicyclo[3.2.1]octane-3,1'-cyclobutane]-8-carboxylate
tert-butyl (1R,2'R,3s,3'S,5S)-2'-hydroxy-3'-((R)-5H-imidazo[5,1-a]isoindol-5-yl)-8-azaspiro[bicyclo[3.2.1]octane-3,1'-cyclobutane]-8-carboxylate
tert-butyl (1R,2'S,3r,3'S,5S)-2'-hydroxy-3'-((R)-5H-imidazo[5,1-a]isoindol-5-yl)-8-azaspiro[bicyclo[3.2.1]octane-3,1'-cyclobutane]-8-carboxylate
tert-butyl (1R,2'R,3s,3'R,5S)-2'-hydroxy-3'-((S)-5H-imidazo[5,1-a]isoindol-5-yl)-8-azaspiro[bicyclo[3.2.1]octane-3,1'-cyclobutane]-8-carboxylate
tert-butyl (1R,2'R,3s,3'R,5S)-2'-hydroxy-3'-((R)-5H-imidazo[5,1-a]isoindol-5-yl)-8-azaspiro[bicyclo[3.2.1]octane-3,1'-cyclobutane]-8-carboxylate
tert-butyl (1R,2'S,3s,3'S,5S)-2'-hydroxy-3'-((S)-5H-imidazo[5,1-a]isoindol-5-yl)-8-azaspiro[bicyclo[3.2.1]octane-3,1'-cyclobutane]-8-carboxylate
tert-butyl (1R,2'S,3s,3'R,5S)-2'-hydroxy-3'-((R)-5H-imidazo[S,1-a]isoindol-5-yl)-8-azaspiro[bicyclo[3.2.1]octane-3,1'-cyclobutane]-8-carboxylate
tert-butyl (1R,2'R,3r,3'S,5S-2'-hydroxy-3'-((S)-5H-imidazo[5,1-a]isoindol-5-yl)-8-azaspiro[bicyclo[3.2.1]octane-3,1'-cyclobutane]-8-carboxylate
tert-butyl (1R,2'S,3s,3'R,5S-2'-hydroxy-3'-((S))-5H-imidazo[5,1-a]isoindol-5-yl)-8-azaspiro[bicyclo[3.2.1]octane-3,1'-cyclobutane]-8-carboxylate
tert-butyl (1R,2'R,3r,3'S,5S)-2'-hydroxy-3'-((R)-5H-imidazo[5,1-a]isoindol-5-yl)-8-azaspiro[bicyclo[3,2,1]octane-3,1'-cyclobutane]-8-carboxylate
tert-butyl (1R,2'S,3s,3'S,5S)-2'-hydroxy-3'-((R)-5H-imidazo[5,1-a]isoindol-5-yl)-8-azaspiro[bicyclo[3,2,1]octane-3,1'-cyclobutane]-8-carboxylate

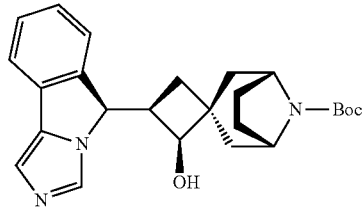

12a

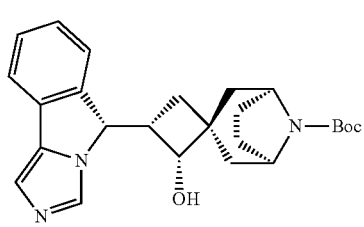

12b

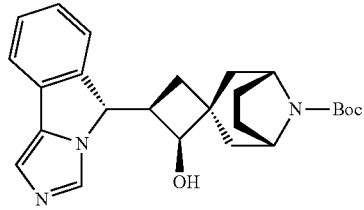

12c

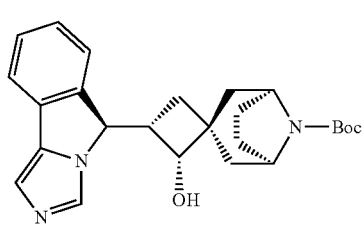

12d

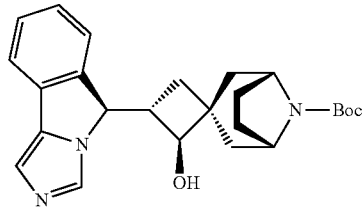

12e

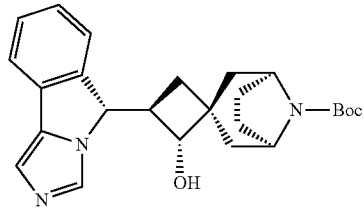

12f

-continued

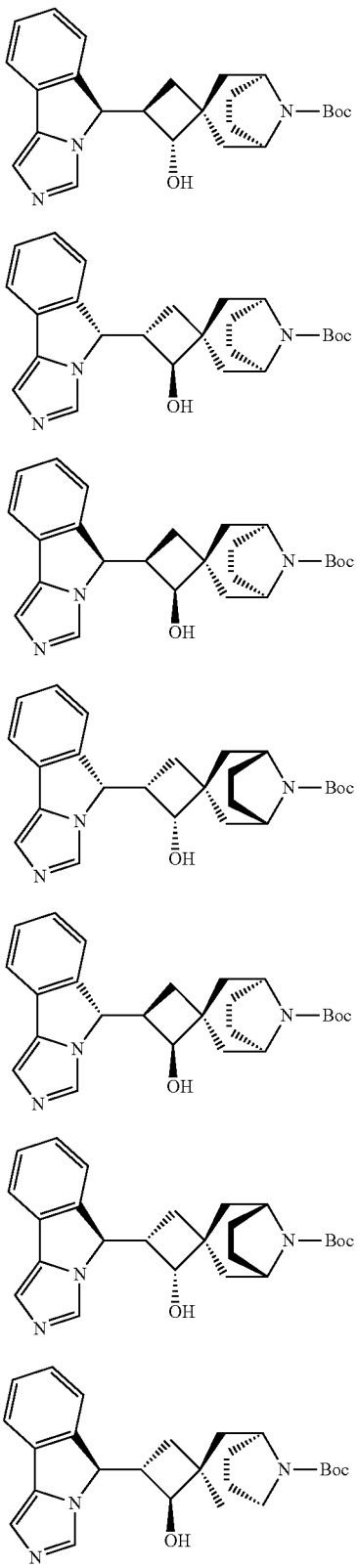

Sodium borohydride (289 mg, 7.63 mmol) was added to a stirred MeOH (38 mL) solution of tert-butyl 3'-(5H-imidazo[1,5b]isoindol-5-yl)-2'-oxo-spiro[8-azabicyclo[3.2.1]octane-3,1'-cyclobutan]-8-carboxylate (1.60 g, 3.81 mmol) at 0° C. The resulting solution was stirred for 2 h at 0° C. The reaction was concentrated and suspended in brine (200 mL). The reaction was quenched by dropwise addition of brine (100 mL) at 0° C. The mixture was extracted with DCM (3×100 mL). The residue was purified by silica gel column eluting with DCM/MeOH (90:10) to afford 1.26 g (78%) of tert-butyl 2'-hydroxy-3'-(5H-imidazo[5,1-a]isoindol-5-yl)-8-azaspiro[bicyclo[3.2.1]octane-3,1'-cyclobutane]-8-carboxylate as a colorless solid. LCMS (ESI) m/z=422.2 [M+H]$^+$.

The product was further isolated by chiral separation to afford 13 of 16 possible stereoisomers as colorless solids.

The absolute configuration of 12a, 12b, 12c, 12d, 12e, 12f, 12g, 12h, 12i, 12j, 12k, 12l, and 12m was assigned arbitrarily.

Example 12a: tert-butyl (1R,2'S,3r,3'R,5S)-2'-hydroxy-3'-((R)-5H-imidazo[5,1-a]isoindol-5-yl)-8-azaspiro[bicyclo[3.2.]octane-3,1'-cyclobutane]-8-carboxylate. LCMS (ESI) m/z=422.2 [M+H]$^+$. $^1$H NMR (400 MHz, DMSO-d$_6$) δ 7.82 (s, 1H), 7.57 (t, J=7.4 Hz, 2H), 7.36 (td, J=7.5, 1.1 Hz, 1H), 7.25 (td, J=7.6, 1.2 Hz, 1H), 7.12 (s, 1H), 5.67 (d, J=8.3 Hz, 1H), 5.34 (d, J=7.3 Hz, 1H), 4.08 (t, J=8.1 Hz, 1H), 3.92 (d, J=5.9 Hz, 2H), 2.27 (s, 2H), 2.15 (s, 1H), 1.80 (s, 2H), 1.70 (s, 2H), J=1.62 (s, 2H), 1.48 (s, 1H), 1.37 (s, 9H), 1.04 (s, 1H). tR=0.784 min (CHIRALCEL OX, MeOH:NH$_4$OH:H$_2$O=24.9:0.1:75, 1.0 mL/min). 12a and 12b are enantiomers.

Example 12b: tert-butyl (1R,2'R,3s,3'S,5S)-2'-hydroxy-3'-((S)-5H-imidazo[5,1-a]isoindol-5-yl)-8-azaspiro[bicyclo[3.2.1]octane-3,1'-cyclobutane]-8-carboxylate. LCMS (ESI) m/z=422.2 [M+H]$^+$. tR=1.086 min (CHIRALCEL OX, MeOH:NH$_4$OH:H$_2$O=24.9:0.1:75, 1.0 mL/min). 12a and 12b are enantiomers.

Example 12c: tert-butyl (1R,2'S,3r,3'R,5S)-2'-hydroxy-3'-((S)-5H-imidazo[5,1-a]isoindol-5-yl)-8-azaspiro[bicyclo[3.2.1]octane-3,1'-cyclobutane]-8-carboxylate. LCMS (ESI) m/z=422.2 [M+H]$^+$. $^1$H NMR (400 MHz, DMSO-d$_6$) δ 7.85 (s, 1H), 7.57 (dd, J=7.7, 6.2 Hz, 2H), 7.46-7.31 (m, 1H), 7.24 (td, J=7.6, 1.2 Hz, 1H), 7.12 (s, 1H), 5.68 (d, J=5.0 Hz, 1H), 5.44 (d, J=9.2 Hz, 1H), 4.09 (d, J=6.5 Hz, 1H), 4.01 (s, 1H), 3.86 (s, 1H), 2.32 (d, J=11.5 Hz, 2H), 1.81 (s, 5H), 1.74-1.58 (m, 3H), 1.40 (s, 10H). tR=0.756 min (Cellulose-3, MeOH:NH$_4$OH:H$_2$O=9.9:0.1:90, 1.0 ml/min). 12c and 12d are enantiomers.

Example 12d: tert-butyl (1R,2'R,3s,3'S,5S)-2'-hydroxy-3'-((R)-5H-imidazo[5,1-a]isoindol-5-yl)-8-azaspiro[bicyclo[3.2.1]octane-3,1'-cyclobutane]-8-carboxylate. LCMS (ESI) m/z=422.2 [M+H]$^+$. tR=1.080 min (Cellulose-3, MeOH:NH$_4$OH:H$_2$O=9.9:0.1:90, 1.0 mL/min). 12c and 12d are enantiomers.

Example 12e: tert-butyl (1R,2'S,3r,3'S,5S)-2'-hydroxy-3'-((R)-5H-imidazo[5,1-a]isoindol-5-yl)-8-azaspiro[bicyclo[3.2.1]octane-3,1'-cyclobutane]-8-carboxylate. LCMS (ESI) m/z=422.2 [M+H]$^+$. $^1$H NMR (400 MHz, DMSO-d6) δ 7.82 (s, 0.1 Hz), 7.61-7.53 (m, 2H), 7.36 (t, J=7.5 Hz, 1H), 7.29-7.20 (m, 1H), 7.12 (s, 1H), 5.35 (d, J=7.6 Hz, 1H), 5.28 (s, 1H), 4.08 (s, 1H), 3.97 (s, 1H), 3.79 (t, J=7.8 Hz, 1H), 2.41 (d, J=12.0 Hz, 1H), 2.15-2.05 (m, 1H), 1.89 (dd, J=13.9, 3.3 Hz, 1H), 1.78 (s, 5H), 1.57 (t, J=10.3 Hz, 1H), 1.39 (s, 9H), 1.37-1.34 (m, 2H). tR=0.927 min (CHIRALCEL OX, MeOH:NH$_4$OH:H$_2$O=24.9:0.1:75, 1.0 mL/min). 12e and 12f are enantiomers.

Example 12f: tert-butyl (1R,2'R,3s,3'R,5S)-2'-hydroxy-3'-((S)-5H-imidazo[5,1-a]isoindol-5-yl)-8-azaspiro[bicyclo[3.2.1]octane-3,1'-cyclobutane]-8-carboxylate. LCMS (ESI)

m/z=422.2 [M+H]⁺. tR=1.029 min (CHIRALCEL OX, MeOH:NH₄OH:H₂O=24.9:0.1:75, 1.0 mL/min). 12e and 12f are enantiomers.

Example 12g: tert-butyl (1R,2'R,3s,3'R,5S)-2'-hydroxy-3'-((R)-5H-imidazo[5,1-a]isoindol-5-yl)-8-azaspiro[bicyclo[3,2,1]octane-3,1'-cyclobutane]-8-carboxylate. LCMS (ESI) m/z=422.2 [M+H]⁺. ¹H NMR (400 MHz, DMSO-d4) δ 7.89 (s, 1H), 7.59 (d, J=7.7 Hz, 1H), 7.42-7.26 (m, 2H), 7.19 (td, J=7.5, 1.2 Hz, 1H), 7.11 (s, 1H), 6.02 (d, J=7.5 Hz, 1H), 5.30 (d, J=10.7 Hz, 1H), 4.28 (s, 1H), 3.97 (s, 2H), 3.31-3.20 (m, 1H), 2.37-2.21 (m, 1H), 2.17 (t, J=10.7 Hz, 1H), 1.90 (s, 1H), 1.84 (s, 1H), 1.78 (s, 3H), 1.69 (td, J=10.6, 9.9, 3.7 Hz, 2H), 1.39 (s, 10H). tR=0.600 min (Cellulose-3, MeOH:NH₄OH:H₂O=9.9:0.1:90, 1.0 mL/min). 12g and 12h are enantiomers.

Example 12h: tert-butyl (1R,2'S,3s,3'S,5S)-2'-hydroxy-3'-((S)-5H-imidazo[5,1-a]isoindol-5-yl)-8-azaspiro[bicyclo[3.2.1]octane-3,1'-cyclobutane]-8-carboxylate. LCMS (ESI) m/z=422.2 [M+H]⁺. tR=1.100 min (Cellulose-3, MeOH:NH₄OH:H₂O=9.9:0.1:90, 1.0 mL/min). 12g and 12h are enantiomers.

Example 12h: tert-butyl (1R,2'S,3s,3'R,5S)-2'-hydroxy-3'-((R)-5H-imidazo[5,1-a]isoindol-5-yl)-8-azaspiro[bicyclo[3.2.1]octane-3,1'-cyclobutane]-8-carboxylate. LCMS (ESI) m/z=422.2 [M+H]⁺. ¹H NMR (400 MHz, DMSO-d₆) δ 7.74 (s, 1H), 7.61 (dd, J=27.2, 7.5 Hz, 2H), 7.37 (td, J=7.5, 1.0 Hz, 1H), 7.26 (td, J=7.6, 1.2 Hz, 1H), 7.11 (s, 1H), 6.01 (d, J=7.2 Hz, 1H), 5.36 (d, J=9.6 Hz, 1H), 4.30 (d, J=8.5 Hz, 1H), 4.01-3.93 (m, 2H), 2.42 (s, 2H), 2.25 (s, 1H), 2.03 (s, 1H), 1.93 (s, 1H), 1.76 (s, 3H), 1.66 (s, 2H), 1.39 (s, 9H), 1.29 (s, 1H). tR=0.928 min (Cellulose-3, MeOH:NH₄OH:H₂O=9.9:0.1:90, 1.0 mL/min). 12i and 12j are enantiomers.

Example 12j: tert-butyl (1R,2'R,3r,3'S,5S)-2'-hydroxy-3'-((S)-5H-imidazo[5,1-a]isoindol-5-yl)-8-azaspiro[bicyclo[3.2.1]octane-3,1'-cyclobutane]-8-carboxylate. LCMS (ESI) m/z=422.2 [M+H]⁺. tR=1.627 min (Cellulose-3, MeOH:NH₄OH:H₂O-9.9:0.1:90, 1.0 mL/min). 12i and 12j are enantiomers.

Example 12k: tert-butyl (1R,2'S,3s,3'R,5S)-2'-hydroxy-3'-((S)-5H-imidazo[5,1-a]isoindol-5-yl)-8-azaspiro[bicyclo[3.2.1]octane-3,1'-cyclobutane]-8-carboxylate. LCMS (ESI) m/z=422.2 [M+H]⁺. ¹H NMR (400 MHz, DMSO-d₆) δ 7.92 (s, 1i), 7.58 (dd, J=7.5, 1.1 Hz, 1H), 7.41-7.31 (m, 2H), 7.22 (td, J=7.5, 1.2 Hz, 1H), 5.65 (d, J=8.5 Hz, 1H), 5.32 (d, J=8.8 Hz, 1H), 3.93 (s, 3H), 2.18 (d, J=9.6 Hz, 1R), 2.14 (s, 2H), 1.82 (s, 2H), 1.69-1.60 (m, 3H), 1.52 (p, J=10.7 Hz, 4H), 1.40 (s, 9H). tR=1.569 min (CHIRALCEL OX, MeOH:NH₄OH:H₂O=24.9:0.1:75, 1.0 mL/min). 12k and 12l are enantiomers.

Example 12l: tert-butyl (1R,2'R,3r,3'S,5S)-2'-hydroxy-3'-((R)-5H-imidazo[5,1-a]isoindol-5-yl)-8-azaspiro[bicyclo[3.2.1]octane-3,1'-cyclobutane]-8-carboxylate. LCMS (ESI) m/z=422.2 [M+H]⁺. tR=1.033 min (CHIRALCEL OX, MeOH:NH₄OH:H₂O=24.9:0.1:75, 1.0 mL/min). 12k and 12l are enantiomers.

Example 12m: tert-butyl (1R,2'S,3s,3'S,5S)-2'-hydroxy-3'-((R)-5H-imidazo[5,1-a]isoindol-5-yl)-8-azaspiro[bicyclo[3,2,1]octane-3,1'-cyclobutane]-8-carboxylate. LCMS (ESI) m/z=422.2 [M+H]+. ¹H NMR (400 MHz, DMSO-d₆) δ 7.89 (s, 1H), 7.58 (d, J=7.5 Hz, 1H), 7.42-7.33 (m, 2H), 7.24 (td, J=7.5, 1.2 Hz, 1H), 7.09 (s, 1H), 5.34 (d, J=7.9 Hz, 1H), 5.26 (s, 1H), 4.09 (s, 1H), 4.01 (s, 1H), 3.73 (s, 1H), 3.49-3.36 (m, 1H), 3.31 (s, 1I-), 2.27 (q, J=8.2 Hz, 2H), 1.92-1.63 (m, 4H), 1.52 (d, J=13.3 Hz, 1H), 1.47-1.32 (m, 1H), 1.40 (s, 10H). tR=0.992 min (CHIRALCEL OX, MeOH:NH₄OH:H₂O=24.9:0.1:75, 1.0 mL/min).

Example 13: 1-hydroxy-2-(5H-imidazo[5,1-a]isoindol-5-yl)-8-thiaspiro[4.5]decane 8,8-dioxide

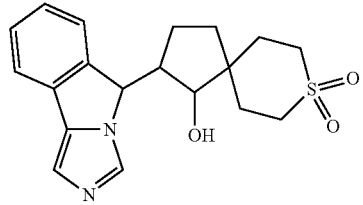 [SMILES: O=S1(=O)CCC2(CCC(C3c4ccccc4-c4cncn43)C2O)CC1]

(1R,2S)-1-hydroxy-2-((S)-5H-imidazo[5,1-a]isoindol-5-yl)-8-thiaspiro[4.5]decane 8,8-dioxide
(1S,2R)-1-hydroxy-2-((R)-5H-imidazo[5,1-a]isoindol-5-yl)-8-thiaspiro[4.5]decane 8,8-dioxide Step 1:
methyl 4-(3-chloropropyl)thiane-4-carboxylate

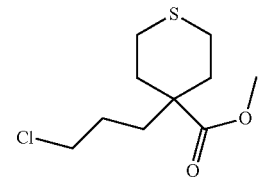

To a solution of methyl thiane-4-carboxylate (500.00 mg, 3.12 mmol) in THF was added LiHMDS (626.56 mg, 3.75 mmol) under nitrogen at −60° C. The resulting solution was stirred for 1 h at −60° C. Then 1-bromo-3-chloropropane was added at −60° C. and stirred for 2 h at room temperature. The reaction was quenched with water (50 mL). The resulting solution was extracted with EtOAc (3×50 mL) and the organic layers combined. The organic layer was dried over anhydrous sodium sulfate and concentrated in vacuo. The residue was purified by flash chromatography on silica gel column eluting with PE/EtOAc (5/1). This resulting in 740 mg (100%) of methyl 4-(3-chloropropyl)thiane-4-carboxylate as a yellow oil. GCMS: m/z=+236.

Step 2:
methyl 4-(3-iodopropyl)thiane-4-carboxylate

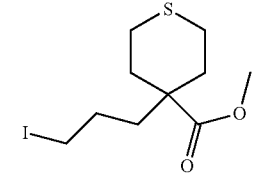

To a solution of methyl 4-(3-chloropropyl)thiane-4-carboxylate (5.56 g, 17 mmol) in DMF (50 mL) was added KI (5.66 g, 34.0 mmol) at 25° C. The resulting solution was stirred for 16 h at 80° C. The resulting mixture was washed with Na₂S₂O₃ (aq). The resulting solution was extracted with ether and the organic layers combined and dried over anhydrous sodium sulfate and concentrated under vacuum. The residue was purified by a silica gel column with PE/EtOAc (5/1). The collected fractions were combined and concentrated under vacuum. This resulted in 2.8 g (50%) of methyl 4-(3-iodopropyl)thiane-4-carboxylate as yellow oil. GCMS: m/z=328.
Step 3:
8-thiaspiro[4.5]decan-1-one

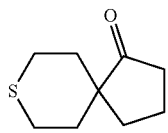 [SMILES: O=C1CCCC12CCSCC2]

To a solution of methyl 4-(3-iodopropyl)thiane-4-carboxylate (500 mg, 1.52 mmol) in THF was added t-BuLi (146.37 mg, 2.26 mmol) at −78° C. under nitrogen. The resulting solution was stirred for 1 h at −78° C. The reaction was quenched with water (20 mL). The resulting solution was extracted with EtOAc (3×20 mL) and the organic layers combined. The organic layer was dried over anhydrous sodium sulfate and concentrated in vacuum. The residue was purified by flash chromatography on silica gel column eluting with PE/EtOAc (5/1). This resulted in 155 mg (60%) of 8-thiaspiro[4.5]decan-1-one as yellow oil. LCMS (ESI) m/z s 171.0 [M+H]$^+$.
Step 4:
(2E)-2-([2-[1-(triphenylmethyl)-1H-imidazol-4-yl]phenyl]methylidene)-8-thiaspiro[4.5]decan-1-one

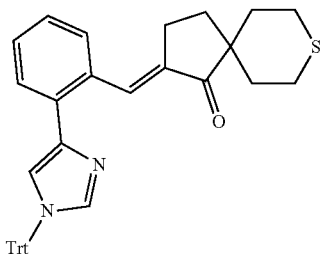

A solution of 8-thiaspiro[4.5]decan-1-one (700 mg, 4.11 mmol) and 2-[1-(triphenylmethyl)-1H-imidazol-4-yl]benzaldehyde (2.6 g, 6.27 mmol) in EtOH (10 mL) was added Ca(OH)$_2$ (762 mg, 10.28 mmol). The resulting solution was stirred for 16 h at 80° C. The mixture was concentrated under vacuum. The residue was purified by silica gel column eluting with PE/EtOAc (1/1). This resulted in 2.3 g (crude) of (2E)-2-([2-[1-(triphenylmethyl)-1H-imidazol-4-yl]phenyl]methylidene)-8-thiaspiro[4.5]decan-1-one as a yellow solid. LCMS (ESI) m/z=567.2 [M+H]$^+$.
Step 5:
2-[5H-imidazo[4,3-a]isoindol-5-yl]-8-thiaspiro[4.5]decan-1-one

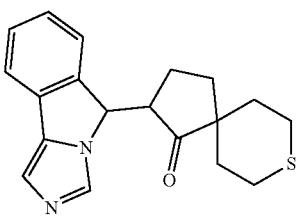 [SMILES: O=C1C(C2c3ccccc3-c3cncn32)CCC12CCSCC2]

A solution of (2E)-2-([2-[1-(triphenylmethyl)-1H-imidazol-4-yl]phenyl]methylidene)-8-thiaspiro[4.5]decan-1-one (2 g, 3.53 mmol) in MeOH (50 mL) and AcOH (10 mL) was stirred for 10 h at 70° C. The resulting mixture was concentrated under vacuum. The residue was purified by silica gel column eluting with DCM/MeOH (10:1). This resulted in 1 g (86%) of 2-[5H-imidazo[4,3-a]isoindol-5-yl]-8-thiaspiro[4.5]decan-1-one as a yellow solid. LCMS (ESI) m/z=325.2 [M+H]$^+$.
Step 6:
2-[5H-imidazo[4,3-a]isoindol-5-yl]-8-lambda-6-thiaspiro[4,5]decane-1,8,8-trione

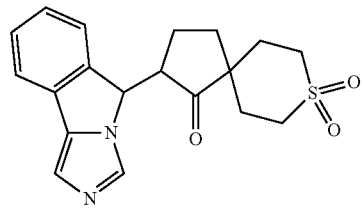 [SMILES: O=C1C(C2c3ccccc3-c3cncn32)CCC12CCS(=O)(=O)CC2]

To a solution of 2-[5H-imidazo[4,3-a]isoindol-5-yl]-8-thiaspiro[4.5]decan-1-one (300 mg, 0.924 mmol) in DCM (15 mL) was added m-CPBA (321 mg, 1.86 mmol) at 25° C. The resulting solution was stirred for 3 h at 25° C. The resulting mixture was washed with Na$_2$S$_2$O$_3$ (aq.). The resulting solution was extracted with EtOAc and the organic layers combined and dried over anhydrous sodium sulfate and concentrated under vacuum. The residue was purified by a silica gel column with ethyl DCM/MeOH (10/1). This resulted in 300 mg (crude) of 2-[5H-imidazo[4,3-a]isoindol-5-yl]-8-lambda-6-thiaspiro[4,5]decane-1,8,8-trione as yellow solid. LCMS (ESI) m/z=357.2 [M+H]$^+$.
Step 7:
(1R,2S)-1-hydroxy-2-((S)-5H-imidazo[5,1-a]isoindol-5-yl)-8-thiaspiro[4.5]decane 8,8-dioxide
(1S,2R)-1-hydroxy-2-((R)-5H-imidazo[5,1-a]isoindol-5-yl)-8-thiaspiro[4.5]decane 8,8-dioxide 13a

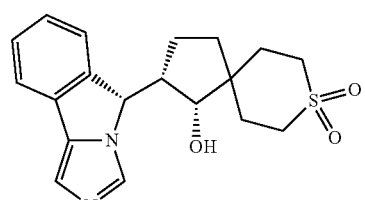

13b

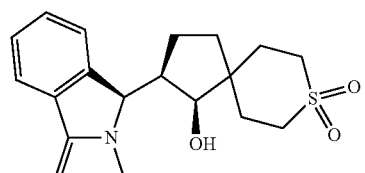

Under nitrogen, a solution of 2-[5H-imidazo[4,3-a]isoindol-5-yl]-8-lambda-6-thiaspiro[4,5]decane-1,8,8-trione (300.00 mg, 0.84 mmol) in THF was added L-Selectride (0.6 mL, 2.5 mmol) at −60° C. The resulting solution was stirred for 2 h at −60 OC. The reaction was quenched with ethanol (5 mL) and diluted with water (100 mL). The resulting solution was extracted with EtOAc (3×200 mL) and the organic layers combined. The organic layer was dried over anhydrous sodium sulfate and concentrated in vacuum. The residue was purified by flash chromatography on silica gel column eluting with DCM/MeOH (10/1). The crude product was further isolated by Prep-HPLC and Chiral-HPLC.

The absolute configuration of 13a-13b was assigned arbitrarily.

Example 13a: (1R,2S)-1-hydroxy-2-((S)-5H-imidazo[5,1-a]isoindol-5-yl)-8-thiaspiro[4.5]decane 8,8-dioxide (16 mg, 2%) as a white solid. LCMS (ESI) m/z=359.2 [M+H]$^+$. $^1$H NMR (300 MHz, DMSO-d6) δ 7.89 (s, 1H), 7.68 (d, J=7.6 Hz, 1H), 7.59 (d, J=7.5 Hz, 1H), 7.38 (t, J=7.2 Hz, 1H), 7.28 (t, J=6.8 Hz, 1H), 7.12 (s, 1H), 5.57 (d, J=5.8 Hz, 1H), 5.41 (d, J=6.9 Hz, 1H), 4.10 (t, J=5.4 Hz, 1H), 3.23-3.08 (m, 1H), 2.99 (d, J=8.0 Hz, 3H), 2.51-2.43 (m, 1H), 2.20-2.01 (m, 1H), 2.01-1.86 (m, 1H), 1.74 (m, 3H), 1.66-1.46 (m, 3H). tR=2.960 min (CHIRALPAK IC-3, 0.46×5 cm; 3 um, Hex(0.1% DEA):EtOH=50:50, 1 mL/min). 13a and 13b are enantiomers.

Example 13b: (1S,2R)-1-hydroxy-2-((R)-5H-imidazo[5,1-a]isoindol-5-yl)-8-thiaspiro[4.5]decane 8,8-dioxide (13.6 mg, 2%) as a white solid. LCMS (ESI) m/z=359.2 [M+H]$^+$. tR=3.724 min (CHIRALPAK IC-3, 0.46×5 cm; 3 um, Hex (0.1% DEA):EtOH=50:50, 1 mL/min). 13a and 13b are enantiomers.

Example 14: 7-((difluoromethyl)sulfonyl)-2-(5H-imidazo[5,1-a]isoindol-5-yl)-7-azaspiro[3.5]nonan-1-ol

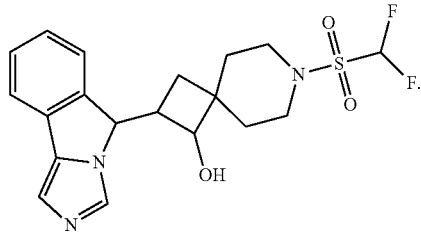 [SMILES: O=S(=O)(C(F)F)N1CCC2(CC1)CC(C1c3ccccc3-c3cncn31)C2O]

(1S,2R)-7-difluoromethanesulfonyl-2-[(5R)-5H-imidazo[4,3-a]isoindol-5-yl]-7-azaspiro[3.5]nonan-1-ol (1R,2S)-7-difluoromethanesulfonyl-2-[(5S)-5H-imidazo[4,3-a]isoindol-5-yl]-7-azaspiro[3.5]nonan-1-ol 14a

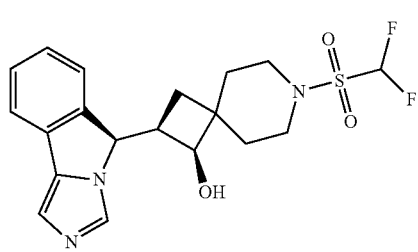

14b

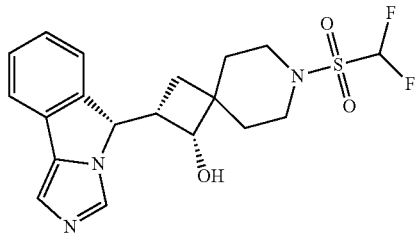

A mixture of 2-(5H-imidazo[1,5-b]isoindol-5-yl)-7-azaspiro[3.5]nonan-3-ol (300.0 mg, 1.02 mmol) and Na$_2$CO$_3$ (323 mg, 3.05 mmol) in DCM (10 mL) and Water (10 mL) was added difluoromethanesulfonyl chloride (1.5 g, 10.16 mmol) and the mixture was stirred at 25° C. for overnight. The reaction was quenched with water (50 mL). The resulting solution was extracted with EtOAc (3×50 mL) and the organic layers combined. The residue was purified by flash chromatography on silica gel eluting with DCM/ MeOH (97:3). The crude product was further isolated by Prep-HPLC and Chiral-HPLC.

The absolute configuration of 14a-14b was assigned arbitrarily.

Example 14a: (1S,2R)-7-difluoromethanesulfonyl-2-[(5R)-5H-imidazo[4,3-a]isoindol-5-yl]-7-azaspiro[3.5]nonan-1-ol (8 mg, 3.9%) as a white solid. LCMS (ESI) m/z=410.1 [M+H]$^+$. $^1$H NMR (300 MHz, DMSO-d6) δ 7.87 (s, 1H), 7.61 (dd, J=11.3, 7.5 Hz, 2H), 7.40-7.37 (m, 1H), 7.35-6.92 (m, 3H), 5.81 (d, J=5.4 Hz, 1H), 5.46 (d, J=8.8 Hz, 1H), 4.16-4.12 (m, 1H), 3.48-3.30 (m, 4H), 2.73-2.50 (m, 1H), 1.97-1.62 (m, 3H), 1.60-1.48 (m, 3H). tR=1.886 min (CHIRALPAK IA-3, 0.46×5 cm; 3 um, Hex(0.1% DEA): EtOH=70:30, 1 mL/min). 14a and 14b are enantiomers.

Example 14b: (1R,2S)-7-difluoromethanesulfonyl-2-[(5S)-5H-imidazo[4,3-a]isoindol-5-yl]-7-azaspiro[3.5] nonan-1-ol (2.2 mg, 1.0%) as a white solid. LCMS (ESI) m/z=410.1 [M+H]$^+$. tR=2.871 min (CHIRALPAK IA-3, 0.46×5 cm; 3 um, Hex(0.1% DEA):EtOH=70:30, 1 mL/min). 14a and 14b are enantiomers.

Example 15: (1-hydroxy-2-(5H-imidazo[5,1]isoindol-5-yl)-7-azaspiro[3.5]nonan-7-yl)dimethylphosphine oxide

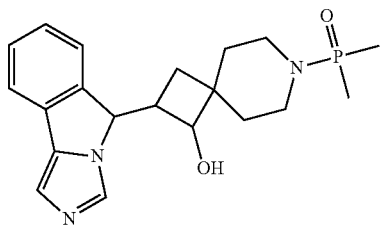 [SMILES: CP(C)(=O)N1CCC2(CC1)CC(C1c3ccccc3-c3cncn31)C2O]

(2S,3R)-7-dimethylphosphoryl-2-[(S)-5H-imidazo[1,5-b]isoindol-5-yl]-7-azaspiro[3.5]nonan-3-ol (2R,3S)-7-dimethylphosphoryl-2-[(5R)-5H-imidazo[1,5-b]isoindol-5-yl]-7-azaspiro[3.5]nonan-3-ol

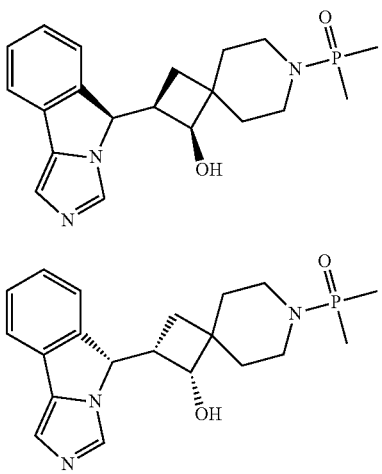

The title compound was prepared by the procedure described in Example 6, by substituting MsCl with dimethylphosphinic chloride in Step 2.

The absolute configuration of 15a-15b was assigned arbitrarily.

Example 15a: (2S,3R)-7-dimethylphosphoryl-2-[(5S)-5H-imidazo[1,5-b]isoindol-5-yl]-7-azaspiro[3.5]nonan-3-ol (40.6 mg, 20%) as a white solid. LCMS (ESI) m/z=372.2 [M+H]+. 1H NMR (400 MHz, DMSO-$d_6$) δ 7.86 (s, 1H), 7.68-7.54 (m, 2H), 7.43-7.20 (m, 2H), 7.13 (s, 1H), 5.68 (d, J=5.5 Hz, 1H), 5.45 (d, J=8.9 Hz, 1H), 4.15-4.03 (m, 1H), 3.01-2.74 (m, 4H), 2.56-2.53 (m, 1H), 1.97-1.59 (m, 3H), 1.48-1.41 (m, 3H), 1.34 (s, 3H), 1.29 (s, 3H). tR=3.765 min (CHIRALPAK IG-3, 0.46×10 cm; 3 um, Hex(0.1% DEA):EtOH=50:50, 1.0 mL/min). 15a and 15b are enantiomers.

Example 15b: (2R,3S)-7-dimethylphosphoryl-2-[(5R)-5H-imidazo[1,5-b]isoindol-5-yl]-7-azaspiro[3.5]nonan-3-ol (41.1 mg, 20%) as a white solid. LCMS (ESI) m/z=372.2 [M+H]+. tR=6.771 min (CHIRALPAK IG-3, 0.46×10 cm; 3 um, Hex(0.1% DEA):EtOH=50:50, 1.0 mL/min). 15a and 15b are enantiomers.

Example 16: 6-(5H imidazo[5,1-a]isoindol-5-yl)-2-(methylsulfonyl)-2-azaspiro[3.4]octan-5-ol

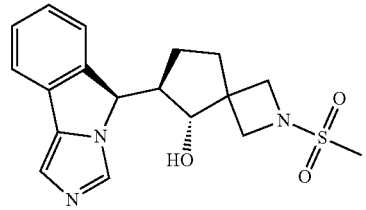

(5R,6R)-6-[(5R)-5H-imidazo[4,3-a]isoindol-5-yl]-2-methanesulfonyl-2-azaspiro[3.4]octan-5-ol Step 1:
6-(5H-imidazo[5,1-a]isoindol-5-yl)-2-azaspiro[3.4]octan-5-ol

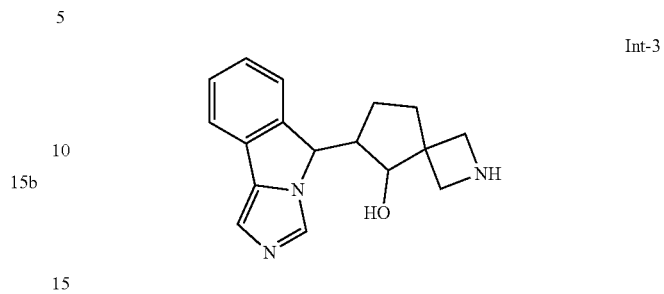

Int-3

To a solution of tert-butyl tert-butyl 5-hydroxy-6-(5H-imidazo[5,1-a]isoindol-5-yl)-2-azaspiro[3.4]octane-2-carboxylate (100.0 mg, 0.260 mmol) in DCM (3 mL) was added a solution of 4N HCl in dioxane (12 mL). The mixture was stirred for 0.5 h at room temperature. The resulting mixture was concentrated under vacuum to give 74 mg of 6-(5H-imidazo[5,1-a]isoindol-5-yl)-2-azaspiro[3.4]octan-5-ol as a yellow oil. The crude product was used in the next step without purification.

tert-butyl 5-hydroxy-6-(5H-imidazo[5,1-a]isoindol-5-yl)-2-azaspiro[3.4]octane-2-carboxylate is a single isomer. The absolute configuration is unknown.

Step 2:
(5R,6R)-6-[(5R)-5H-imidazo[4,3-a]isoindol-5-yl]-2-methanesulfonyl-2-azaspiro[3.4]octan-5-ol 16a To a A solution of (5R,6R)-6-[(5R)-5H-imidazo[4,3-a]isoindol-5-yl]-2-azaspiro[3.4]octan-5-ol (91 mg, 0.327 mmol) in DCM (35 mL) and stirred added TEA (371.8 mg, 3.67 mmol) and MsCl (120.5 mg, 1.05 mmol) at 0° C. The resulting solution was stirred for 2 h at room temperature. The reaction was then quenched by the addition of water (20 mL). The resulting solution was extracted with DCM (3×50 mL) and the organic layers combined. The resulting mixture was washed with brine (20 mL). The organic layer was dried over anhydrous sodium sulfate and concentrated under vacuum. The crude product was further isolated by Prep-HPLC and Chiral HPLC.

The absolute configuration of 16a was assigned arbitrarily.

Example 16a: (5R,6R)-6-[(5R)-5H-imidazo[4,3-a]isoindol-5-yl]-2-methanesulfonyl-2-azaspiro[3.4]octan-5-ol (4.2 mg, 4%) as a white solid. LCMS (ESI) m/z=360.4 [M+H]+. 1H NMR (300 MHz, DMSO-$d_6$) δ 7.88 (s, 1H), 7.67 (d, J=7.6 Hz, 1H), 7.61 (d, J=7.5 Hz, 1H), 7.40 (t, J=7.3 Hz, 1H), 7.31 (td, J=7.5, 1.0 Hz, 1H), 7.13 (s, 1H), 5.82 (d, J=4.9 Hz, 1H), 5.40 (d, J=7.3 Hz, 1H), 4.25 (t, J=4.8 Hz, 1H), 4.08 (d, J=8.2 Hz, 1H), 3.65 (d, J=8.2 Hz, 1H), 3.59-3.45 (m, 2H), 3.00 (s, 3H), 2.18-2.25 (m, 1H), 2.02-1.79 (m, 2H), 1.74-1.54 (m, 1H).

Example 17: 1-(5-hydroxy-6-(5H-imidazo[1,5-a]isoindol-5-yl)-2-azaspiro[3.4]octan-2-yl)ethan-1-one

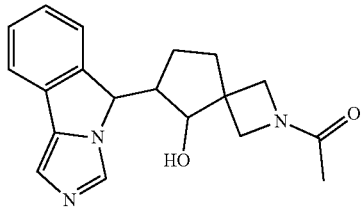 [SMILES: CC(=O)N1CC2(CCC(C3c4ccccc4-c4cncn43)C2O)C1]

1-((5R,6R)-5-hydroxy-6-((R)-5H-imidazo[5,1-a]isoindol-5-yl)-2-azaspiro[3.4]octan-2-yl)ethan-1-one

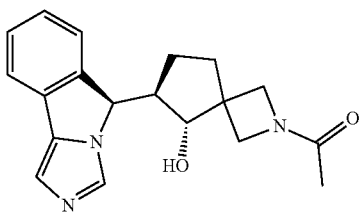

17a

The title compound was prepared by the procedure described in Example 10, by substituting Int-2 with Int-3.

The absolute configuration of 17a was assigned arbitrarily.

Example 17a: 1-((5R,6R)-5-hydroxy-6-((R)-5H-imidazo[5,1-a]isoindol-5-yl)-2-azaspiro[3.4]octan-2-yl)ethan-1-one (13.1 mg, 33%) as a white solid. LCMS (ESI) m/z=324.4 [M+H]$^+$. $^1$H NMR (300 MHz, DMSO-d6) δ 7.92-7.85 (m, 1H), 7.72-7.55 (m, 2H), 7.48-7.23 (m, 2H), 7.13 (s, 1H), 5.74 (s, 1H), 5.40 (d, J=7.4 Hz, 1H), 4.31 (d, J=8.6 Hz, 0.5H), 4.25-4.16 (m, 1H), 4.08 (d, J=9.7 Hz, 0.5H), 3.86 (d, J=8.6 Hz, 0.5H), 3.71 (s, 1H), 3.55 (d, J=9.8 Hz, 0.5H), 3.45 (s, 1H), 2.28-1.53 (m, 8H).

Example 18: 5-hydroxy-6-(5H-imidazo[5,1-a]isoindol-5-yl)-2-azaspiro[3.4]octane-2-sulfonamide

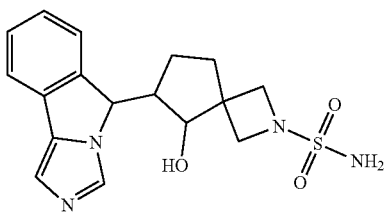 [SMILES: NS(=O)(=O)N1CC2(CCC(C3c4ccccc4-c4cncn43)C2O)C1]

(5R,6R)-5-hydroxy-6-((R)-5H-imidazo[5,1-a]isoindol-5-yl)-2-azaspiro[3.4]octane-2-sulfonamide

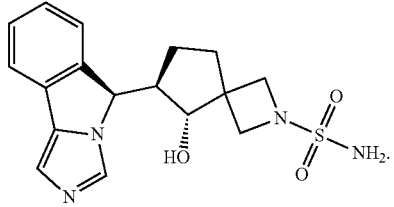

18a

The title compound was prepared by the procedure described in Example 4, by substituting Int-2 with Int-3.

The absolute configuration of 18a was assigned arbitrarily.

Example 18a: (5R,6R)-5-hydroxy-6-((R)-5H-imidazo[5,1-a]isoindol-5-yl)-2-azaspiro[3.4]octane-2-sulfonamide (4.7 mg, 10%) as a light yellow. LCMS (ES) m/z=361.2 [M+H]$^+$. $^1$H NMR (300 MHz, DMSO-d$_6$) δ 7.88 (s, 1H), 7.68 (d, J=7.6 Hz, 1H), 7.61 (d, J=7.4 Hz, 1H), 7.41 (t, J=7.3 Hz, 1H), 7.35-7.26 (m, 1H), 7.13 (s, 1H), 6.85 (s, 2H), 5.73 (d, J=4.9 Hz, 1H), 5.39 (d, J=7.6 Hz, 1H), 4.22 (t, J=4.6 Hz, 1H), 3.93 (d, J=8.0 Hz, 1H), 3.50 (d, J=8.0 Hz, 1H), 3.42-3.26 (m, 3H), 2.18-2.05 (m, 2H), 2.00-1.88 (m, 1H), 1.83-1.57 (m, 3H).

Example 19: 2-methoxyethyl 1-hydroxy-2-(5H-imidazo[5,1-a]isoindol-5-yl)-8-azaspiro[4.5]decane-8-carboxylate

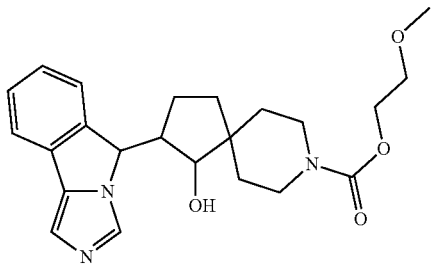 [SMILES: COCCOC(=O)N1CCC2(CCC(C3c4ccccc4-c4cncn43)C2O)CC1]

2-methoxyethyl (3S,4R)-4-hydroxy-3-[(5S)-5H-imidazo[1,5-b]isoindol-5-yl]-8-azaspiro[4.5]decane-8-carboxylate

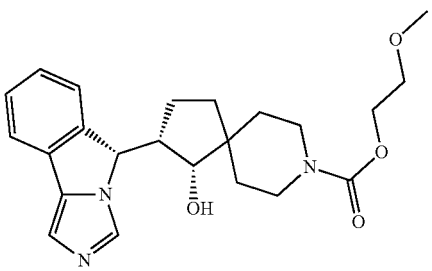

19a

The title compound was prepared by the procedure described in Example 7, by substituting MsCl with 2-methoxyethylchloroformate.

The absolute configuration of 19a was assigned arbitrarily.

Example 19a: 2-methoxyethyl (3S,4R)-4-hydroxy-3-[(5S)-5H-imidazo[1,5-b]isoindol-5-yl]-8-azaspiro[4.5]decane-8-carboxylate (22.4 mg, 22.1%) as a white solid. LCMS (ESI) m/z=412.2 [M+H]⁺. ¹H NMR (400 MHz, MeOH-d) δ 8.01 (s, 1), 7.68-7.57 (m, 2H), 7.44-7.27 (m, 2H), 7.14 (s, 1H), 5.48 (d, J=6.4 Hz, 1H), 4.24-4.17 (m, 2H), 4.05 (d, J=4.9 Hz, 1H), 3.87-3.76 (s, 1H), 3.76-3.65 (s, 1H), 3.61 (t, J=4.7 Hz, 2H), 3.45-3.32 (m, 3H), 3.25-3.15 (m, 2H), 2.53 (d, J=8.1 Hz, 1H), 1.86-1.57 (m, 6H), 1.45-1.28 (m, 2H).

Example 20: cyclopropyl(1-hydroxy-2-(5H-imidazo[5,1-a]isoindol-5-yl)-8-azaspiro[4.5]decan-8-yl)methanone

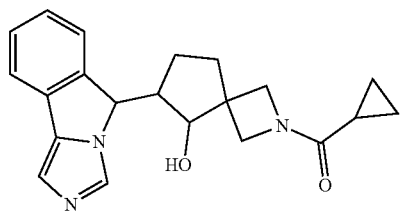

cyclopropyl-[(3S,4R)-4-hydroxy-3-[(5S)-5H-imidazo[,5-b]isoindol-5-yl]-8-azaspiro[4.5]decan-8-yl]methanone 20a

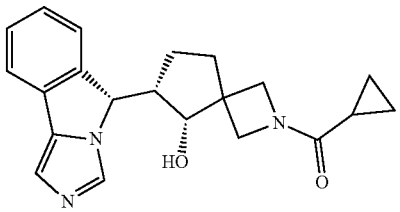 [SMILES: O=C(C1CC1)N1CC2(CCC(C3c4ccccc4-c4cncn43)C2O)C1]

A solution of (3S,4R)-3-[(5S)-5H-imidazo[1,5-b]isoindol-5-yl]-8-azaspiro[4.5]decan-4-ol (105.0 mg, 0.340 mmol) and TEA (343.39 mg, 3.39 mmol) in DCM (10 mL) was stirred at −60° C. Then cyclopropanecarbonyl chloride (42.57 mg, 0.410 mmol) was added and stirred at −60° C. for 2 h. The reaction was quenched by H₂O (100 mL). The resulting solution was extracted with DCM (3×100 mL) and the organic layers were concentrated under vacuum. The crude product was further isolated by Prep-HPLC.

The absolute configuration of 20a was assigned arbitrarily.

Example 20a: cyclopropyl-[(3S,4R)-4-hydroxy-3-[(5S)-5H-imidazo[1,5-b]isoindol-5-yl]-8-azaspiro[4.5]decan-8-yl]methanone (58.4 mg, 45.5%) as a white solid. LCMS (ESI) m/z=378.2 [M+H]⁺. ¹H NMR (400 MHz, MeOH-d) δ 8.04-7.98 (s, 1H), 7.69-7.57 (m, 2H), 7.45-7.27 (m, 2H), 7.14 (s, 1H), 5.51 (d, J=6.6 Hz, 1H), 4.06 (t, J=9.3 Hz, 2H), 3.93 (dt, J=13.7, 4.8 Hz, 1H), 3.55-3.43 (s, 1H), 3.24-3.14 (s, 1H), 2.53 (br, 1H), 1.98-1.68 (m, 7H), 1.45-1.37 (m, 2H), 0.92-0.76 (m, 4H).

Example 21: 2-[[3-hydroxy-2-(5H-imidazo[1,5-b]isoindol-5-yl)-7-azaspiro[3.5]nonan-7-yl]sulfonyl]acetonitrile

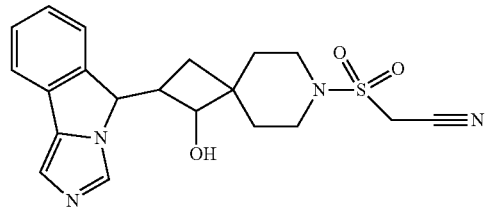 [SMILES: N#CCS(=O)(=O)N1CCC2(CC1)CC(C1c3ccccc3-c3cncn31)C2O]

(2S,3R)-2-[[3-hydroxy-2-((5S)-5H-imidazo[1,5-b]isoindol-5-yl)-7-azaspiro[3.5]nonan-7-yl]sulfonyl]acetonitrile
(2R,3S)-2-[[3-hydroxy-2-((5R)-5H-imidazo[1,5-b]isoindol-5-yl)-7-azaspiro[3.5]nonan-7-yl]sulfonyl]acetonitrile Example 21a: 2-[[3-hydroxy-2-(5H-imidazo[,5-b]isoindol-5-yl)-7-azaspiro[3.5]nonan-7-yl]sulfonyl]acetonitrile

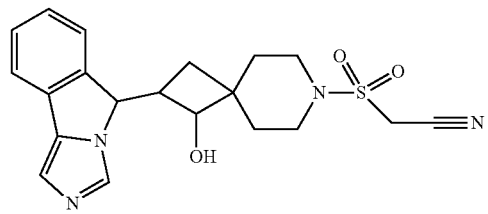 [SMILES: N#CCS(=O)(=O)N1CCC2(CC1)CC(C1c3ccccc3-c3cncn31)C2O]

A solution tert-butyl (1S,2R)-1-hydroxy-2-((R)-5H-imidazo[5,1-a]isoindol-5-yl)-7-azaspiro[3.5]nonane-7-carboxylate and tert-butyl (1R,2S)-1-hydroxy-2-((S)-5H-imidazo[5,1-a]isoindol-5-yl)-7-azaspiro[3.5]nonane-7-carboxylate (Examples 1a and 1b, 50 mg, 0.13 mmol) in 1 mL of DCM was charged with 200 uL of TFA and stirred at room temperature for one hour. The mixture was then concentrated in vacuo and azeotroped twice with MeOH and twice with DCM. The residue was then dissolved in 5 mL of MeOH and charged with 1 g of macroprorous polymer supported Ammonium Carbonate resin and sonicated. The resin was then filtered off by vacuum filtration and the solution was concentrated in vacuo. The residue was then dissolved in 1 mL of dimethylacetamide and charged with cyanomethyl sulfonyl chloride (20 mg, 0.14 mmol) and TEA (42 mg, 0.52 mmol). The crude mixture was then purified by reverse-phase HPLC (0.1% NH₄OH/ACN) to afford the title compound (28 mg, 0.07 mmol, 50% yield) as a white solid.

LCMS (ESI) m/z=399.2 [M+H]⁺. ¹H NMR (400 MHz, DMSO-d₆) δ 7.89 (s, 1H), 7.66-7.52 (m, 21), 7.41-7.32 (m, 1H), 7.30-7.20 (m, 1H), 7.15 (s, 1H), 5.72 (d, J=5.5 Hz, 1H), 5.42 (d, J=8.9 Hz, 1H), 4.10-3.96 (m, 1H), 3.70 (s, 3H), 3.02-2.71 (m, 4H), 2.38 (s, 3H), 2.23 (s, 3H), 1.91-1.75 (m, 2H), 1.74-1.64 (m, 1H), 1.64-1.50 (m, 3H).

Example 21b: (2S,3R)-2-[[3-hydroxy-2-((5S)-5H-imidazo[1,5-b]isoindol-5-yl)-7-azaspiro[3.5]nonan-7-yl]sulfonyl]acetonitrile

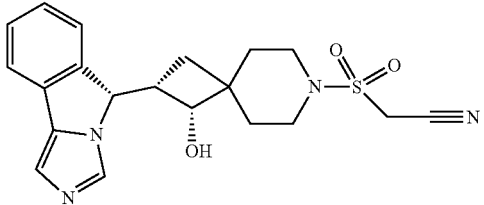 [SMILES: N#CCS(=O)(=O)N1CCC2(CC1)C[C@@H]([C@H]1c3ccccc3-c3cncn31)[C@H]2O]

A solution tert-butyl (1R,2S)-1-hydroxy-2-((S)-5H-imidazo[5,1-a]isoindol-5-yl)-7-azaspiro[3.5]nonane-7-carboxylate (Example 1b, 50 mg, 0.13 mmol) in 1 mL of DCM was charged with 200 uL of TFA and stirred at room temperature for one hour. The mixture was then concentrated in vacuo and azeotroped twice with MeOH and twice with DCM. The residue was then dissolved in 5 mL of MeOH and charged with 1 g of macroprorous polymer supported Ammonium Carbonate resin and sonicated. The resin was then filtered off by vacuum filtration and the solution was concentrated in vacuo. The residue was then dissolved in 1 mL of dimethylacetamide and charged with cyanomethyl sulfonyl chloride (20 mg, 0.14 mmol) and TEA (42 mg, 0.52 mmol). The crude mixture was then purified by reverse-phase HPLC (0.1% NH$_4$OH/ACN) to afford the title compound (28 mg, 0.07 mmol, 50% yield) as a white solid.

LCMS (ESI) m/z=399.2 [M+H]$^+$. $^1$H NMR same as 21a.

Example 21c: (2R,3S)-2-[[3-hydroxy-2-((5R)-5H-imidazo[1,5-b]isoindol-5-yl)-7-azaspiro[3.5]nonan-7-yl]sulfonyl]acetonitrile

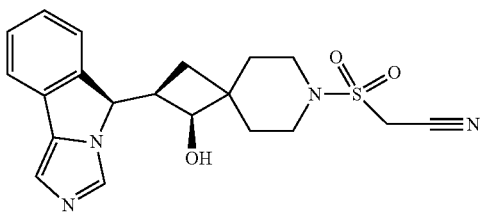 [SMILES: N#CCS(=O)(=O)N1CCC2(CC1)C[C@H]([C@@H]1c3ccccc3-c3cncn31)[C@@H]2O]

The title compound was prepared by the procedure described in Example 21b by replacing tert-butyl (1R,2S)-1-hydroxy-2-((S)-5H-imidazo[5,1-a]isoindol-5-yl)-7-azaspiro[3.5]nonane-7-carboxylate with tert-butyl (1S,2R)-1-hydroxy-2-((R)-5H-imidazo[5,1-a]isoindol-5-yl)-7-azaspiro[3.5]nonane-7-carboxylate LCMS (ESI) m/z=468.2 [M+H]$^+$. $^1$H NMR is same as Example 21a.

Example 22: tert-butyl 2'-hydroxy-3'-(5H-imidazo[5,1-a]isoindol-5-yl)-3-azaspiro[bicyclo[3.2.1]octane-8,1'-cyclobutane]-3-carboxylate

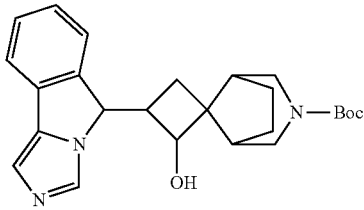 [SMILES: CC(C)(C)OC(=O)N1CC2CCC(C1)C21CC(C2c3ccccc3-c3cncn32)C1O]

tert-butyl (2'S,3'R)-2'-hydroxy-3'-((R)-5H-imidazo[5,1-a]isoindol-5-yl)-3-azaspiro[bicyclo[3,2,1]octane-8,1'-cyclobutane]-3-carboxylate
tert-butyl (2'R,3'S)-2'-hydroxy-3'-((S)-5H-imidazo[5,1-a]isoindol-5-yl)-3-azaspiro[bicyclo[3,2,1]octane-8,1'-cyclobutane]-3-carboxylate
tert-butyl (2'S,3'R)-2'-hydroxy-3'-((S)-5H-imidazo[5,1-a]isoindol-5-yl)-3-azaspiro[bicyclo[3.2.1]octane-8,1'-cyclobutane]-3-carboxylate
tert-butyl (2R,3'S)-2'-hydroxy-3'-((R)-5H-imidazo[5,1-a]isoindol-5-yl)-3-azaspiro[bicyclo[3.2.1]octane-8,1'-cyclobutane]-3-carboxylate
tert-butyl (2'S,3'S)-2'-hydroxy-3'-((R)-5H-imidazo[5,1-a]isoindol-5-yl)-3-azaspiro[bicyclo[3.2.1]octane-8,1'-cyclobutane]-3-carboxylate
tert-butyl (2'R,3) 2'-hydroxy-3'((S)-5H-imidazo[5,1-a]isoindol-5-yl)-3-azaspiro[bicyclo[3.2.1]octane-8,1'-cyclobutane]-3-carboxylate
tert-butyl (2'R,3'R)-2'-hydroxy-3'-((R)-5H-imidazo[5,1-a]isoindol-5-yl)-3-azaspiro[bicyclo[3.2.1]octane-8,1'-cyclobutane]-3-carboxylate
tert-butyl (2'S,3S)-2-hydroxy-3-((S)-5H-imidazo[5,1-a]isoindol-5-yl)-3-azaspiro[bicyclo[3,2,1]octane-8,1'-cyclobutane]-3-carboxylate Step 1:
tert-butyl 2'-oxo-3-azaspiro[bicyclo[3.2.1]octane-8,1'-cyclobutane]-3-carboxylate

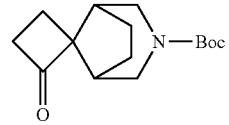

Potassium hydroxide (85 mass %, 3.37 g, 51.0 mmol) was added to a stirred dimethyl sulfoxide (51 mL) solution of tert-butyl 8-oxo-3-azabicyclo[3.2.1]octane-3-carboxylate (5.75 g, 25.5 mmol) and cyclopropyldiphenylsulfonium tetrafluoroborate (8.86 g, 26.8 mmol) at room temperature. After 20 h, the reaction was quenched by dropwise addition of brine (150 mL). The quenched reaction was extracted with isopropyl acetate (3×75 mL). The organic extracts were combined, dried over sodium sulfate, and concentrated. The residue thereby obtained was dissolved in toluene (255 mL). p-Toluenesulfonic acid monohydrate (245 mg, 1.28 mmol) was added to the stirred solution at room temperature. The reaction vessel was fixed with a reflux condenser and warmed to 110° C. After 2 h, the reaction was cooled to room temperature and concentrated. The residue was purified by a silica gel column eluting with heptane/isopropyl acetate (30:70) to afford 5.05 g (75%) tert-butyl 2'-oxo-3-azaspiro[bicyclo[3.2.1]octane-8,1'-cyclobutane]-3-carboxylate as a colorless solid. LCMS (ESI) m/z=266.2 [M+H]+

Step 2:
tert-butyl (E)-2'-oxo-3'-(2-(1-trityl-1H-imidazol-4-yl)benzylidene)-3-azaspiro[bicyclo[3.2.]octane-8,1'-cyclobutane]-3-carboxylate

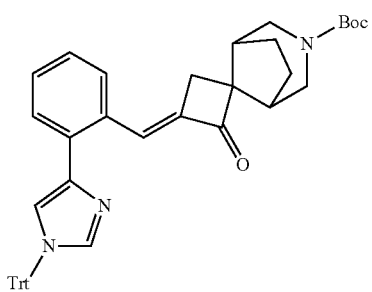

A slurry of tert-butyl 2'-oxospiro[3-azabicyclo[3.2.1]octane-8,1'-cyclobutane]-3-carboxylate (3.00 g, 11.3 mmol), 2-[1-(triphenylmethyl)-5H-imidazol-4-yl]benzaldehyde (4.69 g, 11.3 mmol) and Ca(OH)$_2$ (1.68 g, 22.6 mmol) in EtOH (57 mL) was stirred for 20 h at 80° C. The reaction was cooled to room temperature and insoluble material was removed by filtration. The filtrate was concentrated. The residue was purified by a silica gel column eluting with DCM/methanol (90:10) to afford 6.83 g (91%) tert-butyl (3'E)-2'-oxo-3'-[[2-(1-tritylimidazol-4-yl)phenyl]methylene]spiro[3-azabicyclo[3.2.1]octane-8,1'-cyclobutane]-3-carboxylate as a colorless solid. LCMS (ESI) m/z=662.3 [M+H]+.

Step 3:
tert-butyl 3'-(5H-imidazo[5,1-a]isoindol-5-yl)-2'-oxo-3-azaspiro[bicyclo[3.2.1]octane-8,1'-cyclobutane]-3-carboxylate

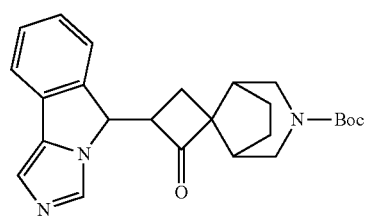 [SMILES: CC(C)(C)OC(=O)N1CC2CCC(C1)C21CC(C2c3ccccc3-c3cncn32)C1=O]

Acetic acid (9.2 mL) was added to a stirred MeOH (92 mL) suspension of tert-butyl (3'E)-2'-oxo-3'-[[2-(1-tritylimidazol-4-yl)phenyl]methylene]spiro[3-azabicyclo[3.2.1]octane-8,1'-cyclobutane]-3-carboxylate (6.10 g, 9.22 mmol) at room temperature. The reaction flask was fixed with a reflux condenser and warmed to 70° C. After 20 h, the reaction was cooled to room temperature and concentrated. The residue was suspended in DCM (300 mL) and saturated aqueous sodium bicarbonate solution (100 mL) was added with stirring. The consequent layers were separated and the organic was washed with brine (100 mL), dried over sodium sulfate, and concentrated. The residue was purified by a silica gel column eluting with DCM/MeOH (97:3) to afford 2.95 g (76%) tert-butyl 3'-(5H-imidazo[1,5-b]isoindol-5-yl)-2'-oxo-spiro[3-azabicyclo[3.2.1]octane-8,1'-cyclobutane]-3-carboxylate as a pale yellow solid. LCMS (ESI) m/z=420.5 [M+H]+.

Step 4:
tert-butyl (2'S,3'R)-2'-hydroxy-3'-((R)-5H-imidazo[5,1-a]isoindol-5-yl)-3-azaspiro[bicyclo[3.2.1]octane-8,1'-cyclobutane]-3-carboxylate tert-butyl (2'R,3'S)-2'-hydroxy-3'-((S)-5H-imidazo[5,1-a]isoindol-5-yl)-3-azaspiro[bicyclo[3.2.1]octane-8,1'-cyclobutane]-3-carboxylate tert-butyl (2'S,3'R)-2'-hydroxy-3'-((S)-5H-imidazo[5,1-a]isoindol-5-yl)-3-azaspiro[bicyclo[3.2.1]octane-8,1'-cyclobutane]-3-carboxylate tert-butyl (2'R,3'S)-2'-hydroxy-3'-((R)-5H-imidazo[5,1-a]isoindol-5-yl)-3-azaspiro[bicyclo[3.2.1]octane-8,1'-cyclobutane]-3-carboxylate tert-butyl (2'S,3'S)-2'-hydroxy-3'-((R)-5H-imidazo[5,1-a]isoindol-5-yl)-3-azaspiro[bicyclo[3.2.1]octane-8,1'-cyclobutane]-3-carboxylate tert-butyl (2'R,3'R)-2'-hydroxy-3'-((S)-5H-imidazo[5,1-a]isoindol-5-yl)-3-azaspiro[bicyclo[3.2.1]octane-8,1'-cyclobutane]-3-carboxylate tert-butyl (2'R,3'R)-2'-hydroxy-3'-((R)-5H-imidazo[5,1-a]isoindol-5-yl)-3-azaspiro[bicyclo[3.2.1]octane-8,1'-cyclobutane]-3-carboxylate tert-butyl (2'S,3'S)-2'-hydroxy-3'-((S)-5H-imidazo[5,1-a]isoindol-5-yl)-3-azaspiro[bicyclo[3.2.1]octane-8,1'-cyclobutane]-3-carboxylate

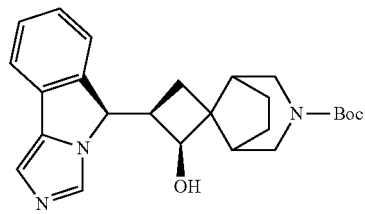

22a

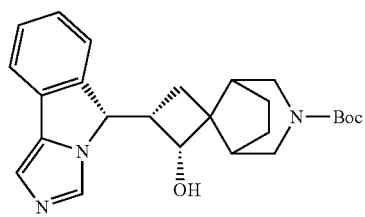

22b

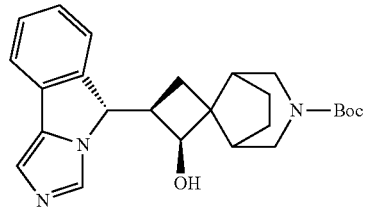

22c

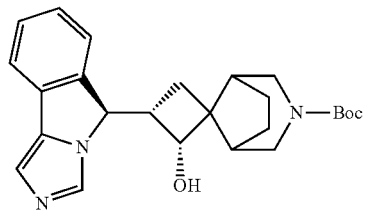

22d

-continued

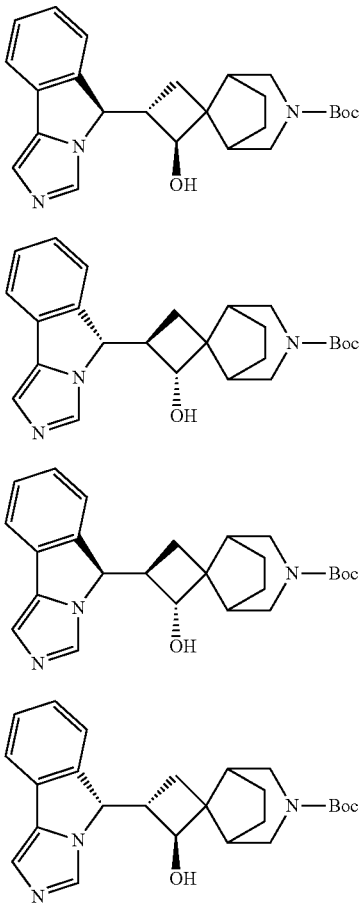

Sodium borohydride (532 mg, 14.1 mmol) was added in five equal portions to a stirred MeOH (70 mL) solution of tert-butyl 3'-(5H-imidazo[1,5-b]isoindol-5-yl)-2'-oxo-spiro[3-azabicyclo[3.2.1]octane-8,1'-cyclobutane]-3-carboxylate (2.95 g, 7.03 mmol) at 0° C. The resulting solution was stirred for 2 h at 0° C. The reaction was concentrated and suspended in brine (200 mL). The resulting suspension was extracted with DCM (3×100 mL). The organic extracts were combined, dried over sodium sulfate, and concentrated. The residue was purified by silica gel column eluting with DCM/MeOH (85:15) to afford 2.75 g (93%) of tert-butyl 2'-hydroxy-3'-(5H-imidazo[1,5-b]isoindol-5-yl)spiro[3-azabicyclo[3.2.]octane-8,1'-cyclobutane]-3-carboxylate as a colorless solid. LCMS (ESI) m/z=422.2 [M+H]+.

The product was further isolated by chiral separation to afford 8 stereoisomers as colorless solids.

The absolute configuration of 22a, 22b, 22c, 22d, 22e, 22f, 22g, and 22h was assigned arbitrarily. The relative configuration of C15 was assigned arbitrarily.

Example 22a: tert-butyl (2'S,3'R)-2'-hydroxy-3'-((R)-5H-imidazo[5,1-a]isoindol-5-yl)-3-azaspiro[bicyclo[3.2.1]octane-8,1'-cyclobutane]-3-carboxylate. LCMS (ESI) m/z=422.2 [M+H]+. 1H NMR (400 MHz, DMSO-d6) δ 7.85 (s, 1H), 7.66-7.54 (m, 2H), 7.41-7.32 (m, 1H), 7.26 (td, J=7.6, 1.2 Hz, 1H), 7.14 (s, 1H), 5.50 (d, J=7.2 Hz, 1H), 5.42 (d, J=6.8 Hz, 1H), 4.55 (t, J=7.0 Hz, 1H), 3.77-3.48 (m, 2H), 3.50-3.41 (m, 2H), 3.26-3.04 (m, 2H), 2.15 (d, J=12.4 Hz, 1H), 1.65 (d, J=13.7 Hz, 2H), 1.41-1.36 (m, 10H), 1.27-1.23 (m, 2H), 0.84 (t, J=10.4 Hz, 1H). tR=0.6 min (OX, MeOH:H2O:IPam=50:49.9:0.1, 4.0 mL/min). 22a and 22b are enantiomers.

Example 22b: tert-butyl (2'R,3'S)-2'-hydroxy-3'-((S)-5H-imidazo[5,1-a]isoindol-5-yl)-3-azaspiro[bicyclo[3.2.1]octane-8,1'-cyclobutane]-3-carboxylate. LCMS (ES) m/z=422.2 [M+H]+. tR=0.8 min (AD, EtOH:H2O:IPam=30:69.9:0.1, 4.0 ml/min). 22a and 22b are enantiomers.

Example 22c: tert-butyl (2'S,3'R)-2'-hydroxy-3'-((S)-5H-imidazo[5,1-a]isoindol-5-yl)-3-azaspiro[bicyclo[3.2.1]octane-8,1'-cyclobutane]-3-carboxylate. LCMS (ESI) m/z=422.2 [M+H]+. 1H NMR (400 MHz, DMSO-d6) δ 7.92 (s, 1H), 7.59 (dt, J=7.4, 1.0 Hz, 1H), 7.43-7.33 (m, 2H), 7.24 (td, J=7.6, 1.2 Hz, 1H), 7.11 (m, 1H), 5.45 (d, J=7.7 Hz, 1H), 5.37 (d, J=8.5 Hz, 1H), 4.45 (q, J=8.4 Hz, 1H), 3.73-3.52 (m, 2H), 3.48-3.42 (m, 2H), 3.25-2.98 (m, 1H), 2.35 (s, 1H), 2.17 (d, J=13.2 Hz, 1H), 1.78 (d, J=13.3 Hz, 1H), 1.73-1.58 (m, 2H), 1.52 (s, 1H), 1.39 (d, J=3.0 Hz, 9H), 1.40-1.26 (m, 2H). tR=1.4 min (OD, McCN:MeOH:H2O:IPam=30:10:59.9:0.1, 4.0 mL/min). 22c and 22d are enantiomers.

Example 22d: tert-butyl (2'R,3'S)-2'-hydroxy-3'-((R)-5H-imidazo[5,1-a]isoindol-5-yl)-3-azaspiro[bicyclo[3.2.1]octane-8,1'-cyclobutane]-3-carboxylate. LCMS (ESI) m/z=422.2 [M+H]+. tR=3.7 min (IC, EtOH:H2O:IPam=25:74.9:0.1, 4.0 mL/min). 22c and 22d are enantiomers.

Example 22e: tert-butyl (2'S,3'S)-2'-hydroxy-3'-((R)-5H-imidazo[5,1-a]isoindol-5-yl)-3-azaspiro[bicyclo[3.2.1]octane-8,1'-cyclobutane]-3-carboxylate. LCMS (ESI) m/z=422.2 [M+H]+. 1H NMR (400 MHz, DMSO-d6) δ 7.86 (s, 1H), 7.64-7.57 (m, 1H), 7.37 (t, J=7.2 Hz, 2H), 7.21 (td, J=7.5, 1.2 Hz, 1H), 7.12 (s, 1H), 5.78 (s, 1H), 5.43 (d, J=10.0 Hz, H), 4.60 (s, 1H), 3.65-3.45 (m, 3H), 3.18-3.04 (m, 1H), 2.23 (s, 2H), 1.88 (s, 1H), 1.79-1.68 (m, 3H), 1.57 (d, J=13.5 Hz, 1H), 1.40 (s, 1H). tR=2.2 min (OD, MeCN:MeOH:H2O:IPam=30:10:59.9:0.1, 4.0 mL/min). 22e and 22f are enantiomers.

Example 22f: tert-butyl (2'R,3'R)-2'-hydroxy-3'-((S)-5H-imidazo[5,1-a]isoindol-5-yl)-3-azaspiro[bicyclo[3.2.1]octane-8,1'-cyclobutane]-3-carboxylate. LCMS (ESI) m/z=422.2 [M+H]+. tR=3.1 min (OD, MeCN:MeOH:H2O:IPam=22.5:7.5:59.9:0.1, 4.0 mL/min). 22e and 22f are enantiomers.

Example 22g: tert-butyl (2'R,3'R)-2'-hydroxy-3'-((R)-5H-imidazo[5,1-a]isoindol-5-yl)-3-azaspiro[bicyclo[3.2.1]octane-8,1-cyclobutane]-3-carboxylate. LCMS (ESI) in/z=422.2 [M+H]+. 1H NMR (400 MHz, DMSO-d6) δ 7.87 (s, 1H), 7.65-7.55 (m, 2H), 7.37 (td, J=7.4, 1.0 Hz, 1H), 7.26 (td, J=7.5, 1.1 Hz, 1H), 7.13 (s, 1H), 5.79 (d, J=6.8 Hz, 1H), 5.49 (d, J=8.5 Hz, 1H), 4.64 (s, 1H), 3.62-3.41 (m, 2H), 3.19-3.06 (m, 1H), 3.06-2.91 (m, 1H), 2.51-2.40 (m, 1H), 2.10 (d, J=23.8 Hz, 1H), 1.88 (s, 2H), 1.64 (d, J=9.8 Hz, 3H), 1.39 (s, 10H). tR=1.4 min (AD, EtOH:H2O:IPam=30:69.9:0.1, 4.0 mL/min). 22g and 22h are enantiomers.

Example 22h: tert-butyl (2'S,3'S)-2'-hydroxy-3'-((S)-5H-imidazo[5,1-a]isoindol-5-yl)-3-azaspiro[bicyclo[3.2.1]octane-8,1'-cyclobutane]-3-carboxylate. LCMS (ESI) m/z=422.2 [M+H]+. tR=2.6 min (IC, EtOH:H2O:IPam=25:74.9:0.1, 4.0 mL/min). 22g and 22h are enantiomers.

Example 23: 2-(5H-imidazo[1,5-b]isoindol-5-yl)-7-(oxetan-3-ylsulfonyl)-7-azaspiro[3.5]nonan-3-ol

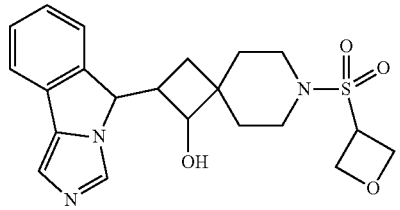 [SMILES: O=S(=O)(C1COC1)N1CCC2(CC1)CC(C1c3ccccc3-c3cncn31)C2O]

Example 23a: 2-(5H-imidazo[1,5-b]isoindol-5-yl)-7-(oxetan-3-ylsulfonyl)-7-azaspiro[3.5]nonan-3-ol

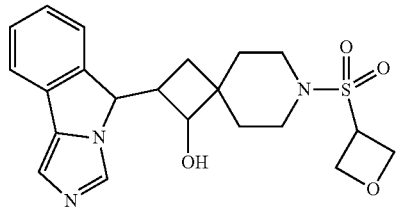 [SMILES: O=S(=O)(C1COC1)N1CCC2(CC1)CC(C1c3ccccc3-c3cncn31)C2O]

The title compound was prepared by the procedure described in Example 21a by substituting cyanomethylsulfanyl chloride with 2-(oxetan-3-ylsulfonyl).

LCMS (ESI) m/z=417.1[M+H]$^+$. $^1$H NMR (400 MHz, DMSO-d$_6$) δ 7.85 (s, 1H), 7.65-7.54 (m, 2H), 7.41-7.32 (m, 1H), 7.25 (td, J=7.5, 1.2 Hz, 1H), 7.13 (s, 1H), 5.73 (d, J=5.4 Hz, 1H), 5.45 (d, J=8.7 Hz, 1H), 4.90-4.62 (m, 4H), 4.10 (td, J=5.9, 5.3, 2.9 Hz, 1H), 3.20-3.09 (m, 1H), 3.09-2.93 (m, 2H), 2.56 (dd, J=9.1, 6.9 Hz, 1H), 1.87 (t, J=10.4 Hz, 1H), 1.81-1.65 (m, 2H), 1.54 (t, J=5.8 Hz, 3H).

Example 23b: (2R,3S)-2-((5S)5H-imidazo[1,5-b]isoindol-5-yl)-7-(oxetan-3-ylsulfonyl)-7-azaspiro[3.5]nonan-3-ol

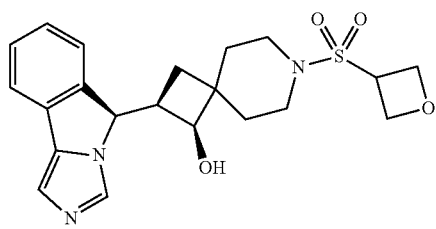 [SMILES: O=S(=O)(C1COC1)N1CCC2(CC1)C[C@H]([C@@H]1c3ccccc3-c3cncn31)[C@@H]2O]

The title compound was prepared by the procedure described in Example 21c by substituting cyanomethylsulfonyl chloride with 2-(oxetan-3-ylsulfonyl).

LCMS (ESI) m/z=417.1 [M+H]$^+$. $^1$H NMR same as 23a.

Example 23c: (2S,3R)-2-[(5S)-5H-imidazo[1,5-b]isoindol-5-yl]-7-(oxetan-3-ylsulfonyl)-7-azaspiro[3.5]nonan-3-ol

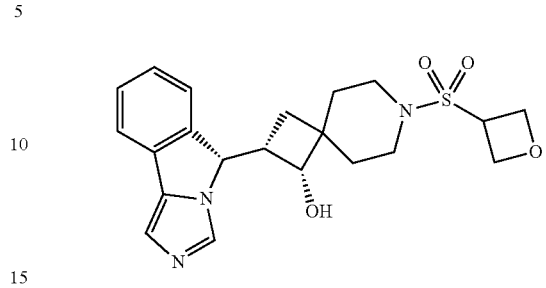

The title compound was prepared by the procedure described in Example 21b by substituting cyanomethylsulfonyl chloride with 2-(oxetan-3-ylsulfonyl).

LCMS (ESI) m/z=417.1 [M+H]$^+$. $^1$H NMR same as 23a.

Example 24: tert-butyl (1-hydroxy-2-(5H-imidazo[5,1-a]isoindol-5-yl)spiro[3.5]nonan-7-yl)carbamate

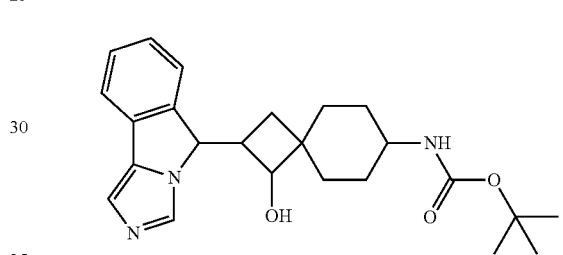

tert-butyl ((1R,2R,4s,7S)-1-hydroxy-2-((R)-5H-imidazo[5,1-a]isoindol-5-yl)spiro[3.5]nonan-7-yl)carbamate
tert-butyl ((1S,2S,4s,7R)-1-hydroxy-2-((S)-5H-imidazo[5,1-a]isoindol-5-yl)spiro[3.5]nonan-7-yl)carbamate
tert-butyl ((1R,2R,4r,7R)-1-hydroxy-2-((S)-5H-imidazo[5,1-a]isoindol-5-yl)spiro[3.5]nonan-7-yl)carbamate
tert-butyl ((1R,2S,4r,7S)-1-hydroxy-2-((R)-5H-imidazo[5,1-a]isoindol-5-yl)spiro[3.5]nonan-7-yl)carbamate
tert-butyl ((1S,2R,4r,7R)-1-hydroxy-2-((S)-5H-imidazo[5,1-a]isoindol-5-yl)spiro[3.5]nonan-7-yl)carbamate
tert-butyl ((1R,2S,4r,7R)-1-hydroxy-2-((R)-5H-imidazo[5,1-a]isoindol-5-yl)spiro[3.5]nonan-7-yl)carbamate
tert-butyl ((1S,2R,4r,7S)-1-hydroxy-2-((S)-5H-imidazo[5,1-a]isoindol-5-yl)spiro[3.5]nonan-7-yl)carbamate
tert-butyl ((1S,2S,4r,7S)-1-hydroxy-2-((R)-5H-imidazo[5,1-a]isoindol-5-yl)spiro[3.5]nonan-7-yl)carbamate
tert-butyl ((1S,2S,4s,7R)-1-hydroxy-2-((S)-5H-imidazo[5,1-a]isoindol-5-yl)spiro[3.5]nonan-7-yl)carbamate
tert-butyl ((1S,2S,4s, 7R)-1-hydroxy-2-((S)-5H-imidazo[5,1-a]isoindol-5-yl)spiro[3.5]nonan-7-yl)carbamate
tert-butyl ((1R,2R,4s,7S)-1-hydroxy-2-((R)-5H-imidazo[5,1-a]isoindol-5-yl)spiro[3.5]nonan-7-yl)carbamate
tert-butyl ((1R,2S,4s,7S)-1-hydroxy-2-((S)-5H-imidazo[5,1-a]isoindol-5-yl)spiro[3.5]nonan-7-yl)carbamate
tert-butyl ((1R,2S,4r,7R)-1-hydroxy-2-((R)-5H-imidazo[5,1-a]isoindol-5-yl)spiro[3.5]nonan-7-yl)carbamate
tert-butyl ((1S,2R,4r,7S)-1-hydroxy-2-((S)-5H-imidazo[5,1-a]isoindol-5-yl)spiro[3.5]nonan-7-yl)carbamate
tert-butyl ((1S,2S,4r,7S)-1-hydroxy-2-((S)-5H-imidazo[5,1-a]isoindol-5-yl)spiro[3.5]nonan-7-yl)carbamate

205
tert-butyl ((1S,2R,4s,7R)-1-hydroxy-2-((R)-5H-imidazo[5,1-a]isoindol-5-yl)spiro[3.5]nonan-7-yl)carbamate
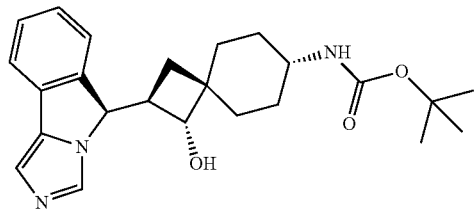
24a
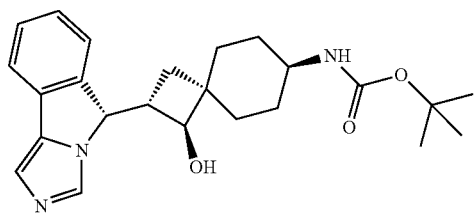
24b
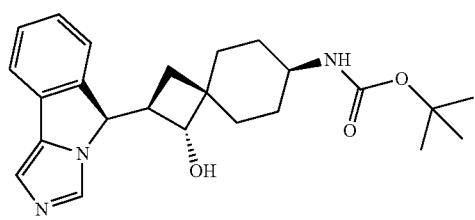
24c
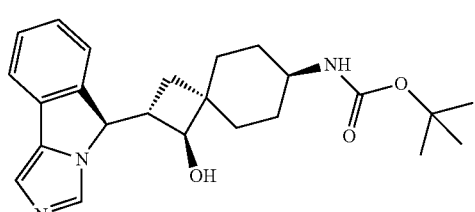
24d
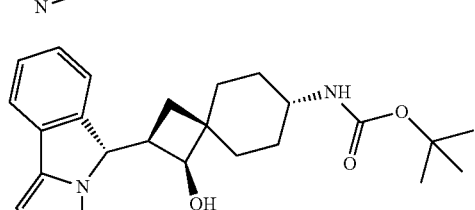
24e
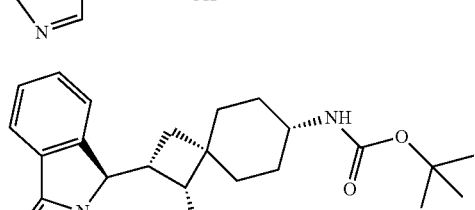
24f
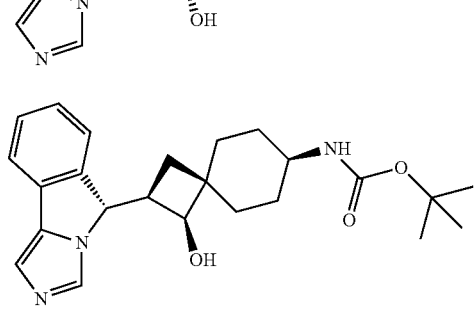
24g
206
-continued
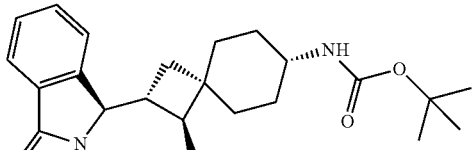
24h
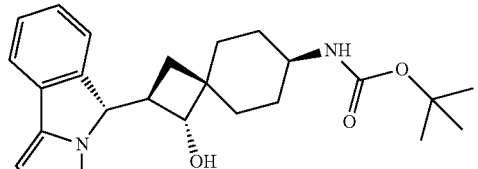
24i
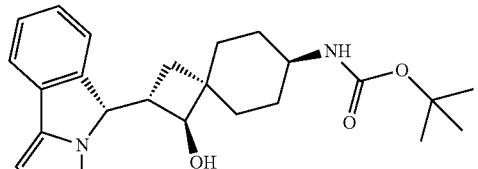
24j
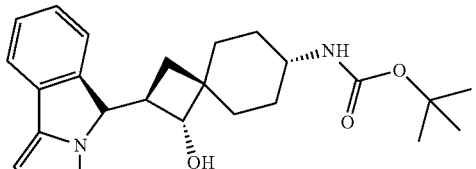
24k
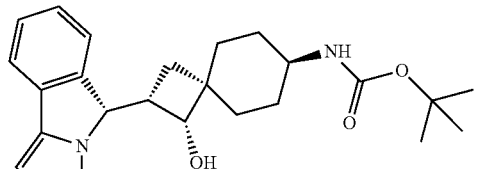
24l
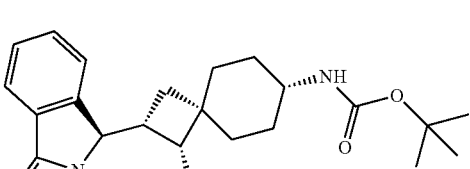
24m
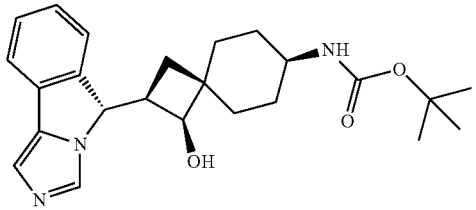
24n -continued

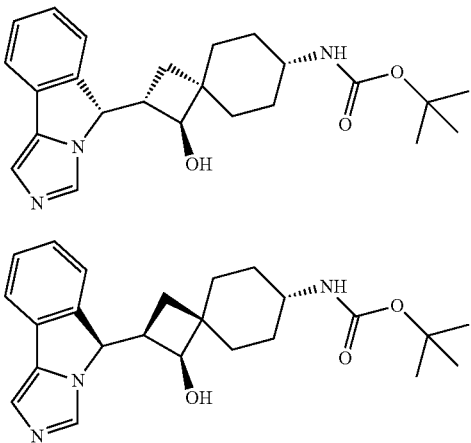

The title compounds were made in a same manner as example 1 by replacing tert-butyl 1-oxo-7-azaspiro[3.5]nonane-7-carboxylate with tert-butyl (1-oxospiro[3.5]nonan-7-yl)carbamate. The absolute configuration of isomers 24g, 24k was determine by X-ray crystallography. The configuration of the rest isomers was assigned arbitrarily.

Example 24a: tert-butyl ((1R,2R,4r,7R)-1-hydroxy-2-((R)-5H-imidazo[5,1-a]isoindol-5-yl)spiro[3.5]nonan-7-yl)carbamate. LCMS (ESI, m/z): 410.2 [M+H]+. 1HNMR (400 MHz, DMSO-d6) δ: 7.87 (s, 1H), 7.66-7.47 (m, 2H), 7.42-7.30 (m, 2H), 7.25 (td, J=7.6, 1.2 Hz, 1H), 7.12 (s, 1H), 6.65 (d, J=7.8 Hz, 1H), 5.57 (s, 1H), 5.43 (d, J=8.6 Hz, 1i), 4.01-3.90 (m, 1H), 1.87-1.66 (m, 3H), 1.58 (p, J=13.3, 12.1 Hz, 3H), 1.23-0.99 (m, 4H), 0.92-0.73 (m, 1H).

Example 24c: tert-butyl ((1R,2R,4r,7R)-1-hydroxy-2-((S)-5H-imidazo[5,1-a]isoindol-5-yl)spiro[3.5]nonan-7-yl)carbamate. LCMS (ESI, m/z): 410.2 [M+H]+. 1HNMR (400 MHz, DMSO-d6) δ: 7.89 (s, 1H), 7.58 (dd, J=7.3, 1.2 Hz, 1H), 7.43-7.32 (m, 2H), 7.24 (td, J=7.5, 1.1 Hz, 1H), 7.09 (s, 1H), 6.65 (d, J=7.8 Hz, 1H), 5.34 (d, J=8.5 Hz, 1H), 5.04 (d, J=6.9 Hz, 1H), 3.84 (t, J=7.3 Hz, 1H), 2.30-2.16 (m, 1H), 1.77 (t, J=10.1 Hz, 1H), 1.69-1.52 (m, 3H), 1.48-1.42 (m, 2H), 1.37 (s, 9H), 1.24 (t, J=7.9 Hz, 3H), 1.16-1.02 (m, 1H).

Example 24d: tert-butyl ((1R,2S,4s,7S)-1-hydroxy-2-((R)-5H-imidazo[5,1-a]isoindol-5-yl)spiro[3.5]nonan-7-yl)carbamate. LCMS (ESI, m/z): 410.2 [M+H]+. 1HNMR (400 MHz, DMSO-d6) δ: 7.83 (s, 1H), 7.60-7.55 (m, 2H), 7.36 (ddd, J=8.3, 7.2, 1.1 Hz, 1H), 7.25 (td, J=7.5, 1.2 Hz, 1H), 7.13 (s, 1H), 6.61 (d, J=7.9 Hz, 1H), 5.37 (d, J=7.1 Hz, 1H), 5.11 (d, J=6.5 Hz, 1H), 3.95 (t, J=7.2 Hz, 1H), 2.43-2.27 (m, 1H), 1.70-1.50 (m, 4H), 1.45 (td, J=13.0, 3.5 Hz, 1H), 1.35 (s, 9H), 1.27-1.08 (m, 3H), 1.08-0.96 (m, 1H), 0.93-0.80 (m, 1H).

Example 24f: tert-butyl ((1R,2S,4r,7R)-1-hydroxy-2-((R)-5H-imidazo[5,1-a]isoindol-5-yl)spiro[3.5]nonan-7-yl)carbamate. LCMS (ESI, m/z): 410.2 [M+H]+. 1HNMR (400 MHz, DMSO-d6) δ: 7.82 (s, 1H), 7.59 (d, J=7.6 Hz, 1H), 7.38 (q, J=7.5 Hz, 2H), 7.23 (td, J=7.5, 1.1 Hz, 1H), 7.11 (s, 1H), 6.67 (d, J=7.8 Hz, 1H), 5.59 (d, J=5.5 Hz, 1H), 5.38 (d, J=10.8 Hz, 1H), 3.90 (td, J=5.9, 2.9 Hz, 1H), 2.31-2.21 (m, 1H), 2.10 (dd, J=11.0, 9.4 Hz, 1H), 1.95-1.78 (m, 2H), 1.73-1.49 (m, 3H), 1.38 (s, 9H), 1.23-1.06 (m, 3H), 0.84 (dt, J=10.8, 6.5 Hz, 1H).

Example 24h: tert-butyl ((1S,2S,4r,7S)-1-hydroxy-2-((R)-5H-imidazo[5,1-a]isoindol-5-yl)spiro[3.5]nonan-7-yl)carbamate. LCMS (ESI, m/z): 410.2 [M+H]). 1HNMR (400 MHz, DMSO-d6) δ: 7.91 (s, 1H), 7.63-7.50 (m, 1H), 7.36 (dt, J=7.4, 3.6 Hz, 2H), 7.22 (td, J=7.6, 1.2 Hz, 1H), 7.09 (s, 1H), 6.59 (d, J=7.0 Hz, 1H), 5.33 (d, J=8.7 Hz, 1H), 4.07 (s, 1H), 3.89 (d, J=7.6 Hz, 1H), 2.30-2.17 (m, 1H), 1.93 (d, J=13.0 Hz, 1H), 1.71-1.47 (m, 6H), 1.37 (s, 9H), 1.27-1.08 (m, 3H).

Example 24k: tert-butyl ((1S,2S,4s,7R)-1-hydroxy-2-((S)-5H-imidazo[5,1-a]isoindol-5-yl)spiro[3.5]nonan-7-yl)carbamate. LCMS (ESI, m/z): 410.2 [M+H]+. 1HNMR (400 MHz, DMSO-d6) δ: 7.82 (s, 1H), 7.57 (dt, J=7.4, 1.4 Hz, 2H), 7.40-7.32 (m, 1H), 7.25 (td, J=7.5, 1.1 Hz, 1H), 7.13 (s, 1H), 6.59 (d, J=6.8 Hz, 1H), 5.36 (d, J=7.1 Hz, 1H), 5.15 (d, J=7.6 Hz, 1H), 3.99 (t, J=7.7 Hz, 1H), 2.42-2.33 (m, 1H), 1.95 (dd, J=12.7, 6.4 Hz, 1H), 1.56 (ddd, J=19.0, 13.6, 9.3 Hz, 4H), 1.37 (s, 9H), 1.31-1.08 (m, 4H), 0.92 (t, J=10.3 Hz, 1H).

Example 24l: tert-butyl ((1R,2S,4s,7S)-1-hydroxy-2-((S)-5H-imidazo[5,1-a]isoindol-5-yl)spiro[3.5]nonan-7-yl)carbamate. LCMS (ESI, m/z): 410.2 [M+H]+. 1HNMR (400 MHz, DMSO-d6) δ: 7.87 (s, 1H), 7.59 (d, J=7.5 Hz, 1H), 7.42-7.31 (m, 2H), 7.21 (td, J=7.5, 1.1 Hz, 1H), 7.11 (s, 1H), 6.69 (d, J=7.4 Hz, 1H), 5.64 (d, J=7.0 Hz, 1H), 5.36 (d, J=10.7 Hz, 1H), 4.02 (td, J=6.5, 3.2 Hz, 1H), 2.32-2.20 (m, 1H), 2.15 (t, J=10.3 Hz, 1H), 2.05 (d, J=12.5 Hz, 1H), 1.75-1.63 (m, 2H), 1.57 (dd, J=14.5, 8.5 Hz, 3H), 1.38 (s, 9H), 1.29 (d, J=12.6 Hz, 2H), 1.14 (dd, J=7.9, 4.4 Hz, 1H).

Example 24n: tert-butyl ((1S,2R,4r,7S)-1-hydroxy-2-((S)-5H-imidazo[5,1-a]isoindol-5-yl)spiro[3.5]nonan-7-yl)carbamate. LCMS (ESI, m/z): 410.2 [M+H]+. 1HNMR (400 MHz, DMSO-d6) δ: 7.87 (s, 1H), 7.59 (dd, J=7.6, 1.1 Hz, 1H), 7.42-7.29 (m, 2H), 7.21 (td, J=7.6, 1.1 Hz, 1H), 7.11 (s, 1H), 6.69 (d, J=6.8 Hz, 1H), 5.64 (d, J=7.0 Hz, 1H), 5.36 (d, J=10.7 Hz, 1H), 4.02 (td, J=6.4, 3.1 Hz, 1H), 2.32-2.21 (m, 1H), 2.15 (t, J=10.3 Hz, 1H), 2.03 (t, J=15.0 Hz, 1H), 1.75-1.63 (m, 2H), 1.59 (d, J=11.6 Hz, 2H), 1.38 (s, 9H), 1.12 (td, J=12.9, 3.8 Hz, 2H), 0.84 (dt, J=10.9, 6.3 Hz, 2H).

Example 25: (2,2-difluorocyclopropyl)(1-hydroxy-2-(5H-imidazo[5,1-a]isoindol-5-yl)-8-azaspiro[4.5]decan-8-yl)methanone

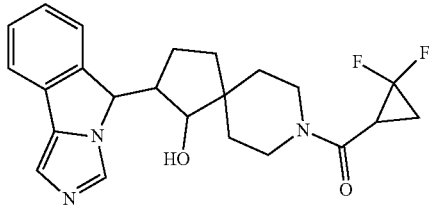 [SMILES: O=C(C1CC1(F)F)N1CCC2(CCC(C3c4ccccc4-c4cncn43)C2O)CC1]

((S)-2,2-difluorocyclopropyl)((1R,2S)-1-hydroxy-2-((S)-5H-imidazo[5,1-a]isoindol-5-yl)-8-azaspiro[4.5]decan-8-yl)methanone ((R)-2,2-difluorocyclopropyl)((1R,2S)-1-hydroxy-2-((S)-5H-imidazo[5,1-a]isoindol-5-yl)-8-azaspiro[4.5]decan-8-yl)methanone

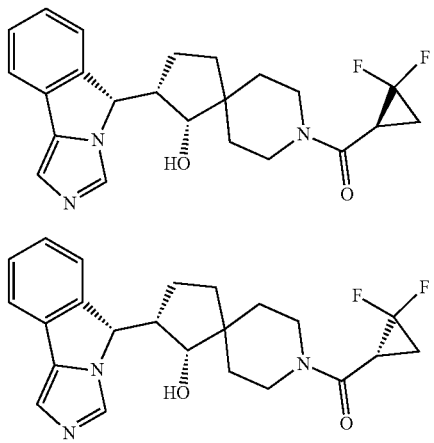

(3S,4R)-3-[(5S)-5H-imidazo[1,5-b]isoindol-5-yl]-8-azaspiro[4.5]decan-4-ol (44.7 mg, 0.145 mmol), 2,2-difluorocyclopropanecarboxylic acid (34.59 mg, 0.28 mmol), 4-hydroxybenzotriazole (57.43 mg, 0.43 mmol), 1-(3-dimethylaminopropyl)-3-ethylcarbodiimidehydrochloride (81.48 mg, 0.43 mmol) and TEA (86.01 mg, 0.85 mmol) were mixed in DCM (10 mL) and stirred at 20° C. for 16 hours. The reaction was quenched with water (100 mL). The resulting solution was extracted with DCM (3×100 mL) and the organic layers were combined. The organic layer was dried over anhydrous sodium sulfate and concentrated under vacuum. The residue was purified by flash chromatography on silica gel column, eluting with DCM/MeOH (10/1) and then by Prep-HPLC and further separated with Chiral-HPLC.

The absolute configuration of 25a-25b was assigned arbitrarily.

Example 25a: ((S)-2,2-difluorocyclopropyl)((1R,2S)-1-hydroxy-2-((S)-5H-imidazo[5,1-a]isoindol-5-yl)-8-azaspiro[4.5]decan-8-yl)methanone (25 mg, 20.1%) as a white solid. LCMS (ESI) m/z=414.3 [M+H]⁺; ¹H NMR (400 MHz, MeOH-d₄) δ 8.02 (d, J=2.7 Hz, 1H), 7.69-7.57 (m, 2H), 7.45-7.27 (m, 2H), 7.14 (s, 1H), 5.52 (d, J=6.3 Hz, 1H), 4.17-3.75 (m, 3H), 3.57-3.33 (m, 21), 3.02-2.84 (m, 1H), 2.65-2.49 (m, 1H), 1.95-1.57 (m, 8H), 1.55-1.28 (m, 2H). tR=2.938 min (CHIRAL Cellulose-SB, 0.46×15 cm; 5 um, Hex(0.1% DEA):EtOH=50:50, 1.0 mL/min).

Example 25b: ((R)-2,2-difluorocyclopropyl)((1R,2S)-1-hydroxy-2-((S)-5H-imidazo[5,1-a]isoindol-5-yl)-8-azaspiro[4.5]decan-8-yl)methanone (15.1 mg, 12.8%) as a white solid. LCMS (ESI) m/z=414.3 [M+H]⁺. tR=3.608 min (CHIRAL Cellulose-SB, 0.46×15 cm; 5 um, Hex(0.1% DEA):EtOH=50:50, 1.0 mL/min).

Example 26: 2-(5H-imidazo[1,5-b]isoindol-5-yl)-7-(1-methylpyrazol-4-ylsulfonyl-7-azaspiro[3.5]nonan-3-ol

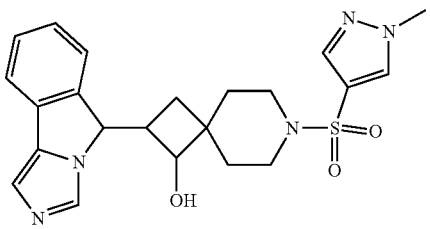 [SMILES: Cn1cc(S(=O)(=O)N2CCC3(CC2)CC(C2c4ccccc4-c4cncn42)C3O)cn1]

The title compound was prepared by the procedure described in Example 21a by substituting cyanomethanesulfonyl chloride with 1-methyl-1H-pyrazole-3-sulfonyl chloride.

LCMS (ESL) m/z=441.0 [M+H]⁺. ¹H NMR (400 MHz, DMSO-d6) δ 8.29 (s, 1H), 7.87-7.71 (m, 2H), 7.57 (td, J=7.3, 0.9 Hz, 2H), 7.40-7.30 (m, 1H), 7.23 (td, J=7.5, 1.2 Hz, 1H), 7.11 (s, 1H), 5.73 (d, J=5.6 Hz, 1H), 5.40 (d, J=8.9 Hz, 1H), 4.01 (td, J=6.3, 3.1 Hz, 1H), 3.90 (s, 3H), 3.29 (s, 1H), 2.95-2.67 (m, 2H), 1.82 (q, J=10.1, 9.5 Hz, 2H), 1.71-1.49 (m, 5H).

Example 27: 2-(5H-imidazo[1,5-b]isoindol-5-yl)-7-(1,3,5-trimethylpyrazol-4-yl)sulfonyl)-7-azaspiro[3.5]nonan-3-ol

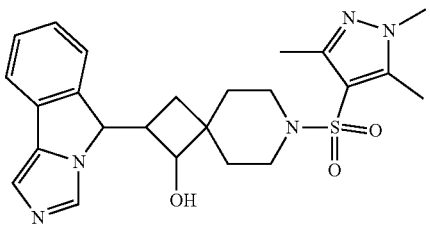 [SMILES: Cc1nn(C)c(C)c1S(=O)(=O)N1CCC2(CC1)CC(C1c3ccccc3-c3cncn31)C2O]

The title compound was prepared by the procedure described in Example 21b, by substituting cyanomethyl sulfonyl chloride with 1,3,5-trimethyl-1H-pyrazole-4-sulphonyl chloride.

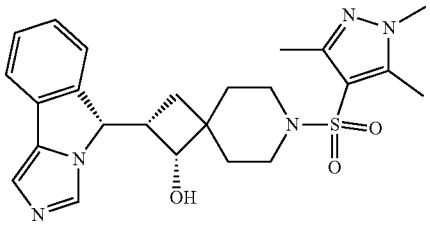 [SMILES: Cc1nn(C)c(C)c1S(=O)(=O)N1CCC2(CC1)C[C@@H]([C@H]1c3ccccc3-c3cncn31)[C@H]2O]

Example 27: (1R,2S)-2-((S)-55H-imidazo[5,1-a]isoindol-5-yl)-7-((1,3,5-trimethyl-1H-pyrazol-4-yl)sulfonyl)-7-azaspiro[3.5]nonan-1-ol. LCMS (ESI) m/z=468.2 [M+H]+. ¹H NMR (400 MHz, DMSO-d6) δ 7.89 (s, 1H), 7.66-7.52 (m, 2H), 7.41-7.32 (m, 1H), 7.30-7.20 (m, 1H), 7.15 (s, 1H), 5.72 (d, J=5.5 Hz, 1H), 5.42 (d, J=8.9 Hz, 1H), 4.10-3.96 (m, 1H), 3.70 (s, 3H), 3.02-2.71 (m, 4H), 2.38 (s, 3H), 2.23 (s, 3H), 1.91-1.75 (m, 2H), 1.74-1.64 (m, 1H), 1.64-1.50 (m, 3H).

Example 28: 7-(2,3-dimethylimidazol-4-yl sulfonyl-2-(5H-imidazo[1,5-b]isoindol-5-yl)-7-azaspiro[3.5]nonan-3-ol

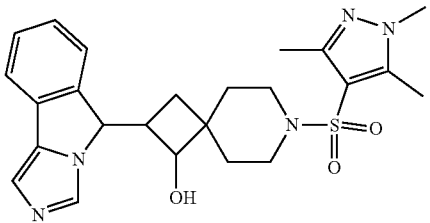 [SMILES: Cc1nn(C)c(C)c1S(=O)(=O)N1CCC2(CC1)CC(C1c3ccccc3-c3cncn31)C2O]

The title compound was prepared by the procedure described in Example 21b by substituting cyanomethylsulfonyl chloride with 2,3-dimethylimidazole-4-sulfonyl chloride.

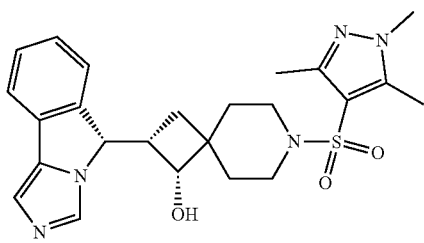 [SMILES: Cc1nn(C)c(C)c1S(=O)(=O)N1CCC2(CC1)C[C@@H]([C@H]1c3ccccc3-c3cncn31)[C@H]2O]

(1R,2S)-2-((S)-5H-imidazo[5,1-a]isoindol-5-yl)-7-((1,3,5-trimethyl-1H-pyrazol-4-yl)sulfonyl)-7-azaspiro[3.5]nonan-1-ol. LCMS (ESI) m/z=454.2 [M+H]+. ¹H NMR (400 MHz, DMSO-d6) δ 8.44 (s, 1H), 7.79-7.56 (m, 2H), 7.52-7.39 (m, 2H), 7.35 (d, J=3.4 Hz, 2H), 5.84 (d, J=5.3 Hz, 1H), 5.59 (d, J=8.7 Hz, 1H), 4.16-3.98 (m, 1H), 3.64 (s, 3H), 3.13-2.84 (m, 4H), 2.75-2.57 (m, 1H), 2.35 (s, 3H), 1.89-1.66 (m, 3H), 1.66-1.45 (m, 3H).

Example 29: 2-(5H-imidazo[1,5-b]isoindol-5-yl)-7-isopropylsulfonyl-7-azaspiro[3.5]nonan-3-ol

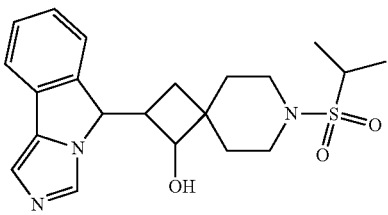 [SMILES: CC(C)S(=O)(=O)N1CCC2(CC1)CC(C1c3ccccc3-c3cncn31)C2O]

The title compound was prepared by the procedure described in Example 21b by substituting cyanomethyl sulfonyl chloride with 2-propanesulfonyl chloride.

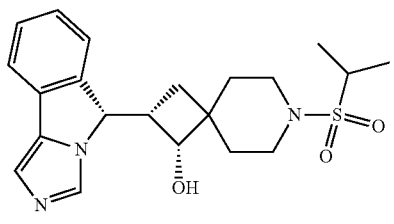 [SMILES: CC(C)S(=O)(=O)N1CCC2(CC1)C[C@@H]([C@H]1c3ccccc3-c3cncn31)[C@H]2O]

Example 29: (1R,2S)-2-((S)-5H-imidazo[5,1-a]isoindol-5-yl)-7-(isopropylsulfonyl)-7-azaspiro[3.5]nonan-1-ol. LCMS (ESI) m/z=402.2 [M+H]+. ¹H NMR (400 MHz, DMSO-d6) δ 8.22 (s, 1H), 7.65 (d, J=7.7 Hz, 2H), 7.48-7.23 (m, 3H), 5.81 (d, J=5.3 Hz, 1H), 5.55 (d, J=8.7 Hz, 1), 4.21-4.01 (m, 1H), 3.19-3.03 (m, 2H), 2.70-2.54 (m, 1H), 1.89 (t, J=10.4 Hz, 1H), 1.84-1.63 (m, 2H), 1.62-1.43 (m, 3H), 1.20 (d, 3-6.8 Hz, 6H).

Example 30: 7-(3,5-dimethylisoxazol-4-yl)sulfonyl-2-(5H-imidazo[1,5-b]isoindol-5-yl)-7-azaspiro[3.5]nonan-3-ol

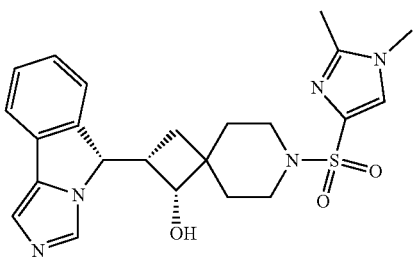 [SMILES: Cc1nc(S(=O)(=O)N2CCC3(CC2)C[C@@H]([C@H]2c4ccccc4-c4cncn42)[C@H]3O)cn1C]

The title compound was prepared by the procedure described in Example 21b by substituting cyanomethyl sulfonyl chloride with 1,2-dimethylimidazole-4-sulfonyl chloride.

Example 30: (1R,2S)-7-((1,2-dimethyl-1H-imidazol-4-yl)sulfonyl)-2-((S)-5H-imidazo[5,1-a]isoindol-5-yl)-7-azaspiro[3.5]nonan-1-ol. LCMS (ESI) m/z=454.2 [M+H]+. ¹H NMR (400 MHz, DMSO-d6) δ 7.83 (s, 1H), 7.69 (s, 1H), 7.65-7.43 (m, 2H), 7.44-7.30 (m, 1H), 7.29-7.17 (m, 1H), 7.12 (s, 1H), 5.72 (d, J=5.5 Hz, 1H), 5.41 (d, J=8.9 Hz, 1H), 4.09-3.92 (m, 1H), 3.61 (s, 3H), 3.15-2.99 (m, 21), 2.96-2.67 (m, 2H), 2.31 (s, 3H), 1.93-1.80 (m, 1H), 1.79-1.72 (m, 1H), 1.71-1.63 (m, 1H), 1.62-1.47 (m, 3H).

Example 31: 7-(1,2-dimethylimidazol-4-ylsulfonyl-2-(5H-imidazo[1,5-b]isoindol-5-yl)-7-azaspiro[3.5]nonan-3-ol

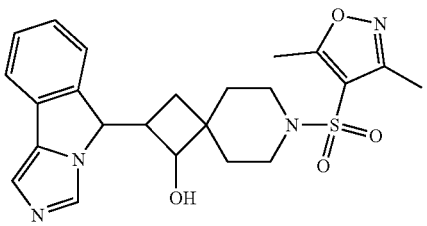 [SMILES: Cc1noc(C)c1S(=O)(=O)N1CCC2(CC1)CC(C1c3ccccc3-c3cncn31)C2O]

The title compound was prepared by the procedure described in Example 21b by substituting cyanomethyl sulfonyl chloride with 3,5-dimethylisoxazole-4-sulfonyl chloride.

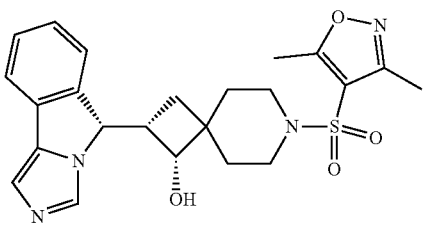 [SMILES: Cc1noc(C)c1S(=O)(=O)N1CCC2(CC1)C[C@@H]([C@H]1c3ccccc3-c3cncn31)[C@H]2O]

Example 31: (1R,2S)-7-((3,5-dimethylisoxazol-4-yl)sulfonyl)-2-((S)-5H-imidazo[5,1-a]isoindol-5-yl)-7-azaspiro[3.5]nonan-1-ol. LCMS (ESI) m/z=455.2 [M+H]+. 1H NMR (400 MHz, DMSO-d6) δ 7.90 (s, 1H), 7.73-7.51 (m, 2H), 7.42-7.29 (m, 1H), 7.32-7.20 (m, 1H), 7.15 (s, 1H), 5.73 (d, J=5.3 Hz, 1H), 5.44 (d, J=8.9 Hz, 1H), 4.13-4.03 (m, 1H), 3.06-2.93 (m, 4H), 2.61 (s, 3H), 2.33 (s, 3H), 1.92-1.68 (m, 4H), 1.65-1.47 (m, 4H).

Example 32: 2-(5H-imidazo[1,5-b]isoindol-5-yl-7-[(4-methyl-3-pyridyl)sulfonyl]-7-azaspiro[3.5]nonan-3-ol

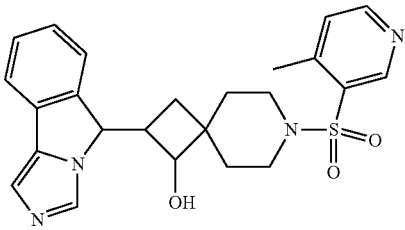

The title compound was prepared by the procedure described in, Example X, by substituting cyanomethyl sulfonyl chloride with 4-methylpyridine-3-sulfonyl chloride in Step X.

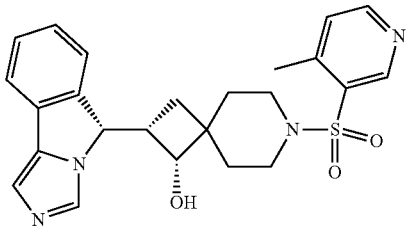 [SMILES: Cc1ccncc1S(=O)(=O)N1CCC2(CC1)C[C@@H]([C@H]1c3ccccc3-c3cncn31)[C@H]2O]

Example 32: (1R,2S)-2-((S)-5H-imidazo[5,1-a]isoindol-5-yl)-7-((4-methylpyridin-3-yl)sulfonyl)-7-azaspiro[3.5]nonan-1-ol. LCMS (ES) m/z=451.2 [M+H]+. 1H NMR (400 MHz, DMSO-d6) δ 8.84 (s, 1H), 8.68 (d, J=5.0 Hz, 1H), 7.82 (s, 1H), 7.65-7.46 (m, 3H), 7.42-7.30 (m, 1H), 7.30-7.17 (m, 1H), 7.11 (s, 1H), 5.73 (d, J=5.4 Hz, 1-), 5.41 (d, J=9.0 Hz, 1H), 4.12-3.99 (m, 1H), 3.23-2.95 (m, 4H), 2.58 (s, 3H), 1.97-1.66 (m, 3H), 1.65-1.42 (m, 3H).

Example 33: 1-[3-hydroxy-2-(5H-imidazo[1,5-b]isoindol-5-yl)-7-azaspiro[3.5]nonan-7-yl]-3-(3-pyridyl)propan-1-one

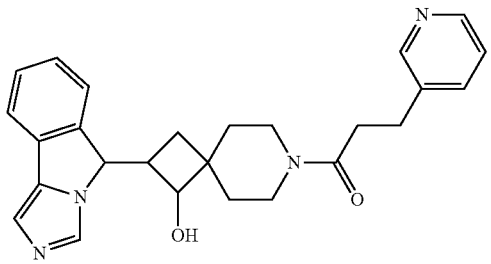 [SMILES: O=C(CCc1cccnc1)N1CCC2(CC1)CC(C1c3ccccc3-c3cncn31)C2O]

A solution of tert-butyl (5R,6S)-5-hydroxy-6-((S)-5H-imidazo[5,1-a]isoindol-5-yl)-2-azaspiro[3.3]heptane-2-carboxylate (50 mg, 0.14 mmol) in 1 mL of DCM was charged with 200 uL of TFA and stirred at room temperature for one hour. The mixture was then concentrated in vacuo and azeotroped twice with MeOH and twice with DCM. The residue was then dissolved in 5 mL of MeOH and charged with 1 g of macroprorous polymer supported Ammonium Carbonate resin and sonicated. The resin was then filtered off by vacuum filtration and the solution was concentrated in vacuo. The residue was then dissolved in 1 mL of dimethylacetamide. In a separate vial, 3-(pyridin-3-yl)propanoic acid (42 mg, 0.28 mmol) was dissolved in 1 ml of dimethylformamide and charged with HATU (106.4 mg, 0.28 mmol) and TEA (42 mg, 0.42 mmol) and stirred at room temperature for 5 minutes. This solution was then added to the formerly mentioned dimethylacetamide solution and stirred at room temperature for one hour. The mixture was then purified by reverse phase HPLC to afford the title compound (17 mg, 0.4 mmol, 29% yield).

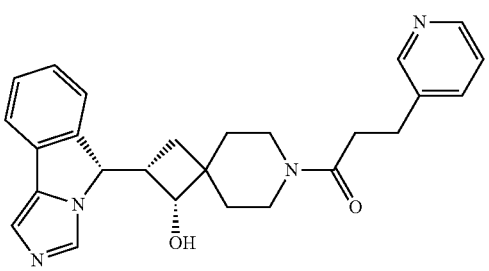

Example 33: 1-((1R,2S)-1-hydroxy-2-((S)-5H-imidazo[5,1-a]isoindol-5-yl)-7-azaspiro[3.5]nonan-7-yl)-3-(pyridin-3-yl)propan-1-one. LCMS (ESI) m/z=429.2 [M+H]+. 1H NMR (400 MHz, DMSO-d6) δ 8.59-8.33 (m, 3H), 7.77-7.59 (m, 3H), 7.60-7.18 (m, 4H), 5.84 (t, J=5.1 Hz, 1H), 5.72-5.50 (m, 1H), 4.19-4.01 (m, 1H), 2.87-2.76 (m, 2H), 2.71-2.58 (m, 3H), 1.92-1.49 (m, 3H), 1.51-1.28 (m, 3H).

Example 34: N-[4-[[3-hydroxy-2-(5H-imidazo[1,5-b]isoindol-5-yl)-7-azaspiro[3.5]nonan-7-yl]sulfonyl]phenyl]-N-methyl-acetamide

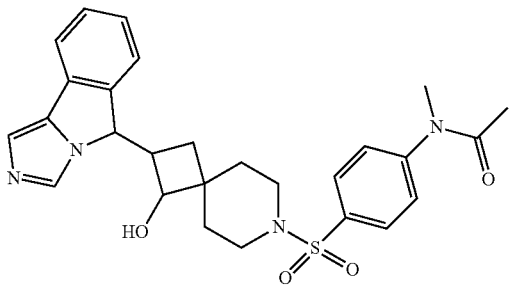 [SMILES: CC(=O)N(C)c1ccc(S(=O)(=O)N2CCC3(CC2)CC(C2c4ccccc4-c4cncn42)C3O)cc1]

The title compound was prepared by the procedure described in Example 21b by substituting cyanomethyl sulfonyl chloride with 4-(N-methylacetamido)benzene-1-sulfonyl chloride.

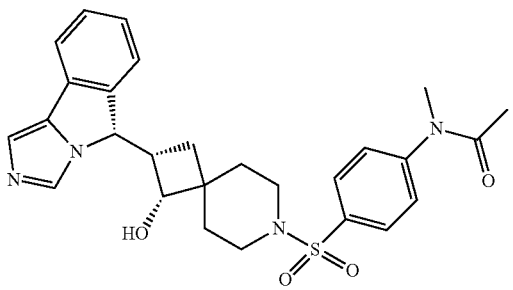 [SMILES: CC(=O)N(C)c1ccc(S(=O)(=O)N2CCC3(CC2)C[C@@H]([C@H]2c4ccccc4-c4cncn42)[C@H]3O)cc1]

Example 34: N-(4-(((1R,2S)-1-hydroxy-2-((S)-5H-imidazo[5,1-a]isoindol-5-yl)-7-azaspiro[3.5]nonan-7-yl)sulfonyl)phenyl)-N-methylacetamide. LCMS (ESI) m/z=507.2 [M+H]+. 1H NMR (400 MHz, DMSO-d6) δ 7.88-7.70 (m, 3H), 7.67-7.48 (m, 4H), 7.40-7.30 (m, 1H), 7.27-7.16 (m, 1H), 7.10 (s, 1H), 5.73 (d, J=5.5 Hz, 1H), 5.38 (d, J=8.9 Hz, 1H), 4.09-3.88 (m, 1H), 3.25 (s, 3H), 3.10-2.77 (m, 5H), 1.97 (d, J=20.2 Hz, 3H), 1.89-1.75 (m, 2H), 1.67-1.41 (m, 4H).

Example 35: 1-[4-[[3-hydroxy-2-(5H-imidazo[1,5-b]isoindol-5-yl)-7-azaspiro[3.5]nonan-7-yl]sulfonyl]-1-piperidyl]ethanone

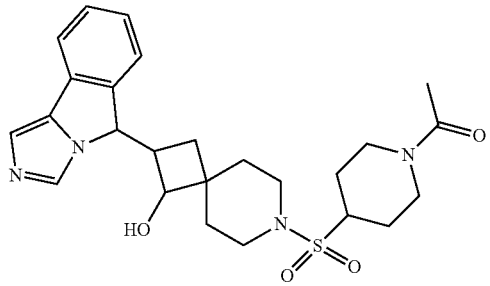 [SMILES: CC(=O)N1CCC(S(=O)(=O)N2CCC3(CC2)CC(C2c4ccccc4-c4cncn42)C3O)CC1]

The title compound was prepared by the procedure described in Example 21b by substituting cyanomethyl sulfonyl chloride with 1-acetylpiperidine-4-sulfonyl chloride.

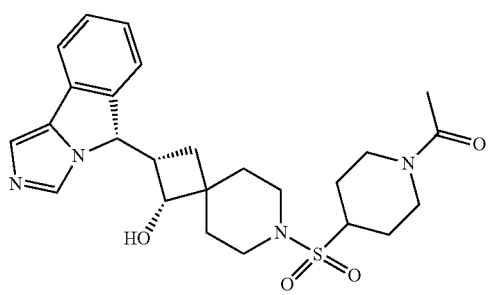 [SMILES: CC(=O)N1CCC(S(=O)(=O)N2CCC3(CC2)C[C@@H]([C@H]2c4ccccc4-c4cncn42)[C@H]3O)CC1]

Example 35: 1-(4-(((1R,2S)-1-hydroxy-2-((S)-5H-imidazo[5,1-a]isoindol-5-yl)-7-azaspiro[3.5]nonan-7-yl)sulfonyl)piperidin-1-yl)ethan-1-one. LCMS (ESI) m/z=485.2 [M+H]+. 1H NMR (400 MHz, DMSO-d6) δ 7.85 (s, 1H), 7.65-7.49 (m, 2H), 7.44-7.19 (m, 2H), 7.13 (s, 1H), 5.74 (d, J=5.3 Hz, 1H), 5.45 (d, J=8.8 Hz, 1H), 4.44 (d, J=12.9 Hz, 1H), 4.27-4.02 (m, 1H), 3.88 (d, J=13.7 Hz, 1H), 3.20-2.95 (m, 3H), 2.00 (s, 3H), 1.98-1.64 (m, 6H), 1.60-1.45 (m, 4H), 1.40-1.21 (m, 2H).

Example 36: 7-cyclobutylsulfonyl-2-(5H-imidazo[1,5-b]isoindol-5-yl)-7-azaspiro[3.5]nonan-3-ol

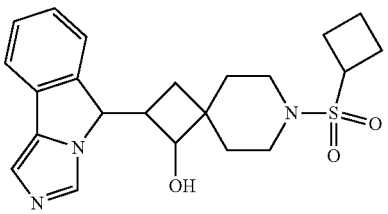 [SMILES: O=S(=O)(C1CCC1)N1CCC2(CC1)C[C@@H]([C@H]1c3ccccc3-c3cncn31)[C@H]2O]

The title compound was prepared by the procedure described in Example 21b by substituting cyanomethyl sulfonyl chloride with cyclobutanesulfonyl chloride.

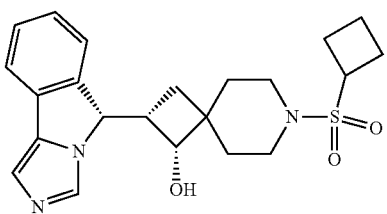

Example 36: (1R,2S)-7-(cyclobutylsulfonyl)-2-((S)-5H-imidazo[5,1-a]isoindol-5-yl)-7-azaspiro[3.5]nonan-1-ol. LCMS (ESI) m/z=414.2 [M+H]⁺. ¹H NMR (400 MHz, DMSO-d6) δ 7.85 (s, 1H), 7.67-7.51 (m, 2H), 7.42-7.21 (m, 2H), 7.13 (s, 1H), 5.75 (s, 1H), 5.44 (d, J=8.8 Hz, 1H), 4.15-4.04 (m, 1H), 4.03-3.86 (m, 1H), 3.23-2.93 (m, 5H), 2.35-2.16 (m, 4H), 2.07 (s, 1H), 2.04-1.84 (m, 2H), 1.82-1.65 (m, 2H), 1.61-1.37 (m, 3H).

Example 37: 5-[[3-hydroxy-2-(5H-imidazo[1,5-b]isoindol-5-yl)-7-azaspiro[3.5]nonan-7-yl]sulfonyl]-1-methyl-indolin-2-one

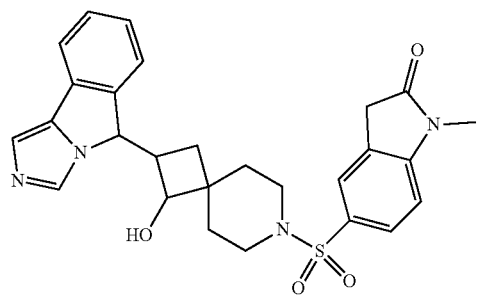 [SMILES: CN1C(=O)Cc2cc(S(=O)(=O)N3CCC4(CC3)CC(C3c5ccccc5-c5cncn53)C4O)ccc21]

The title compound was prepared by the procedure described in Example 21b by substituting cyanomethyl sulfonyl chloride with 1-methyl-2-oxo-5-indolinesulfonyl chloride.

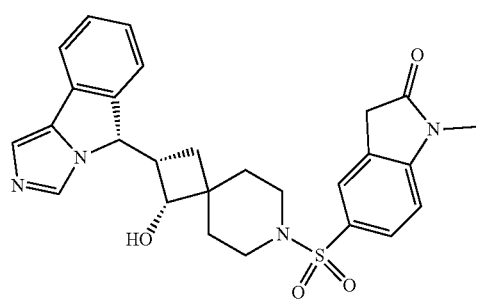 [SMILES: CN1C(=O)Cc2cc(S(=O)(=O)N3CCC4(CC3)C[C@@H]([C@H]3c5ccccc5-c5cncn53)[C@H]4O)ccc21]

Example 37: 5-(((1R,2S)-1-hydroxy-2-((S)-5H-imidazo[5,1-a]isoindol-5-yl)-7-azaspiro[3.5]nonan-7-yl)sulfonyl)-1-methylindolin-2-one. LCMS (ESI) m/z=505.2 [M+H]⁺

Example 38: 6,7-dihydro-5H-pyrazolo[5,1-b][1,3]oxazin-3-yl-[3-hydroxy-2-(5H-imidazo[1,5-b]isoindol-5-yl)-7-azaspiro[3.5]nonan-7-yl]methanone

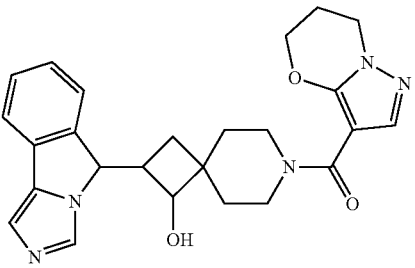 [SMILES: O=C(c1cnn2c1OCCC2)N1CCC2(CC1)CC(C1c3ccccc3-c3cncn31)C2O]

The title compound was prepared by the procedure described in Example 33 by substituting 3-(pyridin-3-yl)propanoic acid with 6,7-dihydro-5h-pyrazolo[5,1-b][1,3]oxazine-3-carboxylic acid.

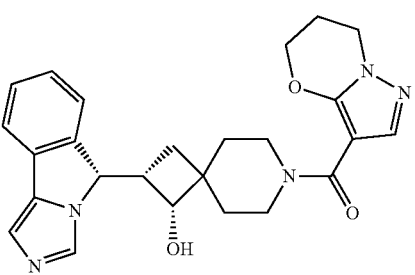 [SMILES: O=C(c1cnn2c1OCCC2)N1CCC2(CC1)C[C@@H]([C@H]1c3ccccc3-c3cncn31)[C@H]2O]

Example 38: (6,7-dihydro-5H-pyrazolo[5,1-b][1,3]oxazin-3-yl)((1R,2S)-1-hydroxy-2-((S)-5H-imidazo[5,1-a]isoindol-5-yl)-7-azaspiro[3.5]nonan-7-yl)methanone. LCMS (ESI) m/z=446.2 [M+H]⁺. ¹H NMR (400 MHz, DMSO-d6) δ 7.86 (s, 1H), 7.72-7.50 (m, 2H), 7.44-7.28 (m, 2H), 7.28-7.22 (m, 1H), 7.13 (s, 1H), 5.74 (s, 1H), 5.45 (d, J=8.7 Hz, 1H), 4.47-4.25 (m, 2H), 4.19-3.98 (m, 4H), 3.55-3.43 (m, 2H), 2.62-2.53 (m, 1H), 2.22-2.11 (m, 2H), 1.98-1.61 (m, 3H), 1.54-1.34 (m, 4H).

Example 39: 1-[2-[3-hydroxy-2-(5H-imidazo[1,5-b]isoindol-5-yl)-7-azaspiro[3.5]nonan-7-yl]-2-oxo-ethyl]piperidin-2-one

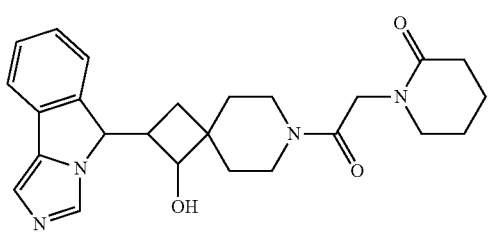 [SMILES: O=C(CN1CCCCC1=O)N1CCC2(CC1)CC(C1c3ccccc3-c3cncn31)C2O]

The title compound was prepared by the procedure described in Example 33 by substituting 3-(pyridin-3-yl)propanoic acid with (2-oxopiperidin-1-yl)acetic acid.

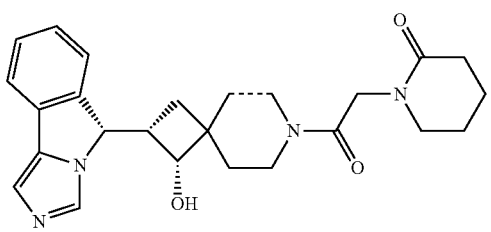

Example 39: 1-(2-((1R,2S)-1-hydroxy-2-((S)-5H-imidazo[5,1-a]isoindol-5-yl)-7-azaspiro[3.5]nonan-7-yl)-2-oxoethyl)piperidin-2-one. LCMS (ESI) m/z=435.3 [M+H]⁺. ¹H NMR (400 MHz, DMSO-d6) δ 8.25 (s, 1H), 7.69-7.58 (m, 2H), 7.52-7.11 (m, 3H), 5.92-5.70 (m, 1H), 5.56 (d, J=8.7 Hz, 1H), 4.23-3.93 (m, 3H), 3.22 (d, J=5.8 Hz, 3H), 2.80-2.53 (m, 2H), 2.26-2.16 (m, 2H), 1.97-1.84 (m, 1H), 1.84-1.57 (m, 5H), 1.57-1.28 (m, 3H).

Example 40: 4-[3-hydroxy-2-(5H-imidazo[1,5-b]isoindol-5-yl)-7-azaspiro[3.5]nonane-7-carbonyl]-1-methyl-piperidin-2-one

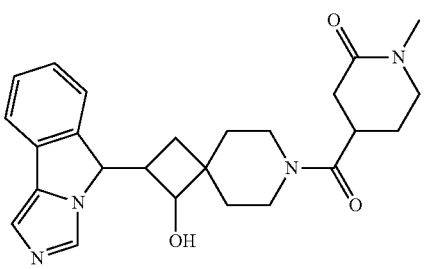 [SMILES: CN1CCC(C(=O)N2CCC3(CC2)CC(C2c4ccccc4-c4cncn42)C3O)CC1=O]

The title compound was prepared by the procedure described in Example 33 by substituting 3-(pyridin-3-yl)propanoic acid with 1-methyl-2-oxopiperidine-4-carboxylic acid.

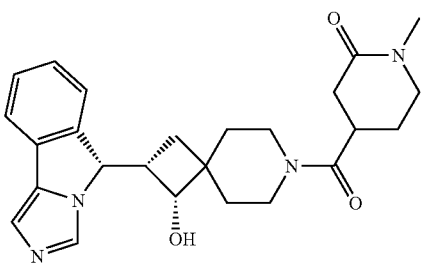 [SMILES: CN1CCC(C(=O)N2CCC3(CC2)C[C@@H]([C@H]2c4ccccc4-c4cncn42)[C@H]3O)CC1=O]

Example 40: 4-((1R,2S)-1-hydroxy-2-((S)-5H-imidazo[5,1-a]isoindol-5-yl)-7-azaspiro[3.5]nonane-7-carbonyl)-1-methylpiperidin-2-one. LCMS (ESI) m/z=435.3. ¹H NMR (400 MHz, DMSO-d6) δ 8.19-7.98 (m, 1H), 7.77-7.56 (m, 2H), 7.46-7.27 (m, 2H), 5.88-5.63 (m, 1H), 5.52 (d, J=8.7 Hz, 1H), 4.20-4.00 (m, 1H), 3.60-3.38 (m, 3H), 3.23-3.12 (m, 2H), 2.78 (d, J=4.8 Hz, 3H), 2.71-2.56 (m, 1H), 2.37-2.12 (m, 2H), 1.98-1.61 (m, 6H), 1.56-1.34 (m, 2H).

Example 41: 1-[3-hydroxy-2-(5H-imidazo[1,5-b]isoindol-5-yl)-7-azaspiro[3.5]nonan-7-yl]-2-(1,2,4-triazol-1-yl)propan-1-one

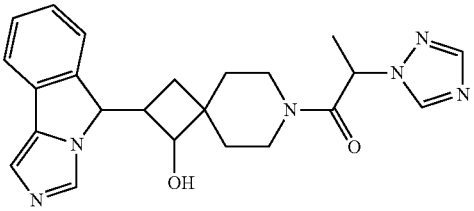 [SMILES: CC(C(=O)N1CCC2(CC1)CC(C1c3ccccc3-c3cncn31)C2O)n1cncn1]

The title compound was prepared by the procedure described in Example 33 by substituting 3-(pyridin-3-yl)propanoic acid with 2-(1h-1,2,4-triazol-1-yl)propanoic acid.

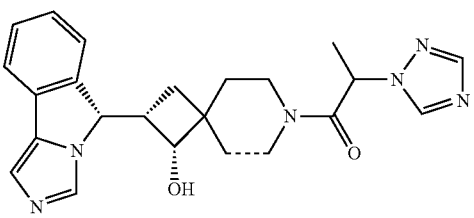

Example 41: 1-((1R,2S)-1-hydroxy-2-((S)-5H-imidazo[5,1-a]isoindol-5-yl)-7-azaspiro[3.5]nonan-7-yl)-2-(1H-1,2,4-triazol-1-yl)propan-1-one. LCMS (ESI) m/z=419.2 [M+H]⁺. ¹H NMR (400 MHz, DMSO-d6) δ 8.67-8.54 (m, 2H), 8.02-7.85 (m, 1H), 7.84-7.63 (m, 2H), 7.63-7.52 (m, 1H), 7.52-7.35 (m, 2H), 5.95-5.82 (m, 1H), 5.78-5.58 (m, 2H), 4.26-4.05 (m, 1H), 3.15-3.02 (m, 1H), 2.89 (s, 1H), 2.77-2.62 (m, 2H), 1.94-1.66 (m, 3H), 1.67-1.33 (m, 7H), 1.33-1.01 (m, 1H).

Example 42: N-[2-[3-hydroxy-2-(5H-imidazo[1,5-b]isoindol-5-yl)-7-azaspiro[3.5]nonan-7-yl]-1-methyl-2-oxo-ethyl]formamide

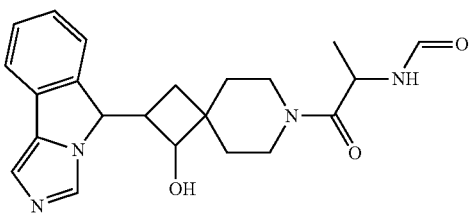 [SMILES: CC(NC=O)C(=O)N1CCC2(CC1)CC(C1c3ccccc3-c3cncn31)C2O]

The title compound was prepared by the procedure described in Example 33 by substituting 3-(pyridin-3-yl)propanoic acid with N-formyl-DL-alanine.

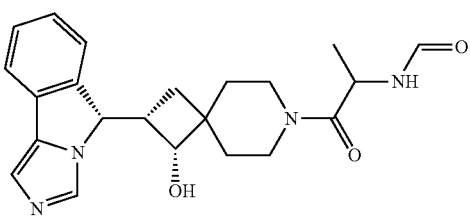

Example 42: N-(1-((1R,2S)-1-hydroxy-2-((S)-5H-imidazo[5,1-a]isoindol-5-yl)-7-azaspiro[3.5]nonan-7-yl)-1-oxopropan-2-yl)formamide. LCMS (ESI) m/z 395.2 [M+H]+. 1H NMR (400 MHz, DMSO-d6) δ 8.05-7.87 (m, 1H), 7.86 (s, 1H), 7.72-7.46 (m, 2H), 7.44-7.30 (m, 1H), 7.30-7.18 (m, 1H), 7.13 (s, 1H), 5.86-5.63 (m, 1H), 5.46 (d, J=8.8 Hz, 1H), 4.88-4.72 (m, 1H), 4.22-4.00 (m, 1H), 2.89 (s, 4H), 2.77-2.64 (m, 1H), 2.62-2.55 (m, 1H), 1.98-1.66 (m, 2H), 1.60-1.36 (m, 3H), 1.25-1.07 (m, 2H).

Example 43: cyclopropyl-[3-hydroxy-2-(5H-imidazo[1,5-b]isoindol-5-yl)-7-azaspiro[3.5]nonan-7-yl]methanone

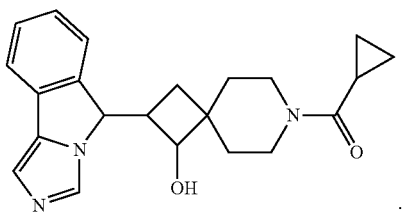 [SMILES: O=C(C1CC1)N1CCC2(CC1)CC(C1c3ccccc3-c3cncn31)C2O]

The title compound was prepared by the procedure described in Example 33 by substituting 3-(pyridin-3-yl) propanoic acid with cyclopropanecarboxylic acid.

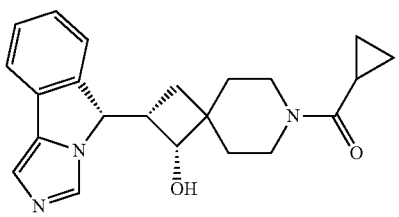

Example 43: cyclopropyl((1R,2S)-1-hydroxy-2-((S)-5H-imidazo[5,1-a]isoindol-5-yl)-7-azaspiro[3.5]nonan-7-yl)methanone. LCMS (ESI) m/z=364.2 [M+H]+. 1H NMR (400 MHz, DMSO-d6) δ 8.58 (s, 1H), 7.81-7.67 (m, 2H), 7.55 (s, 1H), 7.50-7.26 (m, 2H), 5.94-5.80 (m, 1H), 5.67 (d, J=8.6 Hz, 1i), 4.29-3.95 (m, 1H), 3.16-3.00 (m, 1H), 2.78-2.61 (m, 1H), 2.05-1.68 (m, 4H), 1.63-1.35 (m, 3H), 1.28-1.07 (m, 2H), 0.78-0.53 (m, 4H).

Example 44: 2-(5H-imidazo[1,5-b]isoindol-5-yl)-7-(1-methylpyrazol-3-yl)sulfonyl-7-azaspiro[3.5]nonan-3-ol

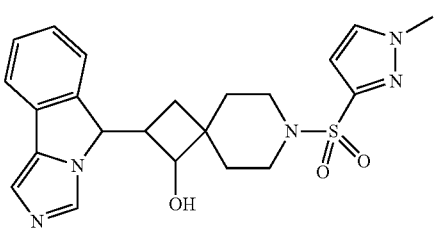 [SMILES: Cn1ccc(S(=O)(=O)N2CCC3(CC2)CC(C2c4ccccc4-c4cncn42)C3O)n1]

The title compound was prepared by the procedure described in Example 21b by substituting cyanomethyl sulfonyl chloride with 1-methyl-1h-pyrazole-3-sulfonyl chloride.

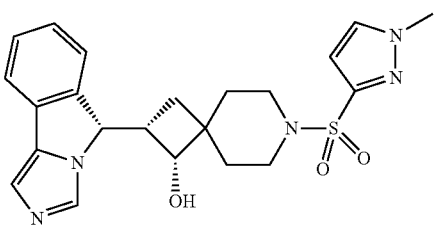 [SMILES: Cn1ccc(S(=O)(=O)N2CCC3(CC2)C[C@@H]([C@H]2c4ccccc4-c4cncn42)[C@H]3O)n1]

Example 44: (1R,2S)-2-((S)-5H-imidazo[5,1-a]isoindol-5-yl)-7-((1-methyl-1H-pyrazol-3-yl)sulfonyl)-7-azaspiro[3.5]nonan-1-ol. LCMS (ESI) m/z=440.2 [M+H]+. 1H NMR (400 MHz, DMSO-d6) δ 7.94 (d, J=2.3 Hz, 1H), 7.82 (s, 1H), 7.65-7.51 (m, 2H), 7.42-7.16 (m, 2H), 7.11 (s, 1H), 6.64 (d, J=2.3 Hz, 1H), 5.74 (d, J=5.5 Hz, 1H), 5.40 (d, J=8.9 Hz, 1H), 4.08-3.97 (m, 1H), 3.94 (s, 3H), 3.17-2.97 (m, 2H), 2.94-2.78 (m, 2H), 1.90-1.44 (m, 6H).

Example 45: [3-hydroxy-2-(5H-imidazo[1,5-b]isoindol-5-yl)-7-azaspiro[3.5]nonan-7-yl]-tetrahydropyran-4-yl-methanone

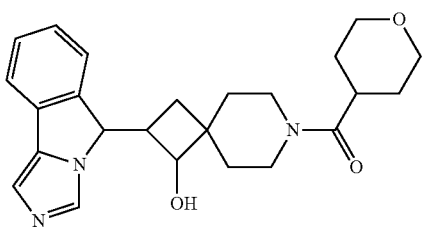 [SMILES: O=C(C1CCOCC1)N1CCC2(CC1)CC(C1c3ccccc3-c3cncn31)C2O]

The title compound was prepared by the procedure described in Example 33 by substituting 3-(pyridin-3-yl) propanoic acid with tetrahydro-pyran-4-carboxylic acid.

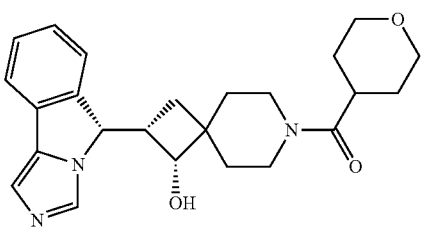

Example 45: ((1R,2S)-1-hydroxy-2-((S)-5H-imidazo[5,1-a]isoindol-5-yl)-7-azaspiro[3.5]nonan-7-yl)(tetrahydro-2H-pyran-4-yl)methanone. LCMS (ESI) m/z=408.2 [M+H]⁺. ¹H NMR (400 MHz, DMSO-d6) δ 8.88-8.66 (m, 1H), 7.81-7.56 (m, 3H), 7.55-7.36 (m, 2H), 7.25-6.87 (m, 1H), 5.98-5.82 (m, 1H), 5.72 (d, J=8.5 Hz, 1H), 4.24-4.02 (m, 1H), 3.91-3.75 (m, 2H), 3.58-3.46 (m, 1H), 2.92-2.61 (m, 3H), 1.97-1.68 (m, 3H), 1.66-1.39 (m, 6H).

Example 46: [3-hydroxy-2-(5H-imidazo[1,5-b]isoindol-5-yl)-7-azaspiro[3.5]nonan-7-yl]-tetrahydro-furan-3-yl-methanone

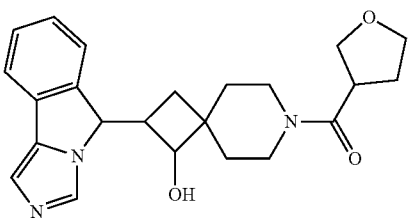 [SMILES: O=C(C1CCOC1)N1CCC2(CC1)CC(C1c3ccccc3-c3cncn31)C2O]

The title compound was prepared by the procedure described in Example 33 by substituting 3-(pyridin-3-yl)propanoic acid with tetrahydro-3-furoic acid.

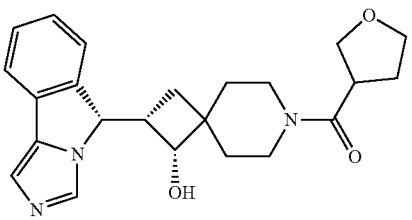 [SMILES: O=C(C1CCOC1)N1CCC2(CC1)C[C@@H]([C@H]1c3ccccc3-c3cncn31)[C@H]2O]

Example 46: ((1R,2S)-1-hydroxy-2-((S)-5H-imidazo[5,1-a]isoindol-5-yl)-7-azaspiro[3.5]nonan-7-yl)tetrahydrofuran-3-yl)methanone. LCMS (ESI) m/z=394.2 [M+H]⁺. ¹H NMR (400 MHz, DMSO-d6) δ 8.78-8.57 (m, 1H), 7.85-7.66 (m, 2H), 7.62 (d, J=4.1 Hz, 1H), 7.51-7.38 (m, 2H), 7.26-6.89 (m, 1H), 5.89 (t, J=5.6 Hz, 1H), 5.75-5.60 (m, 1H), 4.21-4.09 (m, 1H), 3.94-3.80 (m, 1H), 3.75-3.61 (m, 3H), 3.61-3.40 (m, 21H), 2.78-2.64 (m, 1H), 2.12-1.92 (m, 2H), 1.93-1.54 (m, 4H), 1.57-1.34 (m, 3H).

Example 47: 1-[3-hydroxy-2-(5H-imidazo[1,5-b]isoindol-5-yl)-7-azaspiro[3.5]nonan-7-yl]-3-methoxy-propan-1-one

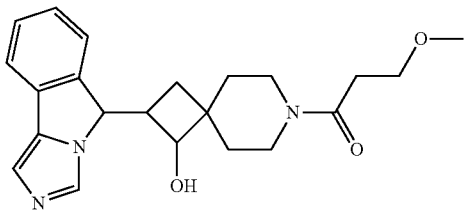 [SMILES: COCCC(=O)N1CCC2(CC1)CC(C1c3ccccc3-c3cncn31)C2O]

The title compound was prepared by the procedure described in Example 33 by substituting 3-(pyridin-3-yl)propanoic acid with 3-methoxypropionic acid.

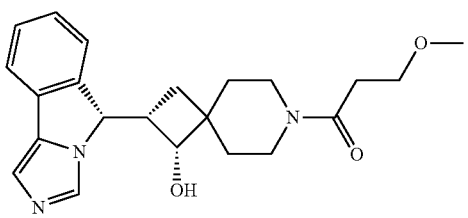

Example 47: 1-((1R,2S)-1-hydroxy-2-((S)-5H-imidazo[5,1-a]isoindol-5-yl)-7-azaspiro[3.5]nonan-7-yl)-3-methoxy-propan-1-one. LCMS (ESI) m/z=382.2 [M+H]⁺. ¹H NMR (400 MHz, DMSO-d6) δ 8.76-8.56 (m, 1H), 7.77-7.63 (m, 2H), 7.63-7.54 (m, 1H), 7.54-7.34 (m, 2H), 5.87 (t, J=5.8 Hz, 1H), 5.68 (d, J=8.5 Hz, 1H), 4.28-4.04 (m, 1H), 3.60-3.45 (m, 2H), 3.21 (d, J=4.1 Hz, 3H), 2.79-2.64 (m, 1H), 2.60-2.51 (m, 5H), 1.95-1.54 (m, 3H), 1.57-1.38 (m, 3H).

Example 48: cyclobutyl-[3-hydroxy-2-(5H-imidazo[1,5-b]isoindol-5-yl)-7-azaspiro[3.5]nonan-7-yl]methanone

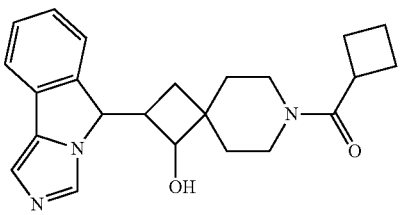 [SMILES: O=C(C1CCC1)N1CCC2(CC1)CC(C1c3ccccc3-c3cncn31)C2O]

The title compound was prepared by the procedure described in Example 33 by substituting 3-(pyridin-3-yl)propanoic acid with cyclobutanecarboxylic acid.

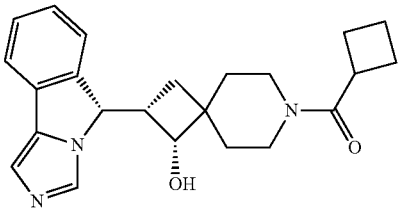 [SMILES: O=C(C1CCC1)N1CCC2(CC1)C[C@@H]([C@H]1c3ccccc3-c3cncn31)[C@H]2O]

Example 48: cyclobutyl((1R,2S)-1-hydroxy-2-((S)-5H-imidazo[5,1-a]isoindol-5-yl)-7-azaspiro[3.5]nonan-7-yl)methanone. LCMS (ESI) m/z=378.2 [M+H]+. ¹H NMR (400 MHz, DMSO-d6) δ 8.86 (d, J=9.5 Hz, 1H), 7.85-7.61 (m, 3H), 7.60-7.33 (m, 2H), 7.21 (s, 1H), 7.08 (s, 1H), 6.96 (s, 1H), 6.00-5.84 (m, 1H), 5.79-5.65 (m, 1H), 4.21-4.05 (m, 1H), 2.89 (s, 1H), 2.73 (s, 1H), 2.23-2.01 (m, 4H), 1.97-1.56 (m, 5H), 1.54-1.36 (m, 2H).

Example 49: 1-[3-hydroxy-2-(5H-imidazo[1,5-b]isoindol-5-yl)-7-azaspiro[3.5]nonan-7-yl]propan-1-one The title compound was prepared by the procedure described in Example 33 by substituting 3-(pyridin-3-yl)propanoic acid with propionic acid.

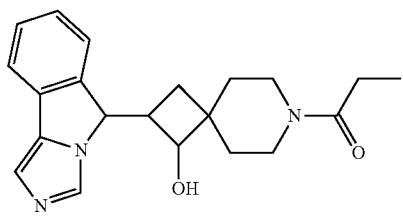 [SMILES: CCC(=O)N1CCC2(CC1)CC(C1c3ccccc3-c3cncn31)C2O]

Example 49: 1-((1R,2S)-1-hydroxy-2-((S)-5H-imidazo[5,1-a]isoindol-5-yl)-7-azaspiro[3.5]nonan-7-yl)propan-1-one. LCMS (ESI) m/z=352.2 [M+H]+. ¹H NMR (400 MHz, DMSO-d6) δ 8.79-8.70 (m, 1H), 7.87-7.59 (m, 3H), 7.55-7.31 (m, 2H), 5.89 (t, J=5.2 Hz, 1H), 5.71 (d, 1-8.5 Hz, 1H), 4.23-4.06 (m, 1H), 3.64-3.43 (m, 1H), 2.36-2.25 (m, 2H), 1.92-1.75 (m, 2H), 1.74-1.56 (m, 1H), 1.55-1.37 (m, 3H), 1.04-0.87 (m, 3H).

Example 50: 4-[3-hydroxy-2-(5H-imidazo[1,5-b]isoindol-5-yl)-7-azaspiro[3.5]nonan-7-yl]-N,N-dimethyl-4-oxo-butanamide

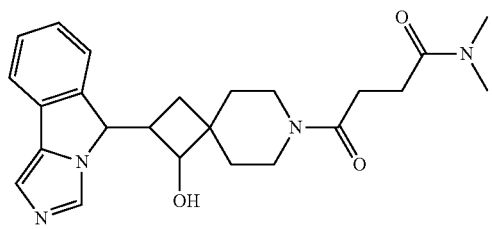 [SMILES: CN(C)C(=O)CCC(=O)N1CCC2(CC1)CC(C1c3ccccc3-c3cncn31)C2O]

The title compound was prepared by the procedure described in Example 33 by substituting 3-(pyridin-3-yl)propanoic acid with N N-dimethylsuccinamic acid.

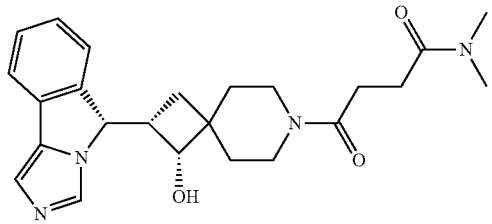

Example 50: 4-((1R,2S)-1-hydroxy-2-((S)-5H-imidazo[5,1-a]isoindol-5-yl)-7-azaspiro[3.5]nonan-7-yl)-N,N-dimethyl-4-oxobutanamide. LCMS (ESI) m/z=423.2 [M+H]+. ¹H NMR (400 MHz, DMSO-d6) δ 8.22 (s, 1H), 7.75-7.51 (m, 2H), 7.50-7.26 (m, 3H), 5.90-5.70 (m, 1H), 5.56 (d, J=8.7 Hz, 1H), 4.20-4.01 (m, 1H), 3.59-3.42 (m, 3H), 2.98 (s, 3H), 2.79 (d, J=1.8 Hz, 3H), 2.67-2.57 (m, 4H), 1.98-1.85 (m, 1H), 1.87-1.57 (m, 2H), 1.56-1.32 (m, 3H).

Example 51: 1-[3-hydroxy-2-(5H-imidazo[1,5-b]isoindol-5-yl)-7-azaspiro[3.5]nonan-7-yl]-2-tetrahydropyran-4-yl-ethanone

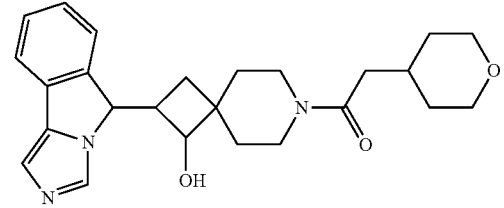 [SMILES: O=C(CC1CCOCC1)N1CCC2(CC1)CC(C1c3ccccc3-c3cncn31)C2O]

The title compound was prepared by the procedure described in Example 33 by substituting 3-(pyridin-3-yl)propanoic acid with (tetrahydro-pyran-4-yl)-acetic acid.

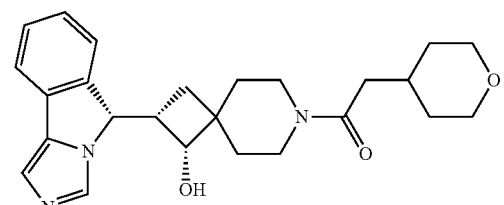

Example 51: 1-((1R,2S)-1-hydroxy-2-((S)-5H-imidazo[5,1-a]isoindol-5-yl)-7-azaspiro[3.5]nonan-7-yl)-2-(tetrahydro-2H-pyran-4-yl)ethan-1-one. LCMS (ESI) m/z=422.3 [M+H]+. ¹H NMR (400 MHz, DMSO-d6) δ 8.05 (s, 1H), 7.70-7.56 (m, 2H), 7.46-7.14 (m, 3H), 5.82-5.65 (m, 1H), 5.51 (d, J=8.7 Hz, 1H), 4.18-4.05 (m, 1H), 3.87-3.77 (m, 2H), 3.65-3.39 (m, 2H), 3.26 (d, J=12.6 Hz, 5H), 2.30-2.16 (m, 2H), 2.01-1.64 (m, 4H), 1.66-1.36 (m, 4H), 1.27-1.08 (m, 2H).

Example 52: 1-[2-[3-hydroxy-2-(5H-imidazo[1,5-b]isoindol-5-yl)-7-azaspiro[3.5]nonan-7-yl]-2-oxo-ethyl]pyrrolidin-2-one

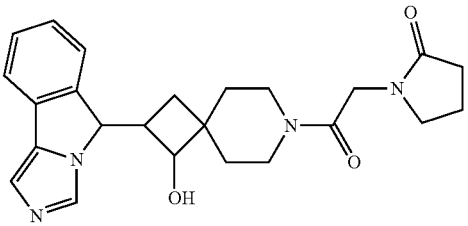 [SMILES: O=C(CN1CCCC1=O)N1CCC2(CC1)CC(C1c3ccccc3-c3cncn31)C2O]

The title compound was prepared by the procedure described in Example 33 by substituting 3-(pyridin-3-yl)propanoic acid with (2-oxopyrrolidin-1-yl)acetic acid.

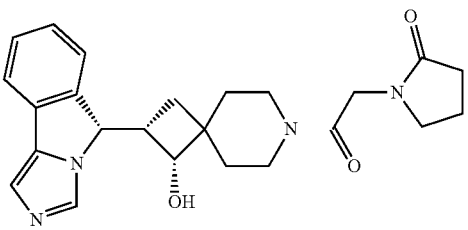

Example 52: 1-(2-((1R,2S)-1-hydroxy-2-((S)-5H-imidazo[5,1-a]isoindol-5-yl)-7-azaspiro[3.5]nonan-7-yl)-2-oxoethyl)pyrrolidin-2-one. LCMS (ESI) m/z=421.2 [M+H]+. ¹H NMR (400 MHz, DMSO-d6) δ 8.23 (s, 1H), 7.79-7.55 (m, 2H), 7.49-7.21 (m, 3H), 5.86-5.74 (m, 1H), 5.56 (d, J=8.7 Hz, 1H), 4.21-3.82 (m, 3H), 3.57-3.36 (m, 3H), 3.16-3.02 (m, 1H), 2.72-2.56 (m, 1H), 2.33-2.06 (m, 2H), 2.07-1.84 (m, 3H), 1.87-1.57 (m, 2H), 1.58-1.36 (m, 3H), 1.20-0.97 (m, 1H).

Example 53: 4-[3-hydroxy-2-(5H-imidazo[1,5-b]isoindol-5-yl)-7-azaspiro[3.5]nonane-7-carbonyl]-1-methyl-pyrrolidin-2-one

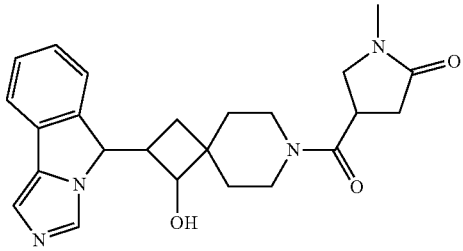 [SMILES: CN1CC(C(=O)N2CCC3(CC2)CC(C2c4ccccc4-c4cncn42)C3O)CC1=O]

The title compound was prepared by the procedure described in Example 33 by substituting 3-(pyridin-3-yl)propanoic acid with 1-methyl-5-oxo-3-pyrrolidinecarboxylic acid.

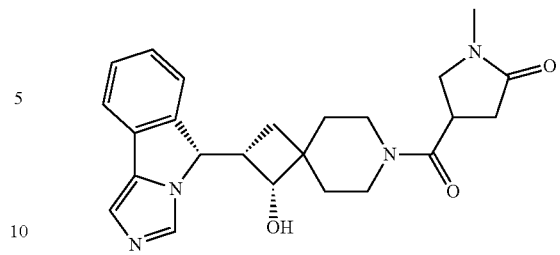

Example 53: 4-((1R,2S)-1-hydroxy-2-((S)-5H-imidazo[5,1-a]isoindol-5-yl)-7-azaspiro[3.5]nonane-7-carbonyl)-1-methylpyrrolidin-2-one. LCMS (ESI) m/z=421.2 [M+H]+. ¹H NMR (400 MHz, DMSO-d6) δ 8.84 (d, J=11.6 Hz, 1H), 7.82-7.66 (m, 3H), 7.55-7.40 (m, 2H), 7.20 (s, 1H), 7.07 (s, 1H), 6.94 (s, 1H), 5.99-5.84 (m, 1H), 5.83-5.62 (m, 1H), 4.29-4.11 (m, 1H), 3.58-3.47 (m, 2H), 2.80-2.61 (m, 4H), 2.46-2.37 (m, 2H), 2.04-1.64 (m, 3H), 1.55-1.36 (m, 3H).

Example 54: 1-[3-hydroxy-2-(5H-imidazo[1,5-b]isoindol-5-yl)-7-azaspiro[3.5]nonan-7-yl]-2-(5-methylisoxazol-3-yl)ethanone

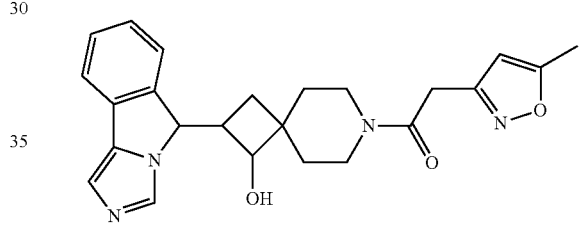

The title compound was prepared by the procedure described in Example 33 by substituting 3-(pyridin-3-yl)propanoic acid with 2-(5-methyl-1,2-oxazol-3-yl)acetic acid.

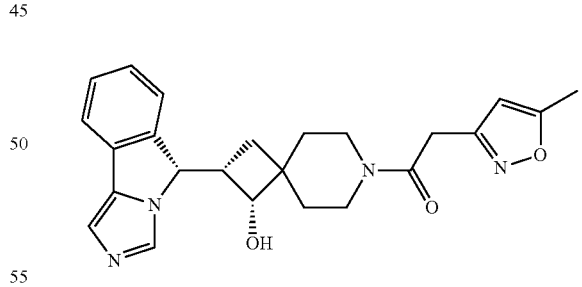

Example 54: 1-((1R,2S)-1-hydroxy-2-((S)-5H-imidazo[5,1-a]isoindol-5-yl)-7-azaspiro[3.5]nonan-7-yl)-2-(5-methyl-isoxazol-3-yl)ethan-1-one. LCMS (ESI) m/z=419.2 [M+H]+. ¹H NMR (400 MHz, DMSO-d6) δ 7.86 (d, J=3.0 Hz, 1H), 7.71-7.55 (m, 2H), 7.45-7.20 (m, 2H), 7.13 (s, 1H), 6.16-6.02 (m, 1H), 5.82-5.63 (m, 1H), 5.45 (d, J=8.8 Hz, 1H), 4.17-3.99 (m, 1H), 3.78-3.69 (m, 2H), 3.59-3.44 (m, 2H), 3.23-3.02 (m, 1H), 2.43-2.26 (m, 3H), 1.99-1.55 (m, 3H), 1.57-1.32 (m, 3H).

Example 55: 1-[3-hydroxy-2-(5H-imidazo[1,5-b]isoindol-5-yl)-7-azaspiro[3.5]nonan-7-yl]-3-(1-methylpyrazol-4-yl)propan-1-one

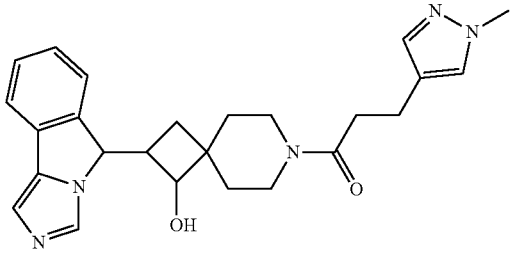 [SMILES: Cn1cc(CCC(=O)N2CCC3(CC2)CC(C2c4ccccc4-c4cncn42)C3O)cn1]

The title compound was prepared by the procedure described in Example 33 by substituting 3-(pyridin-3-yl)propanoic acid with 3-(1-methyl-1h-pyrazol-4-yl)propanoic acid.

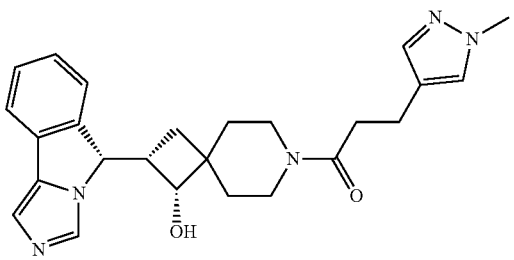 [SMILES: Cn1cc(CCC(=O)N2CCC3(CC2)C[C@@H]([C@H]2c4ccccc4-c4cncn42)[C@H]3O)cn1]

Example 55: 1-((1R,2S)-1-hydroxy-2-((S)-5H-imidazo[5,1-a]isoindol-5-yl)-7-azaspiro[3.5]nonan-7-yl)-3-(1-methyl-1H-pyrazol-4-yl)propan-1-one. LCMS (ESI) m/z=432.2 [M+H]+. ¹H NMR (400 MHz, DMSO-d6) δ 8.15 (s, 1H), 7.73-7.57 (m, 2H), 7.54-7.35 (m, 2H), 7.38-7.26 (m, 2H), 7.23 (d, J=5.9 Hz, 1H), 5.86-5.66 (m, 1H), 5.53 (d, J=8.6 Hz, 1H), 4.17-4.02 (m, 1H), 3.74 (d, J=5.1 Hz, 3H), 3.54-3.41 (m, 1H), 3.26-3.14 (m, 3H), 2.63-2.56 (m, 3H), 1.97-1.81 (m, 1H), 1.85-1.71 (m, 1H), 1.71-1.53 (m, 1H), 1.50-1.36 (m, 3H), 1.22-1.11 (m, 1H).

Example 56: 1-[3-hydroxy-2-(5H-imidazo[1,5-b]isoindol-5-yl)-7-azaspiro[3.5]nonan-7-yl]ethanone

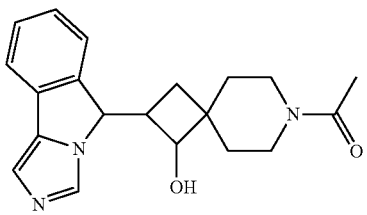 [SMILES: CC(=O)N1CCC2(CC1)CC(C1c3ccccc3-c3cncn31)C2O]

The title compound was prepared by the procedure described in Example 33 by substituting 3-(pyridin-3-yl)propanoic acid with acetic acid.

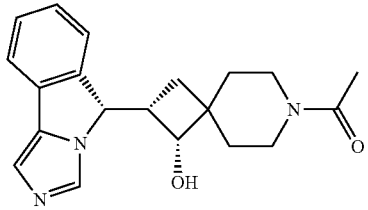 [SMILES: CC(=O)N1CCC2(CC1)C[C@@H]([C@H]1c3ccccc3-c3cncn31)[C@H]2O]

Example 56: 1-((1R,2S)-1-hydroxy-2-((S)-5H-imidazo[5,1-a]isoindol-5-yl)-7-azaspiro[3.5]nonan-7-yl)ethan-1-one. LCMS (ESI) m/z=338.2 [M+H]+. ¹H NMR (400 MHz, DMSO-d6) δ 8.43-8.29 (m, 1H), 7.76-7.64 (m, 2H), 7.52-7.26 (m, 3H), 5.93-5.72 (m, 1H), 5.69-5.52 (m, 1H), 4.26-4.01 (m, 1H), 3.62-3.33 (m, 3H), 2.75-2.59 (m, 1H), 1.97 (d, J=3.6 Hz, 3H), 1.83-1.57 (m, 2H), 1.57-1.30 (m, 3H), 1.18 (t, J=7.3 Hz, 1H).

Example 57: 2,2-difluoroethyl (2S,3R)-3-hydroxy-2-[(5S)-5H-imidazo[1,5-b]isoindol-5-yl]-7-azaspiro[3.5]nonane-7-carboxylate

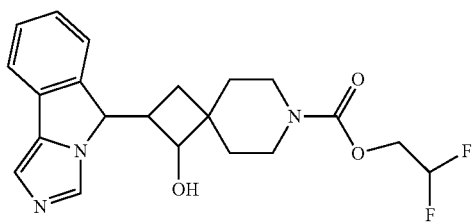 [SMILES: O=C(OCC(F)F)N1CCC2(CC1)CC(C1c3ccccc3-c3cncn31)C2O]

A solution of tert-butyl (5R,6S)-5-hydroxy-6-((S)-5H-imidazo[5,1-a]isoindol-5-yl)-2-azaspiro[3.3]heptane-2-carboxylate (100 mg, 0.28 mmol) in 2 mL of DCM was charged with 500 uL of TFA and stirred at room temperature for one hour. The mixture was then concentrated in vacuo and azeotroped twice with MeOH and twice with DCM. The residue was then dissolved in 5 mL of MeOH and charged with 2 g of macroprorous polymer supported Ammonium Carbonate resin and sonicated. The resin was then filtered off by vacuum filtration and the solution was concentrated in vacuo. The residue was then dissolved in 2 mL of dimethylacetamide. In a separate vial, 2,2-difluoroethan-1-ol (25 mg, 0.3 mmol), triphosgene (36 mg, 0.12 mmol), and pyridine (35 mg, 0.44 mmol) were dissolved in 1 ml of DCM and stirred at 0° C. for 30 minutes. This solution was then added to the formerly mentioned dimethylacetamide solution and charged with TEA (25 mg, 0.24 mmol). The mixture was then stirred at room temperature for one hour. The mixture was then purified by reverse phase HPLC (0.1% NH4OH/ACN) to afford the title compound (35 mg, 0.08 mmol, 35% yield).

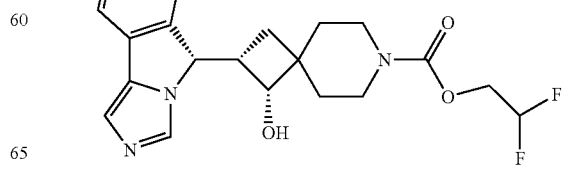

Example 57: 2,2-difluoroethyl (1R,2S)-1-hydroxy-2-((S)-5H-imidazo[5,1-a]isoindol-5-yl)-7-azaspiro[3.5]nonane-7-carboxylate. LCMS (ESI) m/z=404.2 [M+H]⁺. ¹H NMR (400 MHz, DMSO-d6) δ 7.85 (s, 1H), 7.67-7.51 (m, 2H), 7.42-7.21 (m, 2H), 7.13 (s, 1H), 6.23 (tt, J=54.6, 3.4 Hz, 1H), 5.74 (d, J=5.4 Hz, 1H), 5.45 (d, J=8.8 Hz, 1H), 4.27 (td, J=15.3, 3.4 Hz, 2H), 4.11 (td, J=6.1, 3.0 Hz, 1H), 2.56 (td, J=8.8, 6.8 Hz, 1H), 1.92 (t, J=10.4 Hz, 1H), 1.79 (ddd, J=11.3, 8.4, 3.1 Hz, 1H), 1.67 (ddd, J=12.1, 7.9, 3.7 Hz, 1H), 1.64-1.23 (m, 4H).

Example 58: N-(2,2-difluoroethyl)-3-hydroxy-2-(5H-imidazo[1,5-b]isoindol-5-yl)-7-azaspiro[3.5]nonane-7-carboxamide

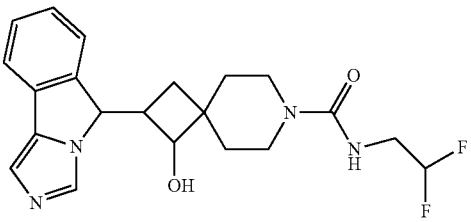 [SMILES: O=C(NCC(F)F)N1CCC2(CC1)CC(C1c3ccccc3-c3cncn31)C2O]

The title compound was prepared by the procedure described in Example 57 by substituting 2,2-difluoroethan-1-ol with 2,2-difluoroethan-1-amine.

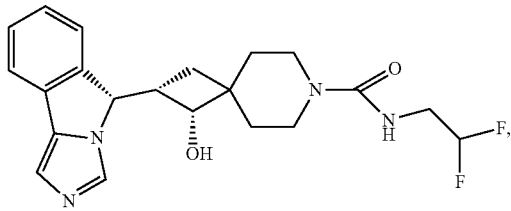 [SMILES: O=C(NCC(F)F)N1CCC2(CC1)C[C@@H]([C@H]1c3ccccc3-c3cncn31)[C@H]2O]

Example 58: (1R,2S)—N-(2,2-difluoroethyl)-1-hydroxy-2-((S)-5H-imidazo[5,1-a]isoindol-5-yl)-7-azaspiro[3.5]nonane-7-carboxamide. LCMS (ESI) m/z=403.2 [M+H]⁺. ¹H NMR (400 MHz, DMSO-d6)) δ 7.85 (s, 1H), 7.67-7.51 (m, 2H), 7.42-7.21 (m, 2H), 7.13 (s, 1H), 6.84 (t, J=5.7 Hz, 1H), 6.21-5.56 (m, 2H), 5.45 (d, J=8.8 Hz, 1H), 4.10 (td, J=6.3, 3.0 Hz, 1H), 3.53-3.25 (m, 2H), 3.32-2.98 (m, 2H), 2.89 (s, 1H), 2.73 (d, J=0.6 Hz, 1H), 2.71-2.33 (m, 1H), 1.90 (t, J=10.4 Hz, 1H), 1.78 (ddd, J=11.3, 8.4, 3.0 Hz, 1H), 1.63 (ddd, J=11.7, 7.9, 3.5 Hz, 1H), 1.59-1.25 (m, 3H).

Example 59: 8-((1H-imidazol-4-yl)sulfonyl)-2-(5H-imidazo[5,1-a]isoindol-5-yl)-8-azaspiro[4.5]decan-1-ol

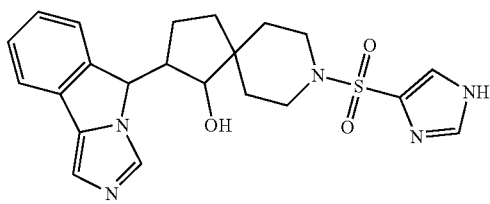 [SMILES: O=S(=O)(c1c[nH]cn1)N1CCC2(CCC(C3c4ccccc4-c4cncn43)C2O)CC1]

The title compound was prepared by the procedure described in Example 7, by substituting MsCl with 1H-imidazole-4-sulfonyl chloride.

The absolute configuration of 59 was assigned arbitrarily.

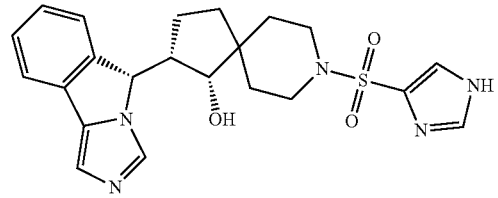 [SMILES: O=S(=O)(c1c[nH]cn1)N1CCC2(CC[C@@H]([C@H]3c4ccccc4-c4cncn43)[C@H]2O)CC1]

Example 59: (1R,2S)-8-((1H-imidazol-4-yl)sulfonyl)-2-(S)-5H-imidazo[5,1-a]isoindol-5-yl)-8-azaspiro[4.5]decan-1-ol. LCMS (ESI) m/z=440.2 [M+H]⁺. ¹H NMR (300 MHz, DMSO-d6) δ 12.85 (s, 1H), 7.90-7.82 (m, 2H), 7.75 (q, J=1.3 Hz, 1H), 7.60 (dd, J=16.3, 7.6 Hz, 2H), 7.36 (t, J=7.5 Hz, 1H), 7.25 (td, J=7.6, 1.2 Hz, 1H), 7.10 (s, 1H), 5.36 (d, J=6.3 Hz, 2H), 3.81 (t, J=5.2 Hz, 1H), 3.30 (s, 1H), 3.21-3.08 (m, 1H), 2.85-2.60 (m, 2H), 2.35-2.19 (m, 1H), 1.80-1.49 (m, 4H), 1.49-1.19 (m, 4H).

Example 60: 2,2-difluoroethyl 1-hydroxy-2-(5H-imidazo[5,1-a]isoindol-5-yl)-8-azaspiro[4.5]decane-8-carboxylate

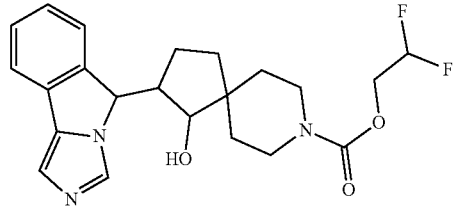 [SMILES: O=C(OCC(F)F)N1CCC2(CCC(C3c4ccccc4-c4cncn43)C2O)CC1]

A solution of (3S,4R)-3-[(5S)-5H-imidazo[1,5-b]isoindol-5-yl]-8-azaspiro[4.5]decan-4-ol (50.0 mg, 0.1400 mmol), 2,2-difluoroethanol (17.8 mg, 0.22 mmol), 1,1'-carbonyldiimidazole (28.14 mg, 0.17 mmol) and TEA (43.9 mg, 0.43 mmol) in THF (15 mL) was stirred at 75° C. for 16 h. The reaction was quenched with water (100 mL). The resulting solution was extracted with EtOAc (3×100 mL) and the organic layers were combined. The crude product was purified by Prep-HPLC.

The absolute configuration of 60 was assigned arbitrarily.

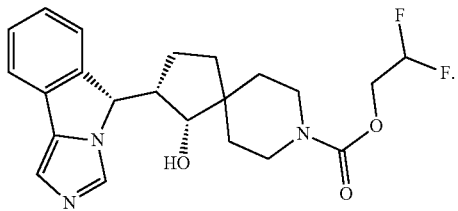 [SMILES: O=C(OCC(F)F)N1CCC2(CC[C@@H]([C@H]3c4ccccc4-c4cncn43)[C@H]2O)CC1]

Example 60: 2,2-difluoroethyl (3S,4R)-4-hydroxy-3-[(5S)-5H-imidazo[1,5-b]isoindol-5-yl]-8-azaspiro[4.5]decane-8-carboxylate (15.5 mg, 25.6%) as a white solid. LCMS (ESI) m/z=418.2 [M+H]⁺. ¹H NMR (400 MHz, MeOH-d₆) δ 8.01 (s, 1H), 7.68-7.57 (m, 2H), 7.36 (dtd, J=35.1, 7.2, 1.1 Hz, 1H), 7.14 (s, 1H), 6.59-5.75 (m, 1H), 5.51 (d, J=6.5 Hz, 1H), 4.29 (td, J=14.3, 3.7 Hz, 2H), 4.05 (d, J=4.9 Hz, 1H), 3.82 (d, J=13.7 Hz, 1H), 3.71 (d, J=13.5 Hz, 1H), 3.23 (m, 2H), 2.53 (s, 1H), 1.84-1.61 (m, 6H), 1.38 (dt, J=10.1, 4.8 Hz, 2H).

Example 61: 1-[3-hydroxy-2-(5H-imidazo[1,5-b]isoindol-5-yl)-7-azaspiro[3.5]nonan-7-carbonyl]cyclopropanecarbonitrile

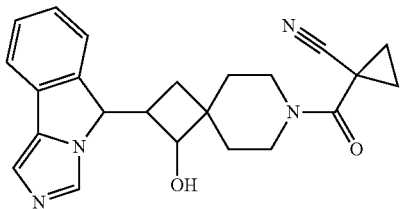 [SMILES: N#CC1(C(=O)N2CCC3(CC2)CC(C2c4ccccc4-c4cncn42)C3O)CC1]

The title compound was prepared by the procedure described in Example 33 by substituting 3-(pyridin-3-yl)propanoic acid with 1-cyano-1-cyclopropanecarboxylic acid.

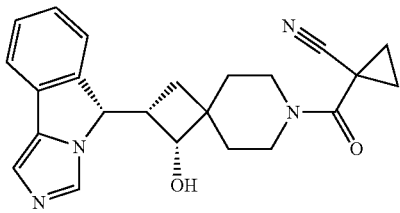 [SMILES: N#CC1(C(=O)N2CCC3(CC2)C[C@@H]([C@H]2c4ccccc4-c4cncn42)[C@H]3O)CC1]

Example 61: 1-((1R,2S)-1-hydroxy-2-((S)-5H-imidazo[5,1-a]isoindol-5-yl)-7-azaspiro[3.5]nonane-7-carbonyl)cyclopropane-1-carbonitrile. LCMS (ESI) m/z=389.2 [M+H]⁺. ¹H NMR (400 MHz, DMSO-d6) δ 8.02 (s, 1H), 7.71-7.52 (m, 2H), 7.50-7.35 (m, 1H), 7.34-7.25 (m, 1H), 7.22 (s, 1H), 5.81 (d, J=5.4 Hz, 1H), 5.51 (d. J=8.7 Hz, 1H), 4.27-3.98 (m, 1H), 3.15-3.01 (m, 2H), 2.68-2.58 (m, 1H), 1.99-1.78 (m, 2H), 1.64-1.50 (m, 6H), 1.50-1.40 (m, 2H), 1.18 (t, J=7.3 Hz, 3H).

Example 62: 1-[3-hydroxy-2-(5H-imidazo[1,5-b]isoindol-5-yl)-7-azaspiro[3.5]nonan-7-yl]-2-(1H-tetrazol-5-yl)ethanone

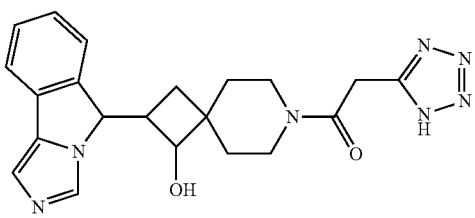 [SMILES: O=C(Cc1nnn[nH]1)N1CCC2(CC1)CC(C1c3ccccc3-c3cncn31)C2O]

The title compound was prepared by the procedure described in Example 33 by substituting 3-(pyridin-3-yl)propanoic acid with 1H-tetrazole-5-acetic acid.

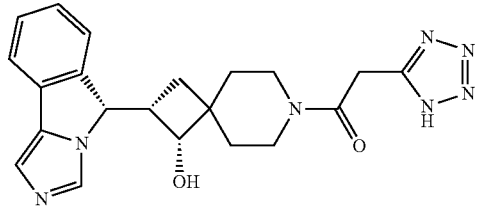

Example 62: 1-((1R,2S)-1-hydroxy-2-((S)-5H-imidazo[5,1-a]isoindol-5-yl)-7-azaspiro[3.5]nonan-7-yl)-2-(1H-tetrazol-5-yl)ethan-1-one. LCMS (ESI) m/z=406.2 [M+H]⁺. ¹H NMR (400 MHz, DMSO-d6) δ 7.88 (s, 1H), 7.73-7.51 (m, 2H), 7.44-7.31 (m, 1H), 7.31-7.18 (m, 1H), 7.14 (s, 1H), 5.75 (s, 1H), 5.45 (d, J=8.8 Hz, 1H), 4.22-3.91 (m, 3H), 3.10-2.94 (m, 1H), 2.64-2.54 (m, 1H), 2.00-1.85 (m, 1H), 1.86-1.57 (m, 2H), 1.57-1.34 (m, 3H), 1.16 (t, J=7.3 Hz, 2H).

Example 63: 1-[3-hydroxy-2-(5H-imidazo[1,5-b]isoindol-5-yl)-7-azaspiro[3.5]nonan-7-yl]-2-(3-methylisoxazol-5-yl)ethanone

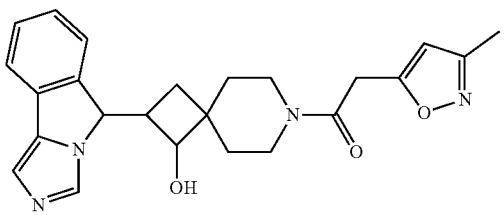 [SMILES: Cc1cc(CC(=O)N2CCC3(CC2)CC(C2c4ccccc4-c4cncn42)C3O)on1]

The title compound was prepared by the procedure described in Example 33 by substituting 3-(pyridin-3-yl)propanoic acid with 3-methyl-5-isoxazoleacetic acid.

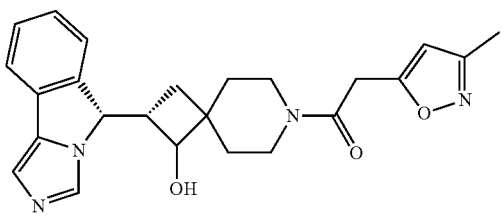

Example 63: 1-((1R,2S)-1-hydroxy-2-((S)-5H-imidazo[5,1-a]isoindol-5-yl)-7-azaspiro[3.5]nonan-7-yl)-2-(3-methyl-isoxazol-5-yl)ethan-1-one. LCMS (ESI) m/z=419.2 [M+H]⁺. ¹H NMR (400 MHz, DMSO-d6) δ 7.86 (d, J=4.4 Hz, 1H), 7.71-7.50 (m, 2H), 7.42-7.32 (m, 1H), 7.32-7.21 (m, 1H), 7.13 (s, 1H), 6.18 (d, J=6.2 Hz, 1H), 5.82-5.69 (m, 1H), 5.46 (d, 3=8.8 Hz, 1H), 4.11 (d, J=9.2 Hz, 1H), 3.92 (d, J=3.5 Hz, 2H), 3.60-3.45 (m, 2H), 2.19 (d, J=4.6 Hz, 3H), 1.99-1.85 (m, 1H), 1.85-1.58 (m, 2H), 1.56-1.28 (m, 3H).

Example 64: 3-[3-hydroxy-2-(5H-imidazo[1,5-b]isoindol-5-yl)-7-azaspiro[3.5]nonane-7-carbonyl]piperidine-1-carboxamide

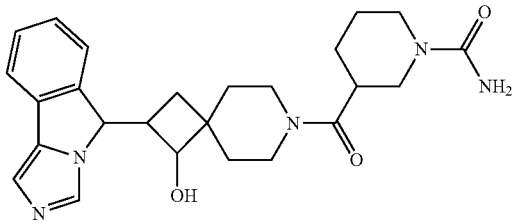

The title compound was prepared by the procedure described in Example 33 by substituting 3-(pyridin-3-yl)propanoic acid with 1-(aminocarbonyl)piperidine-3-carboxylic acid.

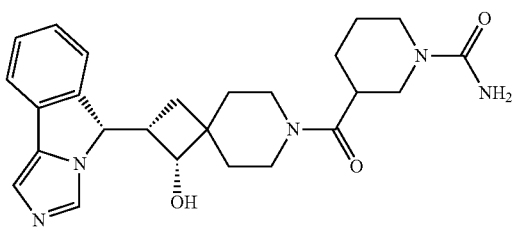 [SMILES: NC(=O)N1CCCC(C(=O)N2CCC3(CC2)C[C@@H]([C@H]2c4ccccc4-c4cncn42)[C@H]3O)C1]

Example 64: 3-((1R,2S)-11-hydroxy-2-((S)-5H-imidazo[5,1-a]isoindol-5-yl)-7-azaspiro[3.5]nonane-7-carbonyl)piperidine-1-carboxamide. LCMS (ESI) m/z=450.3 [M+H]+. 
¹H NMR (400 MHz, DMSO-d6) δ 7.99-7.79 (m, 1H), 7.70-7.48 (m, 2H), 7.44-7.17 (m, 2H), 7.13 (s, 1H), 5.86 (d, J=2.5 Hz, 2H), 5.80-5.64 (m, 1H), 5.46 (d, J=8.8 Hz, 1H), 4.19-4.04 (m, 1H), 3.91 (d, J=13.4 Hz, 2H), 3.59-3.44 (m, 2H), 2.85-2.65 (m, 3H), 2.00-1.74 (m, 2H), 1.74-1.57 (m, 1H), 1.59-1.26 (m, 7H).

Example 65: (1,1-dioxothiolan-3-yl)-[3-hydroxy-2-(5H-imidazo[1,5-b]isoindol-5-yl)-7-azaspiro[3.5]nonan-7-yl]methanone

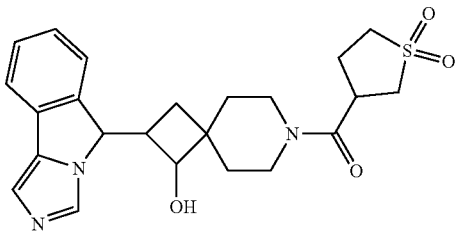

The title compound was prepared by the procedure described in Example 33 by substituting 3-(pyridin-3-yl)propanoic acid with tetrahydrothiophene-3-carboxylic acid 1,1-dioxide.

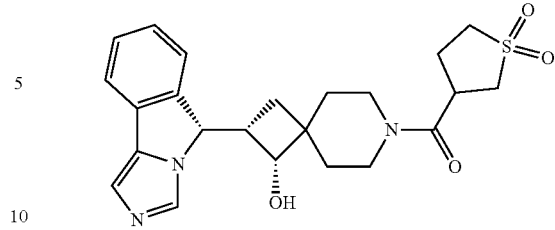

Example 65: (1,1-dioxidotetrahydrothiophen-3-yl)((1R,2S)-1-hydroxy-2-((S)-5H-imidazo[5,1-a]isoindol-5-yl)-7-azaspiro[3.5]nonan-7-yl)methanone. LCMS (ESI) m/z=443.2 [M+H]⁺.

Example 66: 4-[3-hydroxy-2-(5H-imidazo[1,5-b]isoindol-5-yl)-7-azaspiro[3.5]nonane-7-carbonyl]piperidine-1-carboxamide

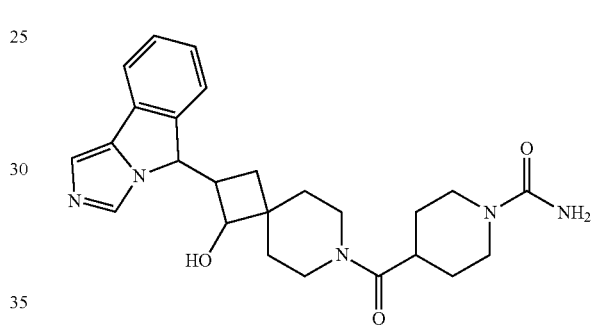

The title compound was prepared by the procedure described in Example 33 by substituting 3-(pyridin-3-yl)propanoic acid with 1-carbamoylpiperidine-4-carboxylic acid 1,1-dioxide.

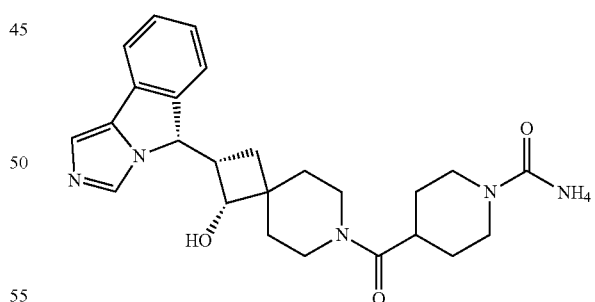

Example 66: 4-((1R,2S)-1-hydroxy-2-((S)-5H-imidazo[5,1-a]isoindol-5-yl)-7-azaspiro[3.5]nonane-7-carbonyl)piperidine-1-carboxamide. LCMS (ESI) m/z=450.3 [M+H]⁺.
¹H NMR (400 MHz, DMSO-d6) δ 7.86 (d, J=2.8 Hz, 1H), 7.71-7.49 (m, 2H), 7.42-7.33 (m, 1H), 7.32-7.18 (m, 1H), 7.13 (s, 1H), 5.86 (d, J=3.1 Hz, 2H), 5.80-5.67 (m, 1H), 5.46 (d, J=8.8 Hz, 1H), 4.19-4.04 (m, 1H), 3.99-3.84 (m, 2H), 3.57-3.41 (m, 2H), 2.83-2.67 (m, 3H), 1.99-1.76 (m, 2H), 1.58-1.32 (m, 7H).

Example 67: [3-hydroxy-2-(5H-imidazo[1,5-b]isoindol-5-yl)-7-azaspiro[3.5]nonan-7-yl]-(5,6,7,8-tetrahydro-[1,2,4]triazolo[4,3-a]pyridin-6-yl)methanone

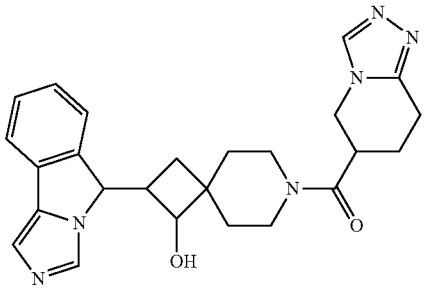

The title compound was prepared by the procedure described in Example 33 by substituting 3-(pyridin-3-yl)propanoic acid with 5,6,7,8-tetrahydro[1,2,4]triazolo[4,3-a]pyridine-6-carboxylic acid.

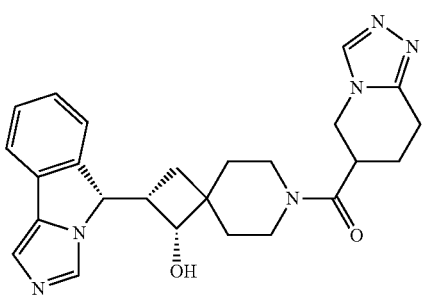 [SMILES: O=C(C1CCc2nncn2C1)N1CCC2(CC1)C[C@@H]([C@H]1c3ccccc3-c3cncn31)[C@H]2O]

Example 67: ((1R,2S)-1-hydroxy-2-((S)-5H-imidazo[5,1-a]isoindol-5-yl)-7-azaspiro[3.5]nonan-7-yl)(5,6,7,8-tetrahydro-[1,2,4]triazolo[4,3-a]pyridin-6-yl)methanone. LCMS (ESI) m/z=445.2 [M+H]$^+$. $^1$H NMR (400 MHz, DMSO-d6) δ 8.39-8.25 (m, 1H), 7.92-7.79 (m, 1H), 7.71-7.51 (m, 2H), 7.44-7.32 (m, 1H), 7.32-7.17 (m, 1H), 7.13 (s, 1H), 5.87-5.66 (m, 1H), 5.46 (d, J=8.7 Hz, 1H), 4.21-4.12 (m, 2H), 4.06-3.92 (m, 1H), 3.62-3.37 (m, 5H), 2.96-2.78 (m, 1H), 2.63-2.53 (m, 1H), 2.12-1.70 (m, 4H), 1.66-1.41 (m, 3H).

Example 68: 1-[4-[3-hydroxy-2-(5H-imidazo[1,5-b]isoindol-5-yl)-7-azaspiro[3.5]nonane-7-carbonyl]-1-piperidyl]ethanone

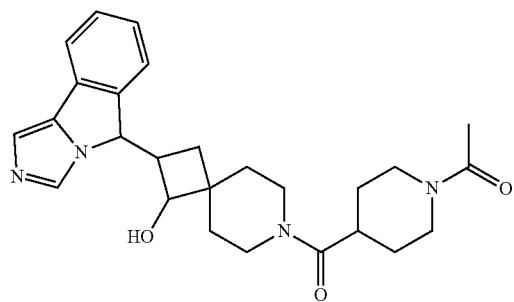 [SMILES: CC(=O)N1CCC(C(=O)N2CCC3(CC2)CC(C2c4ccccc4-c4cncn42)C3O)CC1]

The title compound was prepared by the procedure described in Example 33 by substituting 3-(pyridin-3-yl)propanoic acid with 1 acetylpiperidine-4-carboxylic acid.

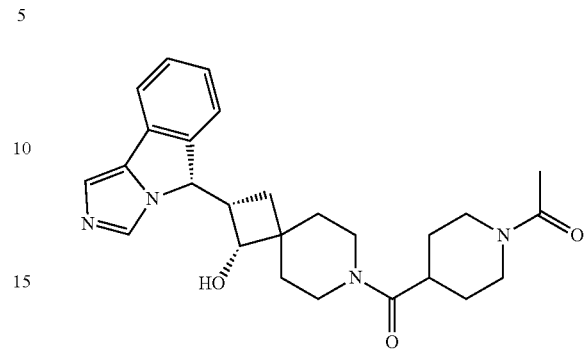

Example 68: 1-(4-((1R,2S)-1-hydroxy-2-((S)-5H-imidazo[5,1-a]isoindol-5-yl)-7-azaspiro[3.5]nonane-7-carbonyl)piperidin-1-yl)ethan-1-one. LCMS (ESI) m/z=449.3[M+H]$^+$ Example 69: 2,2-difluoro-1-[3-hydroxy-2-(5H-imidazo[1,5-b]isoindol-5-yl)-7-azaspiro[3.5]nonan-7-yl]ethanone

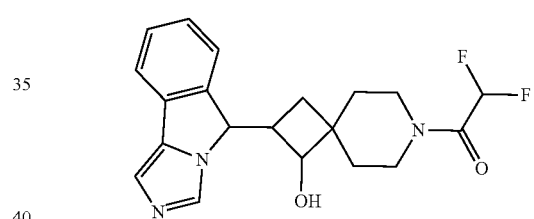

The title compound was prepared by the procedure described in Example 33 by substituting 3-(pyridin-3-yl)propanoic acid with difluoroacetic acid.

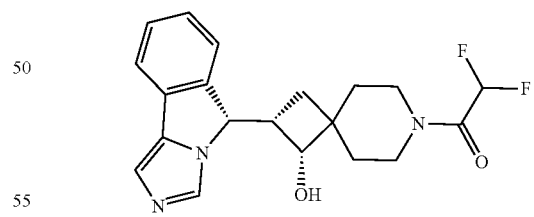

Example 69: 2,2-difluoro-1-((1R,2S)-1-hydroxy-2-((S)-5H-imidazo[5,1-a]isoindol-5-yl)-7-azaspiro[3.5]nona-7-yl)ethan-1-one. LCMS (ESI) m/z=374.2 [M+H]$^+$. $^1$H NMR (400 MHz, DMSO-d$_6$) δ 8.24 (s, 1H), 7.66 (d, J=7.6 Hz, 2H), 7.48-7.21 (m, 3H), 6.92-6.50 (m, 1H), 5.86 (t, J=4.7 Hz, 1H), 5.65-5.51 (m, 1H), 4.27-3.87 (m, 1H), 3.16-3.02 (m, 4H), 2.74-2.59 (m, 1H), 1.87-1.61 (m, 2H), 1.61-1.47 (m, 3H), 1.18 (t, J=7.3 Hz, 5H).

Example 70: 3'(5H-imidazo[5,1-a]isoindol-5-yl)-3-(methylsulfonyl)-3-azaspiro[bicyclo[3.2.1]octane-8,1'-cyclobutan]-2'-ol

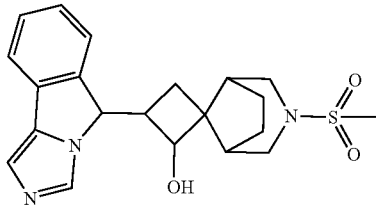 [SMILES: CS(=O)(=O)N1CC2CCC(C1)C21CC(C2c3ccccc3-c3cncn32)C1O]

Step 1:

(2'R,3'R)-3'-((R)-5H-imidazo[5,1-a]isoindol-5-yl)-3-azaspiro[bicyclo(3.2.1 octane-8,1'-cyclobutan]-2'-ol

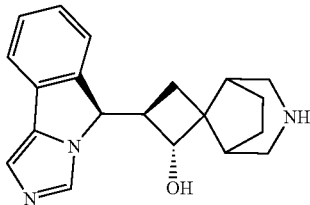

Hydrogen chloride (4 N solution in 1,4-dioxane, 1.06 mL, 4.22 mmol) was added to a stirred MeOH (4.2 mL) solution of tert-butyl (2'R,3'R)-2'-hydroxy-3'-((R)-5H-imidazo[5,1-a]isoindol-5-yl)-3-azaspiro[bicyclo[3.2.1]octane-8,1'-cyclobutane]-3-carboxylate (178 mg, 0.422 mmol) at room temperature. After 4 h, the reaction mixture was concentrated. The residue thereby obtained was used directly in the following step without purification. LCMS (ESI) m/z=322.2 [M+H]$^+$.

Step 2:
(2'R,3'R)-3'-((R)-5H-imidazo[5,1-a]isoindol-5-yl)-3-(methylsulfonyl)-3-azaspiro[bicyclo[3.2.1]octane-8,1'-cyclobutan]-2'-ol

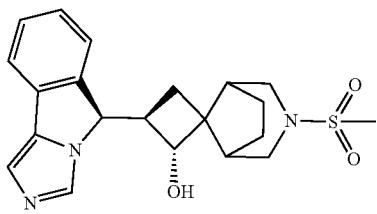

Methanesulfonyl chloride (0.049 mL, 0.63 mmol) was added dropwise to a stirred THF (4.2 mL) solution of (2'R,3'R)-3'-((R)-5H-imidazo[5,1-a]isoindol-5-yl)-3-azaspiro[bicyclo[3.2.1]octane-8,1'-cyclobutan]-2'-ol (136 mg, 0.42 mmol) and triethylamine (0.30 mL, 2.1 mmol) at room temperature. After 30 min, the reaction was quenched by addition of saturated aqueous ammonium chloride solution (25 mL). The biphasic mixture was extracted with DCM (3×25 mL). The organic extracts were combined, dried over sodium sulfate, and concentrated. The residue was purified by silica gel column eluting with DCM/MeOH (90:10) to afford 14 mg (8%) of (2'R,3'R)-3'-((R)-5H-imidazo[5,1-a]isoindol-5-yl)-3-(methylsulfonyl)-3-azaspiro[bicyclo[3.2.1] octane-8,1'-cyclobutan]-2'-ol as a colorless solid. LCMS (ESI) m/z=400.2 [M+H]$^+$.

The absolute configuration of 70 was assigned arbitrarily. The relative configuration of C15 was assigned arbitrarily.

Example 70: (2'R,3'R)-3'-((R)-5H-imidazo[5,1-a]isoindol-5-yl)-3-(methylsulfonyl)-3-azaspiro[bicyclo[3.2.1]octane-8,1'-cyclobutan]-2'-ol. LCMS (ESI) m/z=400.2 [M+H]$^+$. $^1$H NMR (400 MHz, DMSO-d$_6$) δ 7.86 (s, 1H), 7.61 (dd, J=15.8, 7.5 Hz, 2H), 7.42-7.33 (m, 1H), 7.27 (td, J=7.5, 1.2 Hz, 1H), 7.13 (s, 1H), 5.83 (d, J=6.8 Hz, 1H), 5.49 (d, J=9.0 Hz, 1H), 4.64 (td, J=6.8, 3.2 Hz, 1H), 3.19-2.99 (m, 3H), 2.85 (s, 3H), 2.51-2.38 (m, 1H), 2.24 (t, J=4.3 Hz, 1H), 2.03-1.93 (m, 2H), 1.70 (ddt, J=11.8, 9.0, 3.9 Hz, 2H), 1.58-1.37 (m, 3H), 1.22 (t, J=7.1 Hz, 1H).

IDO1 and TDO2 Cell Assay

The NFK GreenScreen™ (NTRC, Netherlands) uses a specific chemical probe that binds to N-Formylkynurenine (NFK), a product of tryptophan catabolism facilitated by IDO or TDO and causes fluorescence at 510 nm when excited at 410 nm. The assay is used to assess compound inhibition of TDO and IDO leading to decreased levels of NFK in SW48 cells (high TDO expressing cells) and to determine whether compounds are selective against A172+IFNg cells (high IDO expressing cells) or are dual inhibitors in cells. The assay is multiplexed with Cell Titer-Glo® (Promega) to determine if compounds are cytotoxic. Briefly, SW48 or A172 cells are harvested in growth media, RPMI 1640 with 10% FBS, 2 mM L-glutamine, and 1× pen/strep. Cells are re-suspended in assay media, tryptophan-free RPMI 1640 supplemented with 2% dialyzed FBS, 2 mM L-glutamine, and 1× pen/strep. Cells are counted on a Vi-Cell (Beckman Coulter). SW48 cells are diluted to 1×10^6 cells/ml in assay media. A172 cells are diluted to 0.24×10^6 cells/ml in assay media. 25 ul of cells are dispensed with a Multi-Flo (Bio-Tek) dispenser to a 384 well greiner μclear plate (Greiner, 781091) with 14 compounds in duplicate. Compounds are dispensed into plates with an Echo® (Labcyte) starting at the highest concentration of 25 uM and are diluted approximately 3× in a 10 point titration. 5 ul of assay media containing 1.2 mM tryptophan are added to the SW48 cells for a final concentration of 200 uM tryptophan in each well. 5 ul of assay media containing 600 uM tryptophan and 600 ng/ml IFNγ are added to the A172 cells for a final concentration of 100 uM tryptophan and 100 ng/ml IFNγ in each well. The final DMSO concentration is 0.5%. Cell plates are placed at room temperature in a closed TC hood with the blower off to allow cells to settle for approximately 30 min. Plates are then moved to an incubator set at 37° C., 5% CO$_2$ for 24 hours. After the 24 hour compound incubation, 8 ul of NFK green reagent is added to each well with a Multidrop™ Combi dispenser (Thermo Scientific). Plates are sealed and incubated at 37° C., 5% CO$_2$ for 5 hours, then read on a PHERAstar® (BMG labtech). Data are analyzed by normalizing to DMSO and high inhibitor controls. After the plates have been read for NFK green, 25 ul of Cell Titer-Glo® (Promega) are added to each well, incubated for 15 minutes at room temperature, and read on the Envision (Perkin Elmer). Cell Titer-Glo data are analyzed by normalizing to the DMSO controls. Four-parameter curve fitting is used and EC50 data are reported.

TABLE 1

| Ex. # | IDO cell Fluor EC50 [μM] | TDO2 Cell Fluor EC50 [μM] |
|---|---|---|
| 1a | 4.3 | 6.3 |
| 1b | 0.0279 | 0.3 |
| 2a | 6.6 | 15.0 |
| 2b | 0.41 | 0.24 |
| 2c | 0.0515 | 0.107 |
| 2d | 1.6 | 3.7 |
| 3a | 25.0 | 25.0 |
| 3b | 1.1 | 0.072 |
| 3c | 13.0 | 14.0 |
| 3d | 4.0 | 0.13 |
| 3e | 7.1 | 14.0 |
| 3f | 0.17 | 0.13 |
| 3g | 8.2 | 14.0 |
| 3h | 0.2 | 1.2 |
| 4a | 25.0 | 25.0 |
| 4b | 16.0 | 0.51 |
| 4c | 6.2 | 4.6 |
| 4d | 0.11 | 0.073 |
| 5 | 0.46 | 0.23 |
| 6a | 5.9 | 0.4 |
| 6b | 25.0 | 25.0 |
| 6c | 25.0 | 25.0 |
| 6d | 9.3 | 0.54 |
| 6e | 3.2 | 6.8 |
| 6f | 0.024 | 0.12 |
| 6g | 4.68 | 1.23 |
| 6h | 6.5 | 8.6 |
| 7a | 3.9 | 0.37 |
| 7b | 25.0 | 25.0 |
| 7c | 0.115 | 0.133 |
| 7d | 25.0 | 25.0 |
| 8a | 17.0 | 15.0 |
| 8b | 0.048 | 0.12 |
| 9a | 18.0 | 21.0 |
| 9b | 0.13 | 0.1 |
| 10a | 25.0 | 24.0 |
| 10b | 0.24 | 0.17 |
| 11a | 20.0 | 0.66 |
| 11b | 25.0 | 25.0 |
| 11c | 25.0 | 25.0 |
| 11d | 25.0 | 3.0 |
| 11e | 6.8 | 12.0 |
| 11f | 0.0585 | 0.182 |
| 11g | 4.7 | 0.93 |
| 11h | 25.0 | 11.0 |
| 12a | 0.92 | 1.2 |
| 12b | 8.1 | 21.0 |
| 12c | 1.9 | 0.52 |
| 12d | 4.3 | 9.8 |
| 12e | 3.9 | 1.5 |
| 12f | 1.9 | 11.0 |
| 12g | 4.7 | 2.1 |
| 12h | 7.0 | 13.0 |
| 12i | 5.8 | 13.0 |
| 12j | 0.12 | 0.74 |
| 12k | 13.0 | 15.0 |
| 12l | 12.0 | 0.41 |
| 12m | 2.0 | 15,0 |
| 13a | 0.29 | 0.16 |
| 13b | 7.2 | 3.3 |
| 14a | 25.0 | 25.0 |
| 14b | 0.068 | 0.13 |
| 15a | 25.0 | 25.0 |
| 15b | 1.1 | 1.5 |
| 16 | 0.22 | 0.095 |
| 17 | 1.3 | 0.67 |
| 18 | 0.58 | 0.11 |
| 19 | 0.099 | 0.094 |
| 20 | 0.14 | 0.1 |
| 21a | 0.15 | 0.18 |
| 21b | 0.075 | 0.1 |
| 21c | 4.8 | 5.9 |
| 22a | 2.1 | 0.41 |
| 22b | 12.0 | 5.0 |
| 22c | 8.8 | 25.0 |
| 22d | 1.4 | 0.44 |
| 22e | 8.5 | 17.0 |
| 22f | 0.092 | 1.4 |
| 22g | 0.041 | 0.16 |
| 22h | 2.8 | 4.0 |
| 23a | 0.15 | 0.33 |
| 23b | 2.5 | 3.2 |
| 23c | 0.05 | 0.09 |
| 24a | 4.4 | 6.9 |
| 24b | 1.3 | 2.1 |
| 24c | 5.2 | 0.73 |
| 24d | 1.1 | 2.5 |
| 24e | 10.0 | 16.0 |
| 24f | 6.0 | 14.0 |
| 24g | 1.8 | 1.1 |
| 24h | 5.4 | 16.0 |
| 24i | 0.96 | 0.26 |
| 24j | 0.64 | 0.14 |
| 24k | 5.0 | 14.0 |
| 24l | 1.9 | 8.6 |
| 24m | 0.039 | 0.26 |
| 24n | 0.24 | 1.1 |
| 24o | 25.0 | 20.0 |
| 24p | 0.92 | 3.3 |
| 25a | 0.034 | 0.081 |
| 25b | 0.16 | 0.15 |
| 26 | 0.11 | 0.22 |
| 27 | 0.03 | 0.14 |
| 28 | 0.065 | 0.24 |
| 29 | 0.059 | 0.24 |
| 30 | 0.32 | 0.49 |
| 31 | 0.15 | 2.2 |
| 32 | 0.049 | 0.3 |
| 33 | 0.49 | 0.84 |
| 34 | 0.032 | 0.48 |
| 35 | 0.14 | 0.46 |
| 36 | 0.035 | 0.15 |
| 37 | 0.23 | 1.1 |
| 38 | 0.63 | 2.3 |
| 39 | 3.3 | 3.9 |
| 40 | 7.0 | 9.2 |
| 41 | 1.5 | 3.4 |
| 42 | 1.1 | 4.1 |
| 43 | 0.36 | 0.85 |
| 44 | 0.082 | 0.28 |
| 45 | 2.4 | 2.1 |
| 46 | 2.0 | 2.4 |
| 47 | 0.85 | 0.85 |
| 48 | 0.35 | 0.73 |
| 49 | 0.56 | 0.53 |
| 50 | 1.5 | 1.3 |
| 51 | 0.39 | 0.22 |
| 52 | 3.9 | 3.7 |
| 53 | 6.7 | 9.9 |
| 54 | 0.24 | 0.37 |
| 55 | 0.51 | 0.81 |
| 56 | 0.66 | 0.79 |
| 57 | 0.087 | 0.26 |
| 58 | 0.35 | 0.34 |
| 59 | 2.8 | 2.0 |
| 60 | 0.04 | 0.056 |
| 61 | 0.12 | 0.47 |
| 62 | 25.0 | 25.0 |
| 63 | 0.16 | 0.31 |
| 64 | 17.0 | 13.0 |
| 65 | 6.3 | 9.0 |
| 66 | 13.0 | 14.0 |
| 67 | 25.0 | 23.0 |
| 68 | 3.4 | 5.7 |
| 69 | 0.35 | 0.37 |
| 70 | 0.15 | 0.14 |

The invention claimed is:
1. A compound of formula (I):

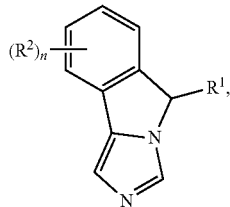

(I)

or a stereoisomer thereof, or a pharmaceutically acceptable salt thereof, wherein $R^1$ is

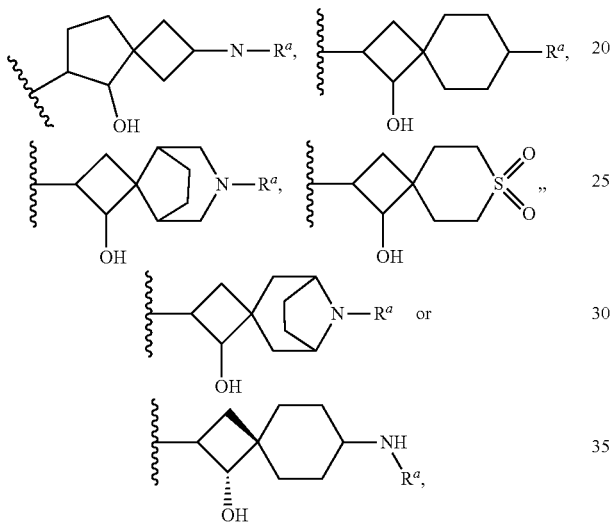

wherein
wherein each $R^a$ is independently oxo, halogen, cyano, nitro, $C_{1-6}$ alkyl, —$C_{1-6}$haloalkyl, $C_{1-6}$alkyl-cyano, —OR, —$NR_2$, —SR, —C(O)OR, —C(O)N(R)$_2$, —C(O)R, —N(R)C(O)R, —S(O)R, —S(O)OR, —S(O)N(R)$_2$, —S(O)$_2$R, —S(O)$_2$OR, —S(O)$_2$N(R)$_2$, —P(O)R$_2$, —OC(O)R, —OC(O)OR, —OC(O)N(R)$_2$, —N(R)C(O)R, —N(R)C(O)OR or —N(R)C(O)N(R)$_2$;
n is 0, 1, 2, 3 or 4;
each $R^2$ is independently halogen, cyano, $C_{1-6}$ alkyl, $C_3$cycloalkyl, —$C_{1-6}$ haloalkyl, —OR, —$NR_2$ or —SR; and
each R is independently hydrogen, $C_{1-6}$ alkyl, $C_{1-6}$ haloalkyl, $C_{1-6}$alkyl-O—$C_{1-6}$ alkyl, —$C_{1-6}$alkyl-NHC(O)H, optionally substituted $C_{3-6}$ cycloalkyl, optionally substituted 4-10 membered heterocycloalkyl, optionally substituted —$C_{1-6}$alkyl-(4-10 membered heterocycloalkyl), optionally substituted heteroaryl, optionally substituted —$C_{1-6}$alkyl-heteroaryl.
2. The compound of claim 1, wherein n is 0, 1, 2 or 3.
3. The compound of claim 1, wherein n is 1.
4. The compound of claim 1, wherein each $R^a$ is independently oxo, halogen, cyano, nitro, $C_{1-6}$ alkyl, —$C_{1-6}$ haloalkyl, $C_{1-6}$alkyl-cyano, —OR, —$NR_2$, —SR, —C(O)OR, —C(O)N(R)$_2$, —C(O)R, —N(R)C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR or —N(R)C(O)N(R)$_2$.

5. The compound of claim 1, wherein each $R^a$ is independently $C_{1-6}$ alkyl, —C(O)OR, —C(O)N(R)$_2$, —C(O)R, —N(R)C(O)R, —S(O)N(R)$_2$, —S(O)$_2$R, —P(O)R$_2$, —OC(O)R, —OC(O)OR or —OC(O)N(R)$_2$.
6. The compound of claim 1, wherein each $R^a$ is independently —C(O)OR, —C(O)R, —N(R)C(O)R, —S(O)N(R)$_2$, —S(O)$_2$R or —P(O)R$_2$.
7. The compound of claim 1 of formula (Ia),

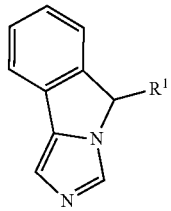

(Ia)

or a stereoisomeric mixture thereof.
8. The compound of claim 1, wherein each R is independently hydrogen, methyl, ethyl, isopropyl, tert-butyl, fluoromethyl, difluoromethyl, —CH$_2$CHF$_2$, —(CH$_2$)$_2$—O—CH$_3$, —CH(CH$_3$)NHC(O)H, —(CH$_2$)$_2$—C(O)NMe$_2$, —CH$_2$CN, cyclopropyl, difluorocyclopropyl, cyclopropane-1-carbonitrile, cyclobutyl, 1-methylpyrazol-4-yl, 1-methyl-1H-pyrazol-3-yl, 1,3,5-trimethylpyrazol-4-yl, 1,3,5-trimethyl-1H-pyrazol-4-yl, 1,2-dimethyl-1H-imidazol-4-yl, 3,5-dimethylisoxazol-4-yl, 4-methylpyridin-3-yl, —(CH$_2$)$_2$-pyridin-3-yl, phenyl-N-methylacetamide, —CH$_2$-piperidin-1-yl, 1-methylindolin-2-one, 6,7-dihydro-5H-pyrazolo[5,1-b][1,3]oxazinyl, —CH$_2$-piperidin-2-one, 1-methylpiperidin-2-one, —CH(CH$_3$)-(1H-1,2,4-triazol-1-yl), 1-methyl-1H-pyrazol-3-yl, tetrahydro-2H-pyran-4-yl, tetrahydrofuran-3-yl, —CH$_2$-(tetrahydro-2H-pyran-4-yl), —CH$_2$-(pyrrolidin-2-one), —CH$_2$-(1-methylpyrrolidin-2-one), —CH$_2$-(5-methylisoxazol-3-yl), —(CH$_2$)$_2$-(1-methyl-1H-pyrazol-4-yl), 1H-imidazol-4-yl, —CH$_2$-(1H-tetrazol-5-yl), —CH$_2$-(3-methylisoxazol-5-yl), piperidine-1-carboxamide, 1,1-dioxidotetrahydrothiophen-3-yl or 5,6,7,8-tetrahydro-[1,2,4]triazolo[4,3-a]pyridin-6-yl.
9. The compound of claim 7, wherein each R is independently hydrogen, methyl, ethyl, isopropyl, tert-butyl, fluoromethyl, difluoromethyl, —CH$_2$CHF$_2$, —(CH$_2$)$_2$—O—CH$_3$, —CH(CH$_3$)NHC(O)H, —(CH$_2$)$_2$—C(O)NMe$_2$ or —CH$_2$CN.
10. The compound of claim 1, wherein each R is independently hydrogen, methyl, cyclopropyl, difluorocyclopropyl, cyclopropane-1-carbonitrile, cyclobutyl, 1-methylpyrazol-4-yl, 1-methyl-1H-pyrazol-3-yl, 1,3,5-trimethylpyrazol-4-yl, 1,3,5-trimethyl-1H-pyrazol-4-yl, 1,2-dimethyl-1H-imidazol-4-yl, 3,5-dimethylisoxazol-4-yl, 4-methylpyridin-3-yl, —(CH$_2$)$_2$-pyridin-3-yl, phenyl-N-methylacetamide, —CH$_2$-piperidin-1-yl, 1-methylindolin-2-one, 6,7-dihydro-5H-pyrazolo[5,1-b][1,3]oxazinyl, —CH$_2$-piperidin-2-one, 1-methylpiperidin-2-one, —CH(CH$_3$)-(1H-1,2,4-triazol-1-yl), 1-methyl-1H-pyrazol-3-yl, tetrahydro-2H-pyran-4-yl, tetrahydrofuran-3-yl, —CH$_2$-(tetrahydro-2H-pyran-4-yl), —CH$_2$-(pyrrolidin-2-one), —CH$_2$-(1-methylpyrrolidin-2-one), —CH$_2$-(5-methylisoxazol-3-yl), —(CH$_2$)$_2$-(1-methyl-1H-pyrazol-4-yl), 1H-imidazol-4-yl, —CH$_2$-(1H-tetrazol-5-yl), —CH$_2$-(3-methylisoxazol-5-yl), piperidine-1-carboxamide, 1,1-dioxidotetrahydrothiophen-3-yl or 5,6,7,8-tetrahydro-[1,2,4]triazolo[4,3-a]pyridin-6-yl.

11. A compound that is
tert-butyl 1-hydroxy-2-(5H-imidazo[5,1-a]isoindol-5-yl)-7-azaspiro[3.5]nonane-7-carboxylate;
tert-butyl 1-hydroxy-2-(5H-imidazo[5,1-a]isoindol-5-yl)-8-azaspiro[4.5]decane-8-carboxylate;
tert-butyl 5-hydroxy-6-(5H-imidazo[4,3-a]isoindol-5-yl)-2-azaspiro[3.4]octane-2-carboxylate;
6-(5H-imidazo[1,5-b]isoindol-5-yl)-2-methylsulfonyl-2-azaspiro[3.3]heptan-7-ol;
7-fluoromethanesulfonyl-2-(5H-imidazo[4,3-a]isoindol-5-yl)-7-azaspiro[3.5]nonan-1-ol;
methyl 1-hydroxy-2-(5H-imidazo[4,3-a]isoindol-5-yl)-8-azaspiro[4.5]decane-8-carboxylate;
1-(1-hydroxy-2-(5H-imidazo[4,3-a]isoindol-5-yl)-8-azaspiro[4.5]decan-8-yl)ethan-1-one;
tert-butyl 2'-hydroxy-3'-(5H-imidazo[5,1-a]isoindol-5-yl)-8-azaspiro[bicyclo[3.2.1]octane-3,1'-cyclobutane]-8-carboxylate;
1-hydroxy-2-(5H-imidazo[5,1-a]isoindol-5-yl)-8-thiaspiro[4.5]decane 8,8-dioxide;
7-((difluoromethyl)sulfonyl)-2-(5H-imidazo[5,1-a]isoindol-5-yl)-7-azaspiro[3.5]nonan-1-ol;
(1-hydroxy-2-(5H-imidazo[5,1-a]isoindol-5-yl)-7-azaspiro[3.5]nonan-7-yl)dimethylphosphine oxide;
6-(5H-imidazo[5,1-a]isoindol-5-yl)-2-(methylsulfonyl)-2-azaspiro[3.4]octan-5-ol;
1-(5-hydroxy-6-(5H-imidazo[5,1-a]isoindol-5-yl)-2-azaspiro[3.4]octan-2-yl)ethan-1-one;
5-hydroxy-6-(5H-imidazo[5,1-a]isoindol-5-yl)-2-azaspiro[3.4]octane-2-sulfonamide;
2-methoxyethyl 1-hydroxy-2-(5H-imidazo[5,1-a]isoindol-5-yl)-8-azaspiro[4.5]decane-8-carboxylate;
cyclopropyl(1-hydroxy-2-(5H-imidazo[5,1-a]isoindol-5-yl)-8-azaspiro[4.5]decan-8-yl)methanone;
2-[[3-hydroxy-2-(5H-imidazo[1,5-b]isoindol-5-yl)-7-azaspiro[3.5]nonan-7-yl]sulfonyl]acetonitrile;
tert-butyl 2'-hydroxy-3'-(5H-imidazo[5,1-a]isoindol-5-yl)-3-azaspiro[bicyclo[3.2.1]octane-8,1'-cyclobutane]-3-carboxylate;
2-(5H-imidazo[1,5-b]isoindol-5-yl)-7-(oxetan-3-ylsulfonyl)-7-azaspiro[3.5]nonan-3-ol;
tert-butyl (1-hydroxy-2-(5H-imidazo[5,1-a]isoindol-5-yl)spiro[3.5]nonan-7-yl)carbamate;
(2,2-difluorocyclopropyl)(1-hydroxy-2-(5H-imidazo[5,1-a]isoindol-5-yl)-8-azaspiro[4.5]decan-8-yl)methanone;
2-(5H-imidazo[1,5-b]isoindol-5-yl)-7-(1-methylpyrazol-4-yl)sulfonyl-7-azaspiro[3.5]nonan-3-ol;
2-(5H-imidazo[1,5-b]isoindol-5-yl)-7-(1,3,5-trimethylpyrazol-4-yl)sulfonyl-7-azaspiro[3.5]nonan-3-ol;
7-(2,3-dimethylimidazol-4-yl)sulfonyl-2-(5H-imidazo[1,5-b]isoindol-5-yl)-7-azaspiro[3.5]nonan-3-ol;
2-(5H-imidazo[1,5-b]isoindol-5-yl)-7-isopropylsulfonyl-7-azaspiro[3.5]nonan-3-ol;
7-(3,5-dimethylisoxazol-4-yl)sulfonyl-2-(5H-imidazo[1,5-b]isoindol-5-yl)-7-azaspiro[3.5]nonan-3-ol;
7-(1,2-dimethylimidazol-4-yl)sulfonyl-2-(5H-imidazo[1,5-b]isoindol-5-yl)-7-azaspiro[3.5]nonan-3-ol;
2-(5H-imidazo[1,5-b]isoindol-5-yl)-7-[(4-methyl-3-pyridyl)sulfonyl]-7-azaspiro[3.5]nonan-3-ol;
1-[3-hydroxy-2-(5H-imidazo[1,5-b]isoindol-5-yl)-7-azaspiro[3.5]nonan-7-yl]-3-(3-pyridyl)propan-1-one;
N-[4-[[3-hydroxy-2-(5H-imidazo[1,5-b]isoindol-5-yl)-7-azaspiro[3.5]nonan-7-yl]sulfonyl]phenyl]-N-methylacetamide;
1-[4-[[3-hydroxy-2-(5H-imidazo[1,5-b]isoindol-5-yl)-7-azaspiro[3.5]nonan-7-yl]sulfonyl]-1-piperidyl]ethanone;
7-cyclobutylsulfonyl-2-(5H-imidazo[1,5-b]isoindol-5-yl)-7-azaspiro[3.5]nonan-3-ol;
5-[[3-hydroxy-2-(5H-imidazo[1,5-b]isoindol-5-yl)-7-azaspiro[3.5]nonan-7-yl]sulfonyl]-1-methyl-indolin-2-one;
6,7-dihydro-5H-pyrazolo[5,1-b][1,3]oxazin-3-yl-[3-hydroxy-2-(5H-imidazo[1,5-b]isoindol-5-yl)-7-azaspiro[3.5]nonan-7-yl]methanone;
1-[2-[3-hydroxy-2-(5H-imidazo[1,5-b]isoindol-5-yl)-7-azaspiro[3.5]nonan-7-yl]-2-oxo-ethyl]piperidin-2-one;
4-[3-hydroxy-2-(5H-imidazo[1,5-b]isoindol-5-yl)-7-azaspiro[3.5]nonane-7-carbonyl]-1-methyl-piperidin-2-one;
1-[3-hydroxy-2-(5H-imidazo[1,5-b]isoindol-5-yl)-7-azaspiro[3.5]nonan-7-yl]-2-(1,2,4-triazol-1-yl)propan-1-one;
N-[2-[3-hydroxy-2-(5H-imidazo[1,5-b]isoindol-5-yl)-7-azaspiro[3.5]nonan-7-yl]-1-methyl-2-oxo-ethyl]formamide;
cyclopropyl-[3-hydroxy-2-(5H-imidazo[1,5-b]isoindol-5-yl)-7-azaspiro[3.5]nonan-7-yl]methanone;
2-(5H-imidazo[1,5-b]isoindol-5-yl)-7-(1-methylpyrazol-3-yl)sulfonyl-7-azaspiro[3.5]nonan-3-ol;
[3-hydroxy-2-(5H-imidazo[1,5-b]isoindol-5-yl)-7-azaspiro[3.5]nonan-7-yl]-tetrahydropyran-4-yl-methanone;
[3-hydroxy-2-(5H-imidazo[1,5-b]isoindol-5-yl)-7-azaspiro[3.5]nonan-7-yl]-tetrahydrofuran-3-yl-methanone;
1-[3-hydroxy-2-(5H-imidazo[1,5-b]isoindol-5-yl)-7-azaspiro[3.5]nonan-7-yl]-3-methoxy-propan-1-one;
cyclobutyl-[3-hydroxy-2-(5H-imidazo[1,5-b]isoindol-5-yl)-7-azaspiro[3.5]nonan-7-yl]methanone;
1-[3-hydroxy-2-(5H-imidazo[1,5-b]isoindol-5-yl)-7-azaspiro[3.5]nonan-7-yl]propan-1-one;
4-[3-hydroxy-2-(5H-imidazo[1,5-b]isoindol-5-yl)-7-azaspiro[3.5]nonan-7-yl]-N,N-dimethyl-4-oxo-butanamide;
1-[3-hydroxy-2-(5H-imidazo[1,5-b]isoindol-5-yl)-7-azaspiro[3.5]nonan-7-yl]-2-tetrahydropyran-4-yl-ethanone;
1-[2-[3-hydroxy-2-(5H-imidazo[1,5-b]isoindol-5-yl)-7-azaspiro[3.5]nonan-7-yl]-2-oxo-ethyl]pyrrolidin-2-one;
4-[3-hydroxy-2-(5H-imidazo[1,5-b]isoindol-5-yl)-7-azaspiro[3.5]nonane-carbonyl]-1-methyl-pyrrolidin-2-one;
1-[3-hydroxy-2-(5H-imidazo[1,5-b]isoindol-5-yl)-7-azaspiro[3.5]nonan-7-yl]-2-(5-methylisoxazol-3-yl)ethanone;
1-[3-hydroxy-2-(5H-imidazo[1,5-b]isoindol-5-yl)-7-azaspiro[3.5]nonan-7-yl]-3-(1-methylpyrazol-4-yl)propan-1-one;
1-[3-hydroxy-2-(5H-imidazo[1,5-b]isoindol-5-yl)-7-azaspiro[3.5]nonan-7-yl]ethanone;
2,2-difluoroethyl (2S,3R)-3-hydroxy-2-[(5S)-5H-imidazo[1,5-b]isoindol-5-yl]-7-azaspiro[3.5]nonane-7-carboxylate;
N-(2,2-difluoroethyl)-3-hydroxy-2-(5H-imidazo[1,5-b]isoindol-5-yl)-7-azaspiro[3.5]nonane-7-carboxamide;
8-((1H-imidazo)-4-yl)sulfonyl)-2-(5H-imidazo[5,1-a]isoindol-5-yl)-8-azaspiro[4.5]decan-1-ol;
2,2-difluoroethyl 1-hydroxy-2-(5H-imidazo[5,1-a]isoindol-5-yl)-8-azaspiro[4.5]decane-8-carboxylate;
1-[3-hydroxy-2-(5H-imidazo[1,5-b]isoindol-5-yl)-7-azaspiro[3.5]nonane-7-carbonyl]cyclopropanecarbonitrile;

1-[3-hydroxy-2-(5H-imidazo[1,5-b]isoindol-5-yl)-7-azaspiro[3.5]nonan-7-yl]-2-(1H-tetrazol-5-yl)ethanone;

1-[3-hydroxy-2-(5H-imidazo[1,5-b]isoindol-5-yl)-7-azaspiro[3.5]nonan-7-yl]-2-(3-methylisoxazol-5-yl)ethanone;

3-[3-hydroxy-2-(5H-imidazo[1,5-b]isoindol-5-yl)-7-azaspiro[3.5]nonane-7-carbonyl]piperidine-1-carboxamide;

(1,1-dioxothiolan-3-yl)-[3-hydroxy-2-(5H-imidazo[1,5-b]isoindol-5-yl)-7-azaspiro[3.5]nonan-7-yl]methanone;

4-[3-hydroxy-2-(5H-imidazo[1,5-b]isoindol-5-yl)-7-azaspiro[3.5]nonane-7-carbonyl]piperidine-1-carboxamide;

[3-hydroxy-2-(5H-imidazo[1,5-b]isoindol-5-yl)-7-azaspiro[3.5]nonan-7-yl]-(5,6,7,8-tetrahydro-[1,2,4]triazolo[4,3-a]pyridin-6-yl)methanone;

1-[4-[3-hydroxy-2-(5H-imidazo[1,5-b]isoindol-5-yl)-7-azaspiro[3.5]nonane-7-carbonyl]-1-piperidyl]ethanone;

2,2-difluoro-1-[3-hydroxy-2-(5H-imidazo[1,5-b]isoindol-5-yl)-7-azaspiro[3.5]nonan-7-yl]ethanone;

3'-(5H-imidazo[5,1-a]isoindol-5-yl)-3-(methylsulfonyl)-3-azaspiro[bicyclo[3.2.1]octane-8,1'-cyclobutan]-2'-ol;

or a pharmaceutically acceptable salt thereof, or an enantiomer or diastereoisomer thereof, or a racemic mixture thereof.

12. A compound that is
tert-butyl (1R,2S)-1-hydroxy-2-((S)-5H-imidazo[5,1-a]isoindol-5-yl)-7-azaspiro[3.5]nonane-7-carboxylate;

tert-butyl (1R,2S)-1-hydroxy-2-((S)-5H-imidazo[5,1-a]isoindol-5-yl)-8-azaspiro[4.5]decane-8-carboxylate;

tert-butyl (5S,6R)-5-hydroxy-6-[(5R)-5H-imidazo[1,5-b]isoindol-5-yl]-2-azaspiro[3.4]octane-2-carboxylate;

(1R,2S)-7-fluoromethanesulfonyl-2-[(5S)-5H-imidazo[4,3-a]isoindol-5-yl]-7-azaspiro[3.5]nonan-1-ol;

(5R,6R)-6-[(5R)-5H-imidazo[4,3-a]isoindol-5-yl]-2-methanesulfonyl-2-azaspiro[3.4]octan-5-ol;

2-methoxyethyl (3S,4R)-4-hydroxy-3-[(5S)-5H-imidazo[1,5-b]isoindol-5-yl]-8-azaspiro[4.5]decane-8-carboxylate;

cyclopropyl-[(3S,4R)-4-hydroxy-3-[(5S)-5H-imidazo[1,5-b]isoindol-5-yl]-8-azaspiro[4.5]decan-8-yl]methanone;

(2S,3R)-2-[[3-hydroxy-2-((5S)-5H-imidazo[1,5-b]isoindol-5-yl)-7-azaspiro[3.5]nonan-7-yl]sulfonyl]acetonitrile;

tert-butyl (2'R,3R)—Z-hydroxy-3-((S)-5H-imidazo[5,1-a]isoindol-5-yl)-3-azaspiro[bicyclo[3.2.1]octane-8,1'-cyclobutane]-3-carboxylate;

tert-butyl (2'R,3R)—Z-hydroxy-3-((R)-5H-imidazo[5,1-a]isoindol-5-yl)-3-azaspiro[bicyclo[3.2.1]octane-8,1'-cyclobutane]-3-carboxylate;

(2S,3R)-2-[(5S)-5H-imidazo[1,5-b]isoindol-5-yl]-7-(oxetan-3-ylsulfonyl)-7-azaspiro[3.5]nonan-3-ol;

tert-butyl ((1R,2S,4r,7R)-1-hydroxy-2-((R)-5H-imidazo[5,1-a]isoindol-5-yl)spiro[3.5]nonan-7-yl)carbamate;

((S)-2,2-difluorocyclopropyl)((1R,2S)-1-hydroxy-2-((S)-5H-imidazo[5,1-a]isoindol-5-yl)-8-azaspiro[4.5]decan-8-yl)methanone;

2-(5H-imidazo[1,5-b]isoindol-5-yl)-7-(1,3,5-trimethylpyrazol-4-yl)sulfonyl-7-azaspiro[3.5]nonan-3-ol;

(1R,2S)-2-((S)-5H-imidazo[5,1-a]isoindol-5-yl)-7-((1,3,5-trimethyl-1H-pyrazol-4-yl)sulfonyl)-7-azaspiro[3.5]nonan-1-ol;

(1R,2S)-2-((S)-5H-imidazo[5,1-a]isoindol-5-yl)-7-(isopropylsulfonyl)-7-azaspiro[3.5]nonan-1-ol;

(1R,2S)-2-((S)-5H-imidazo[5,1-a]isoindol-5-yl)-7-((4-methylpyridin-3-yl)sulfonyl)-7-azaspiro[3.5]nonan-1-ol;

N-(4-(((1R,2S)-1-hydroxy-2-((S)-5H-imidazo[5,1-a]isoindol-5-yl)-7-azaspiro[3.5]nonan-7-yl)sulfonyl)phenyl)-N-methylacetamide;

(1R,2S)-7-(cyclobutylsulfonyl)-2-((S)-5H-imidazo[5,1-a]isoindol-5-yl)-7-azaspiro[3.5]nonan-1-ol;

(1R,2S)-2-((S)-5H-imidazo[5,1-a]isoindol-5-yl)-7-((1-methyl-1H-pyrazol-3-yl)sulfonyl)-7-azaspiro[3.5]nonan-1-ol;

2,2-difluoroethyl (1R,2S)-1-hydroxy-2-((S)-5H-imidazo[5,1-a]isoindol-5-yl)-7-azaspiro[3.5]nonane-7-carboxylate;

2,2-difluoroethyl (3S,4R)-4-hydroxy-3-[(5S)-5H-imidazo[1,5-b]isoindol-5-yl]-8-azaspiro[4.5]decane-8-carboxylate;

or a pharmaceutically acceptable salt thereof, or an enantiomer or diastereoisomer thereof, or a racemic mixture thereof.

13. A pharmaceutical composition comprising a compound according to claim 1 and a pharmaceutically acceptable diluent, excipient, or carrier.

14. A method for treating tryptophan 2,3-dioxygenase (TDO2) mediated immunosuppression associated with a disease in a subject in need thereof, comprising administering an effective tryptophan 2,3-dioxygenase inhibiting amount of a compound according to claim 1.

15. The compound of claim 1, wherein n is 0.

16. A pharmaceutical composition comprising a compound according to claim 11 and a pharmaceutically acceptable diluent, excipient, or carrier.

17. A pharmaceutical composition comprising a compound according to claim 12 and a pharmaceutically acceptable diluent, excipient, or carrier.

* * * * *